US012509670B2

(12) United States Patent
Tang et al.

(10) Patent No.: US 12,509,670 B2
(45) **Date of Patent: *Dec. 30, 2025**

(54) GLUCOAMYLASE AND METHODS OF USE THEREOF

(71) Applicant: DANISCO US INC., Palo Alto, CA (US)

(72) Inventors: Zhongmei Tang, Shanghai (CN); Zhenghong Zhang, Shanghai (CN); Jing Ge, Shanghai (CN); Lilia Babe, Palo Alto, CA (US); Xingxiang Xi, Shanghai (CN); Helong Hao, Shanghai (CN); Chao Huang, Shanghai (CN)

(73) Assignee: DANISCO US INC., Palo Alto, CA (US)

( * ) Notice: Subject to any disclaimer, the term of this patent is extended or adjusted under 35 U.S.C. 154(b) by 426 days.

This patent is subject to a terminal disclaimer.

(21) Appl. No.: 17/918,533

(22) PCT Filed: Apr. 19, 2021

(86) PCT No.: PCT/US2021/027894

§ 371 (c)(1),
(2) Date: Oct. 12, 2022

(87) PCT Pub. No.: WO2021/212095

PCT Pub. Date: Oct. 21, 2021

(65) Prior Publication Data

US 2023/0340444 A1 Oct. 26, 2023

(30) Foreign Application Priority Data

Apr. 17, 2020 (WO) ................ PCT/CN2020/085393

(51) Int. Cl.

| | |
|---|---|
| ***C12N 9/34*** | (2006.01) |
| ***A23L 2/38*** | (2021.01) |
| ***A23L 29/00*** | (2016.01) |
| ***A23L 29/30*** | (2016.01) |
| ***C12N 1/16*** | (2006.01) |
| ***C12N 15/81*** | (2006.01) |
| ***C12P 19/02*** | (2006.01) |
| ***C12P 19/14*** | (2006.01) |

(52) U.S. Cl.

CPC ............ *C12N 9/2428* (2013.01); *A23L 2/382* (2013.01); *A23L 29/06* (2016.08); *A23L 29/35* (2016.08); *C12N 1/16* (2013.01); *C12N 15/81* (2013.01); *C12P 19/02* (2013.01); *C12P 19/14* (2013.01); *C12Y 302/01003* (2013.01)

(58) Field of Classification Search

CPC ........ C12N 9/2428; C12N 1/16; C12N 15/81; A23L 2/382; A23L 29/06; A23L 29/35; C12P 19/02; C12P 19/14; C12Y 302/01003; Y02E 50/10

See application file for complete search history.

(56) References Cited

U.S. PATENT DOCUMENTS

| | | | |
|---|---|---|---|
| 5,084,385 A | 1/1992 | Ashikari et al. | |
| 5,223,409 A | 6/1993 | Lander et al. | |
| 6,022,725 A | 2/2000 | Fowler et al. | |
| 11,421,212 B2 * | 8/2022 | Miller | C12N 9/2428 |
| 2011/0020899 A1 | 1/2011 | Aehle et al. | |
| 2013/0323798 A1 | 12/2013 | Ge et al. | |
| 2022/0396783 A1 * | 12/2022 | Tang | A23L 29/06 |

FOREIGN PATENT DOCUMENTS

| | | | |
|---|---|---|---|
| RU | 2394101 | C2 | 7/2010 |
| RU | 2439153 | C2 | 1/2012 |
| WO | 199117243 | A1 | 11/1991 |
| WO | 199206204 | A1 | 4/1992 |
| WO | 1992012645 | A1 | 8/1992 |
| WO | 199517413 | A1 | 6/1995 |
| WO | 199522625 | A1 | 8/1995 |
| WO | 1997016076 | A1 | 5/1997 |
| WO | 2007044968 | A2 | 4/2007 |
| WO | 2012019169 | A1 | 2/2012 |
| WO | 2013169645 | A1 | 11/2013 |
| WO | 2014099415 | A1 | 6/2014 |
| WO | 2016138315 | A1 | 9/2016 |
| WO | 2017112635 | A1 | 6/2017 |
| WO | 2018027131 | A1 | 2/2018 |
| WO | 2019173424 | A1 | 9/2019 |
| WO | 2019191263 | A1 | 10/2019 |

OTHER PUBLICATIONS

Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
GenPept: Glucoamylase, intracellular sporulation-specific [Apophysomyces ossiformis]; GenBank: KAF7727643.1, Oct. 2, 2020, 2 pages.
Whisstock, J.C. et al., Prediction of protein function from protein sequence and structure. Quarterly Reviews of Biophysics 36, 3 2003, p. 307-340.
Witkowski, A. et al., Conversion of a β-Ketoacyl Synthase to a Malonyl Decarboxylase by Replacement of the Active-Site Cysteine with Glutamine Biochemistry, 1999, 38, 11643-11650.
Seffernick, J. L. et al., Melamine Deaminase and Atrazine Chlorohydrolase: 98 Percent Identical but Functionally Different. Journal of Bacteriology, 2001, v.183, No. 8, p. 2405-2410.

(Continued)

*Primary Examiner* — Ganapathirama Raghu

(57) ABSTRACT

Described are a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage. The glucoamylase or 1,4-alpha-D-glucan glucohydrolase (EC 3.2.1.3) is preferably from the Mucorales-clade, especially having high sequence identity to the glucoamylase from *Saksenaea vasiformis.*

11 Claims, 20 Drawing Sheets

Specification includes a Sequence Listing.

(56) References Cited

OTHER PUBLICATIONS

Broun et al., Catalytic Plasticity of Fatty Acid Modification Enzymes Underlying Chemical Diversity of Plant Lipids. Science, 1998, v.282, p. 1315-1317.
Wishart et al., A single mutation converts a novel phospholyrosine binding domain into a dual-specificity phophatase, J.Biol. Chem., 1995, vol. 270(45): 26782-26785 (Year 1995).
Yang et al., Heterologous expression and efficient ethanol production of aglucoamylase gene in; Molecular Biology Reports: An International Journal on Molecular and Cellular Biology, Kluwer Academic Publishers, vol. 38, No. 1, Mar. 18, 2010, pp. 59-64.
Ashikari et al., High expression and efficient secretion ofglucoamylase in the yeast, Applied Microbiology and Biotechnology, Spring, Berlin, DE, vol. 30, No. 5, May 1, 1989, pp. 515-520.
Carroll et al., Comprehensive analysis of fungal diversity and enzyme activity in nuruk, a Korean fermenting starter, for acquiring useful fungi, J. of Microbiology, vol. 55, No. 5, Mar. 20, 2017, pp. 357-365.
Kumar et al., Purification and kinetics of a raw starch-hydrolyzing, thermostable, and neutral glucoamylase of the thermophilic mold thermomucor indicae-seudaticae, Biotechol. Prog. 2003, vol. 19, p. 936-944.

* cited by examiner

```
             1       10        20        30        40        50        60
             |        |         |         |         |         |         |
       AnGA  WLSNEATVARTAILNNIGADGAWVSGADSGIVVASPSTDNPDYFYTWTRDSGLVLKTLVD
      AfuGA  WLGTETTVALNGILANIGADGAYAKSAKPGIIIASPSTSEPDYYYTWTRDAALVTKVLVD
     FraGA1  YIASESPVAKAGVLANIGTEGSLSSGAYSGVVIASPSTVNPDYLYTWVRDSSLTFQALID
   FveABC11  FISKEADISIKGVLANIGADGKRAQGAAPGAVVASPSRTDPDYWYTWTRDSALTYKVLVE
       GtGA  YVGSEGPIAKAGVLANIGPNGSKASGAAAGVVVASPSKSDPDYWYTWTRDSSLVFKSLID
      PoxGA  FIHKEGERSLQGILDNLGGRGKKTPGTAAGLFIASPNTENPNYYYTWTRDSALTAKCLID
       TrGA  FISTETPIALNNLLCNVGPDGCRAFGTSAGAVIASPSTIDPDYYYMWTRDSALVFKNLID
     WcoGA1  YIASESPIAKAGVLANIGADGSLSSGAYSGIVIASPSTVNPNYLYTWTRDSSLTFMELIN
     SvaGA1  WVSKQEDISFSEMLRNVNP-----EGTAKGFVAASLSTAGPDYFYTWTRDAALVSRVIAY
     BciGA1  WSPSQHSISLYAMLRNINP-----PGSAAGFISASLSTSGPDYYYSWTRDSALVAHVIVN
     BciGA2  WIKGQEDTSRSVMLGNINP-----PGSATGFISASLSTSGPDYYYHWTRDAALVAHVIVN
     BpoGA1  WLKSQIGISRYAMLRNINP-----AGSAVGFIAASLSTANPDYYYAWTRDSALTSYVIAN
     CcuGA1  WIDKQIDISRSAMLKNINP-----AGTVKGFIAASLSTSNPDYFYAWTRDAALVAHVVAN
     RstGA1  WIKRQEKISRFAMLRNINP-----PGSAAGFIAASLSTSGPDYYYSWTRDSALTSNLIAY
     MciGA5  WIDGQTSVSRYAMLRNINP-----AGAVSGFIAASMSTSGPDYFYAWTRDSALTSHVVAY
     DelGA1  WADSQHKISWKAMLANINP-----PGSATGFIAASLSTSGPDYYYAWTRDAAMVAHVIVN
     FspGA3  WVNDQLEISWPSLLKNVNP-----SGAVTGFIAASLSTNDPDYFYCWTRDAALVARVMVY
     GpeGA1  WLKGQIETSRFAMLRNINP-----AGTVKGFIAASLSTANPDYFYAWTRDAALVGHVIAN
     MciGA3  WIDGQTSVSRYAMLRNINP-----AGAVTGFIAASMSTSGPDYFYAWTRDSALTSHVVAY
     CumGA1  WVNKQLKISWSDLLQNVNP-----SGTVTGFIAASLSTSNPDYFYCWTRDAAMVARVMTY
     McoGA1  WLKSQEDISRGAMLRNINP-----PGAATGFIAASLSTSGPDYYYAWTRDSALTSHVIAH
     ParGA1  WVNTQFAISWPTLLKNVNP-----SGTVKGFIAASLSTNNPDYFYSWTRDSALVAHTMTY
     RmiGA1  WIKNQEEISRFAMLRNINP-----PGSATGFIAASLSTAGPDYYYSWTRDSALTANVIAY
     SfuGA2  WGSKQDGISFSTMLGNINP-----PGSSKGFIAASLSTAGPNYYYSWTRDSALVARAITY
     SraGA1  WAKSQKDISWKTLLTSLNP-----SGTAKGFIAASLSTSNPDYYYAWTRDSALVARTMVN
     SraGA3  WVKKQEAISWTDLKTNVNP-----EGAAKGFIAASLSTSEPDYYYAWTRDSALVARVMVN
     TinGA1  WIQEQLAISWNTMLTSVNP-----VGAVTGFIAASLSTANPDYYYCWTRDAALVARVMTF
     ZmeGA1  WASAQLDISWPNLMMNVNP-----SGAVTGSIVASLSTSNPDYFYIWTRDAAMVARVMVY
 GAN00808.1  WIDGQTSVSRYAMLRNINP-----AGTVTGFIAASMSTSGPDYFYAWTRDSALTSHVVAY
 ORE14155.1  WIKKQEEISRFAMLRNINP-----PGSATGFIAASLSTAGPDYYYSWTRDSALTANVIAY
 RCH88939.1  WIKNQEEISRFAMLRNINP-----PGSATGFIAASLSTAGPDYYYSWTRDSALTANVIAY
```

Figure 1A

```
                          70        80        90       100       110       120
                           |         |         |         |         |         |
     AnGA    LFRN-------GDTSLLSTIENYISAQAIVQGISNPSGDLSSGAGLGEPKFNVDETAYTG
    AfuGA    LFRN-------GNLGLQKVITEYVNSQAYLQTVSNPSGGLASG-GLAEPKYNVDMTAFTG
   FraGA1    QYV--YG----EDPTLRSLIDEFITAESILQQTTNPSGTVSTG-GLGEPKFNINETAFTG
 FveABC11    RFIH-------GDKSLQRKIDEYVSAQAKLQGVTNPSGGPESG-GLGEPKFHVNLTAFTG
     GtGA    QYTTGID----STSSLRSLIDSFVIAEANIQQVSNPSGTLTTG-GLGEPKFNVDETAFTG
    PoxGA    LFEDSRAKFPIDRKYLETGIRDYVSSQAILQSVSNPSGTLKDGSGLGEPKFEIDLNPFSG
     TrGA    RFTET------YDAGLQRRIEQYITAQVTLQGLSNPSGSLADGSGLGEPKFELTLKPFTG
   WcoGA1    QY--IYG----EDDTLRTLIDEFVSAEATLQQVTNPSGTVSTG-GLGEPKFNINETAFTG
   SvaGA1    KYNTTNA----GDSKIHGVLDDYVNFQINTQSESTPCN------CLGEPKFNPDGSSFTG
   BciGA1    EYNTTYQ----GNSTLLGILKDYVTYSLNAQTTSTVCN------CLGEPKFNPDGSSFTG
   BciGA2    DYNTTLS----GDSSTLQVIKDYVTFSVNSQSESTVCN------CLGEPKFNPDGSSYTG
   BpoGA1    DYNSTLA----GNSTILQIMKDYVTFSVKSQSVSTACN------CLGEPKFNPDGSSYTG
   CcuGA1    DYNRTKS----GDATYLGLLKDYVTFSINSQNTPTACN------CLGEPKFNKDGSGYNG
   RstGA1    EYNTTLS----GNTTILNILKDYVKFSISSQTTSTVCN------CLGEPKFNHDGSSYTG
   MciGA5    DYNTTLA----GNSTILGLLKNYVTFSINSQTTSTVCN------CLGEPKFNKDGSSYTG
   DelGA1    AYNTTKA----GDATTLGVLKDFVTFQIKAMATSTVCN------CLGEPKFNPDGSSYTG
   FspGA3    MYNTTEA----GDTSLRSKLQDYVTFQINSMKTATVCN------CLGEPKFNKDGSGYSG
   GpeGA1    DYNRTLA----GNSTYLGLLKDYVTFSVNSQSTSTICN------CLGEPKFNKDGSGYSG
   MciGA3    DYNTTLA----GNSTILGLLKNYVTFSLNSQTTSTVCN------CLGEPKFNKDGSGYSG
   CumGA1    MYNTTEA----GDSSLESALKDYITFQINSMKTATACN------CLGEPKFNTDGSGYSG
   McoGA1    DYNTTLA----GNTTILNILKDYVTFSVKSQSVSTVCN------CLGEPKFNPDGSSYTG
   ParGA1    LYNTSEA----GDSTIESALKDYVTFSINAMNAATVCN------CLGEPKFNTDGSGYTG
   RmiGA1    EYNTTFA----GNTTLLKYLKDYVTFSVKSQSVSTVCN------CLGEPKFNADGSSYTG
   SfuGA2    KYSTSYQ----NDPKILGLLKDYVTYQVNEQTESTVCN------CLGEPKFNPDGSSFSG
   SraGA1    MYNTTEA----GSASVLGLLQDYVTFQINAMSTSTVCN------CLGEPKFNPDGSSYTG
   SraGA3    KYNTTDA----GDANLLGLLQDYVSFQINAMGESTVCN------CLGEPKFNPDGSSYTG
   TinGA1    MYNTTQA----GDSGLLGILQDYVSFQIHAMGESTVCN------CLGEPKFNPDGSSYTG
   ZmeGA1    MYNTTEA----GDTNLLNALTDYVTFSISSMNVDTVCD------CLGEPKFNVDGSGYTG
GAN00808.1   DYNTTLA----GNSTILGLLKNYVTFSLNSQTTSTVCN------CLGEPKFNKDGSSYTG
ORE14155.1   EYNTTFT----GNTTLLKYLKDYVTFSVKSQSVSTVCN------CLGEPKFNADGSSYTG
RCH88939.1   EYNTTFT----GNTTLLKYLKDYVTFSVKSQSVSTVCN------CLGEPKFNADGSSFTG
```

Figure 1B

```
                   130       140       150       160       170       180
                     |         |         |         |         |         |
      AnGA   SWGRPQRDGPALRATAMIGFGQWLLDN--GYTSTATDIVWPLVRNDLSYVAQYWNQTGYD
     AfuGA   AWGRPQRDGPALRATALIDFGNWLIDN--GYSSYAVNNIWPIVRNDLSYVSQYWSQSGFD
    FraGA1   PWGRPQRDGPALRSTAIITYATYLWNS--GNTSYVSDSLWPIIELDLNYIATYWNFSTFD
  FveABC11   SWGRPQRDGPPLRATALTLYANWLVSH--GDRSKAVNKVWPVIEKDLAYTVKFWNRTGYD
      GtGA   AWGRPQRDGPALRATALITYGNWLLSN--GNTTWVTSTLWPIIQNDLNYVVQYWNQTTFD
     PoxGA   AWGRPQRDGPALRATAMITYANYLISH--GQKSDVSQVMWPIIANDLAYVGQYWNNTGFD
      TrGA   NWGRPQRDGPALRAIALIGYSKWLINN--NYQSTVSNVIWPIVRNDLNYVAQYWNQTGFD
    WcoGA1   PWGRPQRDGPALRATAIMAYATYLYEN--GNTSYVTDTLWPIIELDLGYVAEYWNESTFD
    SvaGA1   PWGRPQNDGPAERASSFMLIADSFLSQ-TKNASYFTNTLKPAIYKDLDYVVDTWSNPCFD
    BciGA1   AWGRPQNDGPAERAVSFIYFADSYLTQ-TSDSSYVTGTLAPAIYKDLDYVVSVWSNGCFD
    BciGA2   AWGRPQNDGPAERATTFIFFADTYLAQ-GGDSSYVTGTLAPAIYADLDYVVNNWSTGCYD
    BpoGA1   AWGRPQNDGPAERATTFILFADSYLKQ-TGDASYVTGTLKPAIFKDLDYVVNTWTNGCFD
    CcuGA1   PWGRPQNDGPAERADTFVLIADSILTQ-TKDVSYVTGTLRPAIYTDLDYVVRTWSNGCFD
    RstGA1   AWGRPQNDGPAERANTFILFADSYLDQ-TKDASYVTGTLKPAIFKDLDYVVNVWSNGCYD
    MciGA5   AWGRPQNDGPASRADTFILIADSILKQ-TGDATYVTGTLAPAIYKDLDYVVSTWSNGCFD
    DelGA1   PWGRPQNDGPAERATTFILFADSYLSQ-TGDAAYVT-TLKRAIFTDLDYVVTTWQDNCFD
    FspGA3   AWGRPQNDGPADRAITLILFADSFIAQ-GGDVSYITNTLKPAIYTNLDYVVNTWSNVCFD
    GpeGA1   AWGRPQNDGPAERADTFILIADSILKQ-TGDATYVTGTLRPAIYKDLDYVVNVWSNGCFD
    MciGA3   AWGRPQNDGPASRADTFILIADSILKQ-TGDATYVTGTLAPAIYKDLDYVVSTWSNGCFD
    CumGA1   PWGRPQNDGPAERATTMILFADSYLAQ-GGDTSYVTNTLKPAIYTNLDYVVGTWSNNCFD
    McoGA1   AWGRPQNDGPAERASTFILFGDSYLKQ-TGDATYVTGTLAPAIYKDLDYVVNTWSNGCFD
    ParGA1   AWGRPQNDGPASRATTMILFADSFLAQ-GGDVSYVINTLKPAIYKDLDYVVSTWSNTCYD
    RmiGA1   PWGRPQNDGPAERAVTFMLIADSYLTQ-TKDASYVTGTLKPAIFKDLDYVVSVWSNGCYD
    SfuGA2   PWGRPQNDGPAERASTMILFAKSYYAQ-TNDVGYVSNTLKPAIYKDLDYIVNVWGNNCFD
    SraGA1   AWGRPQNDGPAERASTFILFADSYIAQ-GGQLSYVTGTLAPAIYKDLNYVVSTWSNNCFD
    SraGA3   AWGRPQNDGPAERASTFILLADSMIAQKSANGSYVSDTLAPAIYKDLAYVASTWENACYD
    TinGA1   AWGRPQNDGPAERASTFIKIADSYLTQ-TGDVSYVTNTLKPAIYEDLDYIVNVWQNTCFD
    ZmeGA1   AWGRPQNDGPAERASTMILIADSYIAQ-GGDVSYVTDTLKPAIYTDLDYVVDTWSNVCFD
GAN00808.1   AWGRPQNDGPASRADTFILIADSILKQ-TGDATYVTGTLAPAIYKDLDYVVSTWSNGCFD
ORE14155.1   PWGRPQNDGPAERAVTFMLIADSYLTQ-TKDASYVTGTLKPAIFKDLDYVVSVWSNGCYD
RCH88939.1   PWGRPQNDGPAERAVTFMLIADSYLTQ-TKDASYVTGTLKPAIFKDLDYVVSVWSNGCYD
```

Figure 1C

```
                     190       200       210       220       230       240
                       |         |         |         |         |         |
     AnGA   LWEEVNGSSFFTIAVQHRALVEGSAFATAVGSSC--SWCDSQAPEILCYLQSFW--TGSF
    AfuGA   LWEEVNSMSFFTVAVQHRALVEGSTFAKRVGASC--SWCDSQAPQILCYMQSFW--TGSY
   FraGA1   LWEEIDSSSFWTTAVQHRALRQGITFANLIGQTSPVSNYETQAGDILCFLQTYWNPTGNY
 FveABC11   LWEEVNGSSFFTLSASHRALVEGAALAKKLGKSC--SDCATNAPRVLCFMQSFW--TGSY
     GtGA   LWEEVNSSSFFTTAVQHRALREGAAFATKIGQTSSVSSYTTQAANLLCFLQSYWNPTSGY
    PoxGA   LWEEVDGSSFFTIAVQHRALVEGSQLAKKLGKSC--DACDSQPPQILCFLQSFW--NGKY
     TrGA   LWEEVNGSSFFTVANQHRALVEGATLAATLGQSG--SAYSSVAPQVLCFLQRFWVSSGGY
   WcoGA1   LWEEIDSSSFFTTAVQHRALRAGVTFANLIGETSDVSNYQENADDLLCFLQSYWNPTGSY
  SvaGA1    LWEEVNGIHFYTLMVMRRSLLDGANFATRNGDNSKASTYSGVAAKIQARLNSFWDAGKNY
  BciGA1    LWEEVNGIHFYTLMFMRRGLLDGANFASRNGDSTRASTYTSTAASIKTKIDGFWVSSGNY
  BciGA2    LWEEVNGIHFYTLMVMRRGLIDGASFASRNGDSTRSSSYTSTAKSIATKIDSFWSASNNY
  BpoGA1    LWEEVNGVHFYTLMVMRKGLIRGANFATRNGDSTRASTYTNTAASIKTKMDSFWSSGNNY
  CcuGA1    LWEEVNGVHFYTLMVMRRALLVGANFASRNGDSARASNYNNAANSIKSKIDSFWSSNNNY
   RstGA1   LWEEVNGVHFYTLMVMRKGLLLGADFAKRNGDSTRASTYTNTASTIATKISSFWVSSSNW
   MciGA5   LWEEVNGVHFYTLMVMRRGLIKGANFASRNGDNTRANTYTNTAASIKTKIDSFWNSNGNY
  DelGA1    LWEEVNGLHMYTLAVMRRSLVDGASFAARNGDNTRASTYTNTAKSIETKLASFYNSSSNY
  FspGA3    LWEEVNGVHIYTLSVMRKGLLEGADFASRNGDSTRANTYRSTASSIKTRLESFWSSSNNY
  GpeGA1    LWEEVNGVHFYTLMVMRRSLILGANFASRNGDSTRASTYTNTANSIKTKIDTFWSSSNNY
  MciGA3    LWEEVNGVHFYTLMVMRRGLVKGANFASRNGDSTRATTYTNTAASIKTKIDSFWNSNGQY
   CumGA1   LWEEVNGVHIFTLAVMRKSLLDGADFAARNGDTSRVSGYQSTASSIKTKLESFWSSSNNY
  McoGA1    LWEEVNGVHFYTLMSMRRGLLDGANFAKRNGDTTRATTYTNTAASIATKIDTFWVSSGNY
  ParGA1    LWEEVNGVHIYTLSVMRRALIDGANFAQRNGDTSRVSGYTSTATTIKTRLESFWSDSNNY
   RmiGA1   LWEEVNGVHFYTLMVMRKGLILGADFAARNGDSSRASTYKNTASTMESKISSFWSDSNNY
  SfuGA2    LWEEVNGVHFYTLMMMRHGLVQGSIFANTLGDSTRANTYKTAAQNIKNRIDTFWESGSNY
   SraGA1   LWEEVNGRHMFTLAVMRRALLDGVNFASRIGDTTYSSTWSSTASSIQSTLSGYYLSSGNY
  SraGA3    LWEEVNGKHMYTLSVMRRALLDGADFASRQGQTANVTSWKSTADKIKSSLEGFFSSDNGY
  TinGA1    LWEEVYGMHMYTLAVMRRGLLDGADFATRNGDTDKASTYTSTATSIQTRLATFWSDSNGY
  ZmeGA1    LWEEVNGIHMYTLSVMRKALLDGANFATRNGDTSRVSGYESTASSIKTRLESFWSSSNNY
GAN00808.1  LWEEVNGVHFYTLMVMRRGLVKGASFASRNGDSTRANTYTNTAASIKTKIDSFWNSNGQY
ORE14155.1  LWEEVNGVHFYTLMVMRKGLILGADFAARNGDSSRASTYKKTASTMESKISSFWSDSNNY
RCH88939.1  LWEEVNGVHFYTLMVMRKGLILGADFAARNGDSSRASTYKKTASTMESKISSFWSDSNNY
```

Figure 1D

```
                250       260       270       280       290       300
                  |         |         |         |         |         |
      AnGA   I--LANFDSSR---SGKDANTLLGSIHTFDPEAACDDSTFQPCSPRALANHKEVVDSFRS
     AfuGA   I--NANTGGGR---SGKDANTVLASIHTFDPEAGCDDTTFQPCSPRALANHKVYTDSFRS
    FraGA1   M--TANTGGGR---SGKDSNTVLASVHTFDPDAGCDSTTFQPCSDKALSNLKVYVDSFRS
  FveABC11   IDSNINVNDGR---KGLDANSILSSIHTFDPSSKCTDSTFQPCSSRALANHKEVVDSFRS
      GtGA   I--TANTGGGR---SGKDANTLLASIHTYDPSAGCDATTFQPCSDKALSNLKVYVDSFRS
     PoxGA   ITSNINTQASR---SGIDLDSVLGSIHTFDPEAACDDATFQPCSARALANHKVYVDSFRS
      TrGA   VDSNINTNEGR---TGKDVNSVLTSIHTFDPNLGCDAGTFQPCSDKALSNLKVVVDSFRS
    WcoGA1   V--TANTGGGR---SGKDANTLLASIHTFDPDAGCNATTFQPCSDKALSNHKVYVDSFRS
    SvaGA1   ITVTQDYKNGVEKPSGLDVSTLIAA-----NVAGMGDGFYTPGSERILATALAFEKSMAS
    BciGA1   VQVSQSVTSGVSK-AGYDASTLIAA-----NQASRGDGFYTPGSDKMLATAVAIESQFSS
    BciGA2   VAVSQSVTSGVSK-AGYDASTIIAA-----NQASLGDGFYTPGSDKMLATSVAVENAFSS
    BpoGA1   IAVSQSVTGGVSK-AGYDVANIIAA-----NVGSLQDGVYTPGSDRILATAVAVEAKFAS
    CcuGA1   VAVSQSVTGGVSK-AGYDVSTLIAA-----NVGSLSDGFYTPGSERMLATAVAIEDKFAN
    RstGA1   IQVSQSVTAGVSK-KGLDVSTLLAA-----NLGSVEDGFFTPGSEKILATAVAIEDAFAS
    MciGA5   VTVSQSVTGGVSK-AGYDASVLIAA-----NLGSVQDGFYTPGSDKMLATAVAIESKFAS
    DelGA1   VVVTKNFAGGVNK-AGLDTSTLIAA-----NTAGLGDGFFTPGSPEILATAAAIEKSFAD
    FspGA3   ITVTQSYSGGVNK-AGLDVSTLLAA-----NGASMNDGFYTPGSDKMLATAVAIENSFAG
    GpeGA1   VAVSQSVTGGVNK-AGYDVANLIAA-----NVGSLDDGFYTPGSERILATAVAVESKFAS
    MciGA3   VSVSQSVTGGVSK-AGYDASVLIAS-----NLGSLQDGFYTPGSDKMLATAVAIESKFAS
    CumGA1   ITVTQSYSGGVQK-AGLDVSTLIAA-----NQGSMGDGFYTPGSDKMLATAVAIENSFAN
    McoGA1   VQVSQSVTGGVSK-AGYDCANILAA-----NMAANHDGFYTPGSSKILATAVAIESKFAS
    ParGA1   ITVTQSYSGGVQK-AGLDVSTLIAA-----NIGSVGDGFYTPGSDKVLATAVAIEKSFAN
    RmiGA1   VQVSQSVTAGVSK-KGLDVSTLLAA-----NIGSLPDGFFTPGSEKILATAVALENAFAS
    SfuGA2   IVVTQNQSAGVNKPSGLDVAVLLAA-----NQGGLGDGVYTPGSDKVLATAVALEKSFAS
    SraGA1   ITTVQNFQSGVSK-AGYDVSTLIAA-----NVAGMGDGFFTPGSDEVLATAVAIENKFSS
    SraGA3   IEVTQDMQGGVQK-KGLDVSTLIAA-----NIGSMGDGFYTPGSDEVLATAVAVEAAFAD
    TinGA1   ITVTQDYQSGVSK-AGLDVSTLIAA-----NVAGMNDGFFTPGSDEILATAVKVEAAFAN
    ZmeGA1   ITVTQSFSGGVSK-AGLDVSTLIAA-----NLASMNDGFYTPGSDEILATAVAIENSFIS
GAN00808.1   VSVSQSVTGGVSK-AGYDASVLIAS-----NLGSLQDGFYTPGSDKMLATAVAIESKFAS
ORE14155.1   IQVSQSVTAGVSK-KGLDVSTLLAA-----NIGSLPDGFFTPGSEKILATAVALENAFAS
RCH88939.1   IQVSQSVTAGVSK-KGLDVSTLLAA-----NIGSLPDGFFTPGSEKILATAVALENAFAS
```

Figure 1E

```
                      310       320       330       340       350       360
                        |         |         |         |         |         |
        AnGA   IYTLNDGLSD-SEAVAVGRYPEDTYYN-----GNPWFLCTLAAAEQLYDALYQWDKQG-S
       AfuGA   VYAINSGIPQ-GAAVSAGRYPEDVYYN-----GNPWFLTTLAAAEQLYDAIYQWKKIG-S
      FraGA1   LYAINDGIAS-DAAVATGRYPEDVYYG-----GNPWYLCTFAVAEQLYDALIVWSSQG-Y
    FveABC11   IYGVNKNRGK-GKAAAVGRYSEDVYYD-----GNPWYLATLAAAEQLYAAVYQWNKIG-S
        GtGA   VYSINSGIAS-NAAVATGRYPEDSYQG-----GNPWYLTTFAVAEQLYDALNVWAAQG-S
       PoxGA   IYKINAGLAE-GSAANVGRYPEDVYQG-----GNPWYLATLGASELLYDALYQWDRLG-K
        TrGA   IYGVNKGIPA-GAAVAIGRYAEDVYYN-----GNPWYLATFAAAEQLYDAIYVWKKTG-S
      WcoGA1   LYAINDDISS-DAAVATGRYPEDVYYN-----GNPWYLCTLAAAEQLYDSLIVWKAQG-Y
     SvaGA1    LYPLNNNLPS-HLGNAIGRYPEDTYNGNGNSQGNPWFLATTAFTELYYRAILEWKNTG--
     BciGA1    LYSINTNKAS-YLGNAIGRYPEDTYNGNGNSQGNPWFLCTNAFGELFYRAISEWNAAG-S
     BciGA2    LYTVNTGKAS-YLGNAIGRYPEDTYNGNGNSQGNPWYLCTNALGELYYRAIKEWNAAG-S
     BpoGA1    LYGVNSNLPG-YLGNSIGRYPEDTYNGNGNSQGNPWFLATNAYAELYYRAIREWYDNG-G
     CcuGA1    LYGINRNLDS-SLGNAIGRYPEDTYNGNGNSQGNPWFIATNAYAELYYRAIKEWNNNG-G
      RstGA1   LYPINSNLPS-YLGNSIGRYPEDTYNGNGNSQGNPWFLAVNGFAELYYRAIKEWVNNG-S
      MciGA5   LYSINQNLNG-YLGNAIGRYPEDTYNGNGNSQGNPWFICTNAFAELYYRAIKEWFNNG-G
     DelGA1    LYGINKQIPN-WLGTAIGRYPEDTYNGNGNSQGNPWFICTATFAELYYRAILEWQHAG-S
     FspGA3    IYAVNQNRPD-WKGTAIGRYPEDTYDGHGNSQGNPWFIATAAYAEMYYRAILEWQQQP-S
     GpeGA1    IYGVNQNLPS-WLGNSIGRYPEDTYNGNGNSQGNPWFIATNTYAELYYRAIKEWTNNG-G
     MciGA3    LYSINQNLNG-YLGNAIGRYPEDTYNGNGNSQGNPWFICTNAFAELYYRAIKEWFNNG-G
      CumGA1   IYTINKNKPS-WLGTAIGRYPEDTYNGNGNGQGNPWFIATATYAELYYRAILEWQQQE-S
     McoGA1    LYSINSGLAS-WLGTAIGRYPEDTYNGNGNSQGNPWFICTNAFAELYYRAIKEWTQAG-S
     ParGA1    LYTINQNKPS-WLGNAIGRYPEDTYDGYGNSKGNPWFIATATYAELYYRAILEWQQQA-S
      RmiGA1   LYPINSNLPS-YLGNSIGRYPEDTYNGNGNSQGNPWFLAVNAYAELYYRAIKEWISNG-K
     SfuGA2    LYPINKNLPS-YYGTAIGRYPEDTYNGNGNSEANPWFIATTTYAELYYRAISEWTNGS-G
      SraGA1   LYGVNANKAS-YLGTAIGRYPEDTYNGYGNGQGNPWFIATAAYAELYYRAILEWQTKS-S
     SraGA3    LYKINQNTNSTGLGTAIGRYPEDTYNGVGNSQGNPWFIATNTFAELYYRAILEWQNKG-T
     TinGA1    LYGININKAS-YLGNAIGRYPEDTYNGNGNSEGNPWFIATAAFAELYYRAIMEWQLRGSS
     ZmeGA1    EYTLNQNRPS-WLSTAIGRYPEDSYDGYGNSQGNPWFIATATYAELYYRAILEWQQQA-S
  GAN00808.1   LYSINQNLNG-YLGNAIGRYPEDTYNGNGNSQGNPWFICTNAFAELYYRAIKEWFNNG-G
  ORE14155.1   LYPINSNLPS-YLGNSIGRYPEDTYNGNGNSQGNPWFLAVNAYAELYYRAISEWISNG-K
  RCH88939.1   LYPINSNLPS-YLGNSIGRYPEDTYNGNGNSQGNPWFLAVNAYAELYYRAIKEWISNG-K
```

Figure 1F

```
                   370       380       390       400       410       420
                     |         |         |         |         |         |
      AnGA  LEVTDVSLDFFKALYSDAATGT-YSSSSSTYSSIVDAVKTFADGFVSIVETHAASNGSMS
     AfuGA  ISITSTSLAFFKDIYSSAAVGT-YASSTSTFTDIINAVKTYADGYVSIVQAHAMNNGSLS
    FraGA1  LEITDLSLAFFQQFDSDVGTGT-YDSGSSTYSTLTSAIRTFADGFVLTNAKYTPTNGSLS
  FveABC11  ITVDSVSLPFFSDLVPKVSKGT-YRKNSKTYKAIIKAVTSYADGFVAVVQTYTPKDGSLA
      GtGA  LNVTSISLPFFQQFSSSVTAGT-YASSSTTYTTLTSAIKSFADGFVAINAQYTPSNGGLA
     PoxGA  LEVSETSLSFFKDFDATVKIGS-YSRNSKTYKKLTQSIKSYADGFIQLVQQYTPSNGSLA
      TrGA  ITVTATSLAFFQELVPGVTAGT-YSSSSSTFTNIINAVSTYADGFLSEAAKYVPADGSLA
    WcoGA1  IEVTSLSLAFFQQFDASVSAGT-YDSSSDTYTTLLDAVQTYADGFVLMVAQYTPANGSLS
    SvaGA1  VTVTPISKDFFVRFDSSAAPGKKYNPGSQEFATLTQSIAAAADRFMSTVQYHQNPNGSLS
    BciGA1  VTVNSVNLAFFKKYDSSTSSGTTYTVGTSAYNNLVQNVALAADAYFSTVKYHALTNGSMS
    BciGA2  VTVNSVNLGFFQKIDSSISSGTTFTLGTSDYSTLVDNVALAADKFFAVVQYHERSNGSMP
    BpoGA1  VTVNSVNLPFFKKFDSSAASGTTYTVGTTAFNTMVSNVAAAADKFFSTVKFHAYTNGSMS
    CcuGA1  VTVTNVNLNFFKKFDGSASVGTKYTAGSAAYNTLTQNIALAADKFFNTVKVHAATNGSMS
    RstGA1  VTVSNISLSFFKKFDSSATAGKTYTAGTADFNNLAQNIALGADRFLSTVQTHAFNNGSLA
    MciGA5  VTVTSISLNFFKKFDSSAAVGTKYTVGTSAFNSLVQNVAVAADAFFSTVKFHAATNGSMS
    DelGA1  VTVNNVNLPFFKKFDSSTSSGTTYTVGTSSFDSLISKVAYAADNFFSTIKYHAATNGSMS
    FspGA3  ITVNSINLSFFKKFDSSAAVGTVYKPGTQAFNNMVSNVAFAADEFFSTMNFHSATNGSMS
    GpeGA1  VTVTNVNFNFFKKFDSSASVGTKYTVGTSAFNTLTQNVALAADNFFSTVKVHAATNGSMS
    MciGA3  VTVTSISLNFFKKFDSSAAVGTKYTVGTSSFNSLVQNVAVAADAFFSTIKFHAATNGSMS
    CumGA1  VTVNSVNFDFFSKFDSSAKVGTVYTPGTDTFNTMVSNVAFAADEFLSTMEHYAATNGSMS
    McoGA1  VTVDSTSLNFFKKFDSSAAAGTKYTVGTSAFTNLVQNIANGADKFLSTSKFHAATNGSMS
    ParGA1  VTVNSINLGFFSKFDSSASVGTVYTPGTDSFANMVSNVAFAADEFLSTIDYHAMNNGSMH
    RmiGA1  VTVSNISLPFFKKFDSSATSGKTYTAGTSDFNNLAQNIALGADRFLSTVKFHAYNNGSLS
    SfuGA2  VTVNSINKEFFSKFDASATNGKVYTPGSDSFNSLVNNVAIAADNFLSTVRYHQTSNGSLS
    SraGA1  IVVNSKNLGFFSKFDSSAAVGTTYTPGTTAYSNMVQNVALAADRFLSTVQLHAATNGSMS
    SraGA3  ITVNSVNAAFFSKFDSSAKAGTTYKSGSTEFDSLINKVALAADAFLNTVQTYAASNGSMS
    TinGA1  ITVNSVNQGFFTKFDPSATAGTTYTPGTDAFNSLIDNVALAADQFFSTIHLHRATNGSMS
    ZmeGA1  ISVNSVNLGFFSKFDSDASVGTVYTPGTEDFANMVSNVAFAADEFLATIENHSAVNGSLS
GAN00808.1  VTVTSISLNFFKKFDSSAAVGTKYTVGTSAFNSLVQNVAVAADAFFSTIKFHAATNGSMS
ORE14155.1  VTVSNISLPFFKKFDPSATSGKTYTAGTSDFDNLAQNIALGADRFLSTVKFHAYTNGSLS
RCH88939.1  VTVSNISLPFFKKFDSSATSGKTYTAGTSDFNNLAQNIALGADRFLSTVKFHAYTNGSLS
```

Figure 1G

```
                      430       440       450       460       470       480
                        |         |         |         |         |         |
     AnGA   EQYDKSDGEQLSARDLTWSYAALLTANNRRNSVVPASWGETSASSVPGTCAATSAIGTYS
    AfuGA   EQFDKSSGLSLSARDLTWSYAAFLTANMRRNGVVPAPWGAASANSVPSSCSMGSATGTYS
   FraGA1   EEYTSADGTPISAYDLTWSYASALTVFAAEAGTTYGSWGAAGL-TVPSTC---TSG----
 FveABC11   EQFDKSTGTPKSAVHLTWSYASFVGAAERRTGVVPPAWGESNANKVPAVCEAAPACDT--
     GtGA   EQFSRSNGAPVSAVDLTWSYASALTAFEARNNTQFAGWGAVGL-TVPTSCSSNSGGGG--
    PoxGA   EQYDRNTAAPLSANDLTWSFASFLTATQRRDAVVPPSWGAKSANKVPTTCSASPVVGTYK
     TrGA   EQFDRNSGTPLSALHLTWSYASFLTATARRAGIVPPSWANSSASTIPSTCSGASVVGSYS
   WcoGA1   EQYAKADGSPTSAYDLTWSFAAALTAFAARDGKTYGSWGAADL-S--STCSGSTDT----
   SvaGA1   EEFDRSSGYMTGARDLTWSHAAFITAAQARAG----------------------------
   BciGA1   EQYDRSSGMATGARDLTWSHAAMITALKAKSG----------------------------
   BciGA2   EQFGREDGLPTGARDLTWSHAAMISAARAKAG----------------------------
   BpoGA1   EQFGRNDGLCTGARDLTWSHASLISAALAKAG----------------------------
   CcuGA1   EQYHRDTGSMTGARDLTWSHASLITAALAKAG----------------------------
   RstGA1   EEYDRTTGVSTGARDLTWSHASLITAAYAKAG----------------------------
   MciGA5   EQYGRSDGLMTGARDLTWSHASLISASYAKAG----------------------------
   DelGA1   EQFNRDTGFMTGARDLTWSHAAFITAAKAKAG----------------------------
   FspGA3   EQYNRNTGIMQGARDLTWSHAAFITAAKAKLG----------------------------
   GpeGA1   EQFGRDSGVMTGARDLTWSHASLITAALAKTG----------------------------
   MciGA3   EQYGRTDGLMTGARDLTWSHASLISASYAKAG----------------------------
   CumGA1   EQFNRETGSLTGARDLTWSHAAFITAGKAKLG----------------------------
   McoGA1   EQYNRDSGLMTGARDLTWSHASLISASRAKAG----------------------------
   ParGA1   EQYNRDTGISQGARDLTWSHAAFITAAKAKLG----------------------------
   RmiGA1   EEYDRSTGMSTGARDLTWSHASLITAAYAKAG----------------------------
   SfuGA2   EQFNRYTGFMTGARDLTWSHAAMVTALAAKAG----------------------------
   SraGA1   EQFNRDTGVMQGARDLTWSHSAFITAARAKLG----------------------------
   SraGA3   EQYNRDTGALTGARDLTWSHASLITAANAKLG----------------------------
   TinGA1   EQYNRDTGFMQGARDLTWSHAAFITAAKAKQG----------------------------
   ZmeGA1   EQYNRDTGIMQGARDLTWSHAAFITAAKAKQG----------------------------
GAN00808.1  EQYGRTDGLMTGARDLTWSHASLISASYAKAG----------------------------
ORE14155.1  EEYDRSTGMSTGARDLTWSHASLITAAYAKAG----------------------------
RCH88939.1  EEYDRSTGMSTGARDLTWSHASLITAAYAKAG----------------------------
```

Figure 1H

```
                 490       500       510       520       530       540
                   |         |         |         |         |         |
      AnGA   SVTVTSWPSIVATGGTTTTATPTGSGSVTSTSKTTATASKTSTSTSSTSCTTPTAVAVTF
     AfuGA   TATATSWPSTLTSG---------SPGSTTTVGTTTST---TSGTAAETACATPTAVAVTF
    FraGA1   -------------------------------------------------------VAVTF
  FveABC11   --------------------------------------------------------TITF
      GtGA   ----------------------------------------------------GSTVAVTF
     PoxGA   APTATF-------------------------------------SSKTKCVPAKDIVPITF
      TrGA   RPTATSFFPPSQTP---------KPGVP------------SGTPYTPLPCATPTSVAVTF
    WcoGA1   -------------------------------------------------------VAVTF
    SvaGA1   ------------------------------------------------------------
    BciGA1   ------------------------------------------------------------
    BciGA2   ------------------------------------------------------------
    BpoGA1   ------------------------------------------------------------
    CcuGA1   ------------------------------------------------------------
    RstGA1   ------------------------------------------------------------
    MciGA5   ------------------------------------------------------------
    DelGA1   ------------------------------------------------------------
    FspGA3   ------------------------------------------------------------
    GpeGA1   ------------------------------------------------------------
    MciGA3   ------------------------------------------------------------
    CumGA1   ------------------------------------------------------------
    McoGA1   ------------------------------------------------------------
    ParGA1   ------------------------------------------------------------
    RmiGA1   ------------------------------------------------------------
    SfuGA2   ------------------------------------------------------------
    SraGA1   ------------------------------------------------------------
    SraGA3   ------------------------------------------------------------
    TinGA1   ------------------------------------------------------------
    ZmeGA1   ------------------------------------------------------------
GAN00808.1   ------------------------------------------------------------
ORE14155.1   ------------------------------------------------------------
RCH88939.1   ------------------------------------------------------------
```

Figure 1I

```
                      550       560       570       580       590       600
                        |         |         |         |         |         |
     AnGA  DL-TATTTYGENIYLVGSISQLGDWETSDGIALSADKYTSSDPLWYVTVT-LPAGESFEY
    AfuGA  NE-IATTTYGENVYIVGSISELGNWDTSKAVALSASKYTSSNNLWYVSVT-LPAGTTFEY
   FraGA1  EV-DYDTEYGENVYITGSVNALENWSATNALIMSAADY----PTWSITVY-LPPSTTIQY
FveABC11  NVKNVDVTSDQKVYIVGGITQLSNWAPADGIALEESTSTK--GLWTVKVK-IPSDTSFEY
     GtGA  NV-NAQTVWGENIYITGSVDALSNWSPDNALLLSSANY----PTWSITVN-LPASTAIQY
    PoxGA  YL-IENTYYGENVFMSGNITALGNWDAKKGFPLTANLYTQDQNLWFASVEFIPAGTPFEY
     TrGA  HE-LVSTQFGQTVKVAGNAAALGNWSTSAAVALDAVNYADNHPLWIGTVN-LEAGDVVEY
  WcoGA1  EV-QYDTQYGENLYITGSVSQLEDWSADDALIMSSADY----PTWSITVD-LPPSTLIQY
  SvaGA1  ------------------------------------------------------------
  BciGA1  ------------------------------------------------------------
  BciGA2  ------------------------------------------------------------
  BpoGA1  ------------------------------------------------------------
  CcuGA1  ------------------------------------------------------------
   RstGA1  ------------------------------------------------------------
   MciGA5  ------------------------------------------------------------
  DelGA1  ------------------------------------------------------------
  FspGA3  ------------------------------------------------------------
  GpeGA1  ------------------------------------------------------------
  MciGA3  ------------------------------------------------------------
   CumGA1  ------------------------------------------------------------
  McoGA1  ------------------------------------------------------------
  ParGA1  ------------------------------------------------------------
   RmiGA1  ------------------------------------------------------------
  SfuGA2  ------------------------------------------------------------
   SraGA1  ------------------------------------------------------------
  SraGA3  ------------------------------------------------------------
  TinGA1  ------------------------------------------------------------
  ZmeGA1  ------------------------------------------------------------
GAN00808.1  ------------------------------------------------------------
ORE14155.1  ------------------------------------------------------------
RCH88939.1  ------------------------------------------------------------
```

Figure 1J

```
                    610        620   626
                     |          |     |
     AnGA   KFIRIESDDSVEWESDPNREYTVPQA(SEQ ID NO:105)
    AfuGA   KYIRKESDGSIVWESDPNRSYTVPAA(SEQ ID NO:106)
   FraGA1   KYLT-QYNGEVTWEDDPNNEITTPAS(SEQ ID NO:107)
FveABC11   KYIKKTSDGTVTWESDPNNSAATGSK(SEQ ID NO:108)
     GtGA   KYIR-KNNGAVTWESDPNNSITTPAS(SEQ ID NO:109)
    PoxGA   KYYKVEPNGDITWEKGPNRVFVAPTG(SEQ ID NO:110)
     TrGA   KYINVGQDGSVTWESDPNHTYTVPAV(SEQ ID NO:111)
   WcoGA1   KYLT-KYNGDVTWEDDPNNEITTPAS(SEQ ID NO:112)
  SvaGA1   ----------------------SPSF(SEQ ID NO:81)
  BciGA1   ----------------------TPVY(SEQ ID NO:82)
  BciGA2   ----------------------TPVY(SEQ ID NO:83)
  BpoGA1   ----------------------TPSV(SEQ ID NO:84)
  CcuGA1   ----------------------TPVA(SEQ ID NO:85)
   RstGA1   ----------------------SPAA(SEQ ID NO:86)
   MciGA5   ----------------------SPAA(SEQ ID NO:87)
  DelGA1   ----------------------TPVY(SEQ ID NO:88)
  FspGA3   ----------------------TPVF(SEQ ID NO:89)
  GpeGA1   ----------------------APVA(SEQ ID NO:90)
  MciGA3   ----------------------SPAA(SEQ ID NO:91)
   CumGA1   ----------------------IPSF(SEQ ID NO:92)
  McoGA1   ----------------------SPSL(SEQ ID NO:93)
  ParGA1   ----------------------APAF(SEQ ID NO:94)
   RmiGA1   ----------------------SPAA(SEQ ID NO:95)
  SfuGA2   ----------------------TPSP(SEQ ID NO:96)
   SraGA1   ----------------------SPVY(SEQ ID NO:97)
  SraGA3   ----------------------TPYN(SEQ ID NO:98)
  TinGA1   ----------------------TPSF(SEQ ID NO:99)
  ZmeGA1   ----------------------APIH(SEQ ID NO:100)
GAN00808.1  ----------------------SPAA(SEQ ID NO:101)
ORE14155.1  ----------------------SPAA(SEQ ID NO:102)
RCH88939.1  ----------------------SPAA(SEQ ID NO:103)
```

Figure 1K

*Mucorales*-clade GA motif 1A (SEQ ID NO: 114):

57Y-58N-59T-60T-61X-62A-63G-64D, wherein X is any amino acid

*Mucorales*-clade GA sequence motif 2A (SEQ ID NO: 116):

244S-245T-246L-247I-248A-249A-250N-251X-252A, wherein wherein X is any amino acid

*Mucorales*-clade GA motif 3A (SEQ ID NO: 118):

304N-305G-306N-307G-308N-309S-310Q

```
                   10        20        30        40        50        60
AnGA      WLSNEATVARTAILNNIGADGAWVSGADSGIVVASPSTDNPDYFYTWTRDSGLVLKTLVD
AfuGA     WLGTETTVALNGILANIGADGAYAKSAKPGIIIASPSTSEPDYYYTWTRDAALVTKVLVD
FraGA1    YIASESPVAKAGVLANIGTEGSLSSGAYSGVVIASPSTVNPDYLYTWVRDSSLTFQALID
FveABC11  FISKEADISIKGVLANIGADGKRAQGAAPGAVVASPSRTDPDYWYTWTRDSALTYKVLVE
GtGA      YVGSEGPIAKAGVLANIGPNGSKASGAAAGVVVASPSKSDPDYWYTWTRDSSLVFKSLID
PoxGA     FIHKEGERSLQGILDNLGGRGKKTPGTAAGLFIASPNTENPNYYYTWTRDSALTAKCLID
TrGA      FISTETPIALNNLLCNVGPDGCRAFGTSAGAVIASPSTIDPDYYYMWTRDSALVFKNLID
WcoGA1    YIASESPIAKAGVLANIGADGSLSSGAYSGIVIASPSTVNPNYLYTWTRDSSLTFMELIN
SvaGA1    WVSKQEDISFSEMLRNVNP-----EGTAKGFVAASLSTAGPDYFYTWTRDAALVSRVIAY
SobGA1    WVSKQEGISFSEMLRNVNP-----PGTAKGFVAASLSTAGPDYFYTWTRDAALVSRVIAY
AosGA3    WVSSQEDISFSVMLGNINP-----PGTVKGFVAASLSTAGPDYFYSWVRDSALVSRVVTH
AelGA1    WVSSQEDISFSVMLGNINP-----PGTVKGFVAASLSTAGPDYFYSWVRDSALVSRVVTH
AvaGA1    WVSSQEDISFSVMLGNINP-----PGTVKGFVAASLSTAGPDYFYSWVRDSALVSRVVTH
AtrGA1    WVSSQEDISFSVMLGNINP-----PGTVKGFVAASLSTAGPDYFYSWVRDSALVSRVVTH

                   70        80        90       100       110       120
AnGA      LFRN-------GDTSLLSTIENYISAQAIVQGISNPSGDLSSGAGLGEPKFNVDETAYTG
AfuGA     LFRN-------GNLGLQKVITEYVNSQAYLQTVSNPSGGLASG-GLAEPKYNVDMTAFTG
FraGA1    QYVYG------EDPTLRSLIDEFITAESILQQTTNPSGTVSTG-GLGEPKFNINETAFTG
FveABC11  RFIH-------GDKSLQRKIDEYVSAQAKLQGVTNPSGGPESG-GLGEPKFHVNLTAFTG
GtGA      QYTTGID----STSSLRSLIDSFVIAEANIQQVSNPSGTLTTG-GLGEPKFNVDETAFTG
PoxGA     LFEDSRAKFPIDRKYLETGIRDYVSSQAILQSVSNPSGTLKDGSGLGEPKFEIDLNPFSG
TrGA      RFTET------YDAGLQRRIEQYITAQVTLQGLSNPSGSLADGSGLGEPKFELTLKPFTG
WcoGA1    QYIYG------EDDTLRTLIDEFVSAEATLQQVTNPSGTVSTG-GLGEPKFNINETAFTG
SvaGA1    KYNTTNA----GDSKIHGVLDDYVNFQINTQSESTPCN------CLGEPKFNPDGSSFTG
SobGA1    KYNTTNA----GDNNIHGALQDYVTFQINTQTESTPCN------CLGEPKFNPDGSSFTG
AosGA3    KYNTTET----GNSTVAGFLEDYVHFQINTQTESTVCN------CLGEPKFNPDGSSYTG
AelGA1    KYNTTET----GNSTVAGFLQDYVHFQINTQTESTVCN------CLGEPKFNPDGSSYTG
AvaGA1    KYNTTET----GNSTVAGFLQDYVHFQINTQTESTVCN------CLGEPKFNPDGSSYTG
AtrGA1    KYNTTET----GNSTVAGFLQDYVHFQINTQTESTVCN------CLGEPKFNPDGSSYTG

                  130       140       150       160       170       180
AnGA      SWGRPQRDGPALRATAMIGFGQ-WLLDNGYTSTATDIVWPLVRNDLSYVAQYWNQTGYDL
AfuGA     AWGRPQRDGPALRATALIDFGN-WLIDNGYSSYAVNNIWPIVRNDLSYVSQYWSQSGFDL
FraGA1    PWGRPQRDGPALRSTAIITYAT-YLWNSGNTSYVSDSLWPIIELDLNYIATYWNFSTFDL
FveABC11  SWGRPQRDGPPLRATALTLYAN-WLVSHGDRSKAVNKVWPVIEKDLAYTVKFWNRTGYDL
GtGA      AWGRPQRDGPALRATALITYGN-WLLSNGNTTWVTSTLWPIIQNDLNYVVQYWNQTTFDL
PoxGA     AWGRPQRDGPALRATAMITYAN-YLISHGQKSDVSQVMWPIIANDLAYVGQYWNNTGFDL
TrGA      NWGRPQRDGPALRAIALIGYSK-WLINNNYQSTVSNVIWPIVRNDLNYVAQYWNQTGFDL
WcoGA1    PWGRPQRDGPALRATAIMAYAT-YLYENGNTSYVTDTLWPIIELDLGYVAEYWNESTFDL
SvaGA1    PWGRPQNDGPAERASSFMLIADSFLSQTKNASYFTNTLKPAIYKDLDYVVDTWSNPCFDL
SobGA1    PWGRPQNDGPAERASSMILIADSFLAQTKDTAYVTNTLKPAIYKDLDYVVNTWSNPCFDL
AosGA3    PWGRPQNDGPAERASTMILIADSFLTQTKNTSYVDNTLKPAIYKDLDYVVNTWSNPCFDL
AelGA1    PWGRPQNDGPAERASTMILIADSFLTQTKNTSYVDNTLKPAIYKDLDYVVNTWSNPCFDL
AvaGA1    PWGRPQNDGPAERASTMILIADSFLAQTKNTSYVDNTLKPAIYKDLDYVVNTWSNPCFDL
AtrGA1    PWGRPQNDGPAERASTMILIADSFLTQTKNTSYVDNTLKPAIYKDLDYVVNTWSNPCFDL
```

Figure 6A

```
                      190       200       210       220       230       240
AnGA        WEEVNGSSFFTIAVQHRALVEGSAFATAVGSSC--SWCDSQAPEILCYLQSFW--TGSFI
AfuGA       WEEVNSMSFFTVAVQHRALVEGSTFAKRVGASC--SWCDSQAPQILCYMQSFW--TGSYI
FraGA1      WEEIDSSSFWTTAVQHRALRQGITFANLIGQTSPVSNYETQAGDILCFLQTYWNPTGNYM
FveABC11    WEEVNGSSFFTLSASHRALVEGAALAKKLGKSC--SDCATNAPRVLCFMQSFW--TGSYI
GtGA        WEEVNSSSFFTTAVQHRALREGAAFATKIGQTSSVSSYTTQAANLLCFLQSYWNPTSGYI
PoxGA       WEEVDGSSFFTIAVQHRALVEGSQLAKKLGKSC--DACDSQPPQILCFLQSFW--NGKYI
TrGA        WEEVNGSSFFTVANQHRALVEGATLAATLGQSG--SAYSSVAPQVLCFLQRFWVSSGGYV
WcoGA1      WEEIDSSSFFTTAVQHRALRAGVTFANLIGETSDVSNYQENADDLLCFLQSYWNPTGSYV
SvaGA1      WEEVNGIHFYTLMVMRRSLLDGANFATRNGDNSKASTYSGVAAKIQARLNSFWDAGKNYI
SobGA1      WEEVNGVHFYTLMVMRRGLLDGADFATRNGDASKASSYSDAASKIKTRLDSFWVSDKNYI
AosGA3      WEEVNGIHFYTLMVMRRGLLDGANFATRNGDTSKASSYSSTASQIQNKIDSFWSSNKNYI
AelGA1      WEEVNGIHFYTLMVMRRGLLDGANFATRNGDTSKASSYSSTASQIQNKIDSFWSSSKNYI
AvaGA1      WEEVNGIHFYTLMVMRRGLLDGANFATRNGDTSKASSYSSTASQIQNKIDSFWSSSKNYI
AtrGA1      WEEVNGIHFYTLMVMRRGLLDGANFATRNGDTSKASSYSSTASQIQNKIDSFWSSSKNYI

                      250       260       270       280       290       300
AnGA        --LANFDSS---RSGKDANTLLGSIHTFDPEAACDDSTFQPCSPRALANHKEVVDSFRSI
AfuGA       --NANTGGG---RSGKDANTVLASIHTFDPEAGCDDTTFQPCSPRALANHKVYTDSFRSV
FraGA1      --TANTGGG---RSGKDSNTVLASVHTFDPDAGCDSTTFQPCSDKALSNLKVYVDSFRSL
FveABC11    DSNINVNDG---RKGLDANSILSSIHTFDPSSKCTDSTFQPCSSRALANHKEVVDSFRSI
GtGA        --TANTGGG---RSGKDANTLLASIHTYDPSAGCDATTFQPCSDKALSNLKVYVDSFRSV
PoxGA       TSNINTQAS---RSGIDLDSVLGSIHTFDPEAACDDATFQPCSARALANHKVYVDSFRSI
TrGA        DSNINTNEG---RTGKDVNSVLTSIHTFDPNLGCDAGTFQPCSDKALSNLKVVVDSFRSI
WcoGA1      --TANTGGG---RSGKDANTLLASIHTFDPDAGCNATTFQPCSDKALSNHKVYVDSFRSL
SvaGA1      TVTQDYKNGVEKPSGLDVSTLIAA-----NVAGMGDGFYTPGSERILATALAFEKSMASL
SobGA1      TVTQDYKEGVKKDTGLDVSTLIAA-----NVAGKDDGFYTPGSDKILATAVAFENAMAKL
AosGA3      IVTQDYQNGVQKPSGLDISTLIAA-----NVAGMNDGFYTPGSDKMLATAVAIENAMANL
AelGA1      MVTQDYQNGIQKPSGLDISTLIAA-----NVAGMNDGFYTPGSDKMLATAVAIENAMANL
AvaGA1      MVTQDYQNGVQKPSGLDISTLIAA-----NVAGMNDGFYTPGSDKMLATAVAIENAMANL
AtrGA1      IVTQDYQNGVQKPSGLDVSTLIAA-----NVAGMNDGFYTPGSDKMLATAVAIENAMANL

                      310       320       330       340       350       360
AnGA        YTLNDGLSDSEAVAVGRYPEDTYYN-----GNPWFLCTLAAAEQLYDALYQWDKQGSLEV
AfuGA       YAINSGIPQGAAVSAGRYPEDVYYN-----GNPWFLTTLAAAEQLYDAIYQWKKIGSISI
FraGA1      YAINDGIASDAAVATGRYPEDVYYG-----GNPWYLCTFAVAEQLYDALIVWSSQGYLEI
FveABC11    YGVNKNRGKGKAAAVGRYSEDVYYD-----GNPWYLATLAAAEQLYAAVYQWNKIGSITV
GtGA        YSINSGIASNAAVATGRYPEDSYQG-----GNPWYLTTFAVAEQLYDALNVWAAQGSLNV
PoxGA       YKINAGLAEGSAANVGRYPEDVYQG-----GNPWYLATLGASELLYDALYQWDRLGKLEV
TrGA        YGVNKGIPAGAAVAIGRYAEDVYYN-----GNPWYLATFAAAEQLYDAIYVWKKTGSITV
WcoGA1      YAINDDISSDAAVATGRYPEDVYYN-----GNPWYLCTLAAAEQLYDSLIVWKAQGYIEV
SvaGA1      YPLNNNLPSHLGNAIGRYPEDTYNGNGNSQGNPWFLATTAFTELYYRAILEWKNTG-VTV
SobGA1      YPLNQNLDSHLGNSIGRYPEDTYNGNGNSQGNPWFLATTAFTELYYRAILEWKDSG-VTV
AosGA3      YPLNKNLPSYLGNAIGRYPEDTYNGDGNSQGNPWFLATTAFSELYYRALLEWQETG-VTV
AelGA1      YPLNKNLPSYLGNAIGRYPEDTYNGDGNSQGNPWFLATTAFSELYYRALLEWQETG-VTV
AvaGA1      YPLNKNLPSYLGNAIGRYPEDTYNGDGNSQGNPWFLATTAFSELYYRALLEWQETG-VTV
AtrGA1      YPLNKNLPSYLGNAIGRYPEDTYNGDGNSQGNPWFLATTAFSELYYRALLEWQETG-VTV
```

Figure 6B

```
                    370       380       390       400       410       420
AnGA      TDVSLDFFKALYSDAATG-TYSSSSSTYSSIVDAVKTFADGFVSIVETHAASNGSMSEQY
AfuGA     TSTSLAFFKDIYSSAAVG-TYASSTSTFTDIINAVKTYADGYVSIVQAHAMNNGSLSEQF
FraGA1    TDLSLAFFQQFDSDVGTG-TYDSGSSTYSTLTSAIRTFADGFVLTNAKYTPTNGSLSEEY
FveABC11  DSVSLPFFSDLVPKVSKG-TYRKNSKTYKAIIKAVTSYADGFVAVVQTYTPKDGSLAEQF
GtGA      TSISLPFFQQFSSSVTAG-TYASSSTTYTTLTSAIKSFADGFVAINAQYTPSNGGLAEQF
PoxGA     SETSLSFFKDFDATVKIG-SYSRNSKTYKKLTQSIKSYADGFIQLVQQYTPSNGSLAEQY
TrGA      TATSLAFFQELVPGVTAG-TYSSSSSTFTNIINAVSTYADGFLSEAAKYVPADGSLAEQF
WcoGA1    TSLSLAFFQQFDASVSAG-TYDSSSDTYTTLLDAVQTYADGFVLMVAQYTPANGSLSEQY
SvaGA1    TPISKDFFVRFDSSAAPGKKYNPGSQEFATLTQSIAAAADRFMSTVQYHQNPNGSLSEEF
SobGA1    TPVSKDFFAKFDSNAVAGKKYSPNSEEFATLTANIAAAADRFMSTVKYHQNPNGSLSEQF
AosGA3    TSISKDFFSKFDPNASAGKKYSPGSNEFASLAQNIASAADRFLSTVNYHRNSNGSLSEEF
AelGA1    TSISKDFFSKFDPNASAGKKYSPGSDEFNSLAQNIASAADRFLSTVNYHRNSNGSLSEEY
AvaGA1    TSISKDFFSKFDPNASAGKKYSPGSDEFNSLAQNIASAADRFLSTVNYHRNSNGSLSEEY
AtrGA1    TSISKDFFSKFDPNASAGKKYSPGSNEYASLAQNIASAADRFLSTVNYHRNPNGSLSEEY

                    430       440       450       460       470       480
AnGA      DKSDGEQLSARDLTWSYAALLTANNRRNSVVPASWGETSASSVPGTCAATSAIGTYSSVT
AfuGA     DKSSGLSLSARDLTWSYAAFLTANMRRNGVVPAPWGAASANSVPSSCSMGSATGTYSTAT
FraGA1    TSADGTPISAYDLTWSYASALTVFAAEAGTTYGSWGAAGL-TVPSTCTSG----------
FveABC11  DKSTGTPKSAVHLTWSYASFVGAAERRTGVVPPAWGESNANKVPAVCEAAPACD------
GtGA      SRSNGAPVSAVDLTWSYASALTAFEARNNTQFAGWGAVGL-TVPTSCSSNSGGGGGST--
PoxGA     DRNTAAPLSANDLTWSFASFLTATQRRDAVVPPSWGAKSANKVPTTCSASPVVGTYKAPT
TrGA      DRNSGTPLSALHLTWSYASFLTATARRAGIVPPSWANSSASTIPSTCSGASVVGSYSRPT
WcoGA1    AKADGSPTSAYDLTWSFAAALTAFAARDGKTYGSWGAADL-S--STCSGSTDT-------
SvaGA1    DRSSGYMTGARDLTWSHAAFITAAQARAG-------------------------------
SobGA1    DRHSGYMTGARDLTWSHAAFITAAQARAG-------------------------------
AosGA3    DRNTGYMTGARDLTWSHAAFITAGLARAG-------------------------------
AelGA1    DRNSGYMTGARDLTWSHAAFITAGLARAG-------------------------------
AvaGA1    DRNSGYMTGARDLTWSHAAFITAGLARAG-------------------------------
AtrGA1    DRNTGYMTGARDLTWSHAAFITAGLARAG-------------------------------

                    490       500       510       520       530       540
AnGA      VTSWPSIVATGGTTTTATPTGSGSVTSTSKTTATASKTSTSTSSTSCTTPTAVAVTFDL-
AfuGA     ATSWPSTLTSG---------SPGSTTTVGTTTST---TSGTAAETACATPTAVAVTFNE-
FraGA1    ----------------------------------------------------VAVTFEV-
FveABC11  ----------------------------------------------------TTITFNVK
GtGA      ----------------------------------------------------VAVTFNV-
PoxGA     ATFSSKTKCV-------------------------------------PAKDIVPITFYL-
TrGA      ATSFPPSQTP----------KPGVP------------SGTPYTPLPCATPTSVAVTFHE-
WcoGA1    ----------------------------------------------------VAVTFEV-
SvaGA1    ------------------------------------------------------------
SobGA1    ------------------------------------------------------------
AosGA3    ------------------------------------------------------------
AelGA1    ------------------------------------------------------------
AvaGA1    ------------------------------------------------------------
AtrGA1    ------------------------------------------------------------
```

Figure 6C

```
                    550       560       570       580       590       600
AnGA      TATTTYGENIYLVGSISQLGDWETSDGIALSADKYTSSDPLWYVTVT-LPAGESFEYKFI
AfuGA     IATTTYGENVYIVGSISELGNWDTSKAVALSASKYTSSNNLWYVSVT-LPAGTTFEYKYI
FraGA1    DYDTEYGENVYITGSVNALENWSATNALIMSAADY----PTWSITVY-LPPSTTIQYKYL
FveABC11  NVDVTSDQKVYIVGGITQLSNWAPADGIALEESTSTK--GLWTVKVK-IPSDTSFEYKYI
GtGA      NAQTVWGENIYITGSVDALSNWSPDNALLLSSANY----PTWSITVN-LPASTAIQYKYI
PoxGA     IENTYYGENVFMSGNITALGNWDAKKGFPLTANLYTQDQNLWFASVEFIPAGTPFEYKYY
TrGA      LVSTQFGQTVKVAGNAAALGNWSTSAAVALDAVNYADNHPLWIGTVN-LEAGDVVEYKYI
WcoGA1    QYDTQYGENLYITGSVSQLEDWSADDALIMSSADY----PTWSITVD-LPPSTLIQYKYL
SvaGA1    ------------------------------------------------------------
SobGA1    ------------------------------------------------------------
AosGA3    ------------------------------------------------------------
AelGA1    ------------------------------------------------------------
AvaGA1    ------------------------------------------------------------
AtrGA1    ------------------------------------------------------------

                    610       620
AnGA      RIESDDSVEWESDPNREYTVPQA(SEQ ID NO:105)
AfuGA     RKESDGSIVWESDPNRSYTVPAA(SEQ ID NO:106)
FraGA1    T-QYNGEVTWEDDPNNEITTPAS(SEQ ID NO:107)
FveABC11  KKTSDGTVTWESDPNNSAATGSK(SEQ ID NO:108)
GtGA      R-KNNGAVTWESDPNNSITTPAS(SEQ ID NO:109)
PoxGA     KVEPNGDITWEKGPNRVFVAPTG(SEQ ID NO:110)
TrGA      NVGQDGSVTWESDPNHTYTVPAV(SEQ ID NO:111)
WcoGA1    T-KYNGDVTWEDDPNNEITTPAS(SEQ ID NO:112)
SvaGA1    -------------------SPSF(SEQ ID NO:81)
SobGA1    -------------------TPSF(SEQ ID NO:126)
AosGA3    -------------------TPSF(SEQ ID NO:129)
AelGA1    -------------------TPS-(SEQ ID NO:132)
AvaGA1    -------------------TPSF(SEQ ID NO:135)
AtrGA1    -------------------TPSF(SEQ ID NO:138)
```

Figure 6D

GLUCOAMYLASE AND METHODS OF USE THEREOF

CROSS-REFERENCE TO RELATED APPLICATIONS

This application is a U.S. National Stage Application under 35 U.S.C. § 371 of International Patent Application No. PCT/US2021/027984, filed Apr. 19, 2021, which claims priority to International Patent Application No. PCT/CN2020/085393, filed Apr. 17, 2020, the disclosure of each of which is incorporated by reference herein in its entirety.

INCORPORATION-BY-REFERENCE OF A MATERIAL SUBMITTED ON A READ-ONLY OPTICAL DISC, AS A TEXT FILE OR AN XML FILE VIA THE PATENT ELECTRONIC SYSTEM

The sequence listing provided in the file named 20250313_NB41777WOPCT2_SequenceListing_ST25 with a size of 407 KB which was created on Mar. 14, 2025 and which is filed herewith, is incorporated by reference herein in its entirety.

FIELD OF THE INVENTION

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

BACKGROUND

Glucoamylase (1,4-alpha-D-glucan glucohydrolase, EC 3.2.1.3) is an enzyme which catalyzes the release of D-glucose from the non-reducing ends of starch or related oligo- and poly-saccharide molecules. Glucoamylases are produced by several filamentous fungi and yeast.

The major application of glucoamylase is the saccharification of partially processed starch/dextrin to glucose, which is an essential substrate for numerous fermentation processes. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

Glucoamylase for commercial purposes has traditionally been produced employing filamentous fungi, although a diverse group of microorganisms is reported to produce glucoamylase since they secrete large quantities of the enzyme extracellularly. However, commercially used fungal glucoamylases have certain limitations such as slow catalytic activity or lack of stability that increase process costs.

There continues to be a need for new glucoamylases to improve the efficiency of saccharification and provide a high yield in fermentation products.

SUMMARY

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

1. In one aspect, a method for saccharifying a starch substrate, comprising contacting the starch substrate with a glucoamylase selected from the group consisting of:
   (a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
   (b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
   (c) a polypeptide comprising one or more sequence motifs selected from the group consisting of:
      (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
      (ii) YNTTXAGD (SEQ ID NO: 114), wherein X is any amino acid;
      (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
      (iv) STLIAANXA (SEQ ID NO: 116), wherein wherein X is any amino acid;
      (v) $X_aGXGNX_bX_c$ (SEQ ID NO: 117), wherein X is any amino acid and $X_a$ is N or D; $X_b$ is S or G; and $X_c$ is Q, K, or E; and
      (vi) NGNGNSQ (SEQ ID NO: 118);
      wherein the polypeptide has at least 70% identity to the catalytic domain of SEQ ID NO: 61.
2. In some embodiments of the method of paragraph 1, wherein the polypeptide comprises a substitution, deletion or addition at a position corresponding to position 102 of the polypeptide of SEQ ID NO: 61.
3. In some embodiments of the method of paragraph 2, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.
4. In some embodiments of the method of any one of paragraphs 1-3, the polypeptide comprises a substitution, deletion or addition at a position corresponding to position 66 of the polypeptide of SEQ ID NO: 61.
5. In some embodiments of the method of paragraph 4, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

6. In some embodiments of the method of any one of paragraphs 1-5, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

7. In some embodiments of the method of any one of paragraphs 1-6, wherein the starch substrate is about 15% to 65%, 15% to 60% or 15% to 35% dry solid (DS).

8. In some embodiments of the method of any one of paragraphs 1-7, wherein the starch substrate comprises liquefied starch, gelatinized starch, or granular starch.

9. In some embodiments of the method of any one of paragraphs 1-8, further comprising adding a hexokinase, a xylanase, a glucose isomerase, a xylose isomerase, a phosphatase, a phytase, a pullulanase, a beta-amylase, an alpha-amylase, a protease, a cellulase, a hemicellulase, a lipase, a cutinase, a trehalase, an isoamylase, a redox enzyme, an esterase, a transferase, a pectinase, a hydrolase, an alpha-glucosidase, a beta-glucosidase, or a combination thereof to the starch substrate.

10. In some embodiments of the method of any one of paragraphs 1-9, wherein saccharifying the starch substrate results in a high glucose syrup comprising an amount of glucose selected from the group consisting of at least 95.5% glucose, at least 95.6% glucose, at least 95.7% glucose, at least 95.8% glucose, at least 95.9% glucose, at least 96% glucose, at least 96.1% glucose, at least 96.2% glucose, at least 96.3% glucose, at least 96.4% glucose, at least 96.5% glucose and at least 97% glucose.

11. In some embodiments of the method of any one of paragraphs 1-10, further comprising fermenting the high glucose syrup to an end product.

12. In some embodiments of the method of paragraph 11, wherein saccharifying and fermenting are carried out as a simultaneous saccharification and fermentation (SSF) process.

13. In some embodiments of the method of paragraph 11 or 12, wherein the end product is an alcohol, optionally, ethanol.

14. In some embodiments of the method of paragraph 11 or 12, wherein the end product is a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene.

15. In another aspect, a process of producing a fermentation product from a starch substrate comprising the steps of:

1) liquefying the starch substrate;
2) saccharifying the liquefied starch substrate; and
3) fermenting with a fermenting organism;

wherein step 2) is carried out using at least a glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;

(ii) YNTTXAGD (SEQ ID NO: 114), wherein X is any amino acid;

(iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;

(iv) STLIAANXA (SEQ ID NO: 116), wherein wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61.

16. In some embodiments of the process of paragraph 15, wherein the polypeptide comprises a substitution, deletion or addition at a position corresponding to position 102 of the polypeptide of SEQ ID NO: 61.

17. In some embodiments of the process of paragraph 16, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

18. In some embodiments of the process of any one of paragraphs 15-17, the polypeptide comprises a substitution, deletion or addition at a position corresponding to position 66 of the polypeptide of SEQ ID NO: 61.

19. In some embodiments of the process of paragraph 18, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

20. In some embodiments of the process of any one of paragraphs 15-19, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

21. In another aspect, a process of producing a fermentation product from a starch substrate comprising the steps of:
   1) saccharifying the starch substrate at a temperature below the initial gelatinization temperature of the starch substrate; and
   2) fermenting with a fermenting organism, wherein step 1) is carried out using at least a glucoamylase selected from the group consisting of:
      a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
      b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
      c) a polypeptide comprising one or more signature motifs selected from the group consisting of:
         (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
         (ii) YNTTXAGD (SEQ ID NO: 114), wherein X is any amino acid;
         (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
         (iv) STLIAANXA (SEQ ID NO: 116), wherein wherein X is any amino acid;
         (v) $X_aGXGNX_bX_c$ (SEQ ID NO: 117), wherein X is any amino acid and $X_a$ is N or D; $X_b$ is S or G; and $X_c$ is Q, K, or E; and
         (vi) NGNGNSQ (SEQ ID NO: 118);
         wherein the polypeptide has at least 70% identity to the catalytic domain of SEQ ID NO: 61.

22. In some embodiments of the process of paragraph 21, wherein the polypeptide comprises a substitution, deletion or addition at a position corresponding to position 102 of the polypeptide of SEQ ID NO: 61.

23. In some embodiments of the process of paragraph 22, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

24. In some embodiments of the process of any one of paragraphs 21-23, the polypeptide comprises a substitution, deletion or addition at a position corresponding to position 66 of the polypeptide of SEQ ID NO: 61.

25. In some embodiments of the process of paragraph 24, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

26. In some embodiments of the process of any one of paragraphs 21-25, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

27. In another aspect, a method for increasing starch digestibility in an animal which comprises adding at least one glucoamylase selected from the group consisting of:
   a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
   b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
   c) a polypeptide comprising one or more signature motifs selected from the group consisting of:
      (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
      (ii) YNTTXAGD (SEQ ID NO: 114), wherein X is any amino acid;
      (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
      (iv) STLIAANXA (SEQ ID NO: 116), wherein wherein X is any amino acid;
      (v) $X_aGXGNX_bX_c$ (SEQ ID NO: 117), wherein X is any amino acid and $X_a$ is N or D; $X_b$ is S or G; and $X_c$ is Q, K, or E; and
      (vi) NGNGNSQ (SEQ ID NO: 118);
      wherein the polypeptide has at least 70% identity to the catalytic domain of SEQ ID NO: 61.

28. In some embodiments of the method of paragraph 27, wherein the polypeptide comprises a substitution, deletion or addition at a position corresponding to position 102 of the polypeptide of SEQ ID NO: 61.

29. In some embodiments of the method of paragraph 28, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

30. In some embodiments of the method of any one of paragraphs 27-29, the polypeptide comprises a substitution, deletion or addition at a position corresponding to position 66 of the polypeptide of SEQ ID NO: 61.
31. In some embodiments of the method of paragraph 30, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.
32. In some embodiments of the method of any one of paragraphs 27-31, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.
33. In another aspect, a method of producing a fermented beverage, wherein the method comprises the step of contacting a mash and/or a wort with a glucoamylase selected from the group consisting of:
 a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
 b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
 c) a polypeptide comprising one or more signature motifs selected from the group consisting of:
  (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
  (ii) YNTTXAGD (SEQ ID NO: 114), wherein X is any amino acid;
  (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
  (iv) STLIAANXA (SEQ ID NO: 116), wherein wherein X is any amino acid;
  (v) $X_aGXGNX_bX_c$ (SEQ ID NO: 117), wherein X is any amino acid and $X_a$ is N or D; $X_b$ is S or G; and $X_c$ is Q, K, or E; and
  (vi) NGNGNSQ (SEQ ID NO: 118);
 wherein the polypeptide has at least 70% identity to the catalytic domain of SEQ ID NO: 61.
34. In some embodiments of the method of paragraph 33, wherein the polypeptide comprises a substitution, deletion or addition at a position corresponding to position 102 of the polypeptide of SEQ ID NO: 61.
35. In some embodiments of the method of paragraph 34, wherein the polypeptide comprises a substitution selected from the group consisting of S102P, S102G, S102A, S102V, S102L, 51021, S102F, S102Y, S102W, S102S, S102T, S102C, S102M, S102N, S102Q, S102D, S102E, S102K, S102R, and S102H.
36. In some embodiments of the method of any one of paragraphs 33-35, the polypeptide comprises a substitution, deletion or addition at a position corresponding to position 66 of the polypeptide of SEQ ID NO: 61.
37. In some embodiments of the method of paragraph 36, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.
38. In some embodiments of the method of any one of paragraphs 33-37, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.
39. In another aspect, a composition comprising a starch substrate and a glucoamylase selected from the group consisting of:
a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;
b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and
c) a polypeptide comprising one or more signature motifs selected from the group consisting of:
 (i) $YX_aX_bTXXX_cX_d$ (SEQ ID NO: 113), wherein X is any amino acid and $X_a$ is N or S; $X_b$ is T, S, or R; $X_c$ is G or N; and $X_d$ is D, N, or S;
 (ii) YNTTXAGD (SEQ ID NO: 114), wherein X is any amino acid;
 (iii) $X_aX_bX_cX_cAANXX_d$ (SEQ ID NO: 115), wherein X is any amino acid and $X_a$ is S or A; $X_b$ is T, N, or V; $X_c$ is L or I; and $X_d$ is A or G;
 (iv) STLIAANXA (SEQ ID NO: 116), wherein wherein X is any amino acid;

(v) $X_aGXGNX_bX_c$ (SEQ ID NO: 117), wherein X is any amino acid and $X_a$ is N or D; $X_b$ is S or G; and $X_c$ is Q, K, or E; and (vi) NGNGNSQ (SEQ ID NO: 118);

wherein the polypeptide has at least 70% identity to the catalytic domain of SEQ ID NO: 61; wherein said composition is at a temperature of about 4-40° C. and a pH of about 3-7.

40. In some embodiments of the composition of paragraph 39, wherein the polypeptide comprises a substitution, deletion or addition at a position corresponding to position 102 of the polypeptide of SEQ ID NO: 61.

41. In some embodiments of the composition of paragraph 40, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

42. In some embodiments of the composition of any one of paragraphs 39-41, the polypeptide comprises a substitution, deletion or addition at a position corresponding to position 66 of the polypeptide of SEQ ID NO: 61.

43. In some embodiments of the composition of paragraph 42, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

44. In some embodiments of the composition of any one of paragraphs 39-43, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

45. In another aspect, a recombinant host cell comprising a glucoamylase selected from the group consisting of:

a) a polypeptide having an amino acid sequence at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 61 or SEQ ID NO:142;

b) a polypeptide having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 81; and c) a polypeptide comprising one or more signature motifs selected from the group consisting of:

(i) YXaXbTXXXcXd (SEQ ID NO: 113), wherein X is any amino acid and Xa is N or S; Xb is T, S, or R; Xc is G or N; and Xd is D, N, or S;

(ii) YNTTXAGD (SEQ ID NO: 114), wherein X is any amino acid;

(iii) XaXbXcXcAANXXd (SEQ ID NO: 115), wherein X is any amino acid and Xa is S or A; Xb is T, N, or V; Xc is L or I; and Xd is A or G;

(iv) STLIAANXA (SEQ ID NO: 116), wherein wherein X is any amino acid;

(v) XaGXGNXbXc (SEQ ID NO: 117), wherein X is any amino acid and Xa is N or D; Xb is S or G; and Xc is Q, K, or E; and (vi) NGNGNSQ (SEQ ID NO: 118);

wherein the polypeptide has at least 70% identity to the catalytic domain of SEQ ID NO: 61.

46. In some embodiments of the recombinant host cell of paragraph 45, wherein the polypeptide comprises a substitution, deletion or addition at a position corresponding to position 102 of the polypeptide of SEQ ID NO: 61.

47. In some embodiments of the recombinant host cell of paragraph 46, wherein the polypeptide comprises a substitution selected from the group consisting of S102P, S102G, S102A, S102V, S102L, S102I, S102F, S102Y, S102W, S102S, S102T, S102C, S102M, S102N, S102Q, S102D, S102E, S102K, S102R, and S102H.

48. In some embodiments of the recombinant host cell of any one of paragraphs 45-47, the polypeptide comprises a substitution, deletion or addition at a position corresponding to position 66 of the polypeptide of SEQ ID NO: 61.

49. In some embodiments of the recombinant host cell of paragraph 48, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

50. In some embodiments of the recombinant host cell of any one of paragraphs 45-49, wherein the polypeptide comprises SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:119, SEQ ID NO:120, SEQ ID NO:121, SEQ ID NO:122, SEQ ID NO:123, SEQ ID NO:126, SEQ ID NO:129, SEQ ID NO:132, SEQ ID NO:135, SEQ ID NO: 138, SEQ ID NO:140, SEQ ID NO:141, or SEQ ID NO:142.

51. In some embodiments of the recombinant host cell of any one of paragraphs 45-50, which is an ethanologenic microorganism.

52. In some embodiments of the recombinant host cell of paragraph 51, which is a yeast cell.

53. In some embodiments of the recombinant host cell of any one of paragraphs 45-52, wherein said host cell is not *Saksenaea vasiformis.*

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes

BRIEF DESCRIPTION OF THE DRAWINGS

FIG. 1 provides a multiple amino acid sequence alignment of the catalytic domain regions of Mucorales-clade glucoamylases and various reference fungal glucoamylases.

FIG. 6 provides a multiple amino acid sequence alignment of the catalytic domain regions of additional Mucorales-clade glucoamylases and various reference fungal glucoamylases.

DETAILED DESCRIPTION

Figure 2:
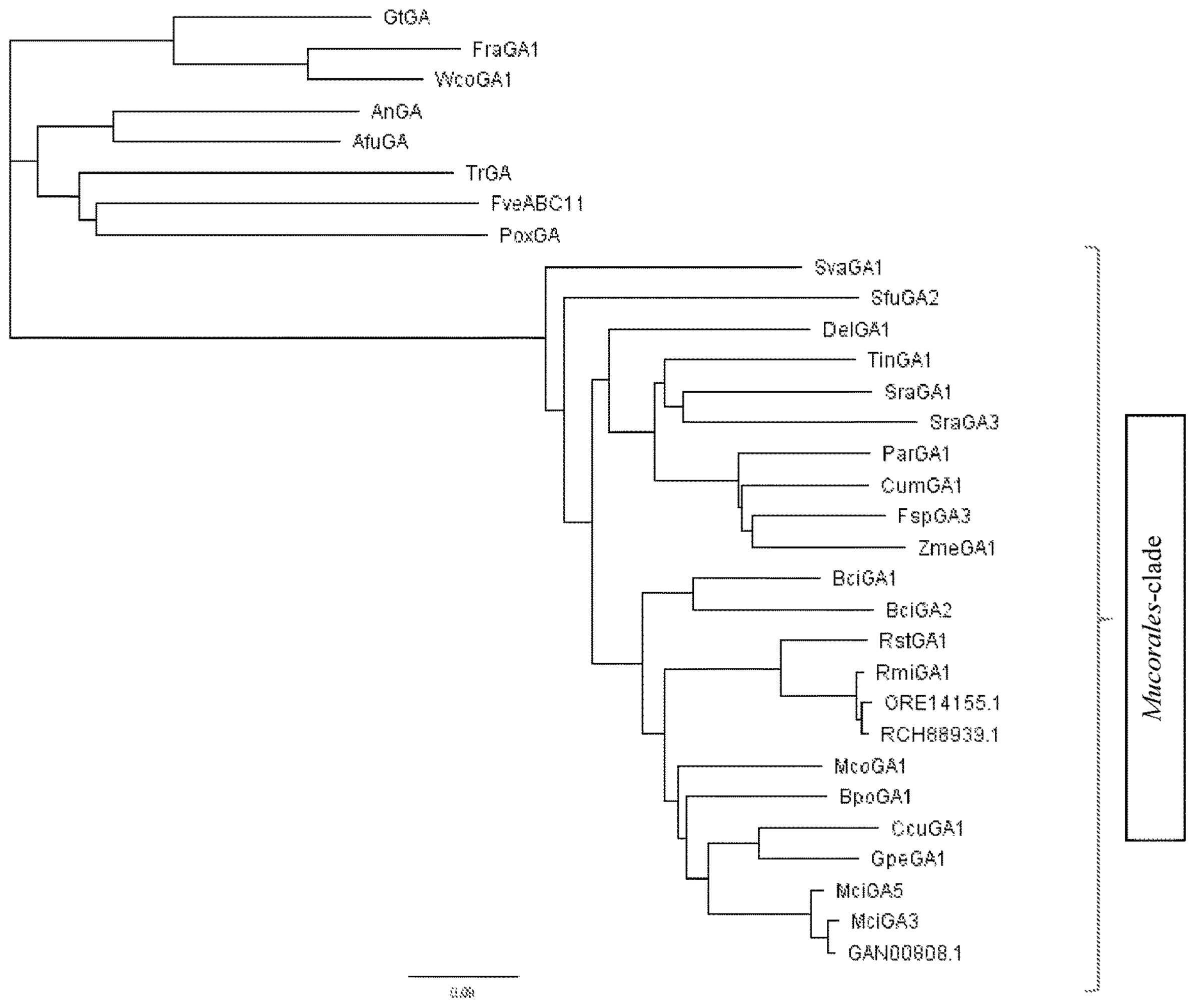
FIG. 2 provides a phylogenetic tree of Mucorales-clade glucoamylases and other fungal glucoamylases.

The present disclosure relates to a recombinant host cell, a composition comprising a glucoamylase and methods of saccharifying the starch substrate using the glucoamylase. Moreover, the disclosure also relates to a process of producing fermentation products and a method for increasing starch digestibility in an animal as well as a method of producing a fermented beverage.

I. Definitions

Prior to describing the compositions and methods in detail, the following terms and abbreviations are defined.

Unless otherwise defined, all technical and scientific terms used have their ordinary meaning in the relevant scientific field. Singleton, et al., Dictionary of Microbiology and Molecular Biology, 2d Ed., John Wiley and Sons, New York (1994), and Hale & Markham, Harper Collins Dictionary of Biology, Harper Perennial, NY (1991) provide the ordinary meaning of many of the terms describing the invention.

The term "glucoamylase (1,4-alpha-D-glucan glucohydrolase, EC 3.2.1.3) activity" is defined herein as an enzyme activity, which catalyzes the release of D-glucose from the non-reducing ends of starch or related oligo- and polysaccharide molecules.

The term "amino acid sequence" is synonymous with the terms "polypeptide", "protein" and "peptide" and are used interchangeably. Where such amino acid sequences exhibit activity, they may be referred to as an "enzyme". The conventional one-letter or three-letter codes for amino acid residues are used, with amino acid sequences being presented in the standard amino-to-carboxy terminal orientation (i.e., N→C).

The term "mature polypeptide" is defined herein as a polypeptide in its final form following translation and any post-translational modifications, such as N-terminal processing, C-terminal truncation, glycosylation, phosphorylation, etc. In one aspect, the predicted mature polypeptide is SEQ ID NO: 61 based on the analysis of SignalP software version 4.0 (Nordahl Petersen et al. (2011) *Nature Methods,* 8:785-786) and SEQ ID NO: 41 is a signal peptide. In another aspect, the mature polypeptide comprises amino acid position 20-468 of SEQ ID NO: 142. In another aspect, the mature polypeptide comprises amino acid position 21-468 of SEQ ID NO: 142. In another aspect, the mature polypeptide comprises amino acid position 22-468 of SEQ ID NO: 142. In another aspect, the mature polypeptide comprises amino acid position 23-468 of SEQ ID NO: 142. In another aspect, the mature polypeptide comprises amino acid position 24-468 of SEQ ID NO: 142. In another aspect, the mature polypeptide comprises amino acid position 25-468 of SEQ ID NO: 142 (SEQ ID NO: 143).

A "signal sequence" or "signal peptide" is a sequence of amino acids attached to the N-terminal portion of a protein, which facilitates the secretion of the protein outside the cell. The mature form of an extracellular protein lacks the signal sequence, which is cleaved off during the secretion process. In some embodiments, SEQ ID NO: 41 is a signal peptide. In other embodiments, the signal peptide comprises amino acid positions 1-20 of SEQ ID NO:142. In other embodiments, the signal peptide comprises amino acid positions 1-21 of SEQ ID NO:142. In other embodiments, the signal peptide comprises amino acid positions 1-22 of SEQ ID NO:142. In other embodiments, the signal peptide comprises amino acid positions 1-23 of SEQ ID NO:142. In other embodiments, the signal peptide comprises amino acid positions 1-24 of SEQ ID NO:142.

The term "nucleic acid" encompasses DNA, RNA, heteroduplexes, and synthetic molecules capable of encoding a polypeptide. Nucleic acids may be single stranded or double stranded, and may be chemically modified. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

The term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

A "synthetic" molecule is produced by in vitro chemical or enzymatic synthesis rather than by an organism.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "expression" refers to the process by which a polypeptide is produced based on a nucleic acid sequence. The process includes both transcription and translation.

The term "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

The term "sequence motif" is a nucleotide or amino-acid sequence pattern that is widespread and has been proven or assumed to have a biological significance. In this invention, the sequence motif is an amino-acid sequence motif identified in the Mucorales-clade glucoamylases.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

"Percent sequence identity" means that a particular sequence has at least a certain percentage of amino acid residues identical to those in a specified reference sequence, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty: OFF.

The term "homologous sequence" is defined herein as a predicted protein having an E value (or expectancy score) of less than 0.001 in a tfasty search (Pearson, W. R., 1999, in Bioinformatics Methods and Protocols, S. Misener and S. A. Krawetz, ed., pp. 185-219) with the glucoamylase of SEQ ID NO: 61.

As used herein with regard to amino acid residue positions, "corresponding to" or "corresponds to" or "correspond to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms, "wild-type", "parental" or "reference" with respect to a polypeptide, refer to a naturally-occurring polypeptide that does not include a man-made substitution, insertion, or deletion at one or more amino acid positions. Similarly, the terms "wild-type", "parental" or "reference" with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

A "slurry" is an aqueous mixture containing insoluble starch granules in water.

The term "total sugar content" refers to the total soluble sugar content present in a starch composition including monosaccharides, oligosaccharides and polysaccharides.

The term "dry solids" (ds) refer to dry solids dissolved in water, dry solids dispersed in water or a combination of both. Dry solids thus include granular starch, and its hydrolysis products, including glucose.

The term "high DS" refers to aqueous starch slurry with a dry solid content greater than 38% (wt/wt).

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+(>DP3) denotes polymers with a degree of polymerization of greater than 3.

The term "contacting" refers to the placing of referenced components (including but not limited to enzymes, substrates, and fermenting organisms) in sufficiently close proximity to affect an expect result, such as the enzyme acting on the substrate or the fermenting organism fermenting a substrate.

As used herein, the terms "yeast cells," "yeast strains," or simply "yeast" refer to organisms from the Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

An "ethanologenic microorganism" refers to a microorganism with the ability to convert a sugar or other carbohydrates to ethanol.

The term "biochemicals" refers to a metabolite of a microorganism, such as citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, iso-butanol, an amino acid, lysine, itaconic acid, other organic acids, 1,3-propanediol, vitamins, or isoprene or other biomaterial.

The term "pullulanase" also called debranching enzyme (E.C. 3.2.1.41, pullulan 6-glucanohydrolase), is capable of hydrolyzing alpha 1-6 glucosidic linkages in an amylopectin molecule.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, in connection with a numerical value, the term "about" refers to a range of −15% to +15% of the numerical value, unless the term is otherwise specifically defined in context.

The following abbreviations/acronyms have the following meanings unless otherwise specified:

EC enzyme commission
CAZy carbohydrate active enzyme
w/v weight/volume
w/w weight/weight
v/v volume/volume
wt % weight percent
° C. degrees Centigrade
g or gm gram
μg microgram
mg milligram
kg kilogram
μL and μl microliter
mL and ml milliliter
mm millimeter
micrometer
mol mole
mmol millimole
M molar
mM millimolar
μM micromolar
nm nanometer
U unit
ppm parts per million
hr and h hour
EtOH ethanol As used herein, the singular terms "a," "an," and "the" include the plural reference unless the context clearly indicates otherwise.

It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

The term "comprising" and its cognates are used in their inclusive sense; that is, equivalent to the term "including" and its corresponding cognates. It is further noted that the term "comprising," as used herein, means including, but not limited to, the component(s) after the term "comprising." The component(s) after the term "comprising" are required or mandatory, but the composition comprising the component(s) can further include other non-mandatory or optional component(s).

It is also noted that the term "consisting essentially of," as used herein refers to a composition wherein the component (s) after the term is in the presence of other known component(s) in a total amount that is less than 30% by weight of the total composition and do not contribute to or interferes with the actions or activities of the component(s).

It is also noted that the term "consisting of," as used herein, means including, and limited to, the component(s) after the term "consisting of" The component(s) after the term "consisting of" are therefore required or mandatory, and no other component(s) are present in the composition.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art to which this invention pertains.

Other definitions of terms may appear throughout the specification.

II. Polypeptides Having Glucoamylase Activity

In a first aspect, the present invention relates to polypeptides comprising an amino acid sequence having preferably at least 70%, at least 75%, at least 80%, at least 85%, at least 90%, at least 92%, at least 93%, at least 94%, at least 95%, at least 96%, at least 97%, at least 98%, and even at least 99%, amino acid sequence identity to the polypeptide of SEQ ID NO: 61 or SEQ ID NO: 142 and having glucoamylase activity. In another aspect, provided herein are polypeptides comprising an amino acid sequence having preferably at least 70%, at least 75%, at least 80%, at least 85%, at least 90%, at least 92%, at least 93%, at least 94%, at least 95%, at least 96%, at least 97%, at least 98%, and even at least 99%, amino acid sequence identity to a polypeptide comprising amino acid position 20-468 of SEQ ID NO: 142, amino acid position 21-468 of SEQ ID NO: 142, amino acid position 22-468 of SEQ ID NO: 142, amino acid position 23-468 of SEQ ID NO: 142, amino acid position 24-468 of SEQ ID NO: 142, or amino acid position 25-468 of SEQ ID NO: 142 (SEQ ID NO: 143).

In some embodiments, the polypeptide comprises an amino acid sequence having at least 70% but less than 100% sequence identity to the polypeptide of SEQ ID NO: 61 or SEQ ID NO: 142. In other embodiments, the polypeptide comprises an amino acid sequence having at least 70% but less than 100% sequence identity to the polypeptide comprising amino acid position 20-468 of SEQ ID NO: 142, amino acid position 21-468 of SEQ ID NO: 142, amino acid position 22-468 of SEQ ID NO: 142, amino acid position 23-468 of SEQ ID NO: 142, amino acid position 24-468 of SEQ ID NO: 142, or amino acid position 25-468 of SEQ ID NO: 142 (SEQ ID NO: 143). In some embodiments, the polypeptide is non-naturally occurring (i.e. does not occur in nature and is a product of human ingenuity).

In some embodiments, the polypeptides of the present invention are homologous polypeptides comprising amino acid sequences that differ by no more than ten amino acids, no more than nine amino acids, no more than eight amino acids, no more than seven amino acids, no more than six amino acids no more than five amino acids, no more than four amino acids, no more than three amino acids, no more than two amino acids, and even no more than one amino acid from the polypeptide of SEQ ID NO: 61, the polypeptide of SEQ ID NO: 142, the polypeptide comprising amino acid position 20-468 of SEQ ID NO: 142, the polypeptide comprising amino acid position 21-468 of SEQ ID NO: 142, the polypeptide comprising amino acid position 22-468 of SEQ ID NO: 142, the polypeptide comprising amino acid position 23-468 of SEQ ID NO: 142, the polypeptide comprising amino acid position 24-468 of SEQ ID NO: 142, or the polypeptide comprising amino acid position 25-468 of SEQ ID NO: 142 (SEQ ID NO: 143).

In some embodiments, the polypeptides of the present invention are the catalytic regions comprising amino acids 18 to 449 of SEQ ID NO: 61, predicted by ClustalX Hypertext Transfer Protocol Secure://world wide web.ncbi.nlm.nih.gov/pubmed/17846036.

In some embodiments, the polypeptides of the present invention have pullulan-hydrolyzing activity.

In a second aspect, the present glucoamylases disclosed herein comprise conservative substitution(s) of one or several amino acid residues relative to the amino acid sequence of SEQ ID NO: 61, the polypeptide of SEQ ID NO: 142, the polypeptide comprising amino acid position 20-468 of SEQ ID NO: 142, the polypeptide comprising amino acid position 21-468 of SEQ ID NO: 142, the polypeptide comprising amino acid position 22-468 of SEQ ID NO: 142, the polypeptide comprising amino acid position 23-468 of SEQ ID NO: 142, the polypeptide comprising amino acid position 24-468 of SEQ ID NO: 142, or the polypeptide comprising amino acid position 25-468 of SEQ ID NO: 142 (SEQ ID NO: 143). Exemplary conservative amino acid substitutions are listed below. Some conservative substitutions (i.e., mutations) can be produced by genetic manipulation while others are produced by introducing synthetic amino acids into a polypeptide by other means.

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the polypeptides of the present invention are the variants of the polypeptide of SEQ ID NO: 61, the polypeptide of SEQ ID NO: 142, the polypeptide comprising amino acid position 20-468 of SEQ ID NO: 142, the polypeptide comprising amino acid position 21-468 of SEQ ID NO: 142, the polypeptide comprising amino acid position 22-468 of SEQ ID NO: 142, the polypeptide comprising amino acid position 23-468 of SEQ ID NO: 142, the polypeptide comprising amino acid position 24-468 of SEQ ID NO: 142, or the polypeptide comprising amino acid position 25-468 of SEQ ID NO: 142 (SEQ ID NO: 143), or a fragment thereof having glucoamylase activity. The variant glucoamylase comprises a deletion, substitution, insertion, or addition of one or a few amino acid residues relative to the amino acid sequence of SEQ ID NO: 61 or SEQ ID NO: 142 or a homologous sequence thereof. In all cases, the expression "one or a few amino acid residues" refers to 10 or less, i.e., 1, 2, 3, 4, 5, 6, 7, 8, 9, or 10, amino acid residues. The amino acid substitutions, deletions and/or insertions of the polypeptide of SEQ ID NO: 61, the polypeptide of SEQ ID NO: 142, the polypeptide comprising amino acid position 20-468 of SEQ ID NO: 142, the polypeptide comprising amino acid position 21-468 of SEQ ID NO: 142, the polypeptide comprising amino acid position 22-468 of SEQ ID NO: 142, the polypeptide comprising amino acid position 23-468 of SEQ ID NO: 142, the polypeptide comprising amino acid position 24-468 of SEQ ID NO: 142, or the polypeptide comprising amino acid position 25-468 of SEQ ID NO: 142 (SEQ ID NO: 143) can be at most 10, at most 9, at most 8, at most 7, at most 6, at most 5, at most 4, at most 3, at most 2, and even at most 1.

In some embodiments, the variant alteration comprises or consists of a substitution at a position corresponding to position 102 of the polypeptide of SEQ ID NO: 61. In some embodiments, the amino acid at a position corresponding to position 102 of the polypeptide of SEQ ID NO: 61 is substituted with Ala, Arg, Asn, Asp, Cys, Gln, Glu, Gly, His, Leu, Ile, Lys, Met, Phe, Pro, Thr, Trp, Tyr, or Val, preferably with Pro. In some embodiments, the variant alteration comprises or consists of the substitution S102P of the polypeptide of SEQ ID NO: 61. In a further embodiment, the variant comprises or consists of the amino acid sequence of SEQ ID NO:104 or SEQ ID NO:141.

In some embodiments, the variant alteration comprises or consists of a substitution at a position corresponding to position 66 of the polypeptide of SEQ ID NO: 61. In some embodiments, the amino acid at a position corresponding to position 85 of the polypeptide of SEQ ID NO: 61 is substituted with Ala, Arg, Asn, Asp, Cys, Gln, Glu, Gly, His, Leu, Ile, Lys, Met, Phe, Pro, Ser, Thr, Trp, or Tyr. In some embodiments, the variant alteration comprises or consists of the substitution V66A of the polypeptide of SEQ ID NO: 61.

In another embodiment, the variant alteration comprises or consists of a substitution at a position corresponding to positions 66 and position 102 of the polypeptide of SEQ ID NO: 61. In some embodiments, the variant alteration comprises or consists of the substitution V66A and S102P of the polypeptide of SEQ ID NO: 61. In a further embodiment, the variant comprises or consists of the amino acid sequence of SEQ ID NO:140.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, Gene 46: 145; Ner et al., 1988, DNA 7: 127).

III. Production of Glucoamylase

The present glucoamylases can be produced in host cells, for example, by secretion or intracellular expression. A cultured cell material (e.g., a whole-cell broth) comprising a glucoamylase can be obtained following secretion of the glucoamylase into the cell medium. Optionally, the glucoamylase can be isolated from the host cells, or even isolated from the cell broth, depending on the desired purity of the final glucoamylase. A gene encoding a glucoamylase can be cloned and expressed according to methods well known in the art. Suitable host cells include bacterial, fungal (including yeast and filamentous fungi), and plant cells (including algae). Particularly useful host cells include *Aspergillus niger, Aspergillus oryzae, Trichoderma reesi*, or *Myceliopthora thermophila*. Other host cells include bacterial cells, e.g., *Bacillus subtilis* or *B. licheniformis*, as well as *Streptomyces*. A suitable yeast host organism can be selected from *Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism.

Additionally, the host may express one or more accessory enzymes, proteins, peptides. These may benefit liquefaction, saccharification, fermentation, SSF, and downstream processes. Furthermore, the host cell may produce ethanol and other biochemicals or biomaterials in addition to enzymes used to digest the various feedstock(s). Such host cells may be useful for fermentation or simultaneous saccharification and fermentation processes to reduce or eliminate the need to add enzymes.

A. Vectors

A DNA construct comprising a nucleic acid encoding a glucoamylase polypeptide can be constructed such that it is suitable to be expressed in a host cell. Because of the known degeneracy in the genetic code, different polynucleotides that encode an identical amino acid sequence can be designed and made with routine skill. It is also known that, depending on the desired host cells, codon optimization may be required prior to attempting expression.

A polynucleotide encoding a glucoamylase polypeptide of the present disclosure can be incorporated into a vector. Vectors can be transferred to a host cell using known transformation techniques, such as those disclosed below.

A suitable vector may be one that can be transformed into and/or replicated within a host cell. For example, a vector comprising a nucleic acid encoding a glucoamylase polypeptide of the present disclosure can be transformed and/or replicated in a bacterial host cell as a means of propagating and amplifying the vector. The vector may also be suitably transformed into an expression host, such that the encoding polynucleotide is expressed as a functional glucoamylase enzyme.

A representative useful vector is pTrex3gM (see, Published US Patent Application 20130323798) and pTTT (see, Published US Patent Application 20110020899), which can be inserted into genome of host. The vectors pTrex3gM and pTTT can both be modified with routine skill such that they comprise and express a polynucleotide encoding a glucoamylase polypeptide of the invention.

An expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the glucoamylase to a host cell organelle such as a peroxisome, or to a particular host cell compartment. For expression under the direction of control sequences, the nucleic acid sequence of the glucoamylase is operably linked to the control sequences in proper manner with respect to expression.

A polynucleotide encoding a glucoamylase polypeptide of the present invention can be operably linked to a promoter, which allows transcription in the host cell. The promoter may be any DNA sequence that shows transcriptional activity in the host cell of choice and may be derived from genes encoding proteins either homologous or heterologous to the host cell. Examples of promoters for directing the transcription of the DNA sequence encoding a glucoamylase, especially in a bacterial host, include the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xylA and xylB genes, and the like.

For transcription in a fungal host, examples of useful promoters include those derived from the gene encoding

*Aspergillus oryzae* TAKA amylase, *Rhizomucor miehei* aspartic proteinase, *Aspergillus niger* neutral α-amylase, *Aspergillus niger* acid stable α-amylase, *Aspergillus niger* glucoamylase, *Rhizomucor miehei* lipase, *Aspergillus oryzae* alkaline protease, *Aspergillus oryzae* triose phosphate isomerase, *Aspergillus nidulans* acetamidase and the like. When a gene encoding a glucoamylase is expressed in a bacterial species such as an *E. coli*, a suitable promoter can be selected, for example, from a bacteriophage promoter including a T7 promoter and a phage lambda promoter. Along these lines, examples of suitable promoters for the expression in a yeast species include but are not limited to the Gal 1 and Gal 10 promoters of *Saccharomyces cerevisiae* and the *Pichia pastoris* AOX1 or AOX2 promoters. Expression in filamentous fungal host cells often involves cbh1, which is an endogenous, inducible promoter from *T. reesei*. See Liu et al. (2008) *Acta Biochim. Biophys. Sin* (*Shanghai*) 40(2): 158-65.

The coding sequence can be operably linked to a signal sequence. The DNA encoding the signal sequence may be a DNA sequence naturally associated with the glucoamylase gene of interest to be expressed, or may be from a different genus or species as the glucoamylase. A signal sequence and a promoter sequence comprising a DNA construct or vector can be introduced into a fungal host cell and can be derived from the same source. For example, the signal sequence may be the *Trichoderma reesei* cbh1 signal sequence, which is operably linked to a cbh1 promoter.

An expression vector may also comprise a suitable transcription terminator and, in eukaryotes, polyadenylation sequences operably linked to the DNA sequence encoding a glucoamylase. Termination and polyadenylation sequences may suitably be derived from the same sources as the promoter.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., Published International PCT Application WO 91/17243.

B. Transformation and Culture of Host Cells

An isolated cell, either comprising a DNA construct or an expression vector, is advantageously used as a host cell in the recombinant production of a glucoamylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium*, and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species.

Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A glucoamylase expressed by a fungal host cell can be glycosylated, i.e., will comprise a glycosyl moiety. The glycosylation pattern can be the same or different as present in the wild-type glucoamylase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding a glucoamylase is stably integrated into a host cell chromosome. Transformants are then selected and purified by known techniques.

C. Expression and Fermentation

A method of producing a glucoamylase may comprise cultivating a host cell under conditions conducive to the production of the enzyme and recovering the enzyme from the cells and/or culture medium.

The medium used to cultivate the cells may be any conventional medium suitable for growing the host cell and obtaining expression of a glucoamylase polypeptide. Suitable media and media components are available from commercial suppliers or may be prepared according to published recipes (e.g., as described in catalogues of the American Type Culture Collection).

Any of the fermentation methods well known in the art can suitably used to ferment the transformed or the derivative fungal strain as described above. In some embodiments, fungal cells are grown under batch or continuous fermentation conditions.

D. Methods for Enriching and Purification

Separation and concentration techniques are known in the art and conventional methods can be used to prepare a concentrated solution or broth comprising a glucoamylase polypeptide of the invention.

After fermentation, a fermentation broth is obtained, the microbial cells and various suspended solids, including residual raw fermentation materials, are removed by conventional separation techniques in order to obtain a glucoamylase solution. Filtration, centrifugation, microfiltration, rotary vacuum drum filtration, ultrafiltration, centrifugation followed by ultrafiltration, extraction, or chromatography, or the like, are generally used.

It may at times be desirable to concentrate a solution or broth comprising a glucoamylase polypeptide to optimize recovery. Use of un-concentrated solutions or broth would typically increase incubation time in order to collect the enriched or purified enzyme precipitate.

IV. Compositions

The present invention also relates to compositions comprising a polypeptide and/or a starch substrate. In some embodiments, a polypeptide comprising an amino acid sequence that is at least about 80%, at least about 85%, at least about 90%, at least about 95%, at least about 96%, at least about 97%, at least about 98%, at least about 99%, identical to that of SEQ ID NO: 61 can also be used in the enzyme composition. Preferably, the compositions are formulated to provide desirable characteristics such as low color, low odor and acceptable storage stability at a temperature of about 4-40° C. and a pH of about 3-7.

The composition may comprise a polypeptide of the present invention as the major enzymatic component. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, alpha-glucosidase, beta-glucosidase, beta-amylase, isoamylase, haloperoxidase, invertase, laccase, lipase, mannosidase, oxidase, pectinolytic enzyme, peptidoglutaminase, peroxidase, phytase, polyphenoloxidase, proteolytic enzyme, pullulanase, ribonuclease, transglutaminase, xylanase or a combination thereof, which may be added in effective amounts well known to the person skilled in the art.

The polypeptide compositions may be prepared in accordance with methods known in the art and may be in the form of a liquid or a dry composition. For instance, the compositions comprising the present glucoamylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc., for example, endogenous plant (including algal) enzymes, residual enzymes from a prior processing step, and the like. The polypeptide to be included in the composition may be stabilized in accordance with methods known in the art.

The composition may be cells expressing the polypeptide, including cells capable of producing a product from fermentation. Such cells may be provided in a liquid or in dry form along with suitable stabilizers. Such cells may further express additional polypeptides, such as those mentioned, above.

Examples are given below of preferred uses of the polypeptides or compositions of the invention. The dosage of the polypeptide composition of the invention and other conditions under which the composition is used may be determined on the basis of methods known in the art.

Above composition is suitable for use in liquefaction, saccharification, and/or fermentation process, preferably in starch conversion, especially for producing syrup and fermentation products, such as ethanol. The composition is also suitable for use in animal nutrition and fermented beverage.

V. Use

The present invention is also directed to use of a polypeptide or composition of the present invention in a liquefaction, a saccharification and/or a fermentation process. The polypeptide or composition may be used in a single process, for example, in a liquefaction process, a saccharification process, or a fermentation process. The polypeptide or composition may also be used in a combination of processes for example in a liquefaction and saccharification process, in a liquefaction and fermentation process, or in a saccharification and fermentation process, preferably in relation to starch conversion.

A. Saccharification

The liquefied starch may be saccharified into a syrup rich in lower DP (e.g., DP1+DP2) saccharides, using alpha-amylases and glucoamylases, optionally in the presence of another enzyme(s). The exact composition of the products of saccharification depends on the combination of enzymes used, as well as the type of starch processed. Advantageously, the syrup obtainable using the provided glucoamylases may contain a weight percent of DP1 of the total oligosaccharides in the saccharified starch exceeding 90%, e.g., 90%-98% or 95%-97%. The weight percent of DP2 in the saccharified starch may be as low as possible, about less than 3%, e.g., 0-3% or 0-2.8%.

Whereas liquefaction is generally run as a continuous process, saccharification is often conducted as a batch process. Saccharification conditions are dependent upon the nature of the liquefact and type of enzymes available. In some cases, a saccharification process may involve temperatures of about 60-65° C. and a pH of about 4.0-4.5, e.g., pH 4.3. Saccharification may be performed, for example, at a temperature between about 40° C., about 50° C., or about 55° C. to about 60° C. or about 65° C., necessitating cooling of the Liquefact. The pH may also be adjusted as needed. Saccharification is normally conducted in stirred tanks, which may take several hours to fill or empty. Enzymes typically are added either at a fixed ratio to dried solids, as the tanks are filled, or added as a single dose at the commencement of the filling stage. A saccharification reaction to make a syrup typically is run over about 24-72 hours, for example, 24-48 hours. A pre-saccharification can be added before saccharification in a simultaneous saccharification and fermentation (SSF), for typically 40-90 minutes at a temperature between 30-65° C., typically about 60° C.

B. Raw Starch Hydrolysis

The present invention provides a use of the glucoamylase of the invention for producing glucoses and the like from raw starch or granular starch. Generally, glucoamylase of the present invention either alone or in the presence of an alpha-amylase can be used in raw starch hydrolysis (RSH) or granular starch hydrolysis (GSH) process for producing desired sugars and fermentation products. The granular starch is solubilized by enzymatic hydrolysis below the gelatinization temperature. Such "low-temperature" systems (known also as "no-cook" or "cold-cook") have been reported to be able to process higher concentrations of dry solids than conventional systems (e.g., up to 45%).

A "raw starch hydrolysis" process (RSH) differs from conventional starch treatment processes, including sequentially or simultaneously saccharifying and fermenting granular starch at or below the gelatinization temperature of the starch substrate typically in the presence of at least an glucoamylase and/or amylase.

The glucoamylase of the invention may also be used in combination with an enzyme that hydrolyzes only alpha-(1, 6)-glucosidic bonds in molecules comprising at least four glucosyl residues. Preferably, the glucoamylase of the invention is used in combination with pullulanase or isoamylase. The use of isoamylase and pullulanase for debranching of starch, the molecular properties of the enzymes, and the potential use of the enzymes together with glucoamylase is described in G. M. A. van Beynum et al., Starch Conversion Technology, Marcel Dekker, New York, 1985, 101-142.

C. Fermentation

The soluble starch hydrolysate, particularly a glucose rich syrup, can be fermented by contacting the starch hydrolysate with a fermenting organism typically at a temperature around 32° C., such as from 30° C. to 35° C. "Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include yeast, such as *Saccharomyces cerevisiae* and bacteria, e.g., *Zymomonas mobilis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27:1049-56. Yeast that can be used for alcohol production include, but are not limited to, *Saccharomyces* spp., including *S. cerevisiae*, as well as *Kluyveromyces*, Lachancea and *Schizosaccharomyces* spp. Numerous yeast strains are commercially available, many of which have been selected or genetically engineered for desired characteristics, such as high alcohol production, rapid growth rate, and the like. The temperature and pH of the fermentation will depend upon the fermenting organism. Microorganisms that produce other metabolites, such as citric acid and lactic acid, by fermentation are also known in the art. See, e.g., Papagianni (2007) *Biotechnol. Adv.* 25:244-63; John et al. (2009) *Biotechnol. Adv.* 27:145-52.

The saccharification and fermentation processes may be carried out as an SSF process. An SSF process can be conducted with fungal cells that express and secrete glucoamylase continuously throughout SSF. The fungal cells expressing glucoamylase also can be the fermenting microorganism, e.g., an ethanologenic microorganism. Ethanol production thus can be carried out using a fungal cell that expresses sufficient glucoamylase so that less or no enzyme has to be added exogenously. The fungal host cell can be selected from an appropriately engineered fungal strains. Fungal host cells that express and secrete other enzymes, in addition to glucoamylase, also can be used. Such cells may express amylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzymes. Fermentation may be followed by subsequent recovery of ethanol.

D. Fermentation Products

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, propylene glycol, butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones.

In a preferred aspect the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred fermentation processes used include alcohol fermentation processes, which are well known in the art. Preferred fermentation processes are anaerobic fermentation processes, which are well known in the art.

E. Brewing

Processes for making beer are well known in the art. See, e.g., Wolfgang Kunze (2004) "Technology Brewing and Malting" Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer.

The brewing composition comprising a glucoamylase, in combination with an amylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

F. Animal Nutrition

The glucoamylases and the compositions described herein can be used as a feed additive for animals to increase starch digestibility. Describe herein is a method for increasing starch digestibility in an animal.

The term "animal" refers to any organism belonging to the kingdom Animalia and includes, without limitation, mammals (excluding humans), non-human animals, domestic animals, livestock, farm animals, zoo animals, breeding stock and the like. For example, there can be mentioned all non-ruminant and ruminant animals. In an embodiment, the animal is a non-ruminant, i.e., a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal is a ruminant animal including, but not limited to, cattle, young calves, goats, sheep, giraffes, bison, moose, elk, yaks, water buffalo, deer, camels, alpacas, llamas, antelope, pronghorn and nilgai.

The terms "animal feed", "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) byproducts from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

The digestibility of starch in feeds is highly variable and dependent on a number of factors including the physical structure of both the starch and feed matrix. It has been found that starch digestibility in an animal's diet can be improved by the use of at least one glucoamylase as a feed additive.

When used as, or in the preparation of, a feed, such as functional feed, the enzyme or feed additive composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

It is also possible that at least one glucoamylase (or an enzyme composition comprising at least one glucoamylase as described herein) described herein can be homogenized to produce a powder. The powder may be mixed with other components known in the art. Optionally, the feedstuff may also contain additional minerals such as, for example, calcium and/or additional vitamins. In some embodiments, the feedstuff is a corn soybean meal mix.

In an alternative preferred embodiment, an enzyme composition comprising at least one glucoamylase can be formulated to granules as described in WO2007/044968 (referred to as TPT granules) or WO1997/016076 or WO1992/012645 incorporated herein by reference. "TPT" means Thermo Protection Technology. When the feed additive composition is formulated into granules, the granules comprise a hydrated barrier salt coated over the protein core. The advantage of such salt coating is improved thermotolerance, improved storage stability and protection against other feed additives otherwise having adverse effect on the enzyme. Preferably, the salt used for the salt coating has a water activity greater than 0.25 or constant humidity greater than 60% at 20° C. In some embodiments, the salt coating comprises $Na_2SO_4$.

Alternatively, the composition is in a liquid formulation suitable for consumption preferably such liquid consumption contains one or more of the following: a buffer, salt, sorbitol and/or glycerol.

Any of the glucoamylases described herein for use as a feed additive may be used alone or in combination with at least one direct fed microbial. Categories of DFMs include *Bacillus*, Lactic Acid Bacteria and Yeasts. Further, any of the glucoamylases described herein for use as a feed additive may be used alone or in combination with at least one essential oil, for example cinnamaldehyde and/or thymol. Still further, any of the glucoamylases described herein for use as a feed additive may be used alone or in combination with at least one additional enzyme. Examples of such enzymes include, without limitation, phytases, xylanases, proteases, amylases, glucanases, or other glucoamylases.

Also disclosed is a method for improving the nutritional value of an animal feed, wherein an effective amount of any of the glucoamylases described herein can be added to animal feed.

The phrase, an "effective amount" as used herein, refers to the amount of an active agent (such as any of the glucoamylase polypeptides disclosed herein) required to confer improved performance on an animal on one or more metrics, either alone or in combination with one or more other active agents (such as, without limitation, one or more additional enzyme(s), one or more DFM(s), one or more essential oils, etc.).

The term "animal performance" as used herein may be determined by any metric such as, without limitation, the feed efficiency and/or weight gain of the animal and/or by the feed conversion ratio and/or by the digestibility of a nutrient in a feed and/or digestible energy or metabolizable energy in a feed and/or by animals' ability to avoid the negative effects of diseases or by the immune response of the subject.

Animal performance characteristics may include but are not limited to: body weight; weight gain; mass; body fat percentage; height; body fat distribution; growth; growth rate; egg size; egg weight; egg mass; egg laying rate; mineral absorption; mineral excretion, mineral retention; bone density; bone strength; feed conversion rate (FCR); average daily feed intake (ADFI); Average daily gain (ADG) retention and/or a secretion of any one or more of copper, sodium, phosphorous, nitrogen and calcium; amino acid retention or absorption; mineralization, bone mineralization carcass yield and carcass quality.

By "improved animal performance on one or more metric" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed comprising the feed additive composition described herein as compared to a feed which does not comprise said feed additive composition.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1

Identification of a Mucorales-Clade Glucoamylase Enzymes

A search for glucoamylase enzymes of the Zygomycetes phylum was performed by scanning annotated protein sequences of the Zygomycetes phylum using dbCAN (Yin et al (2012) "dbCAN: a web resource for automated carbohydrate-active enzyme annoatation: *Nucleic Acids Research* 40:W4450-451) to identify all GH15 proteins based on CAZY family analysis. A number of genes were identified in the genomes of Mucorales order organisms and the sequences were further analyzed. Genes encoding the Mucorales-clade glucoamylases were identified from the sources listed on Table 1, and are assigned SEQ ID NOs shown on Table 1.

TABLE 1

Sequence source and SEQ ID NOs for Mucorales-clade glucoamylases evaluated in this study.

| Sample ID | SEQ ID NO | Gene sequence source *[mycocosm.jgi.doe.gov/cgi-bin/disp GeneModel?db] | Organism |
|---|---|---|---|
| SvaGA1 | 1 | *scaffold_1856:13863-15495, protein ID: 4356 | *Saksenaea vasiformis* B4078 |
| BciGA1 | 2 | *scaffold_261:3283-5849, protein ID: 261628 | *Backusella circina* FSU 941 |
| BciGA2 | 3 | *scaffold_67:52720-55269, protein ID: 183741 | *Backusella circina* FSU 941 |
| BpoGA1 | 4 | *scaffold_1:5688666-5690969, protein ID: 552608 | *Benjaminiella poitrasii* RSA 903 |
| CcuGA1 | 5 | *scaffold_32:142308-144412, protein ID: 565216 | *Choanephora cucurbitarum* NRRL2744 |
| RstGA1 | 6 | world wide web.ncbi.nlm.nih.gov/protein/RCI05434 | *Rhizopus stolonifer* |
| MciGA5 | 7 | world wide webncbi.nlm.nih.gov/protein/EPB90436 | *Mucor circinelloides* f. *circinelloides* 1006PhL |
| DelGA1 | 8 | *scaffold_14:156040-158505, protein ID: 307234 | *Dichotomocladium elegans* RSA 919 |
| FspGA3 | 9 | *scaffold_47:22656-25504, protein ID: 631220 | *Fennellomyces* sp. T-0311 |
| GpeGA1 | 10 | *scaffold_27:154515-156499, protein ID: 572732 | Gilbertella persicaria var. persicaria CBS 190.32-T |
| MciGA3 | 11 | *scaffold_04:2553725-2555899, protein ID: 156167 | Mucor circinelloides CBS277.49 |
| CumGA1 | 12 | *scaffold_36:443143-446327, protein ID: 486055 | *Circinella umbellata* NRRL1351 |
| McoGA1 | 13 | *scaffold_20:482726-484980, protein ID: 382429 | *Mucor cordense* RSA 1222 |
| ParGA1 | 14 | scaffold 11:462211-464919, protein ID: 4368711 | *Phascolomyces articulosus* |
| RmiGA1 | 15 | *scaffold_21:172464-174631, protein ID: 230588 | *Rhizopus microsporus* var. microsporus ATCC52813 |
| SfuGA2 | 16 | *scaffold_162:2818-4664, protein ID: 1870629 | *Spinellus fusiger* NRRL 22323 |
| SraGA1 | 17 | *scaffold_4:869438-871839, protein ID: 545732 | *Syncephalastrum racemosum* NRRL 2496 |
| SraGA3 | 18 | *scaffold_9:632087-633913, protein ID: 558396 | *Syncephalastrum racemosum* NRRL 2496 |
| TinGA1 | 19 | world wide web.ncbi.nlm.nih.gov/nuccore/JSYX01000005 | *Thermomucor indicae-seudaticae* HACC 243 |
| ZmeGA1 | 20 | *scaffold_35:220637-223894, protein ID: 822592 | *Zychaea mexicana* RSA 1403 |

The N-terminal signal peptides were predicted by SignalP software version 4.0 (Nordahl Petersen et al. (2011) *Nature Methods,* 8:785-786). The genes encoding the various Mucorales-clade glucoamylases were codon modified for expression in *Trichoderma reesei*.

TABLE 2

Sequences of Mucorales-clade glucoamylases evaluated in this study. SEQ ID NOs for the nucleotide sequences of expression cassettes, predicted signal peptide and predicted mature polypeptide.

| | SEQ ID Nos | | |
|---|---|---|---|
| Sample ID | codon modified sequences used as expression cassettes | predicted signal peptide | predicted mature protein sequence |
| SvaGA1 | SEQ ID NO: 21 | SEQ ID NO: 41 | SEQ ID NO: 61 |
| BciGA1 | SEQ ID NO: 22 | SEQ ID NO: 42 | SEQ ID NO: 62 |
| BciGA2 | SEQ ID NO: 23 | SEQ ID NO: 43 | SEQ ID NO: 63 |
| BpoGA1 | SEQ ID NO: 24 | SEQ ID NO: 44 | SEQ ID NO: 64 |
| CcuGA1 | SEQ ID NO: 25 | SEQ ID NO: 45 | SEQ ID NO: 65 |
| RstGA1 | SEQ ID NO: 26 | SEQ ID NO: 46 | SEQ ID NO: 66 |

TABLE 2-continued

Sequences of Mucorales-clade glucoamylases evaluated in this study. SEQ ID NOs for the nucleotide sequences of expression cassettes, predicted signal peptide and predicted mature polypeptide.

| Sample ID | SEQ ID Nos codon modified sequences used as expression cassettes | predicted signal peptide | predicted mature protein sequence |
|---|---|---|---|
| MciGA5 | SEQ ID NO: 27 | SEQ ID NO: 47 | SEQ ID NO: 67 |
| DelGA1 | SEQ ID NO: 28 | SEQ ID NO: 48 | SEQ ID NO: 68 |
| FspGA3 | SEQ ID NO: 29 | SEQ ID NO: 49 | SEQ ID NO: 69 |
| GpeGA1 | SEQ ID NO: 30 | SEQ ID NO: 50 | SEQ ID NO: 70 |
| MciGA3 | SEQ ID NO: 31 | SEQ ID NO: 51 | SEQ ID NO: 71 |
| CumGA1 | SEQ ID NO: 32 | SEQ ID NO: 52 | SEQ ID NO: 72 |
| McoGA1 | SEQ ID NO: 33 | SEQ ID NO: 53 | SEQ ID NO: 73 |
| ParGA1 | SEQ ID NO: 34 | SEQ ID NO: 54 | SEQ ID NO: 74 |
| RmiGA1 | SEQ ID NO: 35 | SEQ ID NO: 55 | SEQ ID NO: 75 |
| SfuGA2 | SEQ ID NO: 36 | SEQ ID NO: 56 | SEQ ID NO: 76 |
| SraGA1 | SEQ ID NO: 37 | SEQ ID NO: 57 | SEQ ID NO: 77 |
| SraGA3 | SEQ ID NO: 38 | SEQ ID NO: 58 | SEQ ID NO: 78 |
| TinGA1 | SEQ ID NO: 39 | SEQ ID NO: 59 | SEQ ID NO: 79 |
| ZmeGA1 | SEQ ID NO: 40 | SEQ ID NO: 60 | SEQ ID NO: 80 |

Example 2

Expression of Mucorales-Clade Glucoamylases in *Trichoderma reesei*

The polynucleotides (codon modified sequences used as expression cassettes) encoding the Mucorales-clade glucoamylases genes (SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40) were synthesized by Generay (Generay Biotech Co., Ltd, Shanghai, China) and inserted into the pGX256 expression vector, a derivative vector from pTTT (see, Published US Patent Application 20110020899).

A polynucleotide encoding a variant of SvaGA1 glucoamylase (SEQ ID NO: 61), where a codon change introduced a mutation at amino acid position 102 of Pro in place of Ser (SvaGA1v2, S102P) was constructed. The expression cassette encoding SvaGA1v2 was inserted into the pGX256 (as described above).

All plasmids were transformed into a suitable *Trichoderma reesei* strain using protoplast transformation (Te'o et al., J. Microbiol. Methods 51:393-99, 2002). The transformants were selected and fermented by the methods described in WO 2016/138315. Supernatants from these cultures were used to confirm the protein expression by SDS-PAGE analysis.

Fungal cell cultures were grown in a defined medium as described by Lv et al (2012) in "Construction of teo vectors for gene expression in *Trichoderma reesei*". *Plasmids* 67:67-71. Clarified culture broth were collected after 96 hours by centrifugation. The Mucorales-clade glucoamylases were purified by methods known in the art. The column chromatography fractions containing the target protein were pooled, concentrated and equilibrated to 20 mM sodium acetate pH 5.0, 150 mM sodium chloride using an Amicon Ultra-15 device with 10 K MWCO. The purified samples were approximately 99% pure (by SDS-PAGE analysis) and were stored in 40% glycerol at −80° C. until use.

Example 3

Evaluation of SvaGA1 and SvaGA1v2 Glucoamylases in Saccharification at pH 4.5. 60° C.

The saccharification performance of SvaGA1 and the SvaGA1v2 variant were evaluated at pH 4.5 and 60° C. A sample of GC126 (a DuPont/IFF product) pre-treated corn starch liquefact (prepared at 38% ds, pH 3.3) was used as a starting substrate. The performance of the glucoamylases was tested at the dosage of 30 μg/gds. The glucoamylase *Gloeophyllum trabeum* glucoamylase (GtGA) from EXTENDA® XTRA (a Novozymes product) was included for comparison. For this evaluation, the pullulanase OPTIMAX™ L 1000 (a DuPont product) was dosed at 10 μg/gds, and the alpha-amylase *Aspergillus kawachii* amylase (AkAA, described in WO2013169645, incorporated by reference herein) was dosed at 5 μg/gds for each incubation. The corn starch liquefact substrate and the enzymes (glucoamylase, alpha-amylase and pullulanase) were incubated at pH 4.5, 60° C. for 48 and 65 hours, respectively. All the incubations were quenched by heating at 100° C. for 15 min. Aliquots were removed and diluted 40-fold in 5 mM $H_2SO_4$ for product analysis by HPLC using an Agilent 1200 series system with a Phenomenex Rezex-RFQ Fast Fruit column (cat #00D-0223-K0), run at 80° C. 10 μL samples were loaded on the column and separated with an isocratic gradient of 5 mM $H_2SO_4$ as the mobile phase at a flow rate of 1.0 mL/min. The oligosaccharide products were detected using a refractive index detector, and the standards were run to determine elution times of each DP(n) sugar of interest (DP3+, DP3, DP2 and DP1). The values shown in Table 3 reflect the peak area percentages of each DP(n) as a fraction of the total DP1 to DP3+. The results of DP1 generation and DP3+ hydrolysis by SvaGA1 and SvaGA1v2 glucoamylases outperformed those of the reference GtGA enzyme at pH 4.5, 60° C.

TABLE 3

Sugar composition results for glucoamylases incubated with corn starch liquefact at pH 4.5, 60° C.

| Incubation time | Sample | Percent (%) Dextrose Equivalent (DP) detected DP3+ | DP3 | DP2 | DP1 |
|---|---|---|---|---|---|
| 48 h | SvaGA1 | 0.4 | 1.2 | 2.7 | 95.7 |
| | SvaGA1v2 | 0.4 | 1.2 | 2.7 | 95.7 |
| | GtGA | 0.7 | 1.5 | 3.7 | 94.0 |
| 65 h | SvaGA1 | 0.3 | 1.1 | 2.7 | 95.9 |
| | SvaGA1v2 | 0.3 | 1.0 | 2.9 | 95.8 |
| | GtGA | 0.4 | 1.3 | 2.8 | 95.4 |

Example 4

Specific Activities of Mucorales-Clade Glucoamylase Enzymes on Soluble Starch Glucoamylase specific activity was assayed based on the release of glucose from soluble starch using the coupled glucose oxidase/peroxidase (GOX/HRP) and 2,2'-Azino-bis 3-ethylbenzothiazoline-6-sulfonic acid (ABTS) method (*Anal. Biochem.* 105 (1980), 389-397). Substrate solutions were prepared by mixing 9 mL of soluble starch (1% in water, w/w) and 1 mL of 0.5 M pH 5.0 sodium acetate buffer in a 15-mL conical tube. Coupled enzyme (GOX/HRP) solution with ABTS was prepared in 50 mM sodium acetate buffer (pH 5.0), with the final concentrations of 2.74 mg/mL ABTS, 0.1 U/mL HRP, and 1 U/mL GOX. Serial dilutions of each glucoamylase sample to be evaluated and a glucose standard were prepared in purified water. Each glucoamylase sample (10 μL) was transferred into a new microtiter plate (Corning 3641) containing 90 μL of substrate solution preincubated at 50° C. for 5 min at 600 rpm. The reactions were carried out at 50° C. for 10 min with shaking (600 rpm) in a thermomixer (Eppendorf), 10 μL of reaction mixtures as well as 10 μL of serial dilutions of glucose standard were quickly transferred to new microtiter plates (Corning 3641), respectively, followed by the addition of 100 μL of ABTS/GOX/HRP solution. Absorbance at 405 nm was immediately measured at 11 seconds intervals for 5 min using a SoftMax Pro plate reader (Molecular Device). The output was the reaction rate, Vo, for each enzyme concentration. Linear regression was used to determine the slope of the plot Vo vs. enzyme dose. The specific activity of each glucoamylase was calculated based on the glucose standard curve using Equation below:

$$\text{Specific Activity(Unit/mg)}=\text{Slope(enzyme)/slope (std)}\times 1000 \quad (1),$$

where 1 Unit=1 μmol glucose/min.

Using the method described above, specific activities of the Mucorales-clade Glucoamylases and benchmarks was determined. Results are shown in Table 4.

TABLE 4

Specific activity of Mucorales-clade Glucoamylases on soluble starch after 10-min incubation at pH 5.0, 50°C.

| Sample | Specific activity(U/mg) |
|---|---|
| RmiGA1 | 212.3 |
| SraGA1 | 169.5 |
| BciGA1 | 169.3 |
| SraGA3 | 144.9 |
| BciGA2 | 141.6 |
| MciGA3 | 204.1 |
| McoGA1 | 232.3 |
| DelGA1 | 191.5 |
| GpeGA1 | 233.1 |
| ParGA1 | 144.0 |
| SfuGA2 | 215.7 |
| SvaGA1 | 334.3 |
| TinGA1 | 140.4 |
| AnGA | 191.3 |

Example 5

Analysis of Homologous Mucorales-Clade Glucoamylase Sequences

A multiple amino acid sequence alignment was constructed for the regions encompassing the catalytic domain of the Mucorales-clade glucoamylases:SvaGA1 SEQ ID NO:81, BciGA1 SEQ ID NO:82, BciGA2 SEQ ID NO:83, BpoGA1 SEQ ID NO:84, CcuGA1 SEQ ID NO:85, RstGA1 SEQ ID NO:86, MciGA5 SEQ ID NO:87, DelGA1 SEQ ID NO:88, FspGA3 SEQ ID NO:89, GpeGA1 SEQ ID NO:90, MciGA3 SEQ ID NO:91, CumGA1 SEQ ID NO:92, McoGA1 SEQ ID NO:93, ParGA1 SEQ ID NO:94, RmiGA1 SEQ ID NO:95, SfuGA2 SEQ ID NO:96, SraGA1 SEQ ID NO:97, SraGA3 SEQ ID NO:98, TinGA1 SEQ ID NO:99, and ZmeGA1 SEQ ID NO:100. In the case of SvaGa1, the catalytic domain is 432 residues long and spans amino acids 18 to 449 of the predicted mature protein sequence. The above-mentioned region overlaps the previously defined catalytic domains of fungal glucoamylases, based on studies of *A. awamori* (Aleshin et al, 1994, *J. Mol. Bio.* 238:575-591) and *A. niger* (Lee and Paetzel, 2011, *Acta Cryst. F*67: 188-192) glucoamylase sequences. These sequences were aligned using MUSCLE alignment tool within Geneious 10.2 software with the default parameters. Additional homologous sequences were identified in the public domain: GAN00808.1 SEQ ID NO:101, ORE14155.1 SEQ ID NO:102, and RCH88939.1 SEQ ID NO:103, and their overlapping sequences were also included in this analysis. In addition, the catalytic domains of other glucoamylases, not members of the Mucorales order of fungi, were included in the alignment: *Aspergillus niger* glucoamylase (AnGA) SEQ ID NO:105, *Aspergillus fumigatus* glucoamylase (AfuGA) SEQ ID NO:106, *Fibroporia radiculosa* TFFH 294 glucoamylase (FraGA1) SEQ ID NO:107, *Fusarium verticillioides* glucoamylase (FveABC11) SEQ ID NO:108, *Gloeophyllum trabeum* glucoamylase (GtGA) SEQ ID NO:109, *Penicillium oxalicum* glucoamylase (PoxGA) SEQ ID NO:110, *Trichoderma reesei* glucoamylase (TrGA) SEQ ID NO:111, and *Wolfiporia cocos* MD-104 SS10 glucoamylase (WcoGA1) SEQ ID NO:112, in order to identify regions of sequence similarities and differences. The multiple sequence alignment is shown on FIG. 1 panels A-K. A phylogenetic tree was generated using Geneious 10.2 software from the alignment on FIG. 1 and is shown on FIG. 2.

Figure 3:
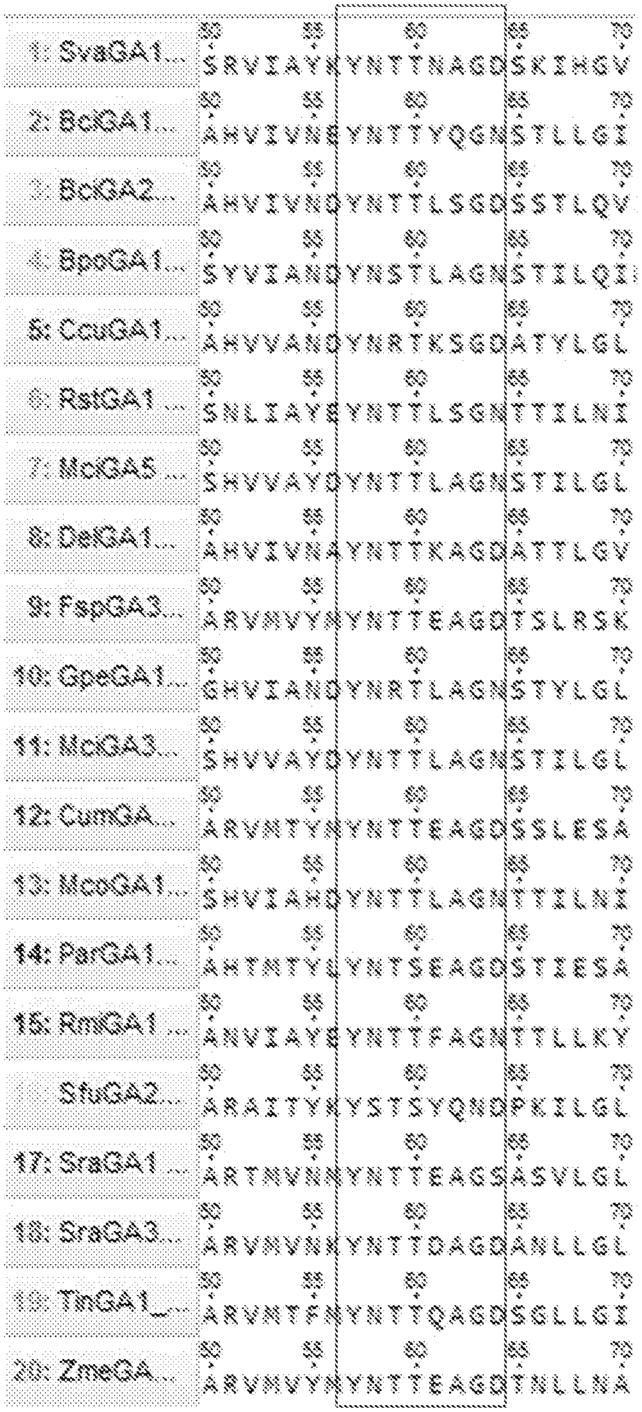
FIG. 3 provides an alignment of Mucorales-clade GA amino acid sequences (numbered according to SvaGa1 catalytic domain region, SEQ ID NO: 81) across region spanning residues 50 to 70, showing motif 1: 57Y-58$X_a$-59$X_b$-60T-61X-62X-63$X_c$-64$X_d$, wherein X is any amino acid and $X_a$ is N or S; $X_b$ is T, S, or R; $X_c$ is G or N; and $X_d$ is D, N, or S.
Figure 4:
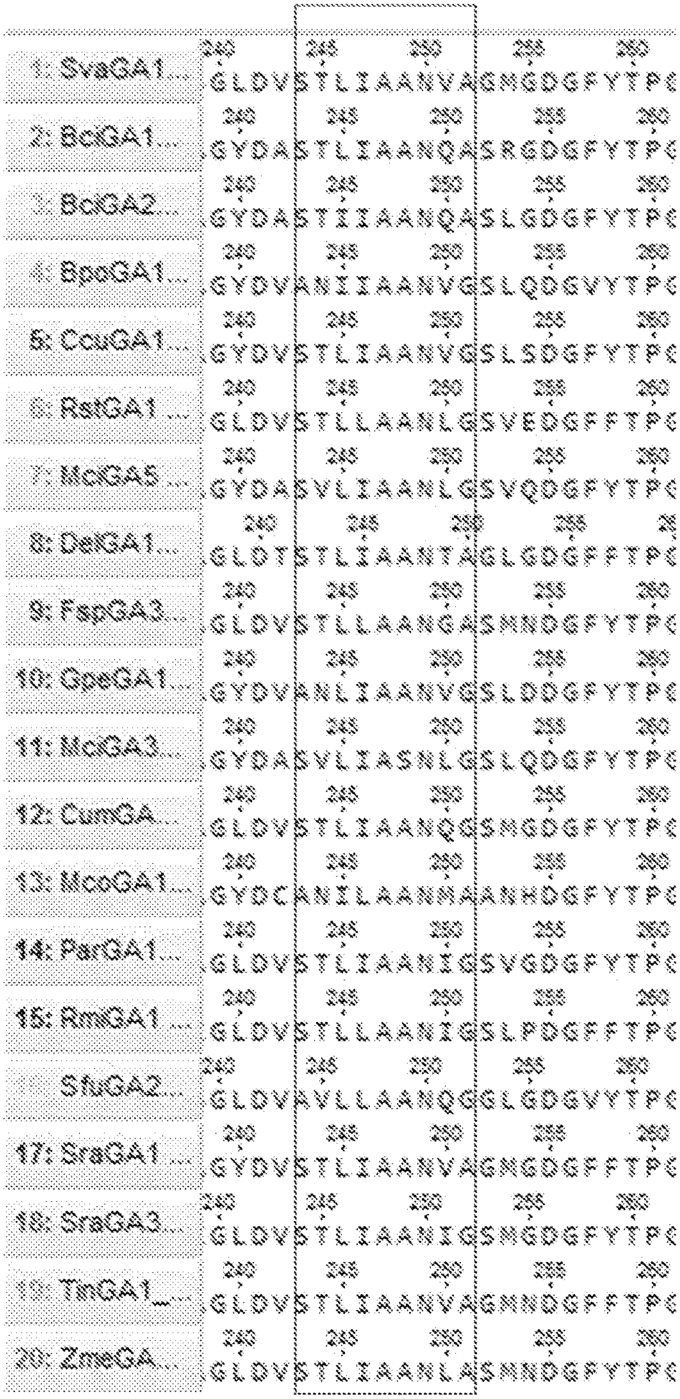
FIG. 4 provides an alignment of Mucorales-clade GA amino acid sequences (numbered according to SvaGa1 catalytic domain region, SEQ ID NO: 81) across region spanning residues 240 to 260, showing motif 2: 244$X_a$-245$X_b$-246$X_c$-247$X_c$-248A-249A-250N-251X-252$X_d$, wherein X is any amino acid and $X_a$ is S or A; $X_b$ is T, N, or V; $X_c$ is L or I; and $X_d$ is A or G.
Figure 5:
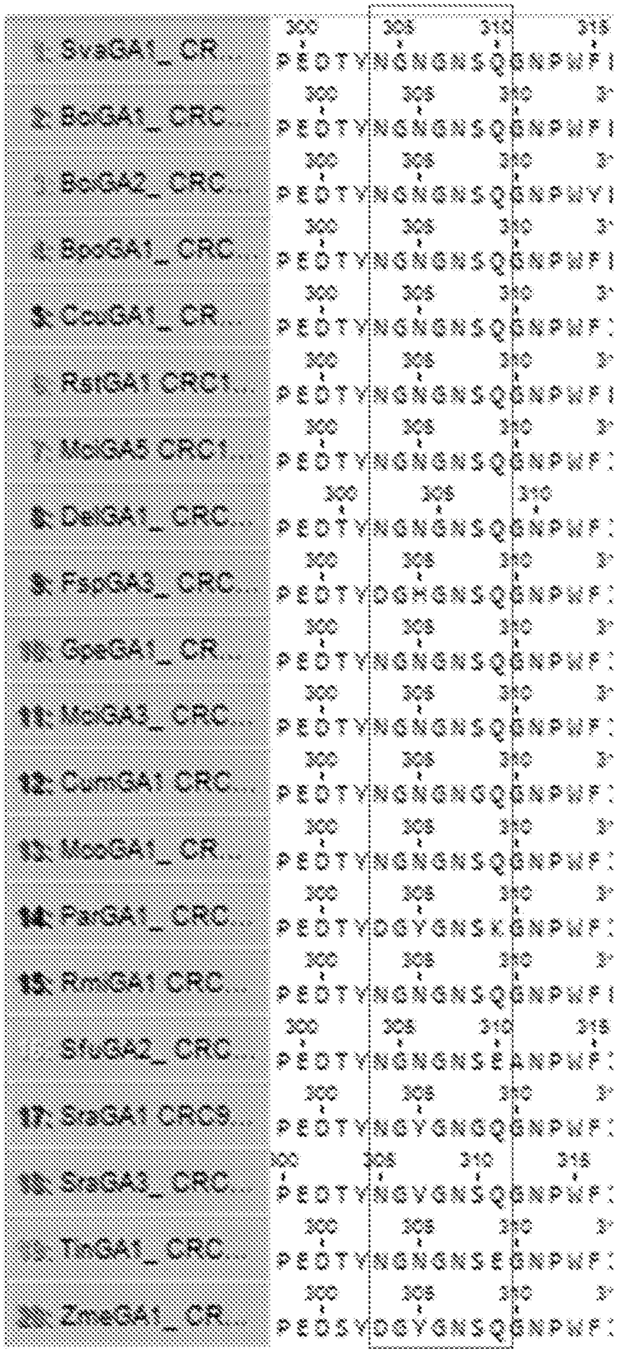
FIG. 5 provides an alignment of Mucorales-clade GA amino acid sequences (numbered according to SvaGa1 catalytic domain region, SEQ ID NO: 81) across region spanning residues 299 to 315, showing motif 3: 304$X_a$-305G-306X-307G-308N-309$X_b$-310$X_c$, wherein X is any amino acid and $X_a$ is N or D; $X_b$ is S or G; and $X_c$ is Q, K, or E.

A series of insertions and deletions and high sequence variability regions were observed on the multiple sequence alignment shown on FIG. 1A-FIG. 1K. Several regions of high similarity among the Mucorales-clade glucoamylases become apparent and sequence motifs have been identified. FIGS. 3, 4 and 5 shows alignments of 3 different regions the Mucorales-clade glucoamylases catalytic domains and highlight the sequence motifs in common. FIG. 3 shows the alignment of Mucorales-clade GA amino acid sequences across the region spanning residues 50 to 70 (numbered according to SEQ ID NO: 81), highlighting the Mucorales-clade GA sequence motif 1 (SEQ ID NO: 113): 57Y-58$X_a$-59$X_b$-60T-61X-62X-63$X_c$-64$X_d$, wherein X is any amino acid and $X_a$ is N or S; $X_b$ is T, S, or R; $X_c$ is G or N; and $X_d$ is D, N, or S. A further refined motif for this region is the Mucorales-clade GA motif 1A (SEQ ID NO: 114): 57Y-58N-59T-60T-61X-62A-63G-64D, wherein X is any amino acid. FIG. 4 shows the alignment of Mucorales-clade GA amino acid sequences (numbered according to SEQ ID NO: 81) across the region spanning residues 240 to 260, describing the Mucorales-clade GA sequence motif 2 (SEQ ID NO: 115): 244$X_a$-245$X_b$-246$X_c$-247$X_c$-248A-249A-250N-251X-252$X_d$, wherein X is any amino acid and $X_a$ is S or A; $X_b$ is T, N, or V; $X_c$ is L or I; and $X_d$ is A or G. A further refined motif for this region is the Mucorales-clade GA sequence motif 2A (SEQ ID NO: 116): 244S-245T-246L-247I-248A-249A-250N-251X-252A, wherein X is any amino acid. FIG. 5 shows the alignment of Mucorales-clade GA amino acid sequences (numbered according to SEQ ID NO: 81) across region spanning residues 299 to 315, describing the Mucorales-clade GA sequence motif 3 (SEQ ID NO: 117): 304$X_a$-305G-306X-307G-308N-309$X_b$-310$X_c$, wherein X is any amino acid and $X_a$ is N or D; $X_b$ is S or G; and $X_c$ is Q, K, or E. A further refined motif for this region is the Mucorales-clade GA motif 3A (SEQ ID NO: 118): 304N-305G-306N-307G-308N-309S-310Q.

Example 6

Thermostability Evaluation of Glucoamylases

Stability Comparison at 60° C.

The thermostability of SvaGA1v2 and SvaGA1v3 was compared with preincubations of the enzyme samples (20 ppm) at 60° C. for 10 min. The preincubation at 4° C. for 10 min was included and set as 100% activity of each glucoamylase sample. The residual activity of the glucoamylase after preincubation was then measured using the same method as described in Example 4 except the pH was 4.5 and the incubation temperature was 60° C. As shown in Table 5, SvaGA1v3 retained 55% of its activity under these conditions.

TABLE 5

SvaGA1v2 and SvaGA1v3 stability preincubated at 60° C. for 10 min followed by residual activity measurement 60° C. for 10 min at pH 4.5

| Sample | 4° C. | 60° C. |
|---|---|---|
| SvaGA1v2 | 100% | 13% |
| SvaGA1v3 | 100% | 55% |

Tm Measurement Using DSC

Differential scanning calorimetry (DSC) measurements were carried out using an ultrasensitive MicroCal™ VP-Capillary DSC System (GE healthcare). Purified SvaGA1, SvaGA1v2 and SvaGA1v3 were diluted to a final concentration of 0.4 mg/mL in 100 mM pH 4.5 sodium acetate buffer. 400 μL of the enzyme solution, as well as a reference containing an identical amount of enzyme-free buffer, were added to a 96-well plate. The plate was then placed in the thermally controlled autosampler compartment kept at 10° C. The enzyme sample and the buffer reference were scanned respectively from 20 to 100° C. at a scan rate of 2° C. per minute. Tm was determined as the temperature at the peak maximum of the transition from the folded to unfolded state. Maximum variation in the Tm was ±0.2° C. The ORIGIN software package (MicroCal, GE Healthcare) was used for baseline subtraction and graph presentation of the data. The DSC result in Table 6 shows that the Tm of SvaGA1v3 is 3 degrees higher than that of SvaGA1v2.

TABLE 6

Tm measurement of SvaGA1v2 and SvaGA1v3 using DSC.

| Sample | Tm (° C.) |
|---|---|
| SvaGA1 | 62 |
| SvaGA1v2 | 64 |
| SvaGA1v3 | 67 |

Example 7

Saccharification Activity Determination

The saccharification performance of SvaGA1v2 and SvaGA1v3 were evaluated at pH 4.5 and 60, 62, 65° C., respectively. All the incubation conditions were the same as described in Example 3, with the exception that the corn starch liquefact was purchased from Cargill. The pullulanase OPTIMAX™ L 1000 (a DuPont product) was dosed at 4 μg/gds, and the alpha-amylase *Aspergillus terreus* amylase (AtAA, described in, for example, International Patent Application Publication Nos. WO2017112635A1 and WO2014099415, incorporated by reference herein) was dosed at 1 μg/gds. The values shown in Table 7 reflect the peak area percentages of each DP(n) as a fraction of the total DP1 to DP3+. The DP1 generation and DP3+ hydrolysis by SvaGA1v3 indicate superior performance when compared to the reference GtGA enzyme under all the selected conditions.

TABLE 7

Sugar composition results for glucoamylases incubated with corn starch liquefact at pH 4.5, 60° C., 62° C., and 65° C., for 24 h, 48 h, and 65 h, respectively.

| GA sample | Incubation temp. (° C.) | Incubation time (h) | DP1 % | DP2 % | DP3 % | DP3+ % |
|---|---|---|---|---|---|---|
| SvaGA1v2 | 60 | 24 | 94.5 | 2.6 | 0.9 | 1.9 |
| | | 48 | 96.7 | 2.2 | 0.7 | 0.4 |
| | | 65 | 96.5 | 2.4 | 0.7 | 0.4 |
| | 62 | 24 | 94.6 | 3.0 | 1.0 | 1.5 |
| | | 48 | 96.7 | 2.1 | 0.8 | 0.4 |
| | | 65 | 96.6 | 2.2 | 0.8 | 0.4 |
| | 65 | 24 | 88.5 | 6.2 | 1.0 | 4.3 |
| | | 48 | 91.1 | 5.8 | 1.1 | 2.0 |
| | | 65 | 92.6 | 4.8 | 1.1 | 1.5 |
| SvaGA1v3 | 60 | 24 | 92.9 | 3.4 | 0.9 | 2.7 |
| | | 48 | 96.7 | 2.2 | 0.7 | 0.3 |
| | | 65 | 96.6 | 2.5 | 0.6 | 0.3 |
| | 62 | 24 | 93.8 | 3.1 | 0.9 | 2.2 |
| | | 48 | 96.7 | 2.2 | 0.7 | 0.3 |
| | | 65 | 96.6 | 2.5 | 0.6 | 0.3 |
| | 65 | 24 | 92.9 | 3.4 | 1.0 | 2.7 |
| | | 48 | 96.3 | 2.2 | 0.8 | 0.6 |
| | | 65 | 96.5 | 2.2 | 0.8 | 0.5 |
| GtGA | 60 | 24 | 91.3 | 3.7 | 1.0 | 4.0 |
| | | 48 | 96.3 | 2.2 | 0.8 | 0.7 |
| | | 65 | 96.6 | 2.3 | 0.6 | 0.5 |
| | 62 | 24 | 92.2 | 3.4 | 1.0 | 3.4 |
| | | 48 | 96.3 | 2.2 | 0.7 | 0.8 |
| | | 65 | 96.3 | 2.5 | 0.7 | 0.5 |
| | 65 | 24 | 92.6 | 3.1 | 0.9 | 3.4 |
| | | 48 | 96.1 | 2.3 | 0.7 | 0.9 |
| | | 65 | 96.2 | 2.5 | 0.6 | 0.7 |

Example 8

Identification of Additional Homologous Mucorales-Clade Glucoamylases

A number of genes were identified in the genomes of Mucorales order organisms and the sequences were further analyzed. Genes encoding the Mucorales-clade glucoamylases were identified from the sources listed on Table 8, and are assigned the SEQ ID NOs shown on Table 9.

TABLE 8

Sequence source and SEQ ID NOs for Mucorales-clade glucoamylases evaluated in this study.

| Sample ID | SEQ ID NO | Gene sequence source *[://world wide web.ncbi.nlm.nih.gov/] | Organism |
|---|---|---|---|
| SobGA1 | 119 | *nuccore/JNEV01000736 | *Saksenaea oblongispora* B3353 |

TABLE 8-continued

Sequence source and SEQ ID NOs for Mucorales-clade glucoamylases evaluated in this study.

| Sample ID | SEQ ID NO | Gene sequence source *[://world wide web.ncbi.nlm.nih.gov/] | Organism |
|---|---|---|---|
| AosGA3 | 120 | *protein/KAF7727643 | *Apophysomyces ossiformis* NRRL A-21654 |
| AelGA1 | 121 | *nuccore/JNDQ01001334.1 | *Apophysomyces elegans* B7760 |
| AvaGA1 | 122 | *nuccore/MZZL01000409.1 | *Apophysomyces variabilis* NCCPF 102052 |
| AtrGA1 | 123 | *nuccore/JNDP01001364.1 | *Apophysomyces trapeziformis* B9324 |

The N-terminal signal peptides were predicted by SignalP software version 4.0 (Nordahl Petersen et al. (2011) Nature Methods, 8:785-786). The genes encoding the various Mucorales-clade glucoamylases were codon modified for expression in *Trichoderma reesei*. Based at least in part on this analysis, a new variant of SvaGA1, named SvaGA1v3, was made and assigned SEQ ID NO:140 as showed in Table 9.

TABLE 9

Sequences of additional Mucorales-clade glucoamylases evaluated in this study. SEQ ID NOs for the nucleotide sequences of expression cassettes, predicted signal peptide and predicted mature polypeptide.

| | SEQ ID Nos | | |
|---|---|---|---|
| Sample ID | codon modified sequences used as expression cassettes | predicted signal peptide | predicted mature protein sequence |
| SobGA1 | SEQ ID NO: 124 | SEQ ID NO: 125 | SEQ ID NO: 126 |
| AosGA3 | SEQ ID NO: 127 | SEQ ID NO: 128 | SEQ ID NO: 129 |
| AelGA1 | SEQ ID NO: 130 | SEQ ID NO: 131 | SEQ ID NO: 132 |
| AvaGA1 | SEQ ID NO: 133 | SEQ ID NO: 134 | SEQ ID NO: 135 |
| AtrGA1 | SEQ ID NO: 136 | SEQ ID NO: 137 | SEQ ID NO: 138 |
| SvaGA1v3 | SEQ ID NO: 139 | SEQ ID NO: 41 | SEQ ID NO: 140 |

Example 9

Expression of Mucorales-Clade Glucoamylases in *Trichoderma reesei*

The polynucleotides (codon modified sequences used as expression cassettes) encoding the Mucorales-clade glucoamylases genes (SEQ ID NO: 124, SEQ ID NO: 127, SEQ ID NO: 130, SEQ ID NO: 133, SEQ ID NO: 136) were synthesized by Generay (Generay Biotech Co., Ltd, Shanghai, China) and inserted into the pGX256 expression vector, a derivative vector from pTTT (see, Published US Patent Application 20110020899).

All plasmids were transformed into a suitable *Trichoderma reesei* strain using protoplast transformation (Te'o et al., J. Microbiol. Methods 51:393-99, 2002). The transformants were selected and fermented by the methods described in WO 2016/138315. Supernatants from these cultures were used to confirm the protein expression by SDS-PAGE analysis.

Fungal cell cultures were grown in a defined medium as described by Lv et al (2012) in "Construction of teo vectors for gene expression in *Trichoderma reesei*". *Plasmids* 67:67-71. Clarified culture broth were collected after 96 hours by centrifugation. The Mucorales-clade glucoamylases were purified by methods known in the art. The column chromatography fractions containing the target protein were pooled, concentrated and equilibrated to 20 mM sodium acetate pH 5.0, 150 mM sodium chloride using an Amicon Ultra-15 device with 10 K MWCO. The purified samples were approximately 99% pure (by SDS-PAGE analysis) and were stored in 40% glycerol at −80° C. until use.

Example 10

Evaluation of Additional Homologous Mucorales-Clade Glucoamylases in Saccharification The saccharification performance of additional homologous Mucorales-clade glucoamylases were evaluated at pH 4.5, 60° C., 62° C., and 65° C., respectively, for 48 h. All the incubation conditions were the same as described in Example 7, except that the glucoamylase samples were dosed at 25 μg/gds. The values shown in Table 10 reflect the peak area percentages of each DP(n) as a fraction of the total DP1 to DP3+. The results of DP1 generation and DP3+ hydrolysis by the Mucorales-clade glucoamylases indicate superior performance when compared to the reference GtGA enzyme when evaluated at pH 4.5, 60° C. for 48 h. When the incubation temperature was increased to 62° C., all the Mucorales-clade GAs also showed better saccharification performance than GtGA enzyme. AtrGA1 could maintain its superior performance when the incubation temperature was raised to 65° C. while GtGA did not.

TABLE 10

Sugar composition results for glucoamylases incubated with corn starch liquefact at pH 4.5, 60, 62, and 65° C., respectively, for 48 h.

| Incubation temp. (° C.) | Sample | DP1 % | DP2 % | DP3 % | DP3+ % |
|---|---|---|---|---|---|
| 60 | AosGA3 | 96.6 | 2.3 | 0.7 | 0.4 |
| | AelGA1 | 96.6 | 2.2 | 0.7 | 0.4 |
| | AvaGA1 | 96.6 | 2.2 | 0.8 | 0.4 |
| | AtrGA1 | 96.7 | 2.2 | 0.7 | 0.4 |
| | SvaGA1 | 96.5 | 2.0 | 0.8 | 0.6 |
| | GtGA | 95.9 | 2.2 | 0.8 | 1.0 |
| 62 | AosGA3 | 96.5 | 2.3 | 0.7 | 0.4 |
| | AelGA1 | 96.4 | 2.3 | 0.8 | 0.5 |
| | AvaGA1 | 96.5 | 2.3 | 0.8 | 0.4 |
| | AtrGA1 | 96.6 | 2.3 | 0.7 | 0.4 |
| | SvaGA1 | 95.3 | 2.9 | 1.0 | 0.9 |
| | GtGA | 96.3 | 2.1 | 0.8 | 0.8 |
| 65 | AosGA3 | 95.7 | 2.6 | 0.9 | 0.8 |
| | AelGA1 | 88.1 | 7.6 | 1.4 | 2.9 |
| | AvaGA1 | 95.0 | 3.0 | 1.0 | 1.0 |
| | AtrGA1 | 96.4 | 2.3 | 0.7 | 0.5 |
| | SvaGA1 | 77.1 | 13.1 | 3.0 | 6.7 |
| | GtGA | 95.8 | 2.2 | 0.8 | 1.1 |

Example 11

Figure 7:
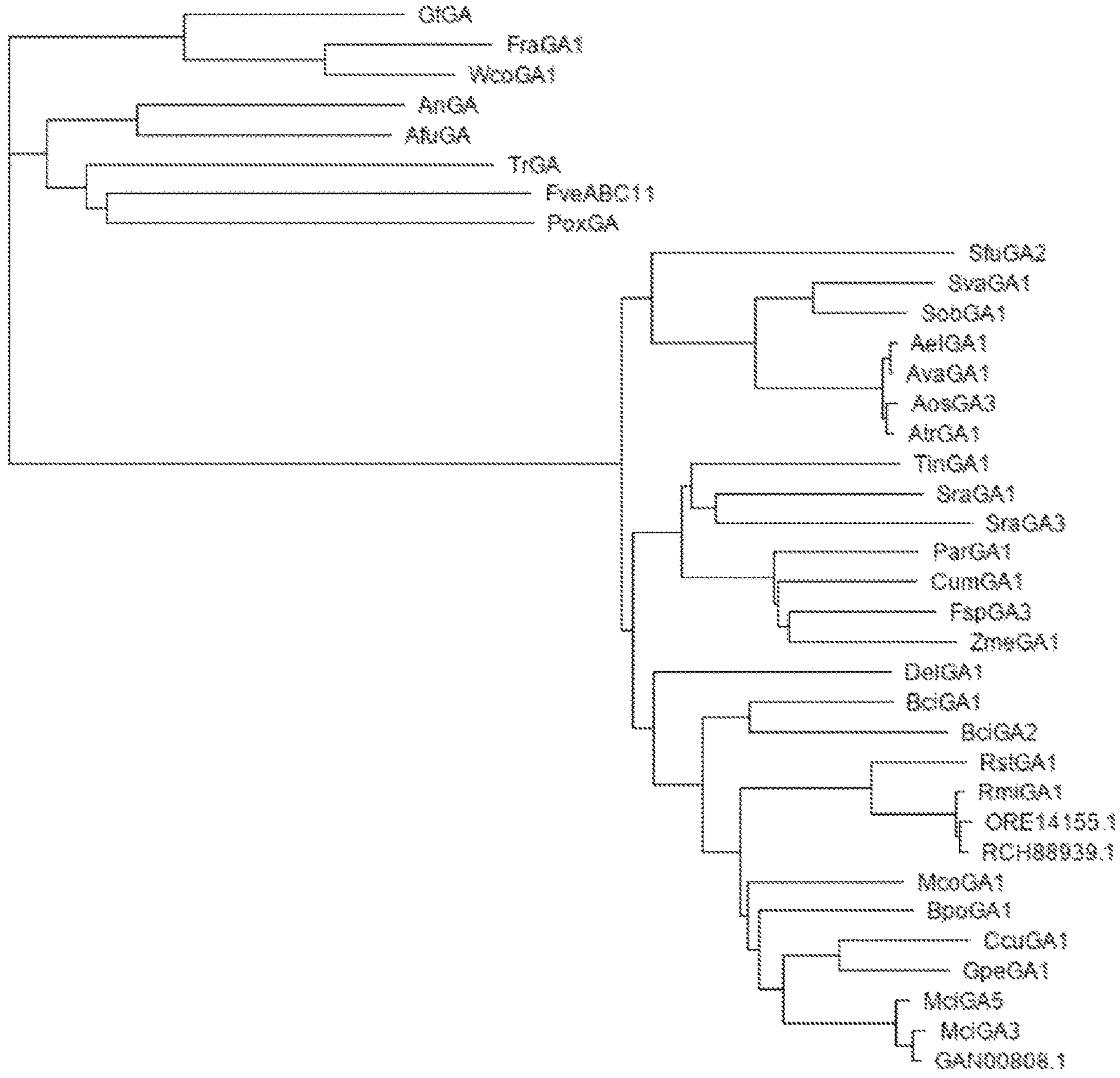
FIG. 7 provides a phylogenetic tree of additional Mucorales-clade glucoamylases and other fungal glucoamylases.

Sequence Analysis of Additional Homologous Mucorales-Clade Glucoamylase Sequences A multiple amino acid sequence alignment was constructed for the regions encompassing the catalytic domain of the Mucorales-clade glucoamylases: SvaGA1 SEQ ID NO:81, SobGA1 SEQ ID NO:119, AosGA3 SEQ ID NO:120, AelGA1 SEQ ID NO:121, AvaGA1 SEQ ID NO:122, and AtrGA1 SEQ ID NO:123 as described in Example 5. These sequences were aligned using MUSCLE alignment tool within Geneious 10.2 software with the default parameters. In addition, the catalytic domains of other glucoamylases, not members of the Mucorales order of fungi, were included in the alignment: *Aspergillus niger* glucoamylase (AnGA) SEQ ID NO:105, *Aspergillus fumigatus* glucoamylase (AfuGA) SEQ ID NO:106, *Fibroporia radiculosa* TFFH 294 glucoamylase (FraGA1) SEQ ID NO:107, *Fusarium verticillioides* glucoamylase (FveABC11) SEQ ID NO:108, *Gloeophyllum trabeum* glucoamylase (GtGA) SEQ ID NO:109, *Penicillium oxalicum* glucoamylase (PoxGA) SEQ ID NO:110, *Trichoderma reesei* glucoamylase (TrGA) SEQ ID NO:111, and *Wolfiporia cocos* MD-104 SS10 glucoamylase (WcoGA1) SEQ ID NO:112, in order to identify regions of sequence similarities and differences. The multiple sequence alignment is shown on FIG. 6 panels A-D. The additional new homologs (SobGA1, AosGA3, AelGA1, AvaGA1, AtrGA1) fall within the motifs outlined in sequences SEQ ID NO:113, SEQ ID NO:115, and SEQ ID NO:117. A phylogenetic tree was generated using Geneious 10.2 software from the alignment of the following sequences: SvaGA1 SEQ ID NO:81, BciGA1 SEQ ID NO:82, BciGA2 SEQ ID NO:83, BpoGA1 SEQ ID NO:84, CcuGA1 SEQ ID NO:85, RstGA1 SEQ ID NO:86, MciGA5 SEQ ID NO:87, DelGA1 SEQ ID NO:88, FspGA3 SEQ ID NO:89, GpeGA1 SEQ ID NO:90, MciGA3 SEQ ID NO:91, CumGA1 SEQ ID NO:92, McoGA1 SEQ ID NO:93, ParGA1 SEQ ID NO:94, RmiGA1 SEQ ID NO:95, SfuGA2 SEQ ID NO:96, SraGA1 SEQ ID NO:97, SraGA3 SEQ ID NO:98, TinGA1 SEQ ID NO:99, ZmeGA1 SEQ ID NO:100, GAN00808.1 SEQ ID NO:101, ORE14155.1 SEQ ID NO:102, and RCH88939.1 SEQ ID NO:103, *Aspergillus niger* glucoamylase (AnGA) SEQ ID NO:105, *Aspergillus fumigatus* glucoamylase (AfuGA) SEQ ID NO:106, *Fibroporia radiculosa* TFFH 294 glucoamylase (FraGA1) SEQ ID NO:107, *Fusarium verticillioides* glucoamylase (FveABC11) SEQ ID NO:108, *Gloeophyllum trabeum* glucoamylase (GtGA) SEQ ID NO:109, *Penicillium oxalicum* glucoamylase (PoxGA) SEQ ID NO:110, *Trichoderma reesei* glucoamylase (TrGA) SEQ ID NO:111, and *Wolfiporia cocos* MD-104 SS10 glucoamylase (WcoGA1) SEQ ID NO:112, SobGA1 SEQ ID NO:119, AosGA3 SEQ ID NO:120, AelGA1 SEQ ID NO:121, AvaGA1 SEQ ID NO:122, and AtrGA1 SEQ ID NO:123, and is shown on FIG. 7.

What is claimed is:

1. An isolated recombinant host cell comprising a glucoamylase selected from the group consisting of:

a) a polypeptide having an amino acid sequence at least 90% identical to SEQ ID NO: 61 or SEQ ID NO: 142;

b) a polypeptide having an amino acid sequence at least 90% identical to SEQ ID NO: 81; and c) a polypeptide comprising amino acid positions 25-468 of SEQ ID NO: 142 (SEQ ID NO: 143).

2. The isolated recombinant host cell of claim 1, wherein the polypeptide comprises a substitution, deletion or addition at a position corresponding to position 102 of the polypeptide of SEQ ID NO: 61.

3. The isolated recombinant host cell of claim 2, wherein the polypeptide comprises a substitution selected from the group consisting of S102P, S102G, S102A, S102V, S102L, SI 021, S102F, S102Y, S102W, S102S, S102T, S102C, S102M, S102N, S102Q, S102D, S102E, S102K, S102R, and S102H.

4. The isolated recombinant host cell of claim 1, wherein the polypeptide comprises a substitution, deletion or addition at a position corresponding to position 66 of the polypeptide of SEQ ID NO: 61.

5. The isolated recombinant host cell of claim 4, wherein the polypeptide comprises a substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

6. The isolated recombinant host cell of claim 3, wherein the polypeptide comprises a further substitution selected from the group consisting of V66P, VS66G, V66A, V66L, V66I, V66F, V66Y, V66W, V66S, V66T, V66C, V66M, V66N, V66Q, V66D, V66E, V66K, V66R, and V66H.

7. The isolated recombinant host cell of claim 1, which is an ethanologenic microorganism.

8. The isolated recombinant host cell of claim 7, which is a yeast cell.

9. The isolated recombinant host cell of claim 1, wherein said host cell is not Saksenaea vasiformis.

10. A method for producing a glucoamylase comprising cultivating the isolated recombinant host cell of claim 1 in a culture medium under conditions conducive for the production of the glucoamylase.

11. The method of claim 10, further comprising recovering the glucoamylase from the culture medium.

* * * * *

SEQUENCE LISTING

```
<160> NUMBER OF SEQ ID NOS: 143

<210> SEQ ID NO 1
<211> LENGTH: 1633
<212> TYPE: DNA
<213> ORGANISM: Saksenaea vasiformis

<400> SEQUENCE: 1

atgccatcct ggaaaaccct tttcttgctc cttgggccga ttgcgactgc agcagctgct     60

ccagtggaca agcagtctct tccaaccgga aattctacca ttagctcctg ggtatccaaa    120

caagaagata ttagcttttc ggaaatgctt cgcaatgtaa accctgaggg aactgcaaaa    180

ggatttgtag ctgcatcttt atccaccgcc ggcccagatt acttctacac atggacacgc    240

gacgctgctt tggtttctcg ggtgattgct tacaagtaca acaccaccaa cgctggcgac    300

agtaagatcc acggggtcct tgatgattat gtcaacttcc aaatcaacac gcaatcggag    360

agtacccctt gcaattgcct tggcgaacca aaatttaatc ccgatggatc aagctttacg    420

ggcccctggg gaaggtaata ctgacctcat tgtgcatggg aaagatacta aataattatt    480

tgttgaaact catcagacca caaaacgatg gtccagctga gcgagcttca agcttcatgt    540

tgattgccga tagcttcctg agccaaacaa aaaatgcgtc gtacttcacg aatacattaa    600

agccaggtac gtctaacctc tccggaaata cgttttcccc tttaatcacc gtctttatta    660

gctatctata aggatctcga ttacgtcgtc gatacctgga gcaatccatg cttcgatctg    720

tggtaagcac acacacttta aaaagttggc gaataaggcc tctaattata ttatagggag    780

gaggtcaatg gtatccattt ctatacettg atggtgatgc gacgtagcct cttggatggt    840

gcaaactttg ccacgcgtaa tggtgacaac tccaaggcca gtacctatag tggcgtcgct    900

gccaaaatcc aagcaagact taattccttc tgggacgctg gcaagaatta tattactgtc    960

acacaagact ataagaacgg tgtcgaaaag ccatctggat tggatgtctc tacattgatt   1020

gctgctaatg tagcaggcat gggcgatggt aacaataacg tagtaaagtc tccaacctta   1080

tactgacata ctattttgct taggcttcta cactcccgga tctgaaagaa ttctcgcaac   1140

tgctctagcc ttcgagaagt ccatggcaag tctataccct cttaacaaca atttgccttc   1200
```

```
tcaccttggt aatgccatcg gtcgctaccc tgaagacact tacaatggca acggaaattc   1260

ccagggcaac ccgtggttcc tggctactac tgcctttaca gaactttact atcgtgccat   1320

tctcgaatgg aagaacacag gtgtgacagt gacgccaatc agcaaagact tctttgtcag   1380

atttgattcc agtgctgcac ccggcaagaa atacaacccc ggctctcaag aatttgccac   1440

gttgacccag agcatcgccg cagctgccga ccgttttatg tcgacagtac aatatcacca   1500

gaatccaaac ggatctcttt ctgaggagtt tgaccgctcc tcaggataca tgaccggtgc   1560

tcgcgatctc acctggtccc acgctgcttt tatcacagct gctcaagcaa gagctggctc   1620

accatccttc taa                                                      1633
```

<210> SEQ ID NO 2
<211> LENGTH: 2498
<212> TYPE: DNA
<213> ORGANISM: Backusella circina

<400> SEQUENCE: 2

```
atgaaacttt ttggtactct aaaggcatct tttgtcttcc ttattggatg catagtgttt     60

gctatggcag acactgtccc tactacccag gttaaactcc agtcctacac ttattctgga    120

ggtgtattgt ctggtacaat ctatgtaaga gaatgattgc ccaagtctat ttcgtttttt    180

tctcttccaa actcatatat tattttgata ggttcaaaat atagactaca ctaaggttgt    240

cactgttatc tattctgatg gttctggtaa ctggaataac aacggcaata ctatctccgc    300

ttcctactct tcctccattt ctggaacaaa ctatgaatac tggacattct cagcatcagt    360

tagtagcatc cagcaatttt acatctcagt aagtgtaaaa cacaaaaaaa gtaggaaatt    420

tcagttattt atgcattaat cgattctttc tttttttttt agtatcttgt agatggtact    480

acctattatg acaacaatgg tggctatggc gccaactatg ctggtaagct caaattcaaa    540

ttttattttc atttacttaa agatgaataa atagtcactg caaccaccac aactgcttca    600

tctactacta aaaccacttc tggtacaaca aagacatcta ctacgtcaac agccactgct    660

acttcaacag gcacatcctc ttttccttct ggtaattcta ccatcagtac ttggagcccc    720

agtcaacaca gtatcagtct ttacgctatg cttcgtaata tcaatcctcc aggaagtgct    780

gctggattca tttctgcctc cttgtctacc tctggacctg attattatta ttcctggaca    840

agagtaaata gttaaaattt aaaatacatc atgctgtttg agtgctcatt ttttgatatt    900

taggattctg cacttgttgc tcatgtcatt gtcaacgaat ataatactac atatcaagga    960

aacagcaccc ttctcggtat tttgaaggat tatgttacct attctcttaa cgctcaaact   1020

acctctactg tttgtaactg tcttggtgag ccaaaattca accctgatgg ttcgagcttc   1080

actggtgcct ggggaaggta aacaagattc atgaagagag acgaaaagat attaaccgtt   1140

tatttagacc tcaaaatgat ggtccagctg agcgtgctgt cagttttatt tattttgcag   1200

atagttatct cactcaaact agcgactcat cttatgttac tggcacactt gcacctggta   1260

agagtcaatt ttttttatga tttttgcaaa tttcaggaat cttattttgt ttcataagct   1320

atttataagg atttggatta tgttgttagc gtatggagta acggttgttt cgatctttgg   1380

taaattgtat ttactttttt ccttaattgt aatactaata tatgtttgaa tttttttttt   1440

agggaggaag taaatggtat ccatttttac acactgatgt ttatgcgcag aggtctcctt   1500

gatggagcca actttgcctc acgaaacggt gactctactc gtgcttccac ttatacctct   1560

accgctgctt ctattaagac caagattgat ggcttctggg tatcgagtgg aaactatgtt   1620
```

-continued

```
caggtcagtc aaagtgttac aagcggtgtc agcaaagctg gatatgacgc ttctacctta   1680

attgctgcaa atcaagccag tcggggtgat ggtaagttgt gtcttttttt ttttaccaaa   1740

aaataaaaaa aagaatctca attaaacaaa attgatgttt aggtttctat acacctggat   1800

ccgataaggt aacgcaatag ataaagttaa aacctctata tgactaacat aaagattaca   1860

gatgctggct acagctgttg ctattgaatc ccaattctca agcttgtact caatcaacac   1920

caacaaggct tcttatctag gaaatgctat tggcaggtga gttcctttaa cactacattt   1980

tcttctaaaa ttctgataat atcatattaa taccttatta aaagatatcc cgaagatacc   2040

tataacggca atggtaactc tcaaggcaac ccttggttct tgtaagtaaa tcattctcat   2100

aaattatata aattgcatat ctttaatttt atttttataa aaggtgcact aatgcatttg   2160

gagagctttt ctatcgcgcc atcagtgaat ggaacgctgc tggtagcgtc accgtaaaca   2220

gcgtcaatct tgccttcttc aagaaatacg attcttctac ctcctctggt acaacgtata   2280

cagttggaac aagtgcttac aataatctcg ttcagaatgt tgctcttgct gctgatgcct   2340

acttctccac cgtcaaatat catgctctta ctaatggttc catgtctgaa caatacgatc   2400

gtagctctgg tatggctaca ggtgcaagag atcttacatg gtcacacgcc gctatgatta   2460

ctgccttgaa ggcaaaatct ggaacaccag tttactaa                           2498
```

<210> SEQ ID NO 3
<211> LENGTH: 2550
<212> TYPE: DNA
<213> ORGANISM: Backusella circina

<400> SEQUENCE: 3

```
atgaagcctt tcggaccaat caagaccact ctttttatta ttattagcca cttctctttg     60

aattctttag ctgatacagt tcctactacc caggtagagg tcaaaactta tacttactcg    120

ggtggagagc tgtctggtac aatctacgta agtttctcgc tctaactttg gctttcttct    180

gtatatcaaa atcttattta aatacacttc cttcatatgt ttaggtcgag aacattgatt    240

atactaaggt tgttacggtc atttatgctg atggttcaga tgactggaat aacaatggca    300

ataccattgc tgccgccttc tctgaatcaa tctctgatac taattacgaa tactggactt    360

tctccagttc tgttaacagc attaaggagt tctatgttaa ggtgaatagt ttattcaata    420

cttttaatta tgattttacc atataaagat tatacatatg cttatcattc acttattaaa    480

tagtatgatg ttgatggaaa cacctactat gacaataatg gaaatgccaa ctaccaaggt    540

attttttttt atcaaactta atatttgtca atgttaacgc taacacatga tcatatagtc    600

tctgcttctt ccactaccac aactactgct acaaagacta caaccactgc aacaaaaacg    660

actgctactg ccacatctac tgccactggt tcaacttcat tcccttctgg taactccact    720

atctcttcct ggattaaggg tcaagaagat accagtcgat ctgttatgct tggcaacatt    780

aacccacctg gaagtgccac tggttttatc tctgcttctt tgtcaactag tggtcctgat    840

tattattatc attggacacg cgtaagtcaa ttccaatttg aacattatag aagttacctc    900

tctaatattc gaaaactaac ttttctcatt tatctatttt catcaggatg ctgctcttgt    960

tgctcacgtt attgtcaatg attataatac tactctttct ggagatagct ctactcttca   1020

agttattaag gattatgtta ctttctctgt taacagccag tctgaatcta ccgtatgcaa   1080

ctgccttggt gagcctaaat tcaatccgga tggatcaagc tacactggtg catggggcag   1140

gtaagatatt atagcattta ataaaatcat gcgcatgtta tattcattat taattttgta   1200

taacattaat cagacctcaa aacgatggtc ctgctgaacg tgccacaaca ttcattttct   1260
```

ttgctgacac ttatctcgca cagggtggtg actctagcta tgtgactggt acacttgccc 1320
caggtatata tagcctttta aaaaacaaat tactttaaaa agtgaatagt attactatgc 1380
taactacatt tatatattct ttactatttt gatttaaata gctatctatg ctgatctgga 1440
ttatgttgta aataactgga gcactggatg ttacgatttg tggtaaagca tctaatatga 1500
agttaatttt tgtgaagtat actcaccaaa agctgatata gggaggaagt taatggtatt 1560
catttctaca ctttgatggt tatgcgcagg ggtcttattg acggtgccag ctttgcctct 1620
cgtaatggtg actctactcg ttcaagcagc tatacttcca ctgctaaatc aattgctacc 1680
aagattgata gtttctggtc agcctccaac aactatgttg ctgtcagtca aagtgtaact 1740
tctggtgtca gtaaggctgg atatgatgct tctaccatta ttgctgctaa ccaagctagt 1800
cttggtgatg gtttctatac tcctggttca gataaggtag gctaatctta atgcaatatt 1860
ataaacgtag aaaaagaaac atgtatatta atgccaattg agtagatgct tgccacctcc 1920
gtcgctgttg agaatgcttt ctcttctctt tacaccgtta atactggaaa ggcttcttac 1980
ttaggaaatg ctattggcag gtgagtgcat ttgacacttc attttcttcg tataatttct 2040
cactaaaaaa actactacca tattaaaaga taccccgaag atacctataa tggtaatggc 2100
aactctcaag gcaacccttg gtatttgtaa gtaaaactct tttatgctcg ataattatcc 2160
cttcctaaca catcattttt atttttaaaa aaaaggtgta ctaacgctct tggtgagtta 2220
tactaccgtg caattaagga atggaatgcc gctggatccg ttacggtcaa cagtgtcaat 2280
ctcggcttct tccaaaagat tgattcctca atttcatctg gcaccacctt taccttaggc 2340
acttctgact acagcaccct cgttgacaat gttgcacttg ctgctgataa gttcttcgcc 2400
gttgtccagt atcatgaacg cagtaatgga tctatgcctg agcaatttgg ccgtgaggac 2460
ggtcttccta ctggtgctag agatcttaca tggtctcatg ctgccatgat ttctgctgcc 2520
cgtgctaagg ctggtactcc tgtgtattag 2550

<210> SEQ ID NO 4
<211> LENGTH: 2256
<212> TYPE: DNA
<213> ORGANISM: Benjaminiella poitrasii

<400> SEQUENCE: 4
atgaagtttt ctcatctctt caggaagcca acgcttctta ttgtgacctt tttgaccgct 60
acggtttttg cagaaactgt tcctacaact tctcaagtca agcttaagag ttatacatat 120
gatggttcca ccttatccgg ccagatttat gtaagttata ttaattattc actttatatt 180 tttttttcc cctgacctgt caaaaatata ctaattttta tttcaaattt taccagattc 240
aaaatattgc ttatacaaag gtggttactg taatctactc tgatgcgtct agcaactgga 300
acaacaatgg aaacacaatt gctgcttcat atactaatgg tatctcagga accaattatg 360
aatactggaa tttcactggt cctgtcagca gcatcaatgc attttacatc aaagtaaatt 420
actgaataat aatgttcaca agcaattata aattctcact ttaattgatt atatagtatg 480
atgttagcgg aaatacatat tatgataaca acaataatgc aaactatcaa ggtaaaatag 540
tcaagagaaa aaaaaaaaga cgcattaacc gaactcaatt tattaatgca ttcttataat 600
agttacaaag acatcaacta caacgactac ttccactgct actgctacta ctactaccaa 660
aacttccaca ccgacttcta ctggtgtccc ctccaatttc cccaccggta acagtactat 720
tagcacatgg ttgaaatcac aaattggcat cagtcgctat gctatgctcc gtaacatcaa 780

```
tcctgctggt tccgctgttg gttttattgc tgcctcttta tcgactgcta accctgacta    840

ctattatgcc tggactcgtg attctgcttt gacctcatat gttattgcca acgattataa    900

ctctactttg gctggtaact caacaatcct tcaaatcatg aaagattacg ttactttctc    960

tgttaagagt caatcggttt ctactgcctg taactgcctt ggtgaaccca aattcaatcc   1020

tgatggatct agttacactg gcgcttgggg aaggtatgta gataatacca tacctttttt   1080

tttttttca taatgatata catgtaaaaa gtttaactaa catgatcaat atgtaaatac    1140

aaagacccca aaatgatggt cctgctgagc gtgctactac atttatatta tttgccgata   1200

gttatcttaa gcaaacaggc gatgctagct atgttactgg aacccttaag ccaggtaaag   1260

ttttttcctt tattacggca tgtatattat gttaacatat acacgtaatt tgaatagcta   1320

ttttcaagga tttggactat gttgtcaaca catggactaa tggatgcttt gatttatggg   1380

aagaggttaa cggtgttcac ttctatacct tgatggtaat gcgtaagggt ttgatcagag   1440

gagctaactt tgccacccgc aacggcgact ctacacgtgc ttctacttac accaacacag   1500

ctgcatccat caaaacaaag atggattcat tctggtcatc tggcaacaac tacattgctg   1560

ttagtcaaag tgttactggt ggtgtcagta aggctggtta cgatgttgct aacattattg   1620

ctgctaatgt tggcagtctc caagatggcg tatatactcc tggttctgat agagtatgta   1680

tcaacagtaa ctttatagta tcaacagaga caatcatatt aaccattgca cccccccttt   1740

tttttctaga ttcttgctac tgctgttgct gttgaagcta aatttgcttc tttatatggt   1800

gttaactcaa acttaccagg ctaccttggt aactccatcg gtcgttatcc cgaagacaca   1860

tataacggta acggaaactc ccaaggtaac ccatggttct tggccacaaa tgcttacgca   1920

gaactttact accgtgccat cagagaatgg tatgacaatg gtggtgttac agtcaacagt   1980

gttaacttgc cgttcttcaa gaaattcgat agttccgctg cttctggtac aacctacact   2040

gtaggtacga ccgccttcaa cacgatggtt tccaatgttg cagctgcagc tgataagttt   2100

ttctcgactg tcaaattcca tgcttacacc aatggctcca tgagcgaaca attcggtcgt   2160

aatgatggtt tatgtacggg ggctcgtgat cttacatggt ctcacgcttc tttgatttct   2220

gctgctcttg caaaggctgg tactccttca gtctaa                             2256
```

<210> SEQ ID NO 5
<211> LENGTH: 1968
<212> TYPE: DNA
<213> ORGANISM: Choanephora cucurbitarum

<400> SEQUENCE: 5

```
atggtttctt ttaacttcct taaaaagcca gtattcattg tgattacttg cttgacagtc     60

tctgtctgtg ctcaatctgt gcctaccagt gaccctgtca aggtcaagac tttcagctac    120

gatggtaact ctttctctgg tcaaatttat gtaagtgtca atacttattt ggaaggtacg    180

ggggtttaat tgtttaattg gatttcgcag atcaaaaata ttgcttatga aaagaccgtt    240

actgtcatct actctgatgg tactggtaat tggaacaaca acaacaacaa gatcgctgct    300

gctttctctg aagccatctc tggttccaac tatgaatact ggactttctc tgcctctgtc    360

cctagcatta aacaatttta tgtcaaggta aagaaacaat agttttaaac ataccaatct    420

aatgtgcctt catagtatga tgtttctggt aaaacttatt acgacaacaa tggtagcaag    480

gactataatg gtaaaatcaa attttcacat gaattaagag tatgttacac taaacctttt    540

tttttttaa tagttgttac ctctggtcct accaccactt ccagtggtcc ctcaaagaca    600

accaccaatg gtcccgctcc tacctccacc aacactaact tcccctccgg taacccttcc    660
```

```
atcacttcat ggatcgataa gcaaattgac atcagtcgct ctgccatgct taagaacatc    720
aaccctgccg gtaccgtcaa gggtttcatt gctgcctctc tctctacctc aaaccccgat    780
tacttctacg cctggacccg tgacgctgcc ttagttgccc atgttgttgc taacgactac    840
aaccgtacca agagcggtga tgccacttac ctcggcctcc tcaaggatta cgttaccttc    900
tctatcaaca gtcaaaacac gcctactgcc tgtaactgtc tcggtgaacc caagttcaac    960
aaggatggtt ctggttacaa cggtccctgg ggtcgtcctc aaaacgatgg tcctgctgaa   1020
cgtgctgaca ctttcgtctt gattgccgac agtatcttga cccaaaccaa ggacgtcagc   1080
tatgtcactg gtaccttgcg ccctgctatc tacactgatc ttgactatgt cgtcagaacc   1140
tggtccaacg gctgtttcga tctctgggaa gaagtcaacg gtgttcactt ctacaccttg   1200
atggtcatgc gtcgtgcctt gcttgtcggt gccaactttg cctctcgtaa cggtgacagt   1260
gctcgtgcca gtaactacaa caacgctgct aactccatca agtccaagat cgacagcttc   1320
tggtcttcca acaacaacta tgttgccgtc agccaaagtg tcactggtgg tgtcagcaag   1380
gccggttacg atgtctctac cttgattgct gccaatgtcg gtagtctctc tgacggtttc   1440
tacacccctg gttctgaaag aatgcttgct actgccgttg ctatcgaaga caagtttgcc   1500
aacctctatg gtatcaaccg taacttggac agcagccttg gtaacgctat cggtcgttac   1560
cctgaagaca cctacaacgg taacggtaac tctcaaggta acccctggtt cattgctacc   1620
aacgcctatg ctgaactcta ctaccgtgcc atcaaggaat ggaacaacaa cggtggtgtg   1680
actgtcacca acgtcaacct caacttcttc aagaagttcg atggtagtgc ctctgtcggt   1740
accaagtaca ctgctggttc tgctgcctac aacaccttga ctcaaaacat tgctcttgct   1800
gctgataagt tcttcaacac cgtcaaggtc catgctgcca ccaacggttc catgtctgaa   1860
caataccacc gtgacaccgg ttccatgaca ggtgctcgtg acttgacttg gtctcatgcc   1920
agtttgatta ctgctgccct tgccaaggct ggtactcccg tagcttaa                1968
```

```
<210> SEQ ID NO 6
<211> LENGTH: 2204
<212> TYPE: DNA
<213> ORGANISM: Rhizopus stolonifer
<220> FEATURE:
<221> NAME/KEY: misc_feature
<222> LOCATION: (171)..(190)
<223> OTHER INFORMATION: Any nucleotide

<400> SEQUENCE: 6

atgaaactgt ttggtttgcc attgaagcct tcgctctttt ttgtggtctc ttatctttct     60
ttcctcgcct ctgctgctag tattcctagt agttctgaag ttcagcttga cacatacgcg    120
tatgatggtg ctaaatttcc aggaaaaatt tatgtgagtt tttttttttt nnnnnnnnnn    180
nnnnnnnnnn tttttttttt tttttttttt ttcttctaaa ggaaggtatc tgatctcaaa    240
taaatttagg tcaaaaacat tgcttatgaa aagactgtca ctgtggtata cgctgatggt    300
tctgataact ggaataacaa tggaaatata atttctgcta ctttctctac cccaatctct    360
ggatctaact acgaatactg gaccttttct tcttctatta gtggtattaa agagttttac    420
attaaggtat agttcatttt ctttatatgt ataatttacc aaccttactt tttacagtat    480
gtggttagtg gtaaaaccta ttacgataac aacggcacta aaaactatca agtttctacc    540
acttcctcta ctaccactgc ttccaccaca accgctactc gtacaactac agctggaact    600
acttcgacct ctactacggc tgcacctaca agcacttcat ccggttcttt cccttcaggt    660
```

aactcgacgg tatcctcttg gattaaacgt caagaaaaaa taagtcgctt cgctatgctt 720
cgtaatatca accctcccgg aagcgctgct ggttttatcg ctgcttctct tagtacctct 780
ggccctgact actactactc atggactcgc gactctgcct taacttccaa cttgattgcc 840
tatgaatata acaccacttt gtctggaaac accactatcc ttaacatcct taaggattac 900
gtcaagttct ctatcagctc tcaaacaact tccactgtat gtaattgtct tggtgaaccc 960
aagttcaacc atgatggctc aagttacaca ggcgcttggg gaaggtagtt acacatattt 1020
ttttctggat gagaacacct gtttattaat attaacttag acctcaaaat gacggacctg 1080
ctgaacgtgc aaatactttt atcttgttcg ctgacagtta ccttgatcaa acaaaggatg 1140
catcttatgt cactggcact cttaaacctg gtaatttttt tgaattttat ttattgtata 1200
gatatgtgta cttatagttt cttaaagcca tttttaagga tttggactac gttgtcaatg 1260
tatggtctaa cggttgttac gatttatggt aaaaaaaaat atgatgtttc tttataggat 1320
cttattgaca gtagaaaata gggaagaagt caacggagtt catttttaca cattgatggt 1380
tatgcgcaag ggcttacttc ttggtgctga ctttgccaag cgtaacggtg actctacacg 1440
tgcatctact tacaccaata ctgcttctac tattgctaca aagatttcta gcttctgggt 1500
atcctctagc aactggattc aagtcagtca aagtgttact gctggcgtta gcaaaaaggg 1560
attggacgta tcaaccttat tggctgctaa tcttggaagt gttgaagacg gtttctttac 1620
cccaggttct gaaaaggtaa ttgtagttta tcatggataa gagtatggtt ttcgagctaa 1680
aatgcacatt taaatagatc cttgctaccg ctgttgctat tgaagatgct tttgcttcat 1740
tgtatcctat caactccaac ttaccttctt accttggtaa ttccatcgga agatatcctg 1800
aagacaccta caacggcaat ggaaattctc aaggcaaccc ttggttcttg gccgtcaatg 1860
gctttgctga gctttactac cgtgctatca aggaatgggt caacaatggt agtgttactg 1920
tgagcaacat cagcttgtct ttttttaaga aatttgactc atctgctact gctggtaaga 1980
cctatactgc cggtactgca gactttaaca atctcgcaca aaacattgca cttggcgccg 2040
atcgtttctt atcaactgtc cagactcatg cctttaacaa cggatctctt gctgaagaat 2100
atgatcgtac aactggagta tctacaggtg ctagagactt gacttggtct catgcctctt 2160
tgattactgc tgcttatgca aaagctggtt cacctgctgc ttaa 2204

<210> SEQ ID NO 7
<211> LENGTH: 2015
<212> TYPE: DNA
<213> ORGANISM: Mucor circinelloides

<400> SEQUENCE: 7
atgaagttct ctaaccttct caagaagcct ctccttttga tcgctggtat tttggccgct 60
actgttgtcg ctgagactgt acctactacc gctgcagtca aagtcaagtc cttcacatat 120
gatggatcca ccttcgctgg tcaaatctac gtacgtacta aaatttcgat ttattgaatt 180
caatgctaaa cccgcattct tcattctata caggtcaaga acattgctta cactaaaact 240
gttaccgtga tttactctga cgcttctaat aattggaata acaatggtaa cacaatcgct 300
gcttcttaca gcgaaggcat ttcaggcacc aattacgaat actggacttt cagtgcccct 360
gtcagtggca tcaagcaatt ctacgtcaag gtaagtctgg gatcactcag tggtcggttg 420
caagtattga gcctataatc tattagtatg ttgtaagcgg taccacctac tatgacaaca 480
acaacagcgg aaactaccaa ggtatttaca ctttcacatg ttgcattagt attgtcatac 540
tgaaaaaaaa attccgtggc attcctttag ttaccactac taccactact actgctccta 600

```
cctctactac ttctggcggt tcttctacaa ccaccggcgg ctctactacc actgctacta    660
gcgtcccaac tggtgttcct tctggtttcc ctactggtaa ctcttctatt agctcttgga    720
tcgacggcca aacatctgtc agtcgttatg ccatgctccg caacatcaac cctgctggcg    780
cagtttctgg tttcattgct gcttccatgt ctacctctgg acctgattac ttttatgcct    840
ggactcgtga ttctgccctg acctctcatg ttgttgctta tgattacaac actactttgg    900
ctggtaactc taccattctc ggcctcttga agaactatgt tactttctct atcaacagtc    960
aaactacttc cactgtttgt aactgtctcg gtgagcccaa gttcaacaag gatggtagca   1020
gttacactgg tgcctggggt agacctcaaa atgatggccc tgctagtcgt gccgatactt   1080
tcattttaat tgctgacagt atcctcaagc aaaccggtga tgctacttat gttactggca   1140
ctcttgctcc tgccatctac aaggatttgg attatgttgt ctcaacttgg tccaacggtt   1200
gtttcgattt atgggaagaa gtcaatggcg ttcactttta cactttgatg gtgatgcgta   1260
gaggtttgat caagggtgct aactttgcct ctcgcaacgg tgacaacact cgtgccaaca   1320
cttacaccaa cactgccgcc tccatcaaga ccaagattga tagcttctgg aactccaatg   1380
gcaactatgt cactgtcagc caaagtgtca ctggcggtgt cagcaaggct ggttatgatg   1440
cctctgtgtt gattgctgcc aacttgggta gtgttcaaga tggtttctac actcctggtt   1500
ctgacaagat gcttgctact gctgttgcca ttgagagcaa gtttgcttcc ctctattcta   1560
tcaaccaaaa cttaaacggt taccttggta atgctatcgg ccgctatcct gaagatactt   1620
acaatggtaa tggtaactct caaggcaacc cttggttcat ctgtaccaat gcctttgctg   1680
agctctacta ccgtgctatc aaggaatggt ttaacaatgg tggtgttact gtcactagta   1740
tcagtttgaa cttcttcaag aaatttgatt cctctgctgc cgttggtacc aaatacactg   1800
ttggtacctc tgctttcaac agcttggtcc aaaatgttgc tgttgctgct gatgccttct   1860
tctccaccgt caagttccat gctgctacta acggctccat gagcgagcaa tatggtcgta   1920
gtgatggttt gatgaccggt gctcgtgatt tgacttggtc tcacgcttca ttgatttctg   1980
cttcttacgc aaaggctggt tcccctgctg cttaa                              2015
```

<210> SEQ ID NO 8
<211> LENGTH: 2398
<212> TYPE: DNA
<213> ORGANISM: Dichotomocladium elegans

<400> SEQUENCE: 8

```
atgaaactta acagtgtttg gaaagcattc agtattttgc ttatggccac catggctttt     60
gctgccaccg ttcctaaaac gcaagtgaag cttgaggcgt acacatactc ggattccata    120
ttctctggta gaattttcgt aagaatctat atctcctcaa atcgtttgta tgcataaagg    180
ctcatatatt gtgaataggt gcaaaacatc gactacacca agattgtaac cgtttactgg    240
tctgatgcat cgaataaatg ggactccagc aaatattata ctgaagctgc ttacacccat    300
tcgatccctg gaactaatta cgaatactgg gatttctcag ccaccattgg tccttcagga    360
atcaagcagt tctacatttc ggtaaccatt tattgaggag aatcggtaaa tccacgcacc    420
tcttttactc atcgtgttcg gatgactttc agtatcaagt ccggggtgtc acttattatg    480
ataacaacgg cggctatggt gtcaattacg gtgagcaaaa cactgtcagc tagtagctct    540
tcatgcccta cttacaaatg cgttgtagac gtcatctcgt cacccccgac cacgtccgat    600
gccactacca ttcctactac taccactagt gctattcctt cttccactac cactattccc    660
```

gccagtactg gggttccttc tggaaactcc actatcaccg tttgggctga ttcgcagcat 720
aagatcagct ggaaagcaat gctcgccaat attaatccac ccggttctgc tactggtttt 780
attgccgcct cgctttcgac ttctggtcca gactactact atgcctggac tcgtgatgct 840
gcgatggttg cgcacgttat tgtcaacgct tacaacacaa ccaaagcagg tgatgcaact 900
actcttggcg ttctgaagga ctttgttacc ttccagatta aggctatggc taccagcacc 960
gtctgcaact gtctcggtga acctaaattc aaccctgtaa gttaccagat agtacagcag 1020
aaagaaaata ccgtctttac catcggtcgt aggatggctc cagctatact ggtccttggg 1080
ggagaccaca aaatgatgga cccgctgagc gtgctactac tttcattcta tttgcggaca 1140
gctatctttc ccagaccgga gacgccgctt atgtcactac cttgaaaaga ggtaagcatc 1200
ctggaagctt caagtgtgca gtgattaacc tgtaaattat gcttcttcca cttcattagc 1260
tatctttacc gatcttgact atgtggtgac cacctggcag gataattgtt ttgatctctg 1320
ggaagaagtg aacggacttc acatgtatac gtaagttgtt attcctcttt ttctcgtatg 1380
cacacgcata cccgcgcccg gagtattagc agaaaaaagc ttaagctact aatggaactc 1440
ttatttcagt ttggcggtaa tgcgccgaag tctggttgat ggagcaagct ttgccgcccg 1500
caatggtgac aatacacgcg ccagtaccta taccaatact gccaaatcca tcgagaccaa 1560
gcttgcaagc ttttacaact cgagtagcaa ctatgtcgtt gtcaccaaga acttcgcagg 1620
tggtgtaaac aaggctggtt tagatacctc cacattgatc gccgcgaaca ctgccggttt 1680
gggtgatggt aagcgggaag catgatgatt aatctgaccc ttagagaggg agaaaataga 1740
tagctctctt ttcaatatgt gattctgact gccagccaac ctctccccaa ggtttcttca 1800
cccccggttc accggagatt ctagctaccg ccgccgcaat cgagaagtca ttcgctgatc 1860
tatacggcat caacaaacaa attcccaact ggttaggcac tgcaattggc cgatacccgg 1920
aagacactta caatggcaac ggcaactcac agggtaaccc ggtaagtatc cctccaacct 1980
ttgtctctct cttcgttgtg ggacctataa tgcgatgctt atctatttaa cctagtggtt 2040
catctgtact gctaccttcg ccgaactcta ttatcgcgcc attctggaat ggcaacacgc 2100
tggctccgtc acagtgaaca acgtgaactt gccattcttc aaaaaattcg atagctccac 2160
ttcctctggc accacctaca ctgtcggcac tagtagcttt gattcactta tctcaaaagt 2220
agcctatgct gcggataact tcttttctac gatcaaatat cacgccgcta cgaatggttc 2280
catgagcgag cagttcaatc gtgataccgg ttttatgact ggcgctagag acttgacctg 2340
gtctcacgcg gcattcatca ccgctgctaa agccaaggct ggcactcctg tatactag 2398

<210> SEQ ID NO 9
<211> LENGTH: 2311
<212> TYPE: DNA
<213> ORGANISM: Fennellomyces sp.

<400> SEQUENCE: 9
atgagaccaa gtcttgtttg gaaaagcctg cttatggttg tgcttaccgc agccatgggc 60
acatatgctc aaactgttcc atctgtgcct atcaagttgg aaagttacac ttactcggat 120
aacgtattcg ccggtcgaat ctttgtaagt agttcgataa tttctgtttg ttaaagagaa 180
aaaaaaactc accccttttt ttcgtcacgt agattcgaaa catcgcttat acaaaagtgg 240
tcaaggtttt ctggtctgat gaatctggca attggaacgg taacggaaac tatgttgatg 300
cctcgtattc ggggtctatt tccggtacca actatgaata ctgggaattt tcaacaacca 360
tcggatccgc cggtattagc caaagctatt tgagagtaaa gagtttgtcc tttttaagtg 420

```
tttcgcaagt ggggaagaga gactaaacag aatattttct ttttagtatg atgtttcagg    480

ttctacgtac tatgataaca atggaaatgc aaactatggt aacgtattaa ctagaagcgg    540

tcaaatttga aatcactcaa agccttcttt tacgtgtttc agatatcgag gaagactcca    600

cacctacgcc caccaccacc actaccagta ctacgacaat aaccactacc actaccagtg    660

gaacttcaac tcctacttct gtccccactg aagttcctgc tggcaatacc actgtcactg    720

actgggtgaa tgatcaattg gaaattagtt ggccatcgct tttaaagaat gtcaatcctt    780

ccggcgcagt aaccggtttc atcgctgctt cgctttccac aaatgatccc gattatttct    840

actgttggac gcgtgatgcc gctttggtcg cacgagtgat ggtttacatg tacaacacaa    900

ccgaagctgg tgacaccagt ttgagaagca agctgcaaga ttatgttaca ttccagatca    960

actccatgaa gactgcaaca gtatgcaact gcttgggtga acccaaattc aataaggtta   1020

gtagtttttt ttttaaatga tgatacactt ttgacaaaaa agaattagga tggttcgggt   1080

tactcgggag catggggtcg cccacaaaat gatggcccgg ctgatcgtgc tatcacgttg   1140

atcctgtttg cggacagttt cattgctcaa ggcggtgatg tctcgtacat taccaacaca   1200

ttgaagccag gtaagtaatc gggtatcacc gtaatccggt ctccaattac taatgtatgc   1260

cacagctatc tacaccaatc tcgactatgt tgttaacacc tggagcaatg tttgctttga   1320

tctatgggaa gaagtcaatg gtgtccatat ctatacgtag gttttttcgg gggagaggga   1380

aacgttaatg tgaaactttt tttttgaagt actcattgaa aatgcttatt tagactttcg   1440

gtcatgcgta agggtttgct tgaaggtgcc gactttgctt ctcgaaacgg cgattccacg   1500

cgtgccaaca cttatagaag caccgcttct tccatcaaga cccgtcttga atctttctgg   1560

tcatcgagca ataattacat cactgttact caatcatact ctggtggtgt gaacaaggcc   1620

ggtttggatg tatccacctt acttgcagcc aacggagcaa gcatgaatga tggttagttt   1680

ttgcttaaaa aaattgactt tgatatttac caaaagaata ctgcgtaggc ttctatactc   1740

ctggctctga caagatgttg gcaaccgctg ttgctattga aaattcgttt gccggtattt   1800

acgctgttaa ccagaatcga cctgattgga aaggtactgc tattggtcga tatcccgaag   1860

atacttatga tggccatggc aattcccaag gcaaccctgt aagtcatata ttccttatca   1920

caagaatgaa ttctaactta gaaaatagtg gttcattgcc acagctgcgt atgctgaaat   1980

gtactaccgt gccatcttgg aatggcaaca gcaaccgtct atcactgtga actcgatcaa   2040

cctgagcttt ttcaaaaagt ttgactcgtc cgccgctgtt ggtactgtgt acaagcccgg   2100

tacccaagct ttcaacaaca tggtttccaa tgttgcgttc gctgctgatg agttcttttc   2160

tactatgaat ttccattccg ccaccaacgg atccatgagc gaacaataca accgcaatac   2220

tggtattatg caaggtgctc gtgatcttac ttggtcccat gctgccttca tcaccgctgc   2280

caaagctaag cttggcacgc cagtattcta g                                  2311
```

<210> SEQ ID NO 10
<211> LENGTH: 1985
<212> TYPE: DNA
<213> ORGANISM: Gilbertella persicaria

<400> SEQUENCE: 10

```
atggttttct ccaagctttt taagaagcct atccttctca ttgtcactta cttgactgtt     60

actgttgtag ctgaaactgt tcctacttca gctcaagttc aagttaagtc cttcaactat    120

gatggctcta ctctttcagg tcaaatttat gtaagtaatt gagaggaagc gaatagtcat    180
```

```
tctgaatttg ctttaggttc aaaacattgc ttacgaaaag actgttactg tcgtttactc    240

tgatggctct gataactgga ataacaatgg taacaccatt gctgccagct attcttcttc    300

tatttcaggt agcaattacg aatactggac tttctcttct tctgttccta gcatcaagca    360

attctatatc aaggtataaa aaaaaaagga aacatgtatg acaaattagc tttactaaca    420

tcatcatctg tattcagtat gtcgttgctg gcaagactta ctatgataac aatggtacaa    480

agaactatca aggtatgtaa ttcacatgtt gcatgaaata tcagttacac taacacaaag    540

gctttaattg tatcaattta gtgagtgcaa gcacccctac taccactact accactactt    600

cttctggagc caccaagact actactacca ttggccctac ttctacaagt actgtcttcc    660

cctctggcaa ctctaccatt tcttcttggc tcaagggtca aattgaaacc agtcgttttg    720

ccatgctccg taacatcaac cctgctggta ctgtcaaggg tttcattgct gcttctttgt    780

ctactgctaa ccctgactat ttctatgcct ggacccgtga tgctgcttta gtcggccatg    840

ttattgccaa tgactacaac cgtaccttag ctggtaacag cacttacctt ggtcttttga    900

aggactatgt tactttctct gtcaactctc aatctacttc tactatctgt aactgtctcg    960

gtgaacccaa gtttaacaag gatggttctg gctacagcgg tgcatggggc cgtcctcaaa   1020

atgatggccc tgctgaacgt gctgatacat tcatcttgat tgctgacagt atcttgaaac   1080

aaactggtga tgctacctat gtaactggta ccttgcgtcc tgctatctac aaggatttgg   1140

actacgttgt caatgtttgg tctaacggtt gtttcgattt gtgggaagaa gttaatggtg   1200

ttcactttta cactttgatg gtcatgcgtc gttctttgat tttgggtgcc aactttgctt   1260

ctcgtaacgg tgattctact cgtgccagta cttacaccaa cactgccaac tctatcaaga   1320

ccaagattga caccttctgg tcttcttcca acaactatgt tgctgtcagt caaagcgtca   1380

ctggtggtgt caacaaggct ggttatgatg ttgctaactt gattgctgct aatgttggta   1440

gtctcgatga cggtttctac actcctggtt ccgaaagaat tctcgctact gctgttgctg   1500

ttgaaagtaa atttgcttct atttacggtg ttaaccaaaa cttgcccagc tggctcggta   1560

actctatcgg tagataccct gaagacactt acaatggtaa cggtaactct caaggtaacc   1620

cttggttcat tgccactaat acttatgctg agctctacta ccgtgctatc aaggaatgga   1680

ccaacaacgg tggtgtcacc gtcactaatg ttaacttcaa cttcttcaag aagtttgata   1740

gcagtgcttc tgttggtacc aagtacactg ttggtacctc tgcctttaac accttgactc   1800

aaaatgttgc tcttgctgct gacaatttct tctctactgt taaggttcat gctgccacca   1860

atggttctat gtctgaacaa ttcggtcgtg atagcggtgt catgactggt gctcgcgatt   1920

tgacttggtc tcacgccagt ttgattactg ctgctcttgc caagacaggt gctcctgtag   1980

cttaa                                                               1985
```

<210> SEQ ID NO 11
<211> LENGTH: 2018
<212> TYPE: DNA
<213> ORGANISM: Mucor circinelloides

<400> SEQUENCE: 11

```
atgaagttct caaatcttct caagaagcct ctccttctga tcgctggtat cttggctgtc     60

actgtagtcg ctgaaactgt ccctactact gaagcagtca aagtcaagtc ctttacctat    120

gatggatcta ccttggctgg tcaaatctat gtaagtgcta gaatcagtac caatcccttc    180

aataaacaca atgctaaata catgctctca acgaatagat caagaacatt gcttacacca    240

agacggttac tgtaatctac tctgatgcct ctgataattg gaacaacaat ggtaacacga    300
```

tcgctgcttc ttacagtgca gccatcgcag gcaccaacta tgaatactgg actttcagtg 360
ctcctgtaag cggcatcaag caattctacg tcaaggtaag tttgggattc ctgtatgctg 420
ggtgctcaga tattaagcct ctgatccgta ttagtatgtt gtcagcggta ctacctacta 480
tgacaacaac aacagcggaa actaccaagg tatattgatt ttcacatgct ggcatttgca 540
ctgtcatact aaacgagctg aatcctctag tttcagtcac caccactacc actactgctc 600
ctaccactac cacttctggc ggttcatcca ctaccactgg cggctccact actactgcta 660
ctagcgtccc cactggtgtt ccttctggtt tccctacagg taactctacc attagctctt 720
ggatcgatgg tcaaacctct gtcagccgtt atgccatgct ccgcaacatc aaccctgctg 780
gtgccgtcac tggtttcatt gctgcctcta tgtctacttc tggtcctgac tacttttatg 840
cctggacgcg tgattctgcc ttgacctctc atgtcgttgc ctacgactac aataccactt 900
tggccggtaa ctctaccatt ctcggtctct tgaagaacta tgttaccttc tctctcaaca 960
gccaaactac ctccactgtc tgtaactgtc tcggtgagcc caagttcaac aaagatggca 1020
gcggttacag cggcgcctgg ggtagacctc aaaatgacgg acctgccagc cgtgccgaca 1080
ctttcatctt gattgccgac agtatcctca agcaaaccgg cgatgctacc tatgttactg 1140
gtaccctcgc tcctgccatc tacaaggatt tggattacgt tgtctctact tggtccaacg 1200
gctgtttcga tttgtgggag gaggtcaacg gtgttcactt ttacactttg atggtgatgc 1260
gcagaggttt ggttaagggt gctaactttg cttctcgcaa tggtgacagc acacgtgcca 1320
ccacttacac caacacagct gcttccatca agaccaagat tgacagcttc tggaactcca 1380
acggtcaata tgtctctgtc agccaaagcg tcactggtgg cgtcagcaag gctggttatg 1440
atgcctctgt cttgattgct tccaacttgg gtagtcttca agatggtttc tatactcctg 1500
gctctgacaa gatgcttgct actgctgttg ccattgagag caagtttgct tctctctact 1560
ctatcaacca aaacttgaac ggttaccttg gtaatgctat cggtcgctac cctgaagaca 1620
cctacaacgg caacggtaac tctcaaggta acccttggtt catctgtacc aacgcctttg 1680
ccgagctcta ctaccgcgct atcaaggaat ggttcaacaa tggcggtgtc actgtcacta 1740
gcatcagttt gaacttcttc aagaagtttg attcctctgc tgctgttggc accaagtaca 1800
ctgtcggcac ctcttctttc aacagcttgg ttcaaaatgt tgctgtcgct gctgatgcct 1860
tcttctctac tatcaagttc catgctgcca ccaacggttc catgagcgag caatacggcc 1920
gcactgatgg cttgatgact ggtgctcgtg atttgacttg gtctcacgct tcattgatct 1980
ctgcttctta tgcaaaggct ggttctcctg ctgcctaa 2018

<210> SEQ ID NO 12
<211> LENGTH: 2946
<212> TYPE: DNA
<213> ORGANISM: Circinella umbellata

<400> SEQUENCE: 12
atgatgccga atcatatttg gaagtgtctg tttctagcca tgaccacagt tttcatgact 60
gtactggtac aaggtgctcc tacttcagaa attgaattgg actcttatac ctacaccggt 120
ggagtatttt ctggtcggtt atatgtatgt ggtatctatt tgtacataat taaaagaaaa 180
attcaagaga atacagtttt gttaatgttg gtaattccca atatatacag gttaaaaata 240
ttgcgtacac caaggaagtg aatgtctatt ggtctgatgc ttctgaagac tgggccaata 300
atggtaatta tgtggcagct acgtattctg aagccatttc gggtacaaat tacgaatatt 360

-continued

```
gggaattctc tgccaaaatt ggatcttctg gtattagtga aagttacata aaggtaaatt    420
actataaatt gtttgaaact ccaaaataca aaataaaaaa tccggcatag ttattaatta    480
ttctttattt ttttcaaata aattcagtac actgtgtctg gctccactta ttatgataat    540
aatgggggta aaaattatgg tatggtcaaa acattttaca cagtaataac gcctttcttg    600
catcatcgaa cttttaaagt atatgcttat tttttttcg tcattttaca atagctatta    660
ctgagacaac tacacccaca ataactgcaa ccccgacatc aacaacggcg acaacgacca    720
tttcttcaac aactactacg gctacttcca ttcctacctc tgttccttcc actgttcctg    780
agggaaatgt tactgtcaca gaatgggtca ataagcaact aaaaatcagc tggtccgatc    840
ttctgcaaaa tgtaggcgta taataactaa aaatacctta tattatattc tatgcatact    900
atctgtaaaa aaaaccttaa aaattattga aaacctgttt ctcattattt atattacttc    960
tatcttatat ataggttaac ccttcaggta cagttactgg ttttattgct gcaagtttaa   1020
gtaccagcaa ccctgattac ttttactgtt ggacaagaga tgctgccatg gttgcacgtg   1080
ttatgactta tatgtataat actactgaag ctggcgactc aagtcttgaa agtgcattaa   1140
aagattatat tacgttccaa atcaattcaa tgaagactgc cactgcatgt aactgcttag   1200
gtgagcccaa gtttaatact gtaagttacg tattagagta agaaataaaa ccccctcgat   1260
tgatcactag acatgttatc tgtatcacgt atcattacaa tgctaatttt ttatttattg   1320
acaaatgtgg tactgtagga tggaagtggt tatagtggcc cttggggtag gcctcaaaat   1380
gatgggcctg gtaagtttaa actatttttt ctattttatt ttactttata agatttttaa   1440
aaatatgttg atcttatgat gatcttatgc cttaacaaaa atgtttttc atatttatac   1500
atatagctga acgtgccact acaatgattt tgtttgctga tagttatctc gctcaagggg   1560
gtgatacttc ctacgttaca aatacattaa aacctggtaa atcattataa taatattttg   1620
tatactataa caaacacaga tagatgtaaa aaaaggcttt ctgtttctca tgtatattaa   1680
caaaaacaat ttacctttt tttttgttat taaaacgatt atatagctat ctataccaat   1740
cttgactatg ttgttggtac ctggtcaaat aattgtttcg atttatggga agaagttaat   1800
ggtgttcata tttgtaagca atatcatgat atttttctaa aaagaacaat acacacacat   1860
acacacacac acacacacac acacacacac acacatatat atatatatat atatatatta   1920
actgctatca acatttttac ttcataaaaa ctaaaataac aataataata ataatagtta   1980
ctctggctgt tatgcgcaag tcattacttg atggtgctga ttttgctgca cgtaatggcg   2040
atacatctcg tgtcagtggt tatcaaagca cagcttcatc tatcaagact aagttagaat   2100
cattctggtc gtccagtaac aattatatca ctgtaactca atcctattct ggaggtgttc   2160
aaaaggccgg attagatgtt tctactttaa ttgctgccaa ccaaggaagt atgggtgatg   2220
gtaagttttt atttttattt tactataata aagtagtttg taatataaaa tacgtaaaaa   2280
agaaaagacg gattttttta tatgaaatat aactattgct ctgtaggatt ctatactcct   2340
ggctctgata aaatgctggc tactgccgtc gctattgaaa actcatttgc aaatatttat   2400
actatcaata aaaacaaacc ttcttggctt ggtactgcta tcgggcgtta tcctgaagac   2460
acatataatg gtaacggcaa tggtcaaggc aacccggtaa gtttatatat aacccattta   2520
ctaaaagaag gtttcatttt atatatgtat ctaatatatt atatggtcac tactattatt   2580
tagtggttta tcgcaacagc aacctatgcc gaattatact accgagctat tttggaatgg   2640
caacaacaag agtctgttac tgtaaactct gtcaactttg atttctttag caagtttgat   2700
tcatcggcta aggttggcac tgtttataca ccaggtacag atacctttaa caccatggtt   2760
```

-continued

```
tcaaacgtag cttttgccgc tgatgaattc ctttcaacaa tggaacatta tgctgctaca   2820

aacgggtcca tgtctgaaca atttaatcga gagactggct ctctcaccgg agcccgtgat   2880

ttgacatggt cccatgccgc atttatcaca gctggtaaag ctaaattagg tattccatca   2940

ttctga                                                              2946


<210> SEQ ID NO 13
<211> LENGTH: 2054
<212> TYPE: DNA
<213> ORGANISM: Mucor cordense

<400> SEQUENCE: 13

atgaagtttt ccaagctctt tacgaagcca actctcttca tagttagcat catcatttct     60

gttgcttcct ctgaaactgt ccctactact gccaatgtcc ttgtcaaatc ttacacttgg    120

gacggtgcca ctttatctgg tcaaatttac gtaagtatat tatgtaatgg cgtgttatag    180

caaaaattga cactgcttgt ctatagatta aaaatcttgc ctatgccaag gttgtctctg    240

tcatttactc tgatgctaat gataactgga ataacaatgg taacaaagta gctgcctcct    300

actctgctgg aattgatgga acaaactacg aatactggac cttttctggc gctgttagcg    360

gtatcaagca attttatgtc aaagtaagta tagatcttct atattcaaat tgaatatata    420

aactaactgt ataatgtagt atgatgttag cggtactagt tactatgata acaatggtac    480

caagaactac caaggtaaaa attagataat gaagtaatcg tatacagatc cttacatgtc    540

gtcttcatag ttaccaagac ctctacaacc accactgctg ctactaccac taccactgcc    600

actactacta ctggtggtac tggtaccact actacaacta ccgctactgc cactgctaca    660

tctactgatt tccctacagg taacagcact atcaccactt ggctcaaatc tcaagaagac    720

atcagtcgtg gtgctatgct ccgcaacatc aaccctcctg gtgccgctac aggtttcatc    780

gccgcctcat tatccacttc cggacctgac tactactatg cctggactcg tgattccgcc    840

ttaacctccc acgtcattgc tcacgactac aacactacat tagccggtaa caccaccatt    900

ctcaacatcc tcaaggacta cgtcactttc tctgtcaaga gtcaatctgt ttccaccgtc    960

tgtaactgtc tcggtgaacc caagttcaac cctgacggct cttcttacac cggcgcttgg   1020

ggtcgtccac aaaacgacgg tcctgctgaa cgtgcttcca cattcatcct ctttggtgac   1080

agttacctca agcaaactgg cgatgctact tacgtcacgg gcacattggc tcctgctatc   1140

tacaaggatt tggactatgt cgtgaatact tggtcaaatg gttgctttga tttatgggaa   1200

gaagtcaatg gtgttcactt ttacaccttg atgagcatgc gtagaggttt gcttgatggt   1260

gctaatttcg ctaagcgtaa tggagatact acacgtgcca ctacttacac aaataccgct   1320

gcttctattg ctacaaagat cgataccttc tgggtctctt ctggtaacta tgttcaagtc   1380

agtcaaagtg tgactggtgg tgtaagcaag gctggttatg attgtgctaa tattctcgct   1440

gccaacatgg ccgccaacca cgatggtttc tatactcctg gttcaagcaa ggtaaatata   1500

catgactcac tatctcttta tgaaagtata ctaaacgttt catatagatt cttgctactg   1560

ctgttgctat tgaatccaag tttgcttcct tatacagcat taactctggt ttggctagct   1620

ggctcggtac agctattggt cgttatcctg aagacactta caacggtaat ggtaactctc   1680

aaggtaaccc ttggttcatc tgtaccaacg cctttgctga actctactac cgcgctatca   1740

aggaatggac tcaagctggt tccgtcactg ttgacagcac tagtcttaac ttctttaaga   1800

aattcgatag ctctgctgct gcaggcacga aatataccgt tggtacttct gctttcacta   1860
```

atttggttca aaatattgct aatggtgctg ataagttttt gtctacttcc aagttccatg 1920
ccgctaccaa tggttccatg tctgaacaat ataaccgtga ttctggtttg atgacgggtg 1980
ctcgtgattt gacttggtct catgcttctt tgatctctgc ttctagagct aaggctggct 2040
ctccttctct ttaa 2054

<210> SEQ ID NO 14
<211> LENGTH: 2709
<212> TYPE: DNA
<213> ORGANISM: Phascolomyces articulosus

<400> SEQUENCE: 14
atgggtgtat tagcagacgt ccctacctct gccaatattg aactggatta ttatacttat 60
aaggataaag tattctctgg tagaatttat gtatgaattt taaaatagag taaaatgaaa 120
gaaaaaaaag atagaagaat gggaatatat aataattaaa ggttataata tatattttat 180
taaataggtt aaaaacattg catatgagaa aacagtagct gtctattggt ccgatgcttc 240
tggtgattgg aataataacg gaaataatgt tgcagcttcg tactctgaat ctatttcagg 300
tactgactat gaatattggg atttctcaac cacaattgga tctggtggta tcaagcaaag 360
ttacttgaag gtacacttga ttgttatcat cctgttattt ttcaaattat aaatatatat 420
actaaaagta cacatactca atagtatact gtatctggta atacttacta tgataataat 480
ggaagcaata actatggtac gtctcaattt aaaaaccata taaacaagta tatttctgta 540
ttcgtattca ggaacgtatg aagctgacat ataagttttt gattatagat attaccgaga 600
ccactgctac tactactact accacaacaa caacaaccac tactggctcc accgcaacaa 660
catcaacaac ttctggtcct accagtacta ccagtaccac acccggccct acacctacca 720
atgttcctga tggcaatgtc actgttacag agtgggttaa cactcaattt gccatcagct 780
ggcctaccct cttgaaaaat gtatctatca aaaaaatata atccttctcc aaaatactca 840
catgttcatt acttatatat cgttttcttt ttaatactaa aggtcaaccc atctggtaca 900
gtgaaaggtt ttatagctgc aagtttaagt accaacaatc ccgattactt ttactcctgg 960
actcgtgaca gtgccttagt ggctcataca atgacatatc tttataatac atcggaagcc 1020
ggtgactcta ctatcgaaag tgcattgaag gattatgtta cattctctat caacgctatg 1080
aatgctgcta ctgtttgtaa ttgtttaggt gaaccgaagt tcaatactgt aagtataagg 1140
ggaaaaaaga gacgatactt taaaaatgat agacttatca ttggatgaaa cttttttttt 1200
aacaaatagg atggaagtgg ttatactgga gcatggggaa ggtaggtttt ttatttacat 1260
gctggctcca gtgcttaaat gatatgatta tttgggagtg aaaaataaat gttgtgagca 1320
accttgctaa acttgtttct attattatta gaccacaaaa tgatggccct gcttcaagag 1380
caacaaccat gattttgttt gctgatagtt tccttgctca aggaggtgat gtttcctatg 1440
tcatcaacac actgaagcca ggtatatact attatatgtc ccaactacat ttattgaaat 1500
ataaagtact aatcttaaca aatattatta tttatcttgc ccaatgatat ttagccatct 1560
ataaagatct tgactatgtt gttagtacct ggtccaatac ttgttatgat ttatgggaag 1620
aagtcaacgg tgttcatatc tgtaagtagt agtatatctc ttaaataatg catcattctg 1680
aatatacata tttatcttca attttttttt taaatagata cattatccgt tatgcgcaga 1740
gcactgattg atggagctaa ctttgctcaa cgtaatggtg atacttctcg cgtgagcggt 1800
tatactagta ctgcaaccac aatcaagaca cgtctcgaat ccttctggtc agatagcaat 1860
aattatatta ctgtcactca atcctattca ggtggtgttc aaaaggctgg attggatgtc 1920
tctactttga ttgcagccaa tatcggaagc gtgggtgatg gtatatttca tctattacta 1980
ctttatttcc atattattgc gttatcggat cgatcttctc tgtcatttta taacgtaata 2040
tttattaata tctcttttct aatatttata ataaggtttc tatactcctg gttcggataa 2100
agtcttggct actgctgttg ctattgaaaa atcatttgcc aatctttaca ccatcaacca 2160
aaacaagcct tcatggcttg gtaatgctat tggtcgttat cccgaagata cttatgatgg 2220
ttatggtaat tccaagggta atcccgtaag tattttttt tatctcttcc gtttatactt 2280
ttaatgcaga taatgatgat atcatcacta tgtccggtcg aatagtaatc catttgttgt 2340
atatagtggt ttattgctac tgcaacttat gccgaattat actatcgtgc cattttggaa 2400
tggcaacaac aagcttctgt tactgtcaac tctatcaatc ttggcttctt tagcaagttt 2460
gattcctctg ctagtgtggg tacagtctat acacctggta cagatagctt tgccaacatg 2520
gtatccaatg tcgcctttgc tgccgacgaa ttcttgtcca ccattgacta tcatgccatg 2580
aacaatggat ccatgcatga acaatacaat agagatactg gtatctctca aggtgctcgt 2640
gatttgactt ggagtcatgc tgctttcatt acagctgcca aagccaaatt aggtgcccca 2700
gcattttaa 2709

<210> SEQ ID NO 15
<211> LENGTH: 2033
<212> TYPE: DNA
<213> ORGANISM: Rhizopus microsporus

<400> SEQUENCE: 15
atgaagttaa tgaactcgtc gatgaagacc tgtgtcttct ttattctctc ctacttttct 60
ttgttggtct cttctgctgc agtccctact agtgctgctg tacaggttga atcttacaaa 120
tatgatggca ctaccttctc tggtcgtatc tttgtaaggc taattgatct catttaaaga 180
aaaagagaga aactgatctc gtcaattagg ttaaaaacat cgcctactca aaggtagtca 240
ctgtcattta ttctgatggc tctgataact ggaacaacaa caataacaag atttctgctg 300
cttactctga agctatctct ggttcaaatt acgaatactg gacattctct gccaagttga 360
gtggtatcaa gcaattctac gtcaaggtaa ttcttttttt ttctctctat ttattgtgta 420
tactaacgcg acctttgata gtatgaagta agtggctcta cctactatga caacaacggt 480
acgaagaatt atcaaggtaa gcatatgctt aagcaatagc atttctttac tgacctatca 540
aatagtccaa gcaacaagcg ctacctctac tactgctact gctactacta ctacatccac 600
cagcactact accactagca ctggcccaac aagcactgcc tccgtctctt tccccactgg 660
taactctact atctcatctt ggattaagaa ccaagaagaa attagccgtt ttgccatgct 720
tcgtaacatc aatcctcccg gaagtgccac aggatttatt gccgcttctt tatctaccgc 780
tggaccagac tactactatt cttggacccg tgattctgca ttgacagcca atgtgatcgc 840
atatgaatac aacaccacct tcgctggtaa caccaccctt ttgaaatacc tcaaggacta 900
cgtcacattc tctgtcaagt cccaatccgt ttctactgtc tgtaactgcc ttggtgaacc 960
caaattcaac gctgatggct ctagctacac tggtccatgg ggaaggcccc aaaacgatgg 1020
acctgctgag cgtgctgtta cttttatgct gattgctgac agctacctta ctcaaacaaa 1080
ggacgcttcc tatgttaccg gtaccttaaa gccagctatc tttaaggatt tggattatgt 1140
tgttagcgta tggtcaaatg gatgttatga cttgtgggaa gaggttaatg gtgttcattt 1200
ctacactttg atggttatgc gcaagggttt gattcttggt gctgattttg ctgctcgtaa 1260

```
tggtgactct tctcgtgctt ctacctacaa gaacactgct tccacaatgg aatctaagat   1320

atccagtttc tggagtgact ccaacaacta tgttcaagtc agtcaaagcg ttactgctgg   1380

tgtcagcaag aagggtttgg atgtttctac tctgctggct gcaaacattg gtagtcttcc   1440

agatggtttt ttcactcctg gttctgaaaa ggtatttgca aaaagtcgct caatatttca   1500

tagattgtaa acgtgatttt atctagatcc ttgctactgc tgtcgctctt gaaaatgcct   1560

ttgcttcatt gtatcccatc aactctaacc ttccctcata cctcggtaac tctattggaa   1620

gatatcctga agacacatac aacggtaatg gtaactctca aggtaaccca tggttcttag   1680

ctgtcaatgc ctacgctgag ctctactacc gtgccatcaa ggaatggatc agcaatggta   1740

aggttactgt gagcaacatc agcttgccct tctttaagaa attcgactcc tctgctactt   1800

ctggaaagac ttacactgct ggcacttctg actttaacaa ccttgctcaa aacattgcct   1860

tgggtgctga tcgcttcttg tccactgtca agttccatgc ctataacaat ggctctttgt   1920

ctgaggagta tgatcgctct actggtatgt ccactggtgc cagagatttg acttggtccc   1980

atgcctcttt gatcactgct gcttatgcaa aggctggctc tcctgctgct taa          2033
```

<210> SEQ ID NO 16
<211> LENGTH: 1469
<212> TYPE: DNA
<213> ORGANISM: Spinellus fusiger

<400> SEQUENCE: 16

```
atgaagtcac cttatagcat gaaaaccgtt ttggcattgt tgtctcttac cccgcttttc     60

acgtcagatg ttgttgctgt gccttctggt aactccacca tcactgcctg gggaagcaag    120

caggacggca ttagtttctc caccatgctt ggtaacatca accctcctgg atctagcaag    180

ggattcattg ctgcctctct ctctactgct ggtcccaatt actactactc atggacccgt    240

gactctgctt tggtagctcg tgccatcacc tacaaataca gcacttctta ccagaacgac    300

cccaagattc tcggtctctt gaaagactat gttacctacc aggtgaacga acaaacagaa    360

agcaccgtct gcaactgtct cggtgagccc aagttcaacc ccgatggttc tagcttcagt    420

ggtccatggg gaagacccca gaatgatggt cctgctgaac gtgcctccac catgattctg    480

tttgccaaga gttactatgc tcagaccaat gatgttggct atgtcagcaa tacactgaag    540

cctgccattt acaaggactt ggattacatt gtgaatgtgt ggggtaacaa ctgctttgat    600

ctctgggaag aagtcaatgg tgtccacttc tataccttga tgatgatgcg ccatggtctt    660

gtccagggct ctatctttgc taacactctc ggtgattcta ccagagccaa cacctacaag    720

acagctgccc agaacatcaa gaacagaatt gatactttct gggaatctgg aagcaactac    780

attgtcgtca ctcagaacca gagtgcaggt gttaacaagc cctctggatt ggatgttgct    840

gttttgcttg ctgccaacca aggtggtctg ggagatggtg tctatactcc tggctctgac    900

aaggtaaatg attatctgct ggtcttttta gacacaccaa actcatccat tttatatgat    960

aggttcttgc tactgctgtt gctcttgaga aatcttttgc cagcttatac cctatcaaca   1020

agaaccttcc ttcttactac ggtactgcca ttggaagata ccccgaagac acctacaatg   1080

gcaatggcaa ctctgaggcc aacccatggt tcattgccac caccacttat gctgagttgt   1140

actaccgtgc tatcagtgaa tggaccaatg gctcaggtgt cactgtaaac agcatcaaca   1200

aggagttctt cagcaagttt gatgccagtg ccaccaacgg aaaggtctac acacctggat   1260

ccgatagctt caacagcctg gtcaacaacg ttgccattgc tgctgataac ttcctttcta   1320

ctgtgagata ccaccaaacc agcaatggct ctttatctga acagttcaac cgctacactg   1380
```

gattcatgac aggtgcccgt gatcttacct ggtcccatgc tgccatggtc actgctcttg 1440
ctgccaaggc cggtactcct tccccttaa 1469

<210> SEQ ID NO 17
<211> LENGTH: 2402
<212> TYPE: DNA
<213> ORGANISM: Syncephalastrum racemosum

<400> SEQUENCE: 17
atgcagctaa acctttactg gaaaagtctg gccgtgctcg ccctgattca gatggtcatg 60
gcggccactg tgccaaccac tcaggttcag ctagactact acacgtactc caacaatgta 120
ctgtcgggcc gcatctatgt aagccgagat agaccaggaa acgccgctga aagagtgctc 180
attacatata tatcttttct tgcaggtgca aaatattgca tactcaaagg tggtcaaagt 240
gatttactca gacgcgtctg gaaactggaa caacaacggc aatactatct ccgcaagcta 300
tgtcgagagt atctctggta ccaactatga gtattgggat ttctcggcca ccattggcac 360
ggctggtatc aagcaattct atcttcgcgt gagtttgtca cctgccttgt ctcttattat 420
taagccatta ggctcgagtg acattaatgc tgtatttcat gtgcatatta gtatgacgta 480
tcaggtagca cttactatga caacaatggt ggggataata acaactacag tacgtattat 540
cggacagcga gagtcactta gccacttatg taacatatta cacatataga cgtcgtcgcg 600
acgacttcaa caacctcgtc atccacaacc acgactacgg ctacaacgac aaccgccaca 660
aagactacta gcaccacaag tgccacagct acgcccacgt catctgcgac ttttcctagc 720
ggcaattcaa cgatcaccac ttgggcaaaa tctcaaaagg atattagctg gaagacactg 780
ctcaccagcc tgaatccctc cggcactgcc aaaggcttca ttgctgcatc gctttccaca 840
tcgaacccag actattatta tgcttggacc cgcgactcgg ccctggttgc caggttggtc 900
gactccattt attgcacttg ggcaagcacc cttcttacgc gacgaattga tggttagaac 960
catggtcaac atgtacaaca ccacggaagc tggaagtgcg tcggttctag gccttttgca 1020
agactatgtc accttccaaa ttaatgccat gagcacttct acggtatgca actgccttgg 1080
tgagcccaag ttcaacccgg atggctcgag ttacaccggt gcctggggcc ggtaattgca 1140
aaatcacgac ggtttgcgtt tcgtaatggt tgatttctgt gtttgtagtc cccagaacga 1200
tggccccgct gaacgtgcca gtaccttcat tctgtttgcc gatagttata tcgctcaagg 1260
tggccagctc tcatatgtga caggaactct cgctcctgct atctacaagg atctcaacta 1320
tgtcgtgagc acctggtcaa ataactgctt tgatctttgg tatgatattg gtcgatattg 1380
catatttccg tcacgtattt ctaactcgtt ctaatatagg gaggaagtca atggccgaca 1440
tatgttcacg taaggaagga tatgcgctaa cgttcctttc tcagatttga tctcatttct 1500
tgtagccttg ctgtcatgcg ccgtgctctc ttggatggtg tcaacttcgc ttcgcgcatc 1560
ggcgatacga cttactcgag cacgtggtcc agtaccgcat cgtctatcca gtcaactttg 1620
tccggctact atttgtcgag cggcaattac attactacgg tgcagaactt ccagtcaggc 1680
gtcagcaaag ccggttatga cgtctcgact ttgattgctg ctaatgtggc cggtatgggc 1740
gatggcttct ttacgcctgg ctcggacgag gtgaaccatc aaaccgcgta aacttcgtag 1800
tagaagactg accgtggtgt aggtactcgc cactgctgtg gctatcgaga acaaattctc 1860
cagcttgtac ggcgtcaacg cgaacaaagc ttcttatctc ggcactgcca tcggacgcta 1920
cccagaggat acctataatg gctatggtaa cggccaagga aacccggtaa gtattactgc 1980

```
acttttcgtt tgtactcaaa catgcagaac cgcgatctaa atggcaggtc cgtatgtagt   2040

ggtttattgc aacggcggca tatgctgagc tgtactatcg tgccattttg gagtggcaga   2100

ccaagtcctc catcgtagtc aactccaaaa acctcggttt cttctccaag tttgattcat   2160

ccgctgcagt gggtactacc tatacgcctg gcaccacagc ttacagcaac atggtgcaaa   2220

atgttgcctt ggctgccgac cggttcttgt cgaccgtaca gctccacgcc gctaccaatg   2280

ggtccatgag cgaacagttc aatcgtgata caggcgttat gcagggtgca cgggatttga   2340

cttggtctca ctctgctttc attaccgctg cgcgcgccaa gcttggttcg cccgtctact   2400

ag                                                                  2402
```

<210> SEQ ID NO 18
<211> LENGTH: 1827
<212> TYPE: DNA
<213> ORGANISM: Syncephalastrum racemosum

<400> SEQUENCE: 18

```
atgcgcgcta caacagctat tctgtctctc tttaccactg cgtccatggc gctggccgcc     60

aacagcactg tcccggatgg caactcaacc acgaccgcct gggtcaagaa gcaagaagcc    120

atctcttgga cagatctcaa gaccaatgtc aaccctgaag gtgcggccaa gggctttatt    180

gctgcgtctc tttccacatc ggagccagat tattactatg cttggacgcg tgattctgct    240

cttgttgcgc ggtatgctca acgtgacatt tacaatgcct aatactgaca taataatatt    300

cagcgtcatg gtcaacaagt acaacacgac cgatgcgggt gacgccaacc tgctaggtct    360

tttgcaagac tatgtgtcgt ttcagatcaa tgccatgggt gaaagcactg tctgcaactg    420

cttgggtgag cccaagttta acccggtaag aagacaaaaa acataagaca gaaaagaaca    480

atcggctgat tctgggacct tgttacacac aggatggctc tagctacact ggagcctggg    540

gccggtgcgt atttgattag atgctcctgt accacgttaa tgttaatatt tgcccacata    600

tagccctcag aacgatggcc ccgcggagcg tgcttcgact tttatcttgc ttgctgatag    660

catgattgct caaaagtcag cgaatggttc ttatgtctcg gataccttag cccctgccat    720

ttacaaggac ttggcctatg ttgcctccac ctgggagaat gcttgctacg atctttggta    780

aggctattcc aatgcaaatt atgtctgcta gcttcatttc taacgaaccg gttctttaat    840

cttttaggga agaagtcaat ggcaagcaca tgtacacgta agtactatat attctttgaa    900

tgattattag taaagtatat atatgactaa tgatgctttg tctttgtatc gctagcctgt    960

ccgtgatgcg ccgcgctctt ctagatggtg ctgattttgc tagccgccag ggtcagacgg   1020

cgaatgtgac ctcgtggaag tcaaccgccg acaagatcaa gtcttcgctc gagggtttct   1080

tctcatccga taatggttac attgaggtga cccaagatat gcagggcggt gtccaaaaga   1140

agggcctcga tgtgtcgacc ttgatcgcag ccaatattgg cagcatgggc gacggtaata   1200

tcttcttatg cgagctatat gcctgcgctc aacaacatta ttaggcttct acaccccggg   1260

ctcagacgag gtgctagcca ctgccgtggc tgtcgaggct gcgttcgctg acctctacaa   1320

gatcaatcag aacacgaact ccaccggcct tggtaccgcc atcggccggt accccgaaga   1380

cacttacaat ggtgtcggca acagccaagg caaccccgta agtcactatc atctttgttg   1440

attatctatt ttaacttcta ttagtggttc attgcaacca acacgtttgc tgaactctac   1500

tatcgcgcta ttcttgagtg gcagaacaag ggtacaatca cggtcaactc ggtcaacgcg   1560

gccttcttct ccaagtttga ttcctcggct aaggctggca ctacatacaa gtcaggcagc   1620

actgaatttg acagcttgat caataaggtg gctttggctg ccgatgcctt cttgaacaca   1680
```

gtccagacgt atgctgcaag caacggctcg atgagtgagc aatacaaccg tgacaccggt 1740
gcgctgacgg gtgctcgcga ccttacttgg tcacacgcca gcttgatcac tgctgcaaac 1800
gccaagctcg gtactcctta taactag 1827

<210> SEQ ID NO 19
<211> LENGTH: 1796
<212> TYPE: DNA
<213> ORGANISM: Thermomucor sp.

<400> SEQUENCE: 19
atgaagcttg gccgtatcgg attcagtatc ctgtcagttg cctccgtctt ttctcaagct 60
gttgttactg ctgctgctgc tgcttcggta ccctccggaa acgcgaccat cacgtcgtgg 120
atccaagagc aactggccat tagctggaac accatgctga cgagcgtcaa tccggttggc 180
gccgtgaccg gcttcattgc cgcgtcgtta tcgaccgcga acccggacta ctactactgc 240
tggacgcgcg acgctgcgct ggtggcacgc gtcatgacgt tcatgtacaa caccacccaa 300
gccggcgaca gtggcctttt gggaatcctg caagactatg tgtcgttcca gatccatgcc 360
atgggtgaat ccacggtttg caactgcctt ggtgagccca aatttaatcc ggtaaatgcg 420
cggccaatcc cccaaacttt ctatacgtat atatattggt tcaagctgaa cgatggttta 480
ggatggttcg agttacactg gcgcatgggg ccggccccag aacgatggac ctgccgagcg 540
ggcgtcgacg tttatcaaaa ttgcagatag ttaccttacc caaaccggtg acgtttcgta 600
cgtcacgaat acgctgaaac caggtgcgta tatatatata tatatatatg tatatatata 660
tagaacagga tacaacaaaa ggtagtagac gaagaactca actttttttc ggacaaagcg 720
atctatgagg atctggacta tatcgtgaat gtttggcaaa atacgtgctt tgatctgtgg 780
gaagaagtct atggcatgca tatgtacacg taagttgtat tctctctatt atgtccattc 840
ctgtggatct tcgtacttat gatgtatgtc catgtaaaga ttggccgtga tgcgccgcgg 900
gttactggac ggcgcggatt tcgcgacgcg caacggcgac accgacaaag ccagcaccta 960
caccagcacg gcaacgtcca tccagacccg gctcgcgacg ttctggtcgg atagcaatgg 1020
ctacattact gtgacgcaag attaccaaag tggggttagc aaagccggac ttgacgtctc 1080
gactctgatt gctgcgaatg tggccggcat gaacgatggg ttctttacgc cgggctcgga 1140
tgaggttcgt gttatacata cttgtacacc aaggaggatg cctattgaca aaaaaagcgc 1200
ggttgttcta gatacttgct acggctgtca aggtggaagc tgcgtttgca aacctttacg 1260
gtatcaacat caacaaggcc agttatcttg gtaatgcaat tggtcggtat cctgaagaca 1320
cgtataacgg caacggcaac tcggaaggca acccggtaag ctatcccatt tttgtccccc 1380
gatttctaag tttgcaactt tctctaacca atgttgcttg gtgttaaaag tggttcattg 1440
ccacagcggc gttcgcggag ctttactacc gggcgatcat ggagtggcaa ttgcgcggca 1500
gcagcatcac ggtgaactcg gtcaaccagg gcttcttcac caagtttgat ccgtcggcta 1560
cggctggcac gacgtatacg ccaggcacgg acgcgtttaa ctcgctgatt gacaatgtgg 1620
cgctggcagc cgatcagttc ttctcgacca tccacctgca ccgtgcgacg aacggctcca 1680
tgagtgagca gtataaccgc gatacggggt tcatgcaagg cgcgcgggat ctgacttggt 1740
cccatgcggc gtttatcacg gccgccaagg cgaagcaggg caccccgtca ttctag 1796

<210> SEQ ID NO 20
<211> LENGTH: 2883
<212> TYPE: DNA

<213> ORGANISM: Zychaea mexicana

<400> SEQUENCE: 20
atgagaccag ttcatctttg gaaaagcctg cttttagctg cggctactgc agtcacgggt 60
acaatagctg ttgatgtacc ttcggtgcct attcagttgg agtcctatac ttattccgaa 120
aatgtattcg ctggtcgaat tttcgtaagt tatggaagcc ataataataa agtggcagga 180
tctatgatgc acaataacta aactctctga ttactcgtta actccctttg tattttgata 240
tctaggttca aaacattgcg tacaccaaag aagtcaacgt gttctggtcc gatgcttctg 300
atgactggaa cgacaatggc aactctgtgg cagctagtta ttccgaatcc atcgcagaca 360
ccaactatga gtactgggaa ttttcaacca cgattggatc tgccggtatc agccaaagtt 420
atttgagagt aagtcccaat cgccatttta tatatattgt gcacgtcagc aatagagctc 480
tgcagtaaag atataacttc agataacctt gacatctatg tctgaacaat ttcgggtttt 540
agtatgacgt atctggatca atctattatg acaataacga cagccagaac tacggtaagc 600
agagtatgag ctacatcttt gaagccttca taatgaagca gctgcacata tactgcctcc 660
taattgggtt gcacgtacaa cgggaaggat tattgctaac tttatatgtt acgtttgtac 720
cagatatcac cgagacatcg acccctacca caaccactgc tgctcccact tctaccacta 780
gcactcctac tactactacg gatggtggat cgacaactac taccactgcg acatctgttc 840
ctacgtctac tggtgttcca gagggcaatg ccaccatcag cgaatgggca agcgctcaat 900
tggatatcag ctggccaaac cttatgatga atgtaagtca acaatactct gtatagtgca 960
gcatacatta caagccattc aattaatcga attttcttac attctctttt tttgttccca 1020
ggtaaaccca tcaggtgcag tgactggctc tatcgttgcc tctttgtcga ctagtaaccc 1080
agattatttt tacatttgga cgcgagatgc tgcaatggtt gcacgcgtga tggtatacat 1140
gtacaacaca accgaagctg gtgacacaaa tctgttaaat gccttgaccg actatgttac 1200
gttctccatc agctccatga atgtggatac cgtctgcgac tgtttgggcg agcccaaatt 1260
caatgtggta agtagagaaa ttttataaaa acagggctaa gtgatactga agagcaagga 1320
taaaaaagtg aggacaaaaa gagtagcaat actagtgtta ataatatacg attcattata 1380
ggatggaagc ggttacaccg gtgcgtgggg aaggtacagt aattatggaa ctagaggaca 1440
gaaaaggctg tattttttgt attatgtgat atgcactgaa aggttggatg aatcttttgt 1500
ttgcaacaat gtactcacat tcatttatgc attagacccc aaaatgatgg acctgcagag 1560
cgtgcttcaa ccatgatttt gatcgcagac agctatatcg ctcagggcgg tgatgtttcc 1620
tatgttactg acacgctgaa gccaggtatg taaattttct atactttact caccatcagc 1680
aacacggagt tttcctgtca tagataacaa acgatcattg acacattatg gtctgtgatc 1740
ttttttatag ccatttacac cgatcttgat tatgttgttg atacttggtc taacgtttgc 1800
ttcgatcttt gggaagaagt gaatggcatt catatgtgta agctatttgt gataatcatt 1860
tttatatgat gtaaaaggaa agtctcttgg ctcactagta tgatgaaaca tagacacctt 1920
gtcggtgatg cgcaaggctc ttctcgatgg cgccaatttt gctacccgca atggcgacac 1980
ctcgcgtgtc agcggttatg aaagcaccgc ttcatccatc aagaccagac tcgaatcatt 2040
ctggtcctct agcaacaact acatcaccgt tacccaatcg ttctcgggag gtgtttcaaa 2100
ggccggcttg gatgtctcta cattgattgc tgccaacctt gcaagcatga acgatggtaa 2160
gtgattactt cacatgaaaa aggtgtatat ttttactcac atatgtctgt cccttgatgg 2220
ttgtaattta ggtttctata ctcctggctc tgatgaaatc ttggccacgg ctgtcgctat 2280
tgaaaactct tttataagtg agtatacgct caatcaaaac agaccatcgt ggctcagcac 2340
agctattggc cgatatcctg aagattctta tgatggctat ggtaactcgc aaggcaatcc 2400
agtaagtaaa aagagtagtt cctttacgta acgctactac tcgtagtgat gatgtgcaca 2460
agagcagcaa atccaattca gctgtagttc gattactgac aatgcaatta tgtcctctag 2520
tggttcattg ccactgccac atatgctgag ctctactacc gtgccatttt ggagtggcaa 2580
caacaagcat ccatcagtgt caactctgtc aacctgggct tctttagcaa gtttgattcc 2640
gatgcttctg tcggcactgt gtacacaccg ggcactgaag attttgccaa catggtctcc 2700
aacgtagcct tcgctgctga cgaattcttg gctaccattg agaaccattc tgccgttaat 2760
ggatccctct ctgagcaata taacagagat actggtatta tgcaaggcgc cagagatctc 2820
acctggtccc atgccgcatt tattactgct gcgaaggcaa agcagggtgc accaatacac 2880
tga 2883

<210> SEQ ID NO 21
<211> LENGTH: 1407
<212> TYPE: DNA
<213> ORGANISM: Artificial Sequence
<220> FEATURE:
<223> OTHER INFORMATION: Sequence is synthesized

<400> SEQUENCE: 21
atgccttctt ggaaaaccct gttcctcctc ctgggcccta tcgccaccgc tgccgctgct 60
cccgttgaca agcagtctct gcctaccggc aacagcacca ttagctcttg ggtcagcaag 120
caggaggaca tcagcttcag cgagatgctc cgaaacgtca accctgaggg caccgccaag 180
ggcttcgttg ccgcgtcgct cagcaccgct ggccccgact acttctacac ctggacccga 240
gacgccgctc tcgtttcccg agttattgct tacaagtaca acaccaccaa cgctggcgac 300
tctaagatcc acggcgttct ggacgactac gttaacttcc agattaacac ccagtctgag 360
tctacccctt gcaactgcct gggcgagcct aagttcaacc ctgacggcag ctctttcacc 420
ggcccttggg gccgccccca gaacgacggc cccgctgagc gagcctccag tttcatgctg 480
attgccgact ctttcctcag ccagaccaag aacgcctctt acttcaccaa caccctcaag 540
cctgccattt acaaggacct cgactacgtc gttgacacct ggtctaaccc ttgcttcgac 600
ctgtgggagg aggttaacgg catccacttc tacaccctca tggttatgcg acgatctctc 660
ctcgacggcg ctaacttcgc cacccgaaac ggcgacaact ccaaggcctc aacctactcc 720
ggcgtcgccg ccaagattca ggctcgactg aactcttttct gggacgccgg caagaactac 780
attaccgtta cccaggacta caagaacggc gttgagaagc ctagcggcct cgacgttagc 840
accctcattg ctgctaacgt cgctggcatg ggcgacggct tctacacccc cggcagcgag 900
cgcatcctcg ctaccgctct ggctttcgag aagagcatgg caagtctgta ccctctgaac 960
aacaacctgc ctagccacct gggcaacgcc attggccgat accccgagga cacctacaac 1020
ggcaacggca actcccaggg caacccttgg ttcctcgcta ccaccgcttt caccgagctg 1080
tactaccgcg ccattctgga gtggaagaac accggcgtta ccgtcacccc tatttctaag 1140
gacttcttcg tccgattcga cagcagcgct gctcctggca agaagtacaa ccccggctcc 1200
caggagttcg ctaccctgac ccagtctatt gctgccgccg ctgaccgatt catgtccacc 1260
gtccagtacc accagaaccc taacggctct ctgtctgagg agttcgaccg atctagcggc 1320
tacatgaccg gcgcccgaga cctgacctgg agtcacgctg ctttcattac cgctgctcag 1380
gcccgagctg gctctccttc tttctaa 1407

<210> SEQ ID NO 22
<211> LENGTH: 1818
<212> TYPE: DNA
<213> ORGANISM: Artificial Sequence
<220> FEATURE:
<223> OTHER INFORMATION: Sequence is synthesized

<400> SEQUENCE: 22
atgaagctgt tcggcaccct gaaggcttct ttcgttttcc tgattggctg cattgttttc 60
gctatggccg acaccgtccc taccacccag gttaagctgc agtcttacac ctactctggc 120
ggcgtcctgt ctggcaccat ctacgtccag aacattgact acaccaaggt tgttaccgtt 180
atatattccg acggctctgg caactggaac aacaacggca acaccattag cgcttcttac 240
agcagctcca tttctggcac caactacgag tactggacct tctctgccag cgtcagctct 300
attcagcagt tctacatctc ttacctcgtt gacggcacca cctactacga caacaacggc 360
ggctacggcg ctaactacgc cgttaccgcc accaccacca ccgcttcttc caccaccaag 420
accacctccg gcaccaccaa gacctccacc accagcaccg ctaccgccac cagcaccggc 480
acctcttcct tccctagcgg caactctacc attagcacct ggagcccttc ccagcacagc 540
attagcctgt acgccatgct gcgaaacatt aaccctcccg gctctgctgc tggcttcatc 600
tctgctagtc tgtctacctc cggccccgac tactactact cttggacccg agacagcgcc 660
ctcgttgctc acgtcatcgt taacgagtac aacaccacct accagggcaa ctccaccctg 720
ctgggcatcc tcaaggacta cgtcacctac agcctgaacg cccagaccac ctctaccgtt 780
tgcaactgcc tgggcgagcc taagttcaac cccgacggct cctccttcac cggcgcttgg 840
ggccgccctc agaacgacgg ccccgctgag cgagctgttt ctttcatata tttcgctgac 900
tcttacctga cccagacctc tgacagctct tacgtcaccg gcaccctcgc cccgctata 960 tacaaggacc tcgactacgt tgtttccgtt tggtctaacg gctgcttcga cctgtgggag 1020
gaagttaacg gcattcactt ctacaccctc atgttcatgc gacgaggcct gctcgacggc 1080
gctaacttcg caagccgaaa cggcgactct acccgagcga gcacctacac ctctaccgct 1140
gctagtatca agaccaagat tgacggcttc tgggtcagca gcggcaacta cgtccaggtt 1200
tcccagtctg ttacctctgg cgtctctaag gctggctacg acgcttccac cctgattgcc 1260
gctaaccagg cctctcgggg cgacggcttc tacacccccg gctccgacaa gatgctcgct 1320
accgccgttg ctattgagtc tcagttcagc agcctgtact ctattaacac caacaaggct 1380
tcttacctgg gcaacgccat tggccgatac cccgaggaca cctacaacgg caacggcaac 1440
tcccagggca acccttggtt cctgtgcacc aacgctttcg gcgagctgtt ctaccgcgcc 1500
attagcgagt ggaacgccgc tggctccgtt accgttaaca gcgttaacct cgctttcttc 1560
aagaagtacg actctagcac cagcagcggc accacctaca ccgttggcac cagcgcttac 1620
aacaacctgg ttcagaacgt tgccctcgct gccgacgctt acttctctac cgtcaagtac 1680
cacgccctga ccaacggctc catgtctgag cagtacgacc gatctagcgg catggctacc 1740
ggcgcaagag acctgacctg gtctcacgcc gccatgatta ccgccctgaa ggccaagtcc 1800
ggcacccccg tttactaa 1818

<210> SEQ ID NO 23
<211> LENGTH: 1809
<212> TYPE: DNA
<213> ORGANISM: Artificial Sequence
<220> FEATURE:
<223> OTHER INFORMATION: Sequence is synthesized

<400> SEQUENCE: 23
atgaagcctt tcggccctat caagaccacc ctgttcatta ttatctctca cttcagcctg 60
aactccctcg ctgacaccgt tcctaccacc caggttgagg tcaagaccta cacctactct 120
ggcggcgagc tgtctggcac catatacgta gagaacatag actacaccaa ggttgttacc 180
gtcatctacg ctgacggctc tgacgactgg aacaacaacg gcaacaccat tgctgccgct 240
ttcagcgagt ccatctctga caccaactac gagtactgga ccttctctag ctctgttaac 300
tctattaaag agttctacgt caagtacgac gttgacggca acacctacta cgacaacaac 360
ggcaacgcta actaccaggt ttctgctagt agcaccacca ccaccaccgc caccaagacc 420
accaccaccg ctaccaagac caccgccacc gctaccagca ccgccaccgg cagcacctct 480
ttccctagcg gcaacagcac catcagctct tggattaagg gccaggaaga cacctcccgg 540
tccgtcatgc tcggcaacat taaccctcct ggctctgcta ccggcttcat tagcgccagc 600
ctgtctacct ctggccccga ctactactac cactggaccc gagacgctgc cctcgttgct 660
cacgttattg ttaacgacta caacaccacc ctgtctggcg actctagcac cctgcaggtc 720
atcaaggact acgttacctt cagcgtcaac tcccagtccg agtctaccgt ttgcaactgc 780
ctgggcgagc ctaagttcaa ccccgacggc tcctcttaca ccggcgcttg ggccgcccc 840 cagaacgacg gccccgctga gcgagctacc accttcattt tcttcgccga cacctacctc 900
gcccagggcg gcgacagctc ttacgttacc ggcaccctcg cccccgctat atatgctgac 960
ctggactacg ttgttaacaa ctggtctacc ggctgctacg acctgtggga agaggttaac 1020
ggcattcact tctacaccct catggttatg cgccgaggcc tcatagatgg cgcttccttc 1080
gcttcccgaa acggcgacag cacccgaagc tcctcttaca cctccaccgc caagtctatt 1140
gctaccaaga ttgactcttt ctggtctgct tctaacaact acgttgctgt ttcccagagc 1200
gttacctctg gcgtctccaa ggctggctac gacgcctcta ctattattgc tgctaaccag 1260
gcgtcgctgg gcgacggctt ctacaccccc ggctccgaca agatgctcgc tacctccgtt 1320
gccgttgaga acgctttcag cagcctgtac accgttaaca ccggcaaggc ttcttacctg 1380
ggcaacgcca ttggccgata ccctgaggac acctacaacg gcaacggcaa ctctcagggc 1440
aacccttggt atctgtgcac caacgccctg ggcgagctgt actaccgcgc catcaaagag 1500
tggaacgctg cgggaagcgt taccgtcaac tccgttaacc tgggcttctt ccagaagatt 1560
gactccagca ttagcagcgg caccaccttc accctgggca cctccgacta cagcaccctc 1620
gttgacaacg tcgccctcgc cgctgacaag ttcttcgccg tcgtccagta ccacgagcga 1680
tctaacggct ccatgcctga gcagttcggc cgagaggacg gcctgcctac cggcgcgaga 1740
gacctgacct ggtctcacgc cgccatgatt agcgctgccc gagctaaggc tggcaccccc 1800
gtttactaa 1809

<210> SEQ ID NO 24
<211> LENGTH: 1806
<212> TYPE: DNA
<213> ORGANISM: Artificial Sequence
<220> FEATURE:
<223> OTHER INFORMATION: Sequence is synthesized

<400> SEQUENCE: 24
atgaagttct ctcacctgtt ccgaaagcct accctcctca ttgttacctt cctgaccgcc 60

```
accgttttcg ccgagaccgt ccctaccacc tcccaggtta agctcaagtc ttacacctac    120
gacggctcta ccctgtctgg ccagatttac atccagaaca ttgcttacac caaggttgtt    180
accgtcattt actctgacgc cagctctaac tggaacaaca acggcaacac cattgctgcc    240
tcttacacca acggcattag cggcaccaac tacgagtact ggaacttcac cggccccgtc    300
agctctatta acgccttcta cattaagtac gacgtttctg gcaacaccta ctacgacaac    360
aacaacaacg ctaactacca ggttaccaag acctccacca ccaccaccac cagcaccgcc    420
accgctacca ccaccaccaa gacctctacc cctacctcca ccggcgttcc ttctaacttc    480
cctaccggca actctaccat cagcacctgg ctcaagtccc agattggcat ctctcgatac    540
gccatgctgc gaaacattaa ccccgctggc tctgccgttg gcttcattgc tgctagcctc    600
agcaccgcta accccgacta ctactacgct tggacccgag acagcgccct gacctcttac    660
gtcatcgcta acgactacaa ctctaccctc gctggcaaca gcaccatcct gcagattatg    720
aaggactacg ttaccttcag cgtcaagtct cagtccgttt ctaccgcttg caactgcctg    780
ggcgagccta agttcaaccc cgacggcagc tcttacaccg gcgcttgggg ccgcccccag    840
aacgacggcc ccgccgagcg agctaccacc ttcatcctgt tcgctgactc ttacctgaag    900
cagaccggcg acgcttctta cgttaccggc accctgaagc ccgctatttt caaggacctc    960
gactacgttg ttaacacctg gaccaacggc tgcttcgacc tgtgggagga ggttaacggc   1020
gtccacttct acaccctcat ggtcatgcga aagggcctga tccgaggcgc caacttcgct   1080
acccgaaacg gcgacagcac ccgagctagc acctacacca acaccgctgc tagcatcaag   1140
accaagatgg actctttctg gagctctggc aacaactaca ttgctgtctc ccagtctgtt   1200
accggcggcg tctccaaggc tggctacgac gttgctaaca ttattgccgc taacgttggc   1260
agcctgcagg acggcgttta cacccccggc tccgaccgca ttctcgccac cgccgttgcc   1320
gttgaggcta agttcgccag cctgtacggc gttaactcta acctccccgg ctacctgggc   1380
aactctattg gccgataccc tgaggacacc tacaacggca acggcaactc ccagggcaac   1440
ccttggttcc tcgccaccaa cgcttacgcc gagctgtact accgcgccat tcgcgagtgg   1500
tacgacaacg gcggcgtcac cgttaactct gttaacctcc ctttcttcaa gaagttcgac   1560
agcagcgctg ctagcggcac cacctacacc gttggcacca ccgctttcaa caccatggtt   1620
tctaacgttg ctgctgccgc tgacaagttc ttcagcaccg tcaagttcca cgcttacacc   1680
aacggctcca tgtctgagca gttcggccga aacgacggcc tgtgcaccgg cgcaagagac   1740
ctgacctggt ctcacgctag cctgattagc gctgccctcg ccaaggctgg caccccctagc   1800
gtctaa                                                               1806
```

<210> SEQ ID NO 25
<211> LENGTH: 1797
<212> TYPE: DNA
<213> ORGANISM: Artificial Sequence
<220> FEATURE:
<223> OTHER INFORMATION: Sequence is synthesized

<400> SEQUENCE: 25

```
atggtttctt tcaacttcct gaagaagcct gttttcattg ttatcacctg cctcaccgtc     60
agcgtttgcg cccagtctgt tcctaccagc gaccccgtta aggttaagac cttctcttac    120
gacggcaact ctttctctgg ccagatttac atcaagaaca ttgcttacga gaagaccgtt    180
accgttattt actccgacgg caccggcaac tggaacaaca acaacaacaa gattgccgct    240
gctttcagcg aggccatctc cggctctaac tacgagtact ggaccttcag cgctagcgtt    300
```

cctagcatca agcagttcta cgtcaagtac gacgtttccg gcaagaccta ctacgacaac 360
aacggctcta aggactacaa cgtcgttacc agcggcccta ccaccaccag ctctggccct 420
agcaagacca ccaccaacgg ccccgctcct accagcacca acaccaactt ccctagcggc 480
aaccctagca ttacctcttg gattgacaag cagattgaca tctcccgatc tgccatgctg 540
aagaacatta accccgctgg caccgttaag ggcttcattg ccgccagcct cagcacctct 600
aaccccgact acttctacgc ttggacccga gacgccgctc tcgttgccca cgttgttgct 660
aacgactaca accgaaccaa gtctggcgac gccacctacc tgggcctcct gaaggactac 720
gtcaccttct ctattaactc ccagaacacc cctaccgctt gcaactgcct gggcgagcct 780
aagttcaaca aggacggctc cggctacaac ggcccttggg gccgccctca gaacgacggc 840
cccgccgagc gagctgacac cttcgtcctc attgccgact ccattctgac ccagaccaag 900
gacgtctctt acgttaccgg caccctgcgc cccgctattt acaccgacct cgactacgtt 960
gtccgaacct ggtctaacgg ctgcttcgac ctgtgggagg aggttaacgg cgtccacttc 1020
tacaccctca tggttatgcg acgagctctc ctcgttggcg ctaacttcgc tagccgaaac 1080
ggcgactctg cccgagcttc taactacaac aacgctgcta actccattaa gtctaagatt 1140
gactctttct ggtcctctaa caacaactac gttgctgttt cccagtctgt taccggcggc 1200
gtttccaagg ctggctacga cgtcagcacc ctcatcgctg ctaacgttgg cagcctgtct 1260
gacggcttct acacccctgg ctctgagcgc atgctcgcca ccgccgtcgc tattgaggac 1320
aagttcgcta acctgtacgg cattaaccga aacctcgaca gcagcctggg caacgccatt 1380
ggccgatacc ccgaggacac ctacaacggc aacggcaact cccagggcaa cccttggttc 1440
atcgccacca acgcttacgc tgagctgtac taccgagcta ttaaggagtg gaacaacaac 1500
ggcggcgtca ccgtcaccaa cgttaacctg aacttcttca agaagttcga cggcagcgct 1560
agcgttggca ccaagtacac cgctggctct gctgcttaca acaccctgac ccagaacatc 1620
gccctcgccg ctgacaagtt cttcaacacc gtcaaggtcc acgctgccac caacggctcc 1680
atgtctgagc agtaccaccg agacaccggc agcatgaccg gcgcaaggga cctgacctgg 1740
tctcacgcta gcctgattac cgccgccctc gccaaggctg gcacccccgt cgcctaa 1797

<210> SEQ ID NO 26
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 26
atgaagctgt tcggcctgcc cctcaagcct agcctgttct tcgtcgtctc ttacctgtct 60
ttcctcgctt ctgctgccag catccctagc agcagcgagg tccagctcga cacctacgct 120
tacgacggcg ccaagttctc tggcaagatt tacgtcaaga acattgctta cgagaagacc 180
gttaccgttg tttacgctga cggctctgac aactggaaca acaacggcaa cattattagc 240
gctaccttca gcacccctat ttccggctct aactacgagt actggacctt cagctctagc 300
attagcggca ttaaggagtt ctacatcaag tacgtcgttt ccggcaagac ctactacgac 360
aacaacggca ccaagaacta ccaggtttcc accaccagct ctaccaccac cgctagcacc 420
accaccgcta cccgaaccac caccgctggc accaccagca cctctaccac cgctgcccct 480
acctctacct ccagcggctc cttccctagc ggcaactcta ccgttagctc ttggattaag 540

```
cgacaggaga agatctcccg attcgccatg ctgcgaaaca ttaacccccc tggcagcgct    600
gctggcttca ttgctgctag cctgtctacc tctggccccg actactacta ctcttggacc    660
cgcgacagcg ccctgacctc taacctgatt gcttacgagt acaacaccac cctgtctggc    720
aacaccacca ttctgaacat cctgaaggac tacgttaagt tctccatcag ctcccagacc    780
accagcaccg tttgcaactg cctgggcgag cctaagttca accacgacgg cagctcttac    840
accggcgctt ggggccgccc ccagaacgac ggccccgctg agcgagctaa caccttcatc    900
ctgttcgccg actcttacct cgaccagacc aaggacgctt cttacgtcac cggcaccctg    960
aagcccgcta ttttcaagga cctcgactac gttgttaacg tttggtctaa cggctgctac   1020
gacctgtggg aggaggttaa cggcgttcac ttctacaccc tcatggtcat gcgaaagggc   1080
ctcctgctgg gcgctgactt cgctaagcga aacggcgact ctacccgagc tagcacctac   1140
accaacaccg ctagcaccat tgctaccaag atctcctctt tctgggttag cagctctaac   1200
tggatccagg tttctcagtc tgttaccgcc ggcgtttcca agaagggcct cgacgtcagc   1260
accctcctcg ctgccaacct gggctccgtt gaggacggct tcttcacccc cggctccgag   1320
aagattctgg ccaccgccgt tgccattgag gacgctttcg ctagcctgta ccctattaac   1380
tctaacctgc cttcttacct gggcaactcc attggccgat accccgagga cacctacaac   1440
ggcaacggca actcccaggg caacccttgg ttcctcgccg ttaacggctt cgccgagctg   1500
tactaccgag ctatcaagga gtgggttaac aacggctccg ttaccgtctc taacatctcc   1560
ctgtccttct tcaagaagtt cgacagcagc gccaccgccg gcaagaccta caccgccggc   1620
accgctgact tcaacaacct cgcccagaac attgctctgg gcgctgaccg attcctgtcc   1680
accgtccaga cccacgcttt caacaacggc tccctcgccg aggagtacga ccgaaccacc   1740
ggcgtcagca ccggcgcccg agacctgacc tggtctcacg ctagcctcat taccgctgct   1800
tacgccaagg ctggcagccc tgccgcctaa                                    1830
```

<210> SEQ ID NO 27
<211> LENGTH: 1827
<212> TYPE: DNA
<213> ORGANISM: Artificial Sequence
<220> FEATURE:
<223> OTHER INFORMATION: Sequence is synthesized

<400> SEQUENCE: 27

```
atgaagttct ctaacctcct gaagaagccc ctcctgctca ttgctggcat tctcgctgcc     60
accgtcgttg ccgagaccgt ccctaccacc gctgctgtta aggttaagtc tttcacctac    120
gacggcagca ccttcgctgg ccagatttac gtcaagaaca tcgcttacac caagaccgtt    180
accgttattt actctgacgc ctctaacaac tggaacaaca acggcaacac cattgccgcc    240
tcttacagcg agggcatctc tggcaccaac tacgagtact ggaccttcag cgcccctgtt    300
tccggcatca agcagttcta cgtcaagtac gttgtcagcg gcaccaccta ctacgacaac    360
aacaactctg gcaactacca ggttaccacc accaccacca ccaccgcccc taccagcacc    420
acctccggcg gctctagcac caccaccggc ggctccacca ccaccgccac ctctgtccct    480
accggcgtcc ctagcggctt ccctaccggc aacagctcta ttagctcttg gattgacggc    540
cagacctccg tttctcgata cgccatgctg cgaaacatta accccgctgg cgctgtttcc    600
ggcttcattg ctgctagcat gtctacctct ggccccgact acttctacgc ttggacccga    660
gacagcgccc tgacctctca cgtcgttgct tacgactaca acaccaccct cgctggcaac    720
tctaccatcc tgggcctcct gaagaactac gttaccttct ctattaactc tcagaccacc    780
```

```
agcaccgttt gcaactgcct gggcgagcct aagttcaaca aggacggcag ctcctacacc    840

ggcgcttggg gccgacccca gaacgacggc cctgctagcc gagctgacac cttcatcctc    900

attgccgact ctattctgaa gcagaccggc gacgctacct acgttaccgg caccctcgcc    960

cccgctattt acaaggacct cgactacgtt gtcagcacct ggtctaacgg ctgcttcgac   1020

ctgtgggagg aggttaacgg cgttcacttc tacaccctca tggtcatgcg acgaggcctg   1080

attaagggcg ctaacttcgc ttcccgaaac ggcgacaaca cccgagctaa cacctacacc   1140

aacaccgccg ctagcatcaa gaccaagatt gactctttct ggaactctaa cggcaactac   1200

gttaccgttt cccagtctgt taccggcggc gtctccaagg ctggctacga cgctagcgtc   1260

ctgattgctg ctaacctggg ctctgtccag gacggcttct acacccctgg ctccgacaag   1320

atgctcgcta ccgctgttgc cattgagtct aagttcgcca gcctgtactc cattaaccag   1380

aacctgaacg gctacctggg caacgccatt ggccgatacc ccgaggacac ctacaacggc   1440

aacggcaact cccagggcaa cccttggttc atttgcacca acgctttcgc cgagctgtac   1500

taccgcgcca ttaaggagtg gttcaacaac ggcggcgtta ccgttacctc catcagcctg   1560

aacttcttca agaagttcga cagctctgct gccgttggca ccaagtacac cgttggcacc   1620

tccgccttca acagcctcgt ccagaacgtc gccgtcgctg ccgacgcttt cttcagcacc   1680

gtcaagttcc acgccgctac caacggctcc atgagcgagc agtacggccg atctgacggc   1740

ctcatgaccg gcgccagaga cctgacctgg tctcacgcta gcctgattag cgcttcttac   1800

gccaaggctg gcagccccgc cgcctaa                                       1827
```

```
<210> SEQ ID NO 28
<211> LENGTH: 1809
<212> TYPE: DNA
<213> ORGANISM: Artificial Sequence
<220> FEATURE:
<223> OTHER INFORMATION: Sequence is synthesized

<400> SEQUENCE: 28
```

```
atgaagctga actccgtttg gaaggctttc agcattctgc tcatggctac tatggctttc     60

gctgctaccg tccccaagac ccaggttaag ttagaggctt acacctactc tgactctatt    120

ttctctggcc gaattttcgt ccagaacatc gactacacca agattgttac cgtttactgg    180

tctgacgcct ctaacaagtg ggacagctct aagtactaca ccgaggccgc ttacacccac    240

agcatccccg gcaccaacta cgagtactgg gacttcagcg ctaccattgg ccctagcggc    300

atcaagcagt tctacatctc ttaccaggtc cgaggcgtca cctactacga caacaacggc    360

ggctacggcg tcaactacga cgtcatctcc agccctccta ccacctctga cgccaccacc    420

attcctacca ccaccacctc cgctattcct agctctacca ccaccatccc tgccagcacc    480

ggcgtcccta gcggcaactc caccattacc gtttgggctg actcccagca caagatttct    540

tggaaggcta tgctcgctaa cattaaccct cccggcagcg ccaccggctt cattgctgcc    600

tccctgtcta cctccggccc tgactactac tacgcttgga cccgagacgc cgcaatggtt    660

gctcacgtta tcgttaacgc ttacaacacc accaaggctg gcgacgctac caccctgggc    720

gttctgaagg acttcgttac cttccagatc aaggctatgg ctacctctac cgtttgcaac    780

tgcctgggcg agcctaagtt caaccccgac ggctcctctt acaccggccc ttggggccgc    840

ccccagaacg acggccctgc tgagcgcgct accaccttca tcctgttcgc cgactcttac    900

ctgtctcaga ccggcgacgc tgcttacgtc accaccctga agcgagccat tttcaccgac    960
```

```
ctcgactacg ttgttaccac ctggcaggac aactgcttcg acctgtggga ggaggttaac   1020

ggcctgcaca tgtacaccct cgctgttatg cgacgatctc tcgttgacgg cgcctctttc   1080

gccgctcgaa acggcgacaa cacccgagcc tctacctaca ccaacaccgc caagtctatt   1140

gagaccaagc tcgcctcttt ctacaacagc tcctctaact acgtcgttgt taccaagaac   1200

ttcgctggcg gcgttaacaa ggctggcctg gacacctcca ccctgattgc tgccaacacc   1260

gctggcctgg gcgacggctt cttcaccccc ggcagccccg agatcctcgc taccgccgct   1320

gccattgaga agtctttcgc cgacctgtac ggcattaaca agcagattcc taactggctg   1380

ggcaccgcta ttggccgata ccccgaggac acctacaacg gcaacggcaa ctctcagggc   1440

aacccttggt tcatttgcac cgccaccttc gccgagctgt actaccgagc tattctggag   1500

tggcagcacg ccggcagcgt taccgtcaac aacgttaacc tgcctttctt caagaagttc   1560

gactctagca cctccagcgg caccacctac accgttggca ccagctcctt cgacagcctg   1620

attagcaagg ttgcttacgc cgctgacaac ttcttctcta ccattaagta ccacgctgcc   1680

accaacggca gcatgtctga gcagttcaac cgagacaccg gcttcatgac cggcgccagg   1740

gacctgacct ggtcgcacgc tgccttcatt accgccgcta aggctaaggc tggcaccccc   1800

gtttactaa                                                           1809
```

<210> SEQ ID NO 29
<211> LENGTH: 1821
<212> TYPE: DNA
<213> ORGANISM: Artificial Sequence
<220> FEATURE:
<223> OTHER INFORMATION: Sequence is synthesized

<400> SEQUENCE: 29

```
atgcgcccta gcctcgtttg gaagtctctc ctgatggttg tcctgaccgc tgcaatgggc     60

acctacgccc agaccgtccc tagcgttcct attaagttag aatcttacac ctactctgac    120

aacgttttcg ctggccgaat tttcatccga aacattgctt acaccaaggt tgtcaaggtt    180

ttctggtctg acgagtccgg caactggaac ggcaacggca actacgttga cgcctcttac    240

tctggctcca tctccggcac caactacgag tactgggagt tcagcaccac cattggctct    300

gccggcatct cccagtctta cctgcgatac gacgtcagcg gctctaccta ctacgacaac    360

aacggcaacg ctaactacga cattgaggag gacagcaccc ctacccctac caccaccacc    420

acctctacca ccaccatcac caccaccacc acctccggca cctctacccc tacctctgtt    480

cctaccgagg tccctgccgg caacaccacc gtcaccgact gggttaacga ccagttagaa    540

atttcttggc ctagcctcct caagaacgtc aaccctagcg gcgctgttac cggcttcatt    600

gctgcatctc tgtctaccaa cgaccccgac tacttctact gctggacccg agacgccgcc    660

ctcgttgccc gcgtcatggt ttacatgtac aacaccaccg aggctggcga cacctccctg    720

cgatctaagt tacaggacta cgttaccttc cagattaact ccatgaaaac cgccaccgtt    780

tgcaactgcc tgggcgagcc taagttcaac aaggacggct ccggctacag cggcgcttgg    840

ggccgccctc agaacgacgg ccccgctgac cgagctatta ccctgattct gttcgctgac    900

tctttcatcg cccagggcgg cgatgtttct tacatcacca acaccctgaa gcctgctatt    960

tacaccaacc tggactacgt tgttaacacc tggtctaacg tttgcttcga cctgtgggag   1020

gaggttaacg gcgtccacat ttacaccctg tctgttatgc gaaagggcct cctggaaggc   1080

gctgacttcg cttctcgaaa cggcgacagc acccgcgcca acacctaccg atctaccgcg   1140

tcctccatca agacccgact ggagtccttc tggagcagct ctaacaacta cattaccgtc   1200
```

```
acccagtctt actctggcgg cgttaacaag gctggcctgg acgtcagcac cctcctcgcc   1260

gctaacggcg ccagcatgaa cgacggcttc tacacccccg gctctgacaa gatgctcgct   1320

accgccgttg ccattgagaa ctccttcgcc ggcatttacg ccgttaacca gaaccgcccc   1380

gactggaagg gcaccgctat tggccgatac cctgaggaca cctacgacgg ccacggcaac   1440

tcccagggca acccttggtt cattgctacc gccgcttacg ctgagatgta ctaccgagct   1500

atactggaat ggcagcagca gccttccatt accgttaact ctattaacct cagcttcttc   1560

aagaagttcg actctagcgc tgctgttggc accgtttaca agcccggcac ccaggctttc   1620

aacaacatgg tttctaacgt tgctttcgct gccgacgagt tcttcagcac catgaacttc   1680

cacagcgcta ccaacggctc tatgagcgag cagtacaacc gaaacaccgg cattatgcag   1740

ggcgcaagag acctgacctg gagccacgct gctttcatta ccgctgctaa ggccaagctg   1800

ggcacccccg ttttctaata a                                              1821
```

<210> SEQ ID NO 30
<211> LENGTH: 1809
<212> TYPE: DNA
<213> ORGANISM: Artificial Sequence
<220> FEATURE:
<223> OTHER INFORMATION: Sequence is synthesized

<400> SEQUENCE: 30

```
atggttttca gcaagctgtt caagaagcct attctcctga ttgttaccta cctgaccgtt     60

accgtcgtcg ccgagaccgt tcctacctct gctcaggtcc aggttaagtc tttcaactac    120

gacggcagca ccctgtccgg ccagatttac gtccagaaca ttgcttacga aaagaccgtt    180

accgttgttt actctgacgg ctccgacaac tggaacaaca acggcaacac cattgctgcc    240

tcttacagct ctagcattag cggctctaac tacgagtact ggaccttcag ctctagcgtc    300

cccagcatta agcagttcta catcaagtac gttgtcgctg gcaagaccta ctacgacaac    360

aacggcacca agaactacca ggtttccgct tccaccccta ccaccaccac caccaccacc    420

tcctctggcg ccaccaagac caccaccacc atcggcccta ccagcaccag caccgttttc    480

cctagcggca acagcaccat cagctcttgg ctgaagggcc agattgagac ctcccgattc    540

gccatgctgc gaaacattaa ccccgctggc accgtcaagg gcttcatcgc cgcctcgctg    600

tctaccgcta accccgacta cttctacgct tggacccgag acgctgctct cgtcggccac    660

gtcattgcta acgactacaa ccgaaccctc gctggcaaca gcacctacct gggcctcctg    720

aaggactacg tcaccttctc tgttaactcc cagtctacct ccaccatttg caactgcctg    780

ggcgagccta agttcaacaa ggacggctct ggctactctg gcgcttgggg ccgccctcag    840

aacgacggcc ccgccgagcg agctgacacc ttcatcctca ttgccgactc catcctgaag    900

cagaccggcg acgccaccta cgttaccggc accctgcgcc ctgctattta caaggacctc    960

gactacgtcg ttaacgtttg gtctaacggc tgcttcgacc tgtgggagga ggttaacggc   1020

gtccacttct acaccctcat ggttatgcga cgatctctga tcctgggcgc taacttcgct   1080

tctcgaaacg gcgacagcac ccgagcgtcc acctacacca acaccgctaa ctctattaag   1140

accaagattg acaccttctg gtcttcctct aacaactacg ttgctgtttc ccagtctgtt   1200

accggcggcg ttaacaaggc tggctacgac gttgctaacc tcatcgccgc taacgttggc   1260

agcctcgacg acggcttcta cacccccggc agcgagcgaa tactcgccac cgctgttgct   1320

gttgagtcta agttcgcttc gatttacggc gtcaaccaga acctgccttc ttggctgggc   1380
```

```
aactccattg gccgataccc cgaggacacc tacaacggca acggcaactc tcagggcaac   1440

ccttggttca ttgctaccaa cacctacgcc gagctgtact accgcgctat taaggagtgg   1500

accaacaacg gcggcgttac cgtcaccaac gttaacttca acttcttcaa gaagttcgac   1560

agctccgctt ctgttggcac caagtacacc gttggcacca gcgctttcaa caccctgacc   1620

cagaacgttg ccctcgctgc cgacaacttc ttctctaccg tcaaggttca cgctgccacc   1680

aacggctcca tgtctgagca gttcggccga gactccggcg tcatgaccgg cgcccgcgac   1740

ctgacctgga gtcacgcatc actgattacc gccgccctcg ccaagaccgg cgcccctgtt   1800

gcctaataa                                                           1809
```

```
<210> SEQ ID NO 31
<211> LENGTH: 1833
<212> TYPE: DNA
<213> ORGANISM: Artificial Sequence
<220> FEATURE:
<223> OTHER INFORMATION: Sequence is synthesized

<400> SEQUENCE: 31

atgaagttct ctaacctcct gaagaagccc ctgctcctga ttgccggcat tctcgctgtt     60

accgtcgttg ccgagaccgt ccctaccacc gaggctgtta aggtcaagtc tttcacctac    120

gacggcagca ccctcgctgg ccagatttac atcaagaaca tcgcttacac caagaccgtt    180

accgttattt actccgacgc ctccgacaac tggaacaaca acggcaacac cattgctgct    240

tcttactccg ctgctattgc tggcaccaac tacgagtact ggaccttcag cgcccccgtg    300

tccggcatta agcagttcta cgtcaagtac gttgtttctg gcaccaccta ctacgacaac    360

aacaactctg gcaactacca ggtttccgtt accaccacca ccaccaccgc ccctaccacc    420

accacctctg gcggctctag caccaccacc ggcggcagca ccaccaccgc cacctccgtc    480

cctaccggcg tccctagcgg cttccctacc ggcaacagca ccattagctc ttggattgac    540

ggccagacct ctgtttcccg atacgccatg ctgcgaaaca ttaaccctgc tggcgctgtt    600

accggcttca ttgccgcatc catgtctacc tctggccccg actacttcta cgcttggacc    660

cgagacagcg ccctgacctc tcacgtcgtt gcttacgact acaacaccac cctcgccggc    720

aacagcacca tcctgggcct cctgaagaac tacgttacct tcagcctgaa ctctcagacc    780

acctctaccg tttgcaactg cctgggcgag cctaagttca acaaggacgg ctctggctac    840

tccggcgctt ggggccgccc ccagaacgac ggccccgcta gtcgagctga caccttcatc    900

ctcatcgctg acagcattct gaagcagacc ggcgacgcca cctacgtcac cggcaccctc    960

gcccccgcta tttacaagga cctcgactac gttgtctcta cctggtctaa cggctgcttc   1020

gacctgtggg aggaggttaa cggcgttcac ttctacaccc tcatggttat gcgacgaggc   1080

ctcgtcaagg gcgctaactt cgcatcccga aacggcgact ctacccgagc taccacctac   1140

accaacaccg ccgcgagcat taagaccaag attgactcct tctggaactc taacggccag   1200

tacgtcagcg tttcccagtc tgttaccggc ggcgtttcca aggctggcta cgacgccagc   1260

gtcctgattg cttctaacct gggctctctc caggacggct tctacacccc tggcagcgac   1320

aagatgctcg ccaccgctgt cgccattgag tccaagttcg ccagcctgta ctccattaac   1380

cagaacctga acggctacct gggcaacgct attggccgat accccgagga cacctacaac   1440

ggcaacggca actcccaggg caacccttgg ttcatttgca ccaacgcttt cgccgagctg   1500

tactaccgag ctattaagga gtggttcaac aacggcggcg ttaccgttac ctccattagc   1560

ctgaacttct tcaagaagtt cgacagctct gccgccgttg gcaccaagta caccgttggc   1620
```

accagctctt tcaacagcct cgtccagaac gttgctgttg ctgccgacgc tttcttcagc 1680
accatcaagt tccacgccgc taccaacggc tccatgagcg agcagtacgg ccgaaccgac 1740
ggcctcatga ccggcgctag agacctgacc tggagtcacg catctctgat cagcgcctct 1800
tacgctaagg ctggctctcc cgctgcctaa taa 1833

<210> SEQ ID NO 32
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 32
atgatgccta accacatttg gaagtgcctg ttcctcgcca tgaccaccgt tttcatgacc 60
gtcctcgtcc agggcgctcc cacctctgag attgaactag actcttacac ctacaccggc 120
ggcgttttct ccggccgact gtacgtcaag aacatcgctt acaccaagga ggttaacgtt 180
tactggtctg acgccagcga ggactgggct aacaacggca actacgttgc cgctacctac 240
tctgaggcta tctccggcac caactacgag tactgggagt tcagcgctaa gattggctct 300
agcggcatca gcgagtctta catcaagtac accgtttccg gctctaccta ctacgacaac 360
aacggcggca agaactacgc catcaccgag accaccaccc ctaccattac cgccacccct 420
acctctacca ccgctaccac caccattagc tctaccacca ccaccgccac ctccatccct 480
acctctgttc ctagcaccgt ccccgagggc aacgttaccg tcaccgagtg ggttaacaag 540
cagctcaaaa tatcttggtc cgacctcttg caaaacgtta acccttctgg caccgttacc 600
ggcttcattg ctgcctcact cagcacctcc aaccccgact acttctactg ctggacccgc 660
gacgccgcaa tggttgcccg cgttatgacc tacatgtaca acaccaccga ggctggcgac 720
agcagcctgg agagcgccct gaaggactac attaccttcc agattaactc tatgaaaacc 780
gctaccgctt gcaactgcct gggcgagcct aagttcaaca ccgacggctc cggctactcc 840
ggcccttggg gccgccccca gaacgacggc cctgctgagc gcgctaccac catgattctg 900
ttcgctgact cttacctcgc ccagggcggc gacacctctt acgttaccaa caccctgaag 960
cctgctattt acaccaacct ggactacgtt gttggcacct ggtctaacaa ctgcttcgac 1020
ctgtgggagg aggttaacgg cgttcacatt ttcaccctcg ccgtcatgcg aaagtctctc 1080
ctcgacggcg ctgacttcgc tgcccgaaac ggcgacacct cccgcgttag cggctaccag 1140
agcaccgctt ctagcattaa gaccaagctg gagtctttct ggtctagctc caacaactac 1200
attaccgtca cccagtctta ctctggcggc gtccagaagg ccggcctgga cgtcagcacc 1260
ctgattgctg ctaaccaggg ctcgatgggc gacggcttct acacccctgg ctctgacaag 1320
atgctcgcca ccgctgttgc tattgagaac tctttcgcta acatttacac cattaacaag 1380
aacaagcctt cttggctggg caccgctatt ggccgatacc ccgaggacac ctacaacggc 1440
aacggcaacg gccagggcaa cccttggttc atcgctaccg ccacctacgc cgagctgtac 1500
taccgagcta ttttggaatg gcagcagcag gagtctgtta ccgttaacag cgtcaacttc 1560
gacttcttct ctaagttcga cagcagcgcc aaggttggca ccgtttacac ccctggcacc 1620
gacaccttca acactatggt ttctaacgtt gctttcgctg ccgacgagtt cctcagcact 1680
atggagcact acgctgccac caacggctct atgtctgagc agttcaaccg agagaccggc 1740
agcctgaccg gcgcccgaga cctgacctgg tcgcacgctg ctttcattac cgctggcaag 1800
gccaagctgg gcattcctag cttctaataa 1830

<210> SEQ ID NO 33
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 33
atgaagttca gcaagctgtt caccaagcct accctgttca tcgtttctat tattatcagc 60
gttgcttcta gcgagaccgt ccctaccacc gctaacgtcc tcgttaagtc ttacacctgg 120
gacggcgcta ccctgtctgg ccagatttac attaagaacc tcgcttacgc caaggttgtt 180
agcgttattt actctgacgc taacgacaac tggaacaaca acggcaacaa ggttgccgct 240
tcttactctg ctggcattga cggcaccaac tacgagtact ggaccttcag cggcgccgtt 300
tccggcatca agcagttcta cgtcaagtac gacgtcagcg gcacctctta ctacgacaac 360
aacggcacca agaactacca ggttaccaag acctctacca ccaccaccgc cgctaccacc 420
accaccaccg ctaccaccac caccggcggc accggcacca ccaccaccac caccgccacc 480
gccaccgcta ccagcaccga cttccctacc ggcaacagca ccattaccac ctggctgaag 540
tcccaggagg acatctcccg aggcgccatg ctccgaaaca ttaacccccc tggcgctgct 600
accggcttca ttgctgccag cctgtctacc tccggccccg actactacta cgcttggacc 660
cgagactccg ccctgacctc tcacgtcatc gctcacgact acaacaccac cctcgctggc 720
aacaccacca tcctgaacat cctgaaggac tacgttacct tctccgtcaa gtcccagtcc 780
gtttctaccg tttgcaactg cctgggcgag cctaagttca accccgacgg cagctcttac 840
accggcgctt ggggccgccc ccagaacgac ggccctgccg agcgagcctc caccttcatc 900
ctgttcggcg actcttacct gaagcagacc ggcgacgcta cctacgttac cggcaccctc 960
gctcctgcca tttacaagga cctcgactac gttgttaaca cctggtctaa cggctgcttc 1020
gacctgtggg aggaggttaa cggcgttcac ttctacaccc tcatgtctat gcgacgaggc 1080
ctcctcgacg gcgccaactt cgccaagcga aacggcgaca ccacccgagc taccacctac 1140
accaacaccg ccgcttccat tgctaccaag attgacacct tctgggttag ctctggcaac 1200
tacgtccagg tttcccagtc tgttaccggc ggcgtcagca aggctggcta cgactgcgct 1260
aacattctcg ctgctaacat ggctgctaac cacgacggct tctacacccc tggcagctct 1320
aagattctcg ctaccgccgt tgccattgag tctaagttcg ccagcctgta ctctattaac 1380
tctggcctcg cttcttggct gggcaccgcc attggccgat accccgagga cacctacaac 1440
ggcaacggca actctcaggg caacccttgg ttcatttgca ccaacgcttt cgctgagctg 1500
tactaccgag ccatcaagga gtggacccag gctggctccg ttaccgttga cagcacctct 1560
ctgaacttct tcaagaagtt cgacagctct gctgccgccg gcaccaagta caccgttggc 1620
acctctgctt tcaccaacct cgtccagaac attgctaacg gcgctgacaa gttcctgtct 1680
acctccaagt tccacgccgc taccaacggc tccatgtctg agcagtacaa ccgagacagc 1740
ggcctcatga ccggcgcccg agacctgacc tggtcgcacg cctcactgat tagcgcctcc 1800
cgagctaagg ctggctctcc tagcctctaa 1830

<210> SEQ ID NO 34
<211> LENGTH: 1845
<212> TYPE: DNA
<213> ORGANISM: Artificial Sequence
<220> FEATURE:
<223> OTHER INFORMATION: Sequence is synthesized

<400> SEQUENCE: 34
atgaagccta ttcacctgtg gcactacctg ttcctcgcca tgaccgctgc cttcatgggc 60
gtcctcgctg acgtccctac ctccgccaac attgaactcg actactacac ctacaaggac 120
aaggttttct ccggccgaat ttacgtcaag aacatcgctt acgaaaaaac cgttgctgtt 180
tactggtctg acgctagtgg cgactggaac aacaacggca acaacgttgc cgcttcttac 240
tctgagtcca tctccggcac cgactacgag tactgggact tcagcaccac cattggctct 300
ggcggcatca agcagtctta cctcaagtac accgttagcg gcaacaccta ctacgacaac 360
aacggctcta acaactacga cattaccgag accaccgcta ccaccaccac caccaccacc 420
accaccacca ccaccggctc taccgccacc acctctacca cctctggccc taccagcacc 480
acctctacca cccccggccc tacccctacc aacgttcccg acggcaacgt taccgtcacc 540
gagtgggtta acacccagtt cgctatttct tggcctaccc tcctgaagaa cgtcaaccct 600
agcggcaccg tcaagggctt cattgctgca tcactcagca ccaacaaccc tgactacttc 660
tactcttgga cccgagacag cgctctcgtt gctcacacca tgacctacct gtacaacacc 720
tctgaggctg gcgacagcac cattgagtct gccctgaagg actacgttac cttcagcatt 780
aacgctatga acgctgctac cgtttgcaac tgcctgggcg agcctaagtt caacaccgac 840
ggctccggct acaccggcgc ttggggccgc ccccagaacg acggccccgc aagtcgagct 900
accaccatga ttctgttcgc cgactccttc ctcgcccagg gcggcgatgt ttcttacgtt 960
attaacaccc tcaagcctgc tatttacaag gacctggact acgtcgttag cacctggtct 1020
aacacctgct acgacctgtg ggaggaggtt aacggcgttc acatttacac cctgtctgtt 1080
atgcgccgcg ccctgattga cggcgctaac ttcgcccagc gaaacggcga cacctcccgc 1140
gtcagcggct acaccagcac cgccaccacc atcaagaccc gactggagtc tttctggagc 1200
gactctaaca actacattac cgttacccag tcttactccg gcggcgtcca gaaggccggc 1260
ctggacgtca gcaccctgat tgctgccaac attggcagcg ttggcgacgg cttctacacc 1320
cccggctctg acaaggtcct cgccaccgcc gtcgccatcg agaagtcctt cgctaacctg 1380
tacaccatta accagaacaa gccttcttgg ctgggcaacg ccattggccg ataccccgag 1440
gacacctacg acggctacgg caactccaag ggcaaccctt ggttcattgc taccgctacc 1500
tacgctgagc tgtactaccg agctatccta gagtggcagc agcaggcttc cgttaccgtt 1560
aactctatta acctgggctt cttctccaag ttcgacagct ctgcctctgt tggcaccgtt 1620
tacacccccg gcaccgactc tttcgccaac atggtttcta acgttgcttt cgctgctgac 1680
gagttcctgt ctaccatcga ctaccacgcc atgaacaacg gctctatgca cgagcagtac 1740
aaccgagaca ccggcatctc ccagggcgca cgcgacctga cctggtcaca cgctgctttc 1800
attaccgctg ccaaggctaa gctgggcgct cccgctttct aataa 1845

<210> SEQ ID NO 35
<211> LENGTH: 1818
<212> TYPE: DNA
<213> ORGANISM: Artificial Sequence
<220> FEATURE:
<223> OTHER INFORMATION: Sequence is synthesized

<400> SEQUENCE: 35
atgaagctca tgaactctag catgaagacc tgcgttttct tcatcctgtc ttacttcagc 60

-continued

```
ctcctcgtca gcagcgctgc cgttcctacc tctgctgctg ttcaggttga gtcctacaag    120

tacgacggca ccaccttcag cggccgaatt ttcgtcaaga acattgctta ctccaaggtt    180

gttaccgtca tatatagcga cggctctgac aactggaaca acaacaacaa caagatcagc    240

gctgcttaca gcgaggctat tagcggctcc aactacgagt actggacctt ctctgctaag    300

ctgtccggca ttaagcagtt ctacgtcaag tacgaggttt ctggctctac ctactacgac    360

aacaacggca ccaagaacta ccaggtccag gctacctctg ccaccagcac caccgccacc    420

gccaccacca ccacctctac cagcaccacc accaccagca ccggccctac cagcaccgca    480

agtgtttctt tccctaccgg caactccacc attagctctt ggattaagaa ccaagaagaa    540

atttcccgat tcgccatgct gcgaaacatt aacccccccg gctccgccac cggcttcatt    600

gctgcctctc tgagcaccgc gggacccgac tactactact cttggacccg agacagcgcc    660

ctgaccgcta acgttattgc ttacgagtac aacaccacct tcgctggcaa caccaccctc    720

ctgaagtacc tgaaggacta cgttaccttc tccgtcaagt ctcagtctgt tagcaccgtt    780

tgcaactgcc tgggcgagcc taagttcaac gccgacggca gctcttacac cggcccttgg    840

ggccgacccc agaacgacgg ccccgccgaa cgggccgtca ccttcatgct cattgctgac    900

tcttacctga cccagaccaa ggacgcttct tacgtcaccg gcaccctgaa gcccgccatt    960

ttcaaggacc tcgactacgt tgtttccgtt tggtctaacg gctgctacga cctgtgggaa   1020

gaagttaacg gcgttcactt ctacaccctg atggttatgc gaaagggcct catcctgggc   1080

gctgacttcg ctgctcgaaa cggcgactct agccgagcct ctacctacaa gaacaccgcg   1140

agcaccatgg agtccaagat ctctagcttc tggtccgact ctaacaacta cgtccaggtt   1200

tcccagtctg ttaccgctgg cgtctccaag aagggcctcg acgttagcac cctcctcgcc   1260

gctaacattg gctccctgcc cgacggcttc ttcacccccg gcagcgagaa gattctggct   1320

accgccgttg ccctagaaaa cgctttcgca tctctgtacc ctattaactc taacctgcct   1380

tcttacctgg gcaactccat tggccgatac cccgaggaca cctacaacgg caacggcaac   1440

tcccagggca acccttggtt cctcgccgtt aacgcttacg ctgagctgta ctaccgagct   1500

attaaagagt ggatctctaa cggcaaggtt accgtctcta acatcagcct ccctttcttc   1560

aagaagttcg acagctccgc cacctctggc aagacctaca ccgctggcac cagcgacttc   1620

aacaacctcg ctcagaacat tgccctgggc gctgaccgat tcctgtctac cgttaagttc   1680

cacgcttaca acaacggcag cctgtctgaa gagtacgacc gatctaccgg catgtctacc   1740

ggcgcacgcg acctgacctg gtctcacgcc tcgctcatca ccgccgctta cgccaaggct   1800

ggcagccccg ctgcctaa                                                 1818
```

<210> SEQ ID NO 36
<211> LENGTH: 1413
<212> TYPE: DNA
<213> ORGANISM: Artificial Sequence
<220> FEATURE:
<223> OTHER INFORMATION: Sequence is synthesized

<400> SEQUENCE: 36

```
atgaagtctc cttacagcat gaaaaccgtc ctcgctctcc tgtccctgac cctctgttc      60

accagcgacg ttgttgccgt tcctagcggc aactccacca tcaccgcttg ggctccaag     120

caggacggca tctctttcag caccatgctg ggcaacatca accctcccgg cagctctaag    180

ggcttcattg ctgcctcgct gtctaccgct ggccctaact actactactc ttggacccga    240

gacagcgctc tcgtcgcccg cgccattacc tacaagtact ccacctctta ccagaacgac    300
```

cccaagattc tgggcctcct gaaggactac gttacctacc aggttaacga gcagaccgag 360
tctaccgttt gcaactgcct cggcgagcct aagttcaacc ccgacggctc tagcttcagc 420
ggcccttggg gccgccctca gaacgacggc cctgctgagc gcgcttccac catgattctg 480
ttcgccaagt cttactacgc ccagaccaac gacgttggct acgtttctaa caccctgaag 540
cccgctattt acaaggacct ggactacatc gttaacgttt ggggcaacaa ctgcttcgac 600
ctgtgggagg aggttaacgg cgtccacttc tacaccctca tgatgatgcg acacggcctc 660
gtccagggca gcattttcgc taacaccctc ggcgacagca cccgagctaa cacctacaag 720
accgccgctc agaacattaa gaaccgaatt gacaccttct gggagtctgg ctctaactac 780
attgttgtta cccagaacca gtctgctggc gttaacaagc cttccggcct cgacgttgcc 840
gtcctgctgg ctgccaacca gggcggcctg ggcgacggcg tttacacccc cggctctgac 900
aaggtcctcg ccaccgccgt cgctctggag aagtctttcg caagcctgta ccccattaac 960
aagaacctgc cttcttacta cggcaccgcc attggccgat accccgagga cacctacaac 1020
ggcaacggca acagcgaggc taacccttgg ttcattgcca ccaccaccta cgctgagctg 1080
tactaccgag ctatttccga gtggaccaac ggctccggcg tcaccgtcaa ctctattaac 1140
aaggagttct tctctaagtt cgacgcctct gccaccaacg gcaaggttta cacccccggc 1200
agcgactctt tcaactccct ggtcaacaac gttgctattg ctgctgacaa cttcctcagc 1260
accgtccgat accaccagac ctccaacggc agcctgtctg agcagttcaa ccgatacacc 1320
ggcttcatga ccggcgcacg ggacctgacc tggtcccacg ccgctatggt taccgctctc 1380
gccgctaagg ctggcacccc tagcccttaa taa 1413

<210> SEQ ID NO 37
<211> LENGTH: 1830
<212> TYPE: DNA
<213> ORGANISM: Artificial Sequence
<220> FEATURE:
<223> OTHER INFORMATION: Sequence is synthesized

<400> SEQUENCE: 37
atgcagctga acctgtactg gaagagcctc gccgtcctcg ctctgattca gatggttatg 60
gctgctaccg tccctaccac ccaggtccag ctcgactact acacctactc taacaacgtc 120
ctgtctggcc gaatctacgt tcagaacatt gcttacagca aggttgttaa ggttatctat 180
agcgacgcct ccggcaactg gaacaacaac ggcaacacca tctccgcttc ttacgtcgag 240
tctatttccg gcaccaacta cgagtactgg gacttcagcg ccaccattgg caccgctggc 300
atcaagcagt tctacctgcg atacgacgtt tccggctcca cctactacga caacaacggc 360
ggcgacaaca acaactacaa cgttgttgct accacctcta ccacctctag ctctaccacc 420
accaccaccg ctaccaccac caccgccacc aagaccacca gcaccacctc tgccaccgct 480
acccctacct ctagcgccac cttccctagc ggcaactcta ccattaccac ctgggccaag 540
tctcagaagg acatttcttg gaagaccctc ctgaccagcc tgaaccctag cggcaccgcc 600
aagggcttca ttgctgcgag tctgtctacc tctaaccctg actactacta cgcttggacc 660
cgagacagcg ctctcgttgc ccgaaccatg gttaacatgt acaacaccac cgaggctggc 720
tctgcttcag tcctgggcct cctgcaggac tacgttacct tccagattaa cgccatgagc 780
accagcaccg tttgcaactg cctgggcgag cctaagttca accccgacgg cagctcttac 840
accggcgctt ggggccgccc ccagaacgac ggccccgctg aacgtgcaag caccttcatc 900
ctgttcgctg actcttacat tgcccagggc ggccagctgt cttacgtcac cggcaccctc 960
gctcccgcca tctacaagga cctgaactac gtcgtttcta cctggtctaa caactgcttc 1020
gacctgtggg aagaggttaa cggccgacac atgttcaccc tcgccgtcat gcgacgcgcc 1080
ctcctggacg gcgttaactt cgcctcccga attggcgaca ccacctactc tagcacctgg 1140
agctctaccg cttctagcat ccagtctacc ctgtctggct actacctgtc ttccggcaac 1200
tacattacca ccgttcagaa cttccagtct ggcgtttcca aggctggcta cgacgtcagc 1260
accctcatcg ctgctaacgt tgcgggcatg ggcgacggct tcttcacccc cggctctgac 1320
gaggttctcg ctaccgccgt tgctattgag aacaagttct ctagcctgta cggcgtcaac 1380
gctaacaagg cttcttacct cggcaccgcc attggccgat accccgagga cacctacaac 1440
ggctacggca acggccaggg caacccttgg ttcattgcta ccgctgctta cgccgagctg 1500
tactaccgag ctattctgga gtggcagacc aagagcagca tcgttgttaa ctccaagaac 1560
ctcggcttct tctccaagtt cgactcttct gccgccgttg gcaccaccta cacccccggc 1620
accaccgctt actctaacat ggtccagaac gtcgccctcg ctgctgaccg attcctcagc 1680
accgtccagc tgcacgctgc caccaacggc tccatgtctg agcagttcaa ccgagacacc 1740
ggcgttatgc agggagcccg tgacctgacc tggtctcaca gcgctttcat taccgctgcc 1800
cgagctaagc tgggcagccc cgtttactaa 1830

<210> SEQ ID NO 38
<211> LENGTH: 1404
<212> TYPE: DNA
<213> ORGANISM: Artificial Sequence
<220> FEATURE:
<223> OTHER INFORMATION: Sequence is synthesized

<400> SEQUENCE: 38
atgcgagcta ccaccgctat tctgtctctg ttcaccaccg cctctatggc tctggctgcc 60
aactctaccg tccctgacgg caactccacc accaccgctt gggtcaagaa gcaagaagcc 120
atctcttgga ccgacctgaa gaccaacgtc aaccctgagg gcgctgctaa gggcttcatt 180
gctgcctctc tgtctaccag cgagcctgac tactactacg cttggacccg agactctgcc 240
ctcgttgctc gcgttatggt taacaagtac aacaccaccg acgctgggga cgccaacctc 300
ctcggcctcc tgcaggacta cgtttctttc cagatcaacg caatgggcga gtctaccgtt 360
tgcaactgcc tgggcgagcc taagttcaac cccgacggca gctcttacac cggcgcttgg 420
ggccgccccc agaacgacgg ccccgccgag cgagcttcta ccttcattct cctcgccgac 480
agcatgattg cccagaagtc tgctaacggc tcttacgtca gcgacaccct ggctcccgct 540
atctacaagg acctggctta cgttgcaagc acctgggaga acgcttgcta cgacctgtgg 600
gaagaggtta acggcaagca catgtacacc ctcagcgtca tgcgacgagc cctcctggac 660
ggcgccgact tcgcttctcg gcagggccag accgccaacg ttacctcttg gaagtctacc 720
gctgacaaga ttaagtctag cctggagggc ttcttcagct ccgacaacgg ctacattgag 780
gttacccagg acatgcaggg cggcgtccag aagaagggcc tggacgtttc caccctcatc 840
gctgctaaca ttggcagcat gggcgacggc ttctacaccc ccggcagcga cgaggttctc 900
gccaccgctg ttgccgttga ggctgccttc gctgacctgt acaagattaa ccagaacacc 960
aactccaccg gcctcggcac cgccatcggc cgataccccg aggacaccta caacggcgtt 1020
ggcaactccc agggcaaccc ttggttcatt gctaccaaca ccttcgctga gctgtactac 1080
cgcgccatcc tggagtggca gaacaagggc accattaccg ttaactccgt taacgctgct 1140
ttcttcagca agtttgactc tagcgctaag gccggtacaa cctacaagtc tggctctacc 1200
gagtttgata gcctcattaa caaggttgct ctggctgctg acgctttcct gaacaccgtc 1260
cagacctacg ctgcttctaa cggctctatg tctgagcagt acaaccgaga caccggcgcc 1320
ctgaccggcg cccgagacct gacctggtct cacgcaagtc tcattaccgc cgctaacgcc 1380
aagctcggca ccccttacaa ctaa 1404

<210> SEQ ID NO 39
<211> LENGTH: 1419
<212> TYPE: DNA
<213> ORGANISM: Artificial Sequence
<220> FEATURE:
<223> OTHER INFORMATION: Sequence is synthesized

<400> SEQUENCE: 39
atgaagctcg gccgaattgg cttctctatt ctgtctgttg cctccgtttt ctctcaggcc 60
gtcgttaccg ctgccgctgc cgcctctgtc cctagcggca acgccaccat tacctcttgg 120
attcaggagc agctcgctat ttcttggaac accatgctga ccagcgttaa ccccgttggc 180
gccgtcaccg gcttcatcgc tgcgagtctg tctaccgcta accccgacta ctactactgc 240
tggacccgag acgctgctct cgtcgcgaga gttatgacct tcatgtacaa caccacccag 300
gctggcgaca gcggcctcct gggcatcctc caggactacg tttccttcca gatccacgca 360
atgggcgagt ctaccgtttg caactgcctg ggcgagccca agttcaaccc cgacggcagc 420
tcttacaccg gcgcttgggg ccgccctcag aacgacggcc ctgctgagcg agcctctacc 480
ttcatcaaga ttgctgactc ttacctgacc cagaccggcg atgtatccta cgttaccaac 540
accctcaagc ccgctattta cgaggacctg gactacattg ttaacgtttg gcagaacacc 600
tgcttcgacc tgtgggagga ggtttacgga atgcacatgt acaccctggc tgttatgcga 660
cgaggcctcc tcgacggcgc cgacttcgct acccgaaacg gcgacaccga caaggcctct 720
acctacacca gcaccgccac cagcatccag acccgactgg ccaccttctg gtctgactcc 780
aacggctaca ttaccgttac ccaggactac cagtccggcg tcagcaaggc tggcctggac 840
gttagcaccc tgattgctgc taacgttgcc ggcatgaacg acggcttctt cacccctggc 900
tctgacgaga ttctcgctac cgccgtcaag gttgaggctg ctttcgctaa cctgtacggc 960
attaacatta acaaggcctc ttacctgggc aacgccattg gccgataccc cgaggacacc 1020
tacaacggca acggcaactc tgagggcaac ccttggttca ttgccaccgc tgctttcgct 1080
gagctgtact accgcgccat tatggagtgg cagctccgag gcagctctat taccgtcaac 1140
tctgttaacc agggcttctt caccaagttc gaccctagcg ccaccgccgg caccacctac 1200
acccccggca ccgacgcttt caactccctc attgacaacg ttgccctcgc tgctgaccag 1260
ttcttcagca ccatccacct ccaccgcgcc accaacggct ctatgtctga gcagtacaac 1320
cgagacaccg gcttcatgca gggcgctcgg gacctgacct ggtcccacgc cgctttcatc 1380
accgccgcta aggctaagca gggcacccct agcttctaa 1419

<210> SEQ ID NO 40
<211> LENGTH: 1842
<212> TYPE: DNA
<213> ORGANISM: Artificial Sequence
<220> FEATURE:
<223> OTHER INFORMATION: Sequence is synthesized

<400> SEQUENCE: 40

```
atgcgccccg ttcacctgtg gaagagcctg ctcctcgccg ctgctaccgc tgttaccggc     60

accatcgccg ttgatgttcc ttctgttcct atccagctag agtcttacac ctactctgag    120

aacgttttcg ccggccgaat tttcgtccag aacattgctt acaccaagga ggttaacgtt    180

ttctggtctg acgcttccga cgactggaac gacaacggca actccgttgc tgcttcttac    240

tccgagtcta ttgctgacac caactacgag tactgggagt tcagcaccac cattggctct    300

gccggcatct cccagtctta cctgcgatac gatgtgtctg gctctattta ctacgacaac    360

aacgactccc agaactacga cattaccgag accagcaccc ctaccaccac caccgctgcc    420

cctacctcta ccacctctac ccctaccacc accaccgacg gcggcagcac caccaccacc    480

accgccacct ccgtccctac ctctaccggc gtccctgagg gcaacgctac cattagcgag    540

tgggcatctg cccagctgga catctcttgg cctaacctca tgatgaacgt taaccctagc    600

ggcgctgtta ccggctccat tgttgcctca ctgtctacct ctaaccctga ctacttctac    660

atttggaccc gagacgctgc gatggttgcc cgcgttatgg tttacatgta caacaccacc    720

gaggctggcg acaccaacct gctcaacgcc ctgaccgact acgttacctt ctctatttcc    780

agcatgaacg ttgacaccgt ttgcgactgc ctgggcgagc ctaagttcaa cgttgacggc    840

tctggctaca ccggcgcttg gggccgcccc cagaacgacg gccccgccga gcgcgcctct    900

accatgatcc tgattgctga ctcttacatc gcccagggcg gcgatgtatc ttacgtcacc    960

gacaccctca agcctgctat ttacaccgac ctggactacg tcgttgacac ctggtctaac   1020

gtttgcttcg acctgtggga ggaggttaac ggcattcaca tgtacaccct cagcgtcatg   1080

cgaaaggccc tcctggacgg cgccaacttc gctacccgaa acggcgacac ctcccgcgtt   1140

agcggctacg agagcaccgc ttcatccatc aagacccgac tggagtcttt ctggtctagc   1200

tctaacaact acattaccgt cacccagtcc ttcagcggcg gcgtttccaa ggccggcctg   1260

gacgtcagca ccctgattgc tgccaacctc gcttccatga acgacggctt ctacaccccc   1320

ggctctgacg agattctcgc taccgccgtt gctattgaga actctttcat ctccgagtac   1380

accctcaacc agaaccgccc ttcttggctg tccaccgcca ttggccgata ccctgaggac   1440

tcttacgacg gctacggcaa ctcccagggc aacccttggt tcatcgctac cgctacctac   1500

gctgagctgt actaccgagc tatcctagag tggcagcagc aggcttcaat tagcgttaac   1560

agcgttaacc tgggcttctt cagcaagttc gactctgacg cttctgttgg caccgtttac   1620

acccccggca ccgaggactt cgccaacatg gtttctaacg tcgctttcgc tgctgacgag   1680

ttcctcgcca ccattgagaa ccacagcgcc gtcaacggca gcctcagcga gcagtacaac   1740

cgagacaccg gcattatgca gggcgcaaga gacctgacct ggtcacacgc tgccttcatt   1800

accgctgcca aggccaagca gggcgctcct attcactaat aa                       1842
```

<210> SEQ ID NO 41
<211> LENGTH: 19
<212> TYPE: PRT
<213> ORGANISM: Saksenaea vasiformis

<400> SEQUENCE: 41

```
Met Pro Ser Trp Lys Thr Leu Phe Leu Leu Leu Gly Pro Ile Ala Thr
1               5                   10                  15

Ala Ala Ala
```

<210> SEQ ID NO 42
<211> LENGTH: 23
<212> TYPE: PRT

<213> ORGANISM: Backusella circina

<400> SEQUENCE: 42

```
Met Lys Leu Phe Gly Thr Leu Lys Ala Ser Phe Val Phe Leu Ile Gly
1               5                   10                  15

Cys Ile Val Phe Ala Met Ala
            20
```

<210> SEQ ID NO 43
<211> LENGTH: 24
<212> TYPE: PRT
<213> ORGANISM: Backusella circina

<400> SEQUENCE: 43

```
Met Lys Pro Phe Gly Pro Ile Lys Thr Thr Leu Phe Ile Ile Ile Ser
1               5                   10                  15

His Phe Ser Leu Asn Ser Leu Ala
            20
```

<210> SEQ ID NO 44
<211> LENGTH: 24
<212> TYPE: PRT
<213> ORGANISM: Benjaminiella poitrasii

<400> SEQUENCE: 44

```
Met Lys Phe Ser His Leu Phe Arg Lys Pro Thr Leu Leu Ile Val Thr
1               5                   10                  15

Phe Leu Thr Ala Thr Val Phe Ala
            20
```

<210> SEQ ID NO 45
<211> LENGTH: 24
<212> TYPE: PRT
<213> ORGANISM: Choanephora cucurbitarum

<400> SEQUENCE: 45

```
Met Val Ser Phe Asn Phe Leu Lys Lys Pro Val Phe Ile Val Ile Thr
1               5                   10                  15

Cys Leu Thr Val Ser Val Cys Ala
            20
```

<210> SEQ ID NO 46
<211> LENGTH: 25
<212> TYPE: PRT
<213> ORGANISM: Rhizopus stolonifer

<400> SEQUENCE: 46

```
Met Lys Leu Phe Gly Leu Pro Leu Lys Pro Ser Leu Phe Phe Val Val
1               5                   10                  15

Ser Tyr Leu Ser Phe Leu Ala Ser Ala
            20                  25
```

<210> SEQ ID NO 47
<211> LENGTH: 24
<212> TYPE: PRT
<213> ORGANISM: Mucor circinelloides

<400> SEQUENCE: 47

```
Met Lys Phe Ser Asn Leu Leu Lys Lys Pro Leu Leu Leu Ile Ala Gly
1               5                   10                  15

Ile Leu Ala Ala Thr Val Val Ala
            20
```

<210> SEQ ID NO 48
<211> LENGTH: 21
<212> TYPE: PRT
<213> ORGANISM: Dichotomocladium elegans

<400> SEQUENCE: 48

Met Lys Leu Asn Ser Val Trp Lys Ala Phe Ser Ile Leu Leu Met Ala
1 5 10 15

Thr Met Ala Phe Ala
20

<210> SEQ ID NO 49
<211> LENGTH: 23
<212> TYPE: PRT
<213> ORGANISM: Fennellomyces sp.

<400> SEQUENCE: 49

Met Arg Pro Ser Leu Val Trp Lys Ser Leu Leu Met Val Val Leu Thr
1 5 10 15

Ala Ala Met Gly Thr Tyr Ala
20

<210> SEQ ID NO 50
<211> LENGTH: 24
<212> TYPE: PRT
<213> ORGANISM: Gilbertella persicaria

<400> SEQUENCE: 50

Met Val Phe Ser Lys Leu Phe Lys Lys Pro Ile Leu Leu Ile Val Thr
1 5 10 15

Tyr Leu Thr Val Thr Val Val Ala
20

<210> SEQ ID NO 51
<211> LENGTH: 24
<212> TYPE: PRT
<213> ORGANISM: Mucor circinelloides

<400> SEQUENCE: 51

Met Lys Phe Ser Asn Leu Leu Lys Lys Pro Leu Leu Leu Ile Ala Gly
1 5 10 15

Ile Leu Ala Val Thr Val Val Ala
20

<210> SEQ ID NO 52
<211> LENGTH: 25
<212> TYPE: PRT
<213> ORGANISM: Circinella umbellata

<400> SEQUENCE: 52

Met Met Pro Asn His Ile Trp Lys Cys Leu Phe Leu Ala Met Thr Thr
1 5 10 15

Val Phe Met Thr Val Leu Val Gln Gly
20 25

<210> SEQ ID NO 53
<211> LENGTH: 24
<212> TYPE: PRT
<213> ORGANISM: Mucor cordense

<400> SEQUENCE: 53

```
Met Lys Phe Ser Lys Leu Phe Thr Lys Pro Thr Leu Phe Ile Val Ser
1               5                   10                  15

Ile Ile Ile Ser Val Ala Ser Ser
            20


<210> SEQ ID NO 54
<211> LENGTH: 23
<212> TYPE: PRT
<213> ORGANISM: Phascolomyces articulosus

<400> SEQUENCE: 54

Met Lys Pro Ile His Leu Trp His Tyr Leu Phe Leu Ala Met Thr Ala
1               5                   10                  15

Ala Phe Met Gly Val Leu Ala
            20


<210> SEQ ID NO 55
<211> LENGTH: 27
<212> TYPE: PRT
<213> ORGANISM: Rhizopus microsporus

<400> SEQUENCE: 55

Met Lys Leu Met Asn Ser Ser Met Lys Thr Cys Val Phe Phe Ile Leu
1               5                   10                  15

Ser Tyr Phe Ser Leu Leu Val Ser Ser Ala Ala
            20                  25


<210> SEQ ID NO 56
<211> LENGTH: 26
<212> TYPE: PRT
<213> ORGANISM: Spinellus fusiger

<400> SEQUENCE: 56

Met Lys Ser Pro Tyr Ser Met Lys Thr Val Leu Ala Leu Leu Ser Leu
1               5                   10                  15

Thr Pro Leu Phe Thr Ser Asp Val Val Ala
            20                  25


<210> SEQ ID NO 57
<211> LENGTH: 21
<212> TYPE: PRT
<213> ORGANISM: Syncephalastrum racemosum

<400> SEQUENCE: 57

Met Gln Leu Asn Leu Tyr Trp Lys Ser Leu Ala Val Leu Ala Leu Ile
1               5                   10                  15

Gln Met Val Met Ala
            20


<210> SEQ ID NO 58
<211> LENGTH: 19
<212> TYPE: PRT
<213> ORGANISM: Syncephalastrum racemosum

<400> SEQUENCE: 58

Met Arg Ala Thr Thr Ala Ile Leu Ser Leu Phe Thr Thr Ala Ser Met
1               5                   10                  15

Ala Leu Ala


<210> SEQ ID NO 59
<211> LENGTH: 20
<212> TYPE: PRT
```

<213> ORGANISM: Thermomucor sp.

<400> SEQUENCE: 59

Met Lys Leu Gly Arg Ile Gly Phe Ser Ile Leu Ser Val Ala Ser Val
1 5 10 15

Phe Ser Gln Ala
20

<210> SEQ ID NO 60
<211> LENGTH: 23
<212> TYPE: PRT
<213> ORGANISM: Zychaea mexicana

<400> SEQUENCE: 60

Met Arg Pro Val His Leu Trp Lys Ser Leu Leu Leu Ala Ala Ala Thr
1 5 10 15

Ala Val Thr Gly Thr Ile Ala
20

<210> SEQ ID NO 61
<211> LENGTH: 449
<212> TYPE: PRT
<213> ORGANISM: Saksenaea vasiformis

<400> SEQUENCE: 61

Ala Pro Val Asp Lys Gln Ser Leu Pro Thr Gly Asn Ser Thr Ile Ser
1 5 10 15

Ser Trp Val Ser Lys Gln Glu Asp Ile Ser Phe Ser Glu Met Leu Arg
20 25 30

Asn Val Asn Pro Glu Gly Thr Ala Lys Gly Phe Val Ala Ala Ser Leu
35 40 45

Ser Thr Ala Gly Pro Asp Tyr Phe Tyr Thr Trp Thr Arg Asp Ala Ala
50 55 60

Leu Val Ser Arg Val Ile Ala Tyr Lys Tyr Asn Thr Thr Asn Ala Gly
65 70 75 80

Asp Ser Lys Ile His Gly Val Leu Asp Asp Tyr Val Asn Phe Gln Ile
85 90 95

Asn Thr Gln Ser Glu Ser Thr Pro Cys Asn Cys Leu Gly Glu Pro Lys
100 105 110

Phe Asn Pro Asp Gly Ser Ser Phe Thr Gly Pro Trp Gly Arg Pro Gln
115 120 125

Asn Asp Gly Pro Ala Glu Arg Ala Ser Ser Phe Met Leu Ile Ala Asp
130 135 140

Ser Phe Leu Ser Gln Thr Lys Asn Ala Ser Tyr Phe Thr Asn Thr Leu
145 150 155 160

Lys Pro Ala Ile Tyr Lys Asp Leu Asp Tyr Val Val Asp Thr Trp Ser
165 170 175

Asn Pro Cys Phe Asp Leu Trp Glu Glu Val Asn Gly Ile His Phe Tyr
180 185 190

Thr Leu Met Val Met Arg Arg Ser Leu Leu Asp Gly Ala Asn Phe Ala
195 200 205

Thr Arg Asn Gly Asp Asn Ser Lys Ala Ser Thr Tyr Ser Gly Val Ala
210 215 220

Ala Lys Ile Gln Ala Arg Leu Asn Ser Phe Trp Asp Ala Gly Lys Asn
225 230 235 240

Tyr Ile Thr Val Thr Gln Asp Tyr Lys Asn Gly Val Glu Lys Pro Ser
245 250 255

Gly Leu Asp Val Ser Thr Leu Ile Ala Ala Asn Val Ala Gly Met Gly
260 265 270

Asp Gly Phe Tyr Thr Pro Gly Ser Glu Arg Ile Leu Ala Thr Ala Leu
275 280 285

Ala Phe Glu Lys Ser Met Ala Ser Leu Tyr Pro Leu Asn Asn Asn Leu
290 295 300

Pro Ser His Leu Gly Asn Ala Ile Gly Arg Tyr Pro Glu Asp Thr Tyr
305 310 315 320

Asn Gly Asn Gly Asn Ser Gln Gly Asn Pro Trp Phe Leu Ala Thr Thr
325 330 335

Ala Phe Thr Glu Leu Tyr Tyr Arg Ala Ile Leu Glu Trp Lys Asn Thr
340 345 350

Gly Val Thr Val Thr Pro Ile Ser Lys Asp Phe Phe Val Arg Phe Asp
355 360 365

Ser Ser Ala Ala Pro Gly Lys Lys Tyr Asn Pro Gly Ser Gln Glu Phe
370 375 380

Ala Thr Leu Thr Gln Ser Ile Ala Ala Ala Ala Asp Arg Phe Met Ser
385 390 395 400

Thr Val Gln Tyr His Gln Asn Pro Asn Gly Ser Leu Ser Glu Glu Phe
405 410 415

Asp Arg Ser Ser Gly Tyr Met Thr Gly Ala Arg Asp Leu Thr Trp Ser
420 425 430

His Ala Ala Phe Ile Thr Ala Ala Gln Ala Arg Ala Gly Ser Pro Ser
435 440 445

Phe

<210> SEQ ID NO 62
<211> LENGTH: 582
<212> TYPE: PRT
<213> ORGANISM: Backusella circina

<400> SEQUENCE: 62

Asp Thr Val Pro Thr Thr Gln Val Lys Leu Gln Ser Tyr Thr Tyr Ser
1 5 10 15

Gly Gly Val Leu Ser Gly Thr Ile Tyr Val Gln Asn Ile Asp Tyr Thr
20 25 30

Lys Val Val Thr Val Ile Tyr Ser Asp Gly Ser Gly Asn Trp Asn Asn
35 40 45

Asn Gly Asn Thr Ile Ser Ala Ser Tyr Ser Ser Ser Ile Ser Gly Thr
50 55 60

Asn Tyr Glu Tyr Trp Thr Phe Ser Ala Ser Val Ser Ser Ile Gln Gln
65 70 75 80

Phe Tyr Ile Ser Tyr Leu Val Asp Gly Thr Thr Tyr Tyr Asp Asn Asn
85 90 95

Gly Gly Tyr Gly Ala Asn Tyr Ala Val Thr Ala Thr Thr Thr Thr Ala
100 105 110

Ser Ser Thr Thr Lys Thr Thr Ser Gly Thr Thr Lys Thr Ser Thr Thr
115 120 125

Ser Thr Ala Thr Ala Thr Ser Thr Gly Thr Ser Ser Phe Pro Ser Gly
130 135 140

Asn Ser Thr Ile Ser Thr Trp Ser Pro Ser Gln His Ser Ile Ser Leu
145 150 155 160

Tyr Ala Met Leu Arg Asn Ile Asn Pro Pro Gly Ser Ala Ala Gly Phe
165 170 175

```
Ile Ser Ala Ser Leu Ser Thr Ser Gly Pro Asp Tyr Tyr Tyr Ser Trp
            180                 185                 190

Thr Arg Asp Ser Ala Leu Val Ala His Val Ile Val Asn Glu Tyr Asn
        195                 200                 205

Thr Thr Tyr Gln Gly Asn Ser Thr Leu Leu Gly Ile Leu Lys Asp Tyr
    210                 215                 220

Val Thr Tyr Ser Leu Asn Ala Gln Thr Thr Ser Thr Val Cys Asn Cys
225                 230                 235                 240

Leu Gly Glu Pro Lys Phe Asn Pro Asp Gly Ser Ser Phe Thr Gly Ala
                245                 250                 255

Trp Gly Arg Pro Gln Asn Asp Gly Pro Ala Glu Arg Ala Val Ser Phe
            260                 265                 270

Ile Tyr Phe Ala Asp Ser Tyr Leu Thr Gln Thr Ser Asp Ser Ser Tyr
        275                 280                 285

Val Thr Gly Thr Leu Ala Pro Ala Ile Tyr Lys Asp Leu Asp Tyr Val
    290                 295                 300

Val Ser Val Trp Ser Asn Gly Cys Phe Asp Leu Trp Glu Glu Val Asn
305                 310                 315                 320

Gly Ile His Phe Tyr Thr Leu Met Phe Met Arg Arg Gly Leu Leu Asp
                325                 330                 335

Gly Ala Asn Phe Ala Ser Arg Asn Gly Asp Ser Thr Arg Ala Ser Thr
            340                 345                 350

Tyr Thr Ser Thr Ala Ala Ser Ile Lys Thr Lys Ile Asp Gly Phe Trp
        355                 360                 365

Val Ser Ser Gly Asn Tyr Val Gln Val Ser Gln Ser Val Thr Ser Gly
    370                 375                 380

Val Ser Lys Ala Gly Tyr Asp Ala Ser Thr Leu Ile Ala Ala Asn Gln
385                 390                 395                 400

Ala Ser Arg Gly Asp Gly Phe Tyr Thr Pro Gly Ser Asp Lys Met Leu
                405                 410                 415

Ala Thr Ala Val Ala Ile Glu Ser Gln Phe Ser Ser Leu Tyr Ser Ile
            420                 425                 430

Asn Thr Asn Lys Ala Ser Tyr Leu Gly Asn Ala Ile Gly Arg Tyr Pro
        435                 440                 445

Glu Asp Thr Tyr Asn Gly Asn Gly Asn Ser Gln Gly Asn Pro Trp Phe
    450                 455                 460

Leu Cys Thr Asn Ala Phe Gly Glu Leu Phe Tyr Arg Ala Ile Ser Glu
465                 470                 475                 480

Trp Asn Ala Ala Gly Ser Val Thr Val Asn Ser Val Asn Leu Ala Phe
                485                 490                 495

Phe Lys Lys Tyr Asp Ser Ser Thr Ser Ser Gly Thr Thr Tyr Thr Val
            500                 505                 510

Gly Thr Ser Ala Tyr Asn Asn Leu Val Gln Asn Val Ala Leu Ala Ala
        515                 520                 525

Asp Ala Tyr Phe Ser Thr Val Lys Tyr His Ala Leu Thr Asn Gly Ser
    530                 535                 540

Met Ser Glu Gln Tyr Asp Arg Ser Ser Gly Met Ala Thr Gly Ala Arg
545                 550                 555                 560

Asp Leu Thr Trp Ser His Ala Ala Met Ile Thr Ala Leu Lys Ala Lys
                565                 570                 575

Ser Gly Thr Pro Val Tyr
            580
```

```
<210> SEQ ID NO 63
<211> LENGTH: 578
<212> TYPE: PRT
<213> ORGANISM: Backusella circina

<400> SEQUENCE: 63

Asp Thr Val Pro Thr Thr Gln Val Glu Val Lys Thr Tyr Thr Tyr Ser
1               5                   10                  15

Gly Gly Glu Leu Ser Gly Thr Ile Tyr Val Glu Asn Ile Asp Tyr Thr
            20                  25                  30

Lys Val Val Thr Val Ile Tyr Ala Asp Gly Ser Asp Asp Trp Asn Asn
        35                  40                  45

Asn Gly Asn Thr Ile Ala Ala Ala Phe Ser Glu Ser Ile Ser Asp Thr
    50                  55                  60

Asn Tyr Glu Tyr Trp Thr Phe Ser Ser Ser Val Asn Ser Ile Lys Glu
65                  70                  75                  80

Phe Tyr Val Lys Tyr Asp Val Asp Gly Asn Thr Tyr Tyr Asp Asn Asn
                85                  90                  95

Gly Asn Ala Asn Tyr Gln Val Ser Ala Ser Ser Thr Thr Thr Thr Thr
            100                 105                 110

Ala Thr Lys Thr Thr Thr Thr Ala Thr Lys Thr Thr Ala Thr Ala Thr
        115                 120                 125

Ser Thr Ala Thr Gly Ser Thr Ser Phe Pro Ser Gly Asn Ser Thr Ile
    130                 135                 140

Ser Ser Trp Ile Lys Gly Gln Glu Asp Thr Ser Arg Ser Val Met Leu
145                 150                 155                 160

Gly Asn Ile Asn Pro Pro Gly Ser Ala Thr Gly Phe Ile Ser Ala Ser
                165                 170                 175

Leu Ser Thr Ser Gly Pro Asp Tyr Tyr Tyr His Trp Thr Arg Asp Ala
            180                 185                 190

Ala Leu Val Ala His Val Ile Val Asn Asp Tyr Asn Thr Thr Leu Ser
        195                 200                 205

Gly Asp Ser Ser Thr Leu Gln Val Ile Lys Asp Tyr Val Thr Phe Ser
    210                 215                 220

Val Asn Ser Gln Ser Glu Ser Thr Val Cys Asn Cys Leu Gly Glu Pro
225                 230                 235                 240

Lys Phe Asn Pro Asp Gly Ser Ser Tyr Thr Gly Ala Trp Gly Arg Pro
                245                 250                 255

Gln Asn Asp Gly Pro Ala Glu Arg Ala Thr Thr Phe Ile Phe Phe Ala
            260                 265                 270

Asp Thr Tyr Leu Ala Gln Gly Gly Asp Ser Ser Tyr Val Thr Gly Thr
        275                 280                 285

Leu Ala Pro Ala Ile Tyr Ala Asp Leu Asp Tyr Val Val Asn Asn Trp
    290                 295                 300

Ser Thr Gly Cys Tyr Asp Leu Trp Glu Glu Val Asn Gly Ile His Phe
305                 310                 315                 320

Tyr Thr Leu Met Val Met Arg Arg Gly Leu Ile Asp Gly Ala Ser Phe
                325                 330                 335

Ala Ser Arg Asn Gly Asp Ser Thr Arg Ser Ser Ser Tyr Thr Ser Thr
            340                 345                 350

Ala Lys Ser Ile Ala Thr Lys Ile Asp Ser Phe Trp Ser Ala Ser Asn
        355                 360                 365

Asn Tyr Val Ala Val Ser Gln Ser Val Thr Ser Gly Val Ser Lys Ala
    370                 375                 380
```

Gly Tyr Asp Ala Ser Thr Ile Ile Ala Ala Asn Gln Ala Ser Leu Gly
385 390 395 400

Asp Gly Phe Tyr Thr Pro Gly Ser Asp Lys Met Leu Ala Thr Ser Val
405 410 415

Ala Val Glu Asn Ala Phe Ser Ser Leu Tyr Thr Val Asn Thr Gly Lys
420 425 430

Ala Ser Tyr Leu Gly Asn Ala Ile Gly Arg Tyr Pro Glu Asp Thr Tyr
435 440 445

Asn Gly Asn Gly Asn Ser Gln Gly Asn Pro Trp Tyr Leu Cys Thr Asn
450 455 460

Ala Leu Gly Glu Leu Tyr Tyr Arg Ala Ile Lys Glu Trp Asn Ala Ala
465 470 475 480

Gly Ser Val Thr Val Asn Ser Val Asn Leu Gly Phe Phe Gln Lys Ile
485 490 495

Asp Ser Ser Ile Ser Ser Gly Thr Thr Phe Thr Leu Gly Thr Ser Asp
500 505 510

Tyr Ser Thr Leu Val Asp Asn Val Ala Leu Ala Ala Asp Lys Phe Phe
515 520 525

Ala Val Val Gln Tyr His Glu Arg Ser Asn Gly Ser Met Pro Glu Gln
530 535 540

Phe Gly Arg Glu Asp Gly Leu Pro Thr Gly Ala Arg Asp Leu Thr Trp
545 550 555 560

Ser His Ala Ala Met Ile Ser Ala Ala Arg Ala Lys Ala Gly Thr Pro
565 570 575

Val Tyr

<210> SEQ ID NO 64
<211> LENGTH: 577
<212> TYPE: PRT
<213> ORGANISM: Benjaminiella poitrasii

<400> SEQUENCE: 64

Glu Thr Val Pro Thr Thr Ser Gln Val Lys Leu Lys Ser Tyr Thr Tyr
1 5 10 15

Asp Gly Ser Thr Leu Ser Gly Gln Ile Tyr Ile Gln Asn Ile Ala Tyr
20 25 30

Thr Lys Val Val Thr Val Ile Tyr Ser Asp Ala Ser Ser Asn Trp Asn
35 40 45

Asn Asn Gly Asn Thr Ile Ala Ala Ser Tyr Thr Asn Gly Ile Ser Gly
50 55 60

Thr Asn Tyr Glu Tyr Trp Asn Phe Thr Gly Pro Val Ser Ser Ile Asn
65 70 75 80

Ala Phe Tyr Ile Lys Tyr Asp Val Ser Gly Asn Thr Tyr Tyr Asp Asn
85 90 95

Asn Asn Asn Ala Asn Tyr Gln Val Thr Lys Thr Ser Thr Thr Thr Thr
100 105 110

Thr Ser Thr Ala Thr Ala Thr Thr Thr Thr Lys Thr Ser Thr Pro Thr
115 120 125

Ser Thr Gly Val Pro Ser Asn Phe Pro Thr Gly Asn Ser Thr Ile Ser
130 135 140

Thr Trp Leu Lys Ser Gln Ile Gly Ile Ser Arg Tyr Ala Met Leu Arg
145 150 155 160

Asn Ile Asn Pro Ala Gly Ser Ala Val Gly Phe Ile Ala Ala Ser Leu
165 170 175

```
Ser Thr Ala Asn Pro Asp Tyr Tyr Tyr Ala Trp Thr Arg Asp Ser Ala
            180                 185                 190

Leu Thr Ser Tyr Val Ile Ala Asn Asp Tyr Asn Ser Thr Leu Ala Gly
        195                 200                 205

Asn Ser Thr Ile Leu Gln Ile Met Lys Asp Tyr Val Thr Phe Ser Val
    210                 215                 220

Lys Ser Gln Ser Val Ser Thr Ala Cys Asn Cys Leu Gly Glu Pro Lys
225                 230                 235                 240

Phe Asn Pro Asp Gly Ser Ser Tyr Thr Gly Ala Trp Gly Arg Pro Gln
                245                 250                 255

Asn Asp Gly Pro Ala Glu Arg Ala Thr Thr Phe Ile Leu Phe Ala Asp
            260                 265                 270

Ser Tyr Leu Lys Gln Thr Gly Asp Ala Ser Tyr Val Thr Gly Thr Leu
        275                 280                 285

Lys Pro Ala Ile Phe Lys Asp Leu Asp Tyr Val Val Asn Thr Trp Thr
    290                 295                 300

Asn Gly Cys Phe Asp Leu Trp Glu Glu Val Asn Gly Val His Phe Tyr
305                 310                 315                 320

Thr Leu Met Val Met Arg Lys Gly Leu Ile Arg Gly Ala Asn Phe Ala
                325                 330                 335

Thr Arg Asn Gly Asp Ser Thr Arg Ala Ser Thr Tyr Thr Asn Thr Ala
            340                 345                 350

Ala Ser Ile Lys Thr Lys Met Asp Ser Phe Trp Ser Ser Gly Asn Asn
        355                 360                 365

Tyr Ile Ala Val Ser Gln Ser Val Thr Gly Gly Val Ser Lys Ala Gly
    370                 375                 380

Tyr Asp Val Ala Asn Ile Ile Ala Ala Asn Val Gly Ser Leu Gln Asp
385                 390                 395                 400

Gly Val Tyr Thr Pro Gly Ser Asp Arg Ile Leu Ala Thr Ala Val Ala
                405                 410                 415

Val Glu Ala Lys Phe Ala Ser Leu Tyr Gly Val Asn Ser Asn Leu Pro
            420                 425                 430

Gly Tyr Leu Gly Asn Ser Ile Gly Arg Tyr Pro Glu Asp Thr Tyr Asn
        435                 440                 445

Gly Asn Gly Asn Ser Gln Gly Asn Pro Trp Phe Leu Ala Thr Asn Ala
    450                 455                 460

Tyr Ala Glu Leu Tyr Tyr Arg Ala Ile Arg Glu Trp Tyr Asp Asn Gly
465                 470                 475                 480

Gly Val Thr Val Asn Ser Val Asn Leu Pro Phe Phe Lys Lys Phe Asp
                485                 490                 495

Ser Ser Ala Ala Ser Gly Thr Thr Tyr Thr Val Gly Thr Thr Ala Phe
            500                 505                 510

Asn Thr Met Val Ser Asn Val Ala Ala Ala Ala Asp Lys Phe Phe Ser
        515                 520                 525

Thr Val Lys Phe His Ala Tyr Thr Asn Gly Ser Met Ser Glu Gln Phe
    530                 535                 540

Gly Arg Asn Asp Gly Leu Cys Thr Gly Ala Arg Asp Leu Thr Trp Ser
545                 550                 555                 560

His Ala Ser Leu Ile Ser Ala Ala Leu Ala Lys Ala Gly Thr Pro Ser
                565                 570                 575

Val
```

<210> SEQ ID NO 65
<211> LENGTH: 574
<212> TYPE: PRT
<213> ORGANISM: Choanephora cucurbitarum

<400> SEQUENCE: 65

Gln Ser Val Pro Thr Ser Asp Pro Val Lys Val Lys Thr Phe Ser Tyr
1               5                   10                  15

Asp Gly Asn Ser Phe Ser Gly Gln Ile Tyr Ile Lys Asn Ile Ala Tyr
            20                  25                  30

Glu Lys Thr Val Thr Val Ile Tyr Ser Asp Gly Thr Gly Asn Trp Asn
        35                  40                  45

Asn Asn Asn Asn Lys Ile Ala Ala Ala Phe Ser Glu Ala Ile Ser Gly
    50                  55                  60

Ser Asn Tyr Glu Tyr Trp Thr Phe Ser Ala Ser Val Pro Ser Ile Lys
65                  70                  75                  80

Gln Phe Tyr Val Lys Tyr Asp Val Ser Gly Lys Thr Tyr Tyr Asp Asn
                85                  90                  95

Asn Gly Ser Lys Asp Tyr Asn Val Val Thr Ser Gly Pro Thr Thr Thr
            100                 105                 110

Ser Ser Gly Pro Ser Lys Thr Thr Thr Asn Gly Pro Ala Pro Thr Ser
        115                 120                 125

Thr Asn Thr Asn Phe Pro Ser Gly Asn Pro Ser Ile Thr Ser Trp Ile
    130                 135                 140

Asp Lys Gln Ile Asp Ile Ser Arg Ser Ala Met Leu Lys Asn Ile Asn
145                 150                 155                 160

Pro Ala Gly Thr Val Lys Gly Phe Ile Ala Ala Ser Leu Ser Thr Ser
                165                 170                 175

Asn Pro Asp Tyr Phe Tyr Ala Trp Thr Arg Asp Ala Ala Leu Val Ala
            180                 185                 190

His Val Val Ala Asn Asp Tyr Asn Arg Thr Lys Ser Gly Asp Ala Thr
        195                 200                 205

Tyr Leu Gly Leu Leu Lys Asp Tyr Val Thr Phe Ser Ile Asn Ser Gln
    210                 215                 220

Asn Thr Pro Thr Ala Cys Asn Cys Leu Gly Glu Pro Lys Phe Asn Lys
225                 230                 235                 240

Asp Gly Ser Gly Tyr Asn Gly Pro Trp Gly Arg Pro Gln Asn Asp Gly
                245                 250                 255

Pro Ala Glu Arg Ala Asp Thr Phe Val Leu Ile Ala Asp Ser Ile Leu
            260                 265                 270

Thr Gln Thr Lys Asp Val Ser Tyr Val Thr Gly Thr Leu Arg Pro Ala
        275                 280                 285

Ile Tyr Thr Asp Leu Asp Tyr Val Val Arg Thr Trp Ser Asn Gly Cys
    290                 295                 300

Phe Asp Leu Trp Glu Glu Val Asn Gly Val His Phe Tyr Thr Leu Met
305                 310                 315                 320

Val Met Arg Arg Ala Leu Leu Val Gly Ala Asn Phe Ala Ser Arg Asn
                325                 330                 335

Gly Asp Ser Ala Arg Ala Ser Asn Tyr Asn Asn Ala Ala Asn Ser Ile
            340                 345                 350

Lys Ser Lys Ile Asp Ser Phe Trp Ser Ser Asn Asn Asn Tyr Val Ala
        355                 360                 365

Val Ser Gln Ser Val Thr Gly Gly Val Ser Lys Ala Gly Tyr Asp Val
    370                 375                 380

```
Ser Thr Leu Ile Ala Ala Asn Val Gly Ser Leu Ser Asp Gly Phe Tyr
385                 390                 395                 400

Thr Pro Gly Ser Glu Arg Met Leu Ala Thr Ala Val Ala Ile Glu Asp
                405                 410                 415

Lys Phe Ala Asn Leu Tyr Gly Ile Asn Arg Asn Leu Asp Ser Ser Leu
            420                 425                 430

Gly Asn Ala Ile Gly Arg Tyr Pro Glu Asp Thr Tyr Asn Gly Asn Gly
        435                 440                 445

Asn Ser Gln Gly Asn Pro Trp Phe Ile Ala Thr Asn Ala Tyr Ala Glu
    450                 455                 460

Leu Tyr Tyr Arg Ala Ile Lys Glu Trp Asn Asn Asn Gly Gly Val Thr
465                 470                 475                 480

Val Thr Asn Val Asn Leu Asn Phe Phe Lys Lys Phe Asp Gly Ser Ala
                485                 490                 495

Ser Val Gly Thr Lys Tyr Thr Ala Gly Ser Ala Ala Tyr Asn Thr Leu
            500                 505                 510

Thr Gln Asn Ile Ala Leu Ala Ala Asp Lys Phe Phe Asn Thr Val Lys
        515                 520                 525

Val His Ala Ala Thr Asn Gly Ser Met Ser Glu Gln Tyr His Arg Asp
    530                 535                 540

Thr Gly Ser Met Thr Gly Ala Arg Asp Leu Thr Trp Ser His Ala Ser
545                 550                 555                 560

Leu Ile Thr Ala Ala Leu Ala Lys Ala Gly Thr Pro Val Ala
                565                 570


<210> SEQ ID NO 66
<211> LENGTH: 584
<212> TYPE: PRT
<213> ORGANISM: Rhizopus stolonifer

<400> SEQUENCE: 66

Ala Ser Ile Pro Ser Ser Ser Glu Val Gln Leu Asp Thr Tyr Ala Tyr
1               5                   10                  15

Asp Gly Ala Lys Phe Ser Gly Lys Ile Tyr Val Lys Asn Ile Ala Tyr
            20                  25                  30

Glu Lys Thr Val Thr Val Val Tyr Ala Asp Gly Ser Asp Asn Trp Asn
        35                  40                  45

Asn Asn Gly Asn Ile Ile Ser Ala Thr Phe Ser Thr Pro Ile Ser Gly
    50                  55                  60

Ser Asn Tyr Glu Tyr Trp Thr Phe Ser Ser Ser Ile Ser Gly Ile Lys
65                  70                  75                  80

Glu Phe Tyr Ile Lys Tyr Val Val Ser Gly Lys Thr Tyr Tyr Asp Asn
                85                  90                  95

Asn Gly Thr Lys Asn Tyr Gln Val Ser Thr Thr Ser Ser Thr Thr Thr
            100                 105                 110

Ala Ser Thr Thr Thr Ala Thr Arg Thr Thr Thr Ala Gly Thr Thr Ser
        115                 120                 125

Thr Ser Thr Thr Ala Ala Pro Thr Ser Thr Ser Ser Gly Ser Phe Pro
    130                 135                 140

Ser Gly Asn Ser Thr Val Ser Ser Trp Ile Lys Arg Gln Glu Lys Ile
145                 150                 155                 160

Ser Arg Phe Ala Met Leu Arg Asn Ile Asn Pro Pro Gly Ser Ala Ala
                165                 170                 175

Gly Phe Ile Ala Ala Ser Leu Ser Thr Ser Gly Pro Asp Tyr Tyr Tyr
            180                 185                 190
```

```
Ser Trp Thr Arg Asp Ser Ala Leu Thr Ser Asn Leu Ile Ala Tyr Glu
        195                 200                 205

Tyr Asn Thr Thr Leu Ser Gly Asn Thr Thr Ile Leu Asn Ile Leu Lys
    210                 215                 220

Asp Tyr Val Lys Phe Ser Ile Ser Ser Gln Thr Thr Ser Thr Val Cys
225                 230                 235                 240

Asn Cys Leu Gly Glu Pro Lys Phe Asn His Asp Gly Ser Ser Tyr Thr
                245                 250                 255

Gly Ala Trp Gly Arg Pro Gln Asn Asp Gly Pro Ala Glu Arg Ala Asn
            260                 265                 270

Thr Phe Ile Leu Phe Ala Asp Ser Tyr Leu Asp Gln Thr Lys Asp Ala
        275                 280                 285

Ser Tyr Val Thr Gly Thr Leu Lys Pro Ala Ile Phe Lys Asp Leu Asp
    290                 295                 300

Tyr Val Val Asn Val Trp Ser Asn Gly Cys Tyr Asp Leu Trp Glu Glu
305                 310                 315                 320

Val Asn Gly Val His Phe Tyr Thr Leu Met Val Met Arg Lys Gly Leu
                325                 330                 335

Leu Leu Gly Ala Asp Phe Ala Lys Arg Asn Gly Asp Ser Thr Arg Ala
            340                 345                 350

Ser Thr Tyr Thr Asn Thr Ala Ser Thr Ile Ala Thr Lys Ile Ser Ser
        355                 360                 365

Phe Trp Val Ser Ser Ser Asn Trp Ile Gln Val Ser Gln Ser Val Thr
    370                 375                 380

Ala Gly Val Ser Lys Lys Gly Leu Asp Val Ser Thr Leu Leu Ala Ala
385                 390                 395                 400

Asn Leu Gly Ser Val Glu Asp Gly Phe Phe Thr Pro Gly Ser Glu Lys
                405                 410                 415

Ile Leu Ala Thr Ala Val Ala Ile Glu Asp Ala Phe Ala Ser Leu Tyr
            420                 425                 430

Pro Ile Asn Ser Asn Leu Pro Ser Tyr Leu Gly Asn Ser Ile Gly Arg
        435                 440                 445

Tyr Pro Glu Asp Thr Tyr Asn Gly Asn Gly Asn Ser Gln Gly Asn Pro
    450                 455                 460

Trp Phe Leu Ala Val Asn Gly Phe Ala Glu Leu Tyr Tyr Arg Ala Ile
465                 470                 475                 480

Lys Glu Trp Val Asn Asn Gly Ser Val Thr Val Ser Asn Ile Ser Leu
                485                 490                 495

Ser Phe Phe Lys Lys Phe Asp Ser Ser Ala Thr Ala Gly Lys Thr Tyr
            500                 505                 510

Thr Ala Gly Thr Ala Asp Phe Asn Asn Leu Ala Gln Asn Ile Ala Leu
        515                 520                 525

Gly Ala Asp Arg Phe Leu Ser Thr Val Gln Thr His Ala Phe Asn Asn
    530                 535                 540

Gly Ser Leu Ala Glu Glu Tyr Asp Arg Thr Thr Gly Val Ser Thr Gly
545                 550                 555                 560

Ala Arg Asp Leu Thr Trp Ser His Ala Ser Leu Ile Thr Ala Ala Tyr
                565                 570                 575

Ala Lys Ala Gly Ser Pro Ala Ala
            580
```

<210> SEQ ID NO 67
<211> LENGTH: 584

<212> TYPE: PRT
<213> ORGANISM: Mucor circinelloides

<400> SEQUENCE: 67

Glu Thr Val Pro Thr Thr Ala Ala Val Lys Val Lys Ser Phe Thr Tyr
1 5 10 15

Asp Gly Ser Thr Phe Ala Gly Gln Ile Tyr Val Lys Asn Ile Ala Tyr
20 25 30

Thr Lys Thr Val Thr Val Ile Tyr Ser Asp Ala Ser Asn Asn Trp Asn
35 40 45

Asn Asn Gly Asn Thr Ile Ala Ala Ser Tyr Ser Glu Gly Ile Ser Gly
50 55 60

Thr Asn Tyr Glu Tyr Trp Thr Phe Ser Ala Pro Val Ser Gly Ile Lys
65 70 75 80

Gln Phe Tyr Val Lys Tyr Val Val Ser Gly Thr Thr Tyr Tyr Asp Asn
85 90 95

Asn Asn Ser Gly Asn Tyr Gln Val Thr Thr Thr Thr Thr Thr Thr Ala
100 105 110

Pro Thr Ser Thr Thr Ser Gly Gly Ser Ser Thr Thr Thr Gly Gly Ser
115 120 125

Thr Thr Thr Ala Thr Ser Val Pro Thr Gly Val Pro Ser Gly Phe Pro
130 135 140

Thr Gly Asn Ser Ser Ile Ser Ser Trp Ile Asp Gly Gln Thr Ser Val
145 150 155 160

Ser Arg Tyr Ala Met Leu Arg Asn Ile Asn Pro Ala Gly Ala Val Ser
165 170 175

Gly Phe Ile Ala Ala Ser Met Ser Thr Ser Gly Pro Asp Tyr Phe Tyr
180 185 190

Ala Trp Thr Arg Asp Ser Ala Leu Thr Ser His Val Val Ala Tyr Asp
195 200 205

Tyr Asn Thr Thr Leu Ala Gly Asn Ser Thr Ile Leu Gly Leu Leu Lys
210 215 220

Asn Tyr Val Thr Phe Ser Ile Asn Ser Gln Thr Thr Ser Thr Val Cys
225 230 235 240

Asn Cys Leu Gly Glu Pro Lys Phe Asn Lys Asp Gly Ser Ser Tyr Thr
245 250 255

Gly Ala Trp Gly Arg Pro Gln Asn Asp Gly Pro Ala Ser Arg Ala Asp
260 265 270

Thr Phe Ile Leu Ile Ala Asp Ser Ile Leu Lys Gln Thr Gly Asp Ala
275 280 285

Thr Tyr Val Thr Gly Thr Leu Ala Pro Ala Ile Tyr Lys Asp Leu Asp
290 295 300

Tyr Val Val Ser Thr Trp Ser Asn Gly Cys Phe Asp Leu Trp Glu Glu
305 310 315 320

Val Asn Gly Val His Phe Tyr Thr Leu Met Val Met Arg Arg Gly Leu
325 330 335

Ile Lys Gly Ala Asn Phe Ala Ser Arg Asn Gly Asp Asn Thr Arg Ala
340 345 350

Asn Thr Tyr Thr Asn Thr Ala Ala Ser Ile Lys Thr Lys Ile Asp Ser
355 360 365

Phe Trp Asn Ser Asn Gly Asn Tyr Val Thr Val Ser Gln Ser Val Thr
370 375 380

Gly Gly Val Ser Lys Ala Gly Tyr Asp Ala Ser Val Leu Ile Ala Ala
385 390 395 400

Asn Leu Gly Ser Val Gln Asp Gly Phe Tyr Thr Pro Gly Ser Asp Lys
405 410 415

Met Leu Ala Thr Ala Val Ala Ile Glu Ser Lys Phe Ala Ser Leu Tyr
420 425 430

Ser Ile Asn Gln Asn Leu Asn Gly Tyr Leu Gly Asn Ala Ile Gly Arg
435 440 445

Tyr Pro Glu Asp Thr Tyr Asn Gly Asn Gly Asn Ser Gln Gly Asn Pro
450 455 460

Trp Phe Ile Cys Thr Asn Ala Phe Ala Glu Leu Tyr Tyr Arg Ala Ile
465 470 475 480

Lys Glu Trp Phe Asn Asn Gly Gly Val Thr Val Thr Ser Ile Ser Leu
485 490 495

Asn Phe Phe Lys Lys Phe Asp Ser Ser Ala Ala Val Gly Thr Lys Tyr
500 505 510

Thr Val Gly Thr Ser Ala Phe Asn Ser Leu Val Gln Asn Val Ala Val
515 520 525

Ala Ala Asp Ala Phe Phe Ser Thr Val Lys Phe His Ala Ala Thr Asn
530 535 540

Gly Ser Met Ser Glu Gln Tyr Gly Arg Ser Asp Gly Leu Met Thr Gly
545 550 555 560

Ala Arg Asp Leu Thr Trp Ser His Ala Ser Leu Ile Ser Ala Ser Tyr
565 570 575

Ala Lys Ala Gly Ser Pro Ala Ala
580

<210> SEQ ID NO 68
<211> LENGTH: 581
<212> TYPE: PRT
<213> ORGANISM: Dichotomocladium elegans

<400> SEQUENCE: 68

Ala Thr Val Pro Lys Thr Gln Val Lys Leu Glu Ala Tyr Thr Tyr Ser
1 5 10 15

Asp Ser Ile Phe Ser Gly Arg Ile Phe Val Gln Asn Ile Asp Tyr Thr
20 25 30

Lys Ile Val Thr Val Tyr Trp Ser Asp Ala Ser Asn Lys Trp Asp Ser
35 40 45

Ser Lys Tyr Tyr Thr Glu Ala Ala Tyr Thr His Ser Ile Pro Gly Thr
50 55 60

Asn Tyr Glu Tyr Trp Asp Phe Ser Ala Thr Ile Gly Pro Ser Gly Ile
65 70 75 80

Lys Gln Phe Tyr Ile Ser Tyr Gln Val Arg Gly Val Thr Tyr Tyr Asp
85 90 95

Asn Asn Gly Gly Tyr Gly Val Asn Tyr Asp Val Ile Ser Ser Pro Pro
100 105 110

Thr Thr Ser Asp Ala Thr Thr Ile Pro Thr Thr Thr Thr Ser Ala Ile
115 120 125

Pro Ser Ser Thr Thr Thr Ile Pro Ala Ser Thr Gly Val Pro Ser Gly
130 135 140

Asn Ser Thr Ile Thr Val Trp Ala Asp Ser Gln His Lys Ile Ser Trp
145 150 155 160

Lys Ala Met Leu Ala Asn Ile Asn Pro Pro Gly Ser Ala Thr Gly Phe
165 170 175

Ile Ala Ala Ser Leu Ser Thr Ser Gly Pro Asp Tyr Tyr Tyr Ala Trp

```
            180                 185                 190

Thr Arg Asp Ala Ala Met Val Ala His Val Ile Val Asn Ala Tyr Asn
        195                 200                 205

Thr Thr Lys Ala Gly Asp Ala Thr Thr Leu Gly Val Leu Lys Asp Phe
    210                 215                 220

Val Thr Phe Gln Ile Lys Ala Met Ala Thr Ser Thr Val Cys Asn Cys
225                 230                 235                 240

Leu Gly Glu Pro Lys Phe Asn Pro Asp Gly Ser Ser Tyr Thr Gly Pro
                245                 250                 255

Trp Gly Arg Pro Gln Asn Asp Gly Pro Ala Glu Arg Ala Thr Thr Phe
            260                 265                 270

Ile Leu Phe Ala Asp Ser Tyr Leu Ser Gln Thr Gly Asp Ala Ala Tyr
        275                 280                 285

Val Thr Thr Leu Lys Arg Ala Ile Phe Thr Asp Leu Asp Tyr Val Val
    290                 295                 300

Thr Thr Trp Gln Asp Asn Cys Phe Asp Leu Trp Glu Glu Val Asn Gly
305                 310                 315                 320

Leu His Met Tyr Thr Leu Ala Val Met Arg Arg Ser Leu Val Asp Gly
                325                 330                 335

Ala Ser Phe Ala Ala Arg Asn Gly Asp Asn Thr Arg Ala Ser Thr Tyr
            340                 345                 350

Thr Asn Thr Ala Lys Ser Ile Glu Thr Lys Leu Ala Ser Phe Tyr Asn
        355                 360                 365

Ser Ser Ser Asn Tyr Val Val Val Thr Lys Asn Phe Ala Gly Gly Val
    370                 375                 380

Asn Lys Ala Gly Leu Asp Thr Ser Thr Leu Ile Ala Ala Asn Thr Ala
385                 390                 395                 400

Gly Leu Gly Asp Gly Phe Phe Thr Pro Gly Ser Pro Glu Ile Leu Ala
                405                 410                 415

Thr Ala Ala Ala Ile Glu Lys Ser Phe Ala Asp Leu Tyr Gly Ile Asn
            420                 425                 430

Lys Gln Ile Pro Asn Trp Leu Gly Thr Ala Ile Gly Arg Tyr Pro Glu
        435                 440                 445

Asp Thr Tyr Asn Gly Asn Gly Asn Ser Gln Gly Asn Pro Trp Phe Ile
    450                 455                 460

Cys Thr Ala Thr Phe Ala Glu Leu Tyr Tyr Arg Ala Ile Leu Glu Trp
465                 470                 475                 480

Gln His Ala Gly Ser Val Thr Val Asn Asn Val Asn Leu Pro Phe Phe
                485                 490                 495

Lys Lys Phe Asp Ser Ser Thr Ser Ser Gly Thr Thr Tyr Thr Val Gly
            500                 505                 510

Thr Ser Ser Phe Asp Ser Leu Ile Ser Lys Val Ala Tyr Ala Ala Asp
        515                 520                 525

Asn Phe Phe Ser Thr Ile Lys Tyr His Ala Ala Thr Asn Gly Ser Met
    530                 535                 540

Ser Glu Gln Phe Asn Arg Asp Thr Gly Phe Met Thr Gly Ala Arg Asp
545                 550                 555                 560

Leu Thr Trp Ser His Ala Ala Phe Ile Thr Ala Ala Lys Ala Lys Ala
                565                 570                 575

Gly Thr Pro Val Tyr
            580
```

<210> SEQ ID NO 69

```
<211> LENGTH: 582
<212> TYPE: PRT
<213> ORGANISM: Fennellomyces sp.

<400> SEQUENCE: 69

Gln Thr Val Pro Ser Val Pro Ile Lys Leu Glu Ser Tyr Thr Tyr Ser
1               5                   10                  15

Asp Asn Val Phe Ala Gly Arg Ile Phe Ile Arg Asn Ile Ala Tyr Thr
            20                  25                  30

Lys Val Val Lys Val Phe Trp Ser Asp Glu Ser Gly Asn Trp Asn Gly
        35                  40                  45

Asn Gly Asn Tyr Val Asp Ala Ser Tyr Ser Gly Ser Ile Ser Gly Thr
    50                  55                  60

Asn Tyr Glu Tyr Trp Glu Phe Ser Thr Thr Ile Gly Ser Ala Gly Ile
65                  70                  75                  80

Ser Gln Ser Tyr Leu Arg Tyr Asp Val Ser Gly Ser Thr Tyr Tyr Asp
                85                  90                  95

Asn Asn Gly Asn Ala Asn Tyr Asp Ile Glu Glu Asp Ser Thr Pro Thr
            100                 105                 110

Pro Thr Thr Thr Thr Thr Ser Thr Thr Thr Ile Thr Thr Thr Thr Thr
        115                 120                 125

Ser Gly Thr Ser Thr Pro Thr Ser Val Pro Thr Glu Val Pro Ala Gly
    130                 135                 140

Asn Thr Thr Val Thr Asp Trp Val Asn Asp Gln Leu Glu Ile Ser Trp
145                 150                 155                 160

Pro Ser Leu Leu Lys Asn Val Asn Pro Ser Gly Ala Val Thr Gly Phe
                165                 170                 175

Ile Ala Ala Ser Leu Ser Thr Asn Asp Pro Asp Tyr Phe Tyr Cys Trp
            180                 185                 190

Thr Arg Asp Ala Ala Leu Val Ala Arg Val Met Val Tyr Met Tyr Asn
        195                 200                 205

Thr Thr Glu Ala Gly Asp Thr Ser Leu Arg Ser Lys Leu Gln Asp Tyr
    210                 215                 220

Val Thr Phe Gln Ile Asn Ser Met Lys Thr Ala Thr Val Cys Asn Cys
225                 230                 235                 240

Leu Gly Glu Pro Lys Phe Asn Lys Asp Gly Ser Gly Tyr Ser Gly Ala
                245                 250                 255

Trp Gly Arg Pro Gln Asn Asp Gly Pro Ala Asp Arg Ala Ile Thr Leu
            260                 265                 270

Ile Leu Phe Ala Asp Ser Phe Ile Ala Gln Gly Gly Asp Val Ser Tyr
        275                 280                 285

Ile Thr Asn Thr Leu Lys Pro Ala Ile Tyr Thr Asn Leu Asp Tyr Val
    290                 295                 300

Val Asn Thr Trp Ser Asn Val Cys Phe Asp Leu Trp Glu Glu Val Asn
305                 310                 315                 320

Gly Val His Ile Tyr Thr Leu Ser Val Met Arg Lys Gly Leu Leu Glu
                325                 330                 335

Gly Ala Asp Phe Ala Ser Arg Asn Gly Asp Ser Thr Arg Ala Asn Thr
            340                 345                 350

Tyr Arg Ser Thr Ala Ser Ser Ile Lys Thr Arg Leu Glu Ser Phe Trp
        355                 360                 365

Ser Ser Ser Asn Asn Tyr Ile Thr Val Thr Gln Ser Tyr Ser Gly Gly
    370                 375                 380

Val Asn Lys Ala Gly Leu Asp Val Ser Thr Leu Leu Ala Ala Asn Gly
```

```
385                 390                 395                 400

Ala Ser Met Asn Asp Gly Phe Tyr Thr Pro Gly Ser Asp Lys Met Leu
                405                 410                 415

Ala Thr Ala Val Ala Ile Glu Asn Ser Phe Ala Gly Ile Tyr Ala Val
            420                 425                 430

Asn Gln Asn Arg Pro Asp Trp Lys Gly Thr Ala Ile Gly Arg Tyr Pro
        435                 440                 445

Glu Asp Thr Tyr Asp Gly His Gly Asn Ser Gln Gly Asn Pro Trp Phe
    450                 455                 460

Ile Ala Thr Ala Ala Tyr Ala Glu Met Tyr Tyr Arg Ala Ile Leu Glu
465                 470                 475                 480

Trp Gln Gln Gln Pro Ser Ile Thr Val Asn Ser Ile Asn Leu Ser Phe
                485                 490                 495

Phe Lys Lys Phe Asp Ser Ser Ala Ala Val Gly Thr Val Tyr Lys Pro
            500                 505                 510

Gly Thr Gln Ala Phe Asn Asn Met Val Ser Asn Val Ala Phe Ala Ala
        515                 520                 525

Asp Glu Phe Phe Ser Thr Met Asn Phe His Ser Ala Thr Asn Gly Ser
    530                 535                 540

Met Ser Glu Gln Tyr Asn Arg Asn Thr Gly Ile Met Gln Gly Ala Arg
545                 550                 555                 560

Asp Leu Thr Trp Ser His Ala Ala Phe Ile Thr Ala Ala Lys Ala Lys
                565                 570                 575

Leu Gly Thr Pro Val Phe
            580


<210> SEQ ID NO 70
<211> LENGTH: 577
<212> TYPE: PRT
<213> ORGANISM: Gilbertella persicaria

<400> SEQUENCE: 70

Glu Thr Val Pro Thr Ser Ala Gln Val Gln Val Lys Ser Phe Asn Tyr
1               5                   10                  15

Asp Gly Ser Thr Leu Ser Gly Gln Ile Tyr Val Gln Asn Ile Ala Tyr
            20                  25                  30

Glu Lys Thr Val Thr Val Val Tyr Ser Asp Gly Ser Asp Asn Trp Asn
        35                  40                  45

Asn Asn Gly Asn Thr Ile Ala Ala Ser Tyr Ser Ser Ser Ile Ser Gly
    50                  55                  60

Ser Asn Tyr Glu Tyr Trp Thr Phe Ser Ser Ser Val Pro Ser Ile Lys
65                  70                  75                  80

Gln Phe Tyr Ile Lys Tyr Val Val Ala Gly Lys Thr Tyr Tyr Asp Asn
                85                  90                  95

Asn Gly Thr Lys Asn Tyr Gln Val Ser Ala Ser Thr Pro Thr Thr Thr
            100                 105                 110

Thr Thr Thr Thr Ser Ser Gly Ala Thr Lys Thr Thr Thr Thr Ile Gly
        115                 120                 125

Pro Thr Ser Thr Ser Thr Val Phe Pro Ser Gly Asn Ser Thr Ile Ser
    130                 135                 140

Ser Trp Leu Lys Gly Gln Ile Glu Thr Ser Arg Phe Ala Met Leu Arg
145                 150                 155                 160

Asn Ile Asn Pro Ala Gly Thr Val Lys Gly Phe Ile Ala Ala Ser Leu
                165                 170                 175
```

```
Ser Thr Ala Asn Pro Asp Tyr Phe Tyr Ala Trp Thr Arg Asp Ala Ala
            180                 185                 190

Leu Val Gly His Val Ile Ala Asn Asp Tyr Asn Arg Thr Leu Ala Gly
        195                 200                 205

Asn Ser Thr Tyr Leu Gly Leu Leu Lys Asp Tyr Val Thr Phe Ser Val
    210                 215                 220

Asn Ser Gln Ser Thr Ser Thr Ile Cys Asn Cys Leu Gly Glu Pro Lys
225                 230                 235                 240

Phe Asn Lys Asp Gly Ser Gly Tyr Ser Gly Ala Trp Gly Arg Pro Gln
                245                 250                 255

Asn Asp Gly Pro Ala Glu Arg Ala Asp Thr Phe Ile Leu Ile Ala Asp
            260                 265                 270

Ser Ile Leu Lys Gln Thr Gly Asp Ala Thr Tyr Val Thr Gly Thr Leu
        275                 280                 285

Arg Pro Ala Ile Tyr Lys Asp Leu Asp Tyr Val Val Asn Val Trp Ser
    290                 295                 300

Asn Gly Cys Phe Asp Leu Trp Glu Glu Val Asn Gly Val His Phe Tyr
305                 310                 315                 320

Thr Leu Met Val Met Arg Arg Ser Leu Ile Leu Gly Ala Asn Phe Ala
                325                 330                 335

Ser Arg Asn Gly Asp Ser Thr Arg Ala Ser Thr Tyr Thr Asn Thr Ala
            340                 345                 350

Asn Ser Ile Lys Thr Lys Ile Asp Thr Phe Trp Ser Ser Ser Asn Asn
        355                 360                 365

Tyr Val Ala Val Ser Gln Ser Val Thr Gly Gly Val Asn Lys Ala Gly
    370                 375                 380

Tyr Asp Val Ala Asn Leu Ile Ala Ala Asn Val Gly Ser Leu Asp Asp
385                 390                 395                 400

Gly Phe Tyr Thr Pro Gly Ser Glu Arg Ile Leu Ala Thr Ala Val Ala
                405                 410                 415

Val Glu Ser Lys Phe Ala Ser Ile Tyr Gly Val Asn Gln Asn Leu Pro
            420                 425                 430

Ser Trp Leu Gly Asn Ser Ile Gly Arg Tyr Pro Glu Asp Thr Tyr Asn
        435                 440                 445

Gly Asn Gly Asn Ser Gln Gly Asn Pro Trp Phe Ile Ala Thr Asn Thr
    450                 455                 460

Tyr Ala Glu Leu Tyr Tyr Arg Ala Ile Lys Glu Trp Thr Asn Asn Gly
465                 470                 475                 480

Gly Val Thr Val Thr Asn Val Asn Phe Asn Phe Phe Lys Lys Phe Asp
                485                 490                 495

Ser Ser Ala Ser Val Gly Thr Lys Tyr Thr Val Gly Thr Ser Ala Phe
            500                 505                 510

Asn Thr Leu Thr Gln Asn Val Ala Leu Ala Ala Asp Asn Phe Phe Ser
        515                 520                 525

Thr Val Lys Val His Ala Ala Thr Asn Gly Ser Met Ser Glu Gln Phe
    530                 535                 540

Gly Arg Asp Ser Gly Val Met Thr Gly Ala Arg Asp Leu Thr Trp Ser
545                 550                 555                 560

His Ala Ser Leu Ile Thr Ala Ala Leu Ala Lys Thr Gly Ala Pro Val
                565                 570                 575

Ala
```

<210> SEQ ID NO 71

<211> LENGTH: 585
<212> TYPE: PRT
<213> ORGANISM: Mucor circinelloides

<400> SEQUENCE: 71

```
Glu Thr Val Pro Thr Thr Glu Ala Val Lys Val Lys Ser Phe Thr Tyr
1               5                   10                  15

Asp Gly Ser Thr Leu Ala Gly Gln Ile Tyr Ile Lys Asn Ile Ala Tyr
            20                  25                  30

Thr Lys Thr Val Thr Val Ile Tyr Ser Asp Ala Ser Asp Asn Trp Asn
        35                  40                  45

Asn Asn Gly Asn Thr Ile Ala Ala Ser Tyr Ser Ala Ala Ile Ala Gly
    50                  55                  60

Thr Asn Tyr Glu Tyr Trp Thr Phe Ser Ala Pro Val Ser Gly Ile Lys
65                  70                  75                  80

Gln Phe Tyr Val Lys Tyr Val Val Ser Gly Thr Thr Tyr Tyr Asp Asn
                85                  90                  95

Asn Asn Ser Gly Asn Tyr Gln Val Ser Val Thr Thr Thr Thr Thr Thr
            100                 105                 110

Ala Pro Thr Thr Thr Thr Ser Gly Gly Ser Ser Thr Thr Thr Gly Gly
        115                 120                 125

Ser Thr Thr Thr Ala Thr Ser Val Pro Thr Gly Val Pro Ser Gly Phe
    130                 135                 140

Pro Thr Gly Asn Ser Thr Ile Ser Ser Trp Ile Asp Gly Gln Thr Ser
145                 150                 155                 160

Val Ser Arg Tyr Ala Met Leu Arg Asn Ile Asn Pro Ala Gly Ala Val
                165                 170                 175

Thr Gly Phe Ile Ala Ala Ser Met Ser Thr Ser Gly Pro Asp Tyr Phe
            180                 185                 190

Tyr Ala Trp Thr Arg Asp Ser Ala Leu Thr Ser His Val Val Ala Tyr
        195                 200                 205

Asp Tyr Asn Thr Thr Leu Ala Gly Asn Ser Thr Ile Leu Gly Leu Leu
    210                 215                 220

Lys Asn Tyr Val Thr Phe Ser Leu Asn Ser Gln Thr Thr Ser Thr Val
225                 230                 235                 240

Cys Asn Cys Leu Gly Glu Pro Lys Phe Asn Lys Asp Gly Ser Gly Tyr
                245                 250                 255

Ser Gly Ala Trp Gly Arg Pro Gln Asn Asp Gly Pro Ala Ser Arg Ala
            260                 265                 270

Asp Thr Phe Ile Leu Ile Ala Asp Ser Ile Leu Lys Gln Thr Gly Asp
        275                 280                 285

Ala Thr Tyr Val Thr Gly Thr Leu Ala Pro Ala Ile Tyr Lys Asp Leu
    290                 295                 300

Asp Tyr Val Val Ser Thr Trp Ser Asn Gly Cys Phe Asp Leu Trp Glu
305                 310                 315                 320

Glu Val Asn Gly Val His Phe Tyr Thr Leu Met Val Met Arg Arg Gly
                325                 330                 335

Leu Val Lys Gly Ala Asn Phe Ala Ser Arg Asn Gly Asp Ser Thr Arg
            340                 345                 350

Ala Thr Thr Tyr Thr Asn Thr Ala Ala Ser Ile Lys Thr Lys Ile Asp
        355                 360                 365

Ser Phe Trp Asn Ser Asn Gly Gln Tyr Val Ser Val Ser Gln Ser Val
    370                 375                 380

Thr Gly Gly Val Ser Lys Ala Gly Tyr Asp Ala Ser Val Leu Ile Ala
```

```
385                 390                 395                 400

Ser Asn Leu Gly Ser Leu Gln Asp Gly Phe Tyr Thr Pro Gly Ser Asp
                405                 410                 415

Lys Met Leu Ala Thr Ala Val Ala Ile Glu Ser Lys Phe Ala Ser Leu
            420                 425                 430

Tyr Ser Ile Asn Gln Asn Leu Asn Gly Tyr Leu Gly Asn Ala Ile Gly
        435                 440                 445

Arg Tyr Pro Glu Asp Thr Tyr Asn Gly Asn Gly Asn Ser Gln Gly Asn
    450                 455                 460

Pro Trp Phe Ile Cys Thr Asn Ala Phe Ala Glu Leu Tyr Tyr Arg Ala
465                 470                 475                 480

Ile Lys Glu Trp Phe Asn Asn Gly Gly Val Thr Val Thr Ser Ile Ser
                485                 490                 495

Leu Asn Phe Phe Lys Lys Phe Asp Ser Ser Ala Ala Val Gly Thr Lys
            500                 505                 510

Tyr Thr Val Gly Thr Ser Ser Phe Asn Ser Leu Val Gln Asn Val Ala
        515                 520                 525

Val Ala Ala Asp Ala Phe Phe Ser Thr Ile Lys Phe His Ala Ala Thr
    530                 535                 540

Asn Gly Ser Met Ser Glu Gln Tyr Gly Arg Thr Asp Gly Leu Met Thr
545                 550                 555                 560

Gly Ala Arg Asp Leu Thr Trp Ser His Ala Ser Leu Ile Ser Ala Ser
                565                 570                 575

Tyr Ala Lys Ala Gly Ser Pro Ala Ala
            580                 585


<210> SEQ ID NO 72
<211> LENGTH: 583
<212> TYPE: PRT
<213> ORGANISM: Circinella umbellata

<400> SEQUENCE: 72

Ala Pro Thr Ser Glu Ile Glu Leu Asp Ser Tyr Thr Tyr Thr Gly Gly
1               5                   10                  15

Val Phe Ser Gly Arg Leu Tyr Val Lys Asn Ile Ala Tyr Thr Lys Glu
            20                  25                  30

Val Asn Val Tyr Trp Ser Asp Ala Ser Glu Asp Trp Ala Asn Asn Gly
        35                  40                  45

Asn Tyr Val Ala Ala Thr Tyr Ser Glu Ala Ile Ser Gly Thr Asn Tyr
    50                  55                  60

Glu Tyr Trp Glu Phe Ser Ala Lys Ile Gly Ser Ser Gly Ile Ser Glu
65                  70                  75                  80

Ser Tyr Ile Lys Tyr Thr Val Ser Gly Ser Thr Tyr Tyr Asp Asn Asn
                85                  90                  95

Gly Gly Lys Asn Tyr Ala Ile Thr Glu Thr Thr Thr Pro Thr Ile Thr
            100                 105                 110

Ala Thr Pro Thr Ser Thr Thr Ala Thr Thr Thr Ile Ser Ser Thr Thr
        115                 120                 125

Thr Thr Ala Thr Ser Ile Pro Thr Ser Val Pro Ser Thr Val Pro Glu
    130                 135                 140

Gly Asn Val Thr Val Thr Glu Trp Val Asn Lys Gln Leu Lys Ile Ser
145                 150                 155                 160

Trp Ser Asp Leu Leu Gln Asn Val Asn Pro Ser Gly Thr Val Thr Gly
                165                 170                 175
```

```
Phe Ile Ala Ala Ser Leu Ser Thr Ser Asn Pro Asp Tyr Phe Tyr Cys
            180                 185                 190

Trp Thr Arg Asp Ala Ala Met Val Ala Arg Val Met Thr Tyr Met Tyr
        195                 200                 205

Asn Thr Thr Glu Ala Gly Asp Ser Ser Leu Glu Ser Ala Leu Lys Asp
    210                 215                 220

Tyr Ile Thr Phe Gln Ile Asn Ser Met Lys Thr Ala Thr Ala Cys Asn
225                 230                 235                 240

Cys Leu Gly Glu Pro Lys Phe Asn Thr Asp Gly Ser Gly Tyr Ser Gly
                245                 250                 255

Pro Trp Gly Arg Pro Gln Asn Asp Gly Pro Ala Glu Arg Ala Thr Thr
            260                 265                 270

Met Ile Leu Phe Ala Asp Ser Tyr Leu Ala Gln Gly Gly Asp Thr Ser
        275                 280                 285

Tyr Val Thr Asn Thr Leu Lys Pro Ala Ile Tyr Thr Asn Leu Asp Tyr
    290                 295                 300

Val Val Gly Thr Trp Ser Asn Asn Cys Phe Asp Leu Trp Glu Glu Val
305                 310                 315                 320

Asn Gly Val His Ile Phe Thr Leu Ala Val Met Arg Lys Ser Leu Leu
                325                 330                 335

Asp Gly Ala Asp Phe Ala Ala Arg Asn Gly Asp Thr Ser Arg Val Ser
            340                 345                 350

Gly Tyr Gln Ser Thr Ala Ser Ser Ile Lys Thr Lys Leu Glu Ser Phe
        355                 360                 365

Trp Ser Ser Ser Asn Asn Tyr Ile Thr Val Thr Gln Ser Tyr Ser Gly
    370                 375                 380

Gly Val Gln Lys Ala Gly Leu Asp Val Ser Thr Leu Ile Ala Ala Asn
385                 390                 395                 400

Gln Gly Ser Met Gly Asp Gly Phe Tyr Thr Pro Gly Ser Asp Lys Met
                405                 410                 415

Leu Ala Thr Ala Val Ala Ile Glu Asn Ser Phe Ala Asn Ile Tyr Thr
            420                 425                 430

Ile Asn Lys Asn Lys Pro Ser Trp Leu Gly Thr Ala Ile Gly Arg Tyr
        435                 440                 445

Pro Glu Asp Thr Tyr Asn Gly Asn Gly Asn Gly Gln Gly Asn Pro Trp
    450                 455                 460

Phe Ile Ala Thr Ala Thr Tyr Ala Glu Leu Tyr Tyr Arg Ala Ile Leu
465                 470                 475                 480

Glu Trp Gln Gln Gln Glu Ser Val Thr Val Asn Ser Val Asn Phe Asp
                485                 490                 495

Phe Phe Ser Lys Phe Asp Ser Ser Ala Lys Val Gly Thr Val Tyr Thr
            500                 505                 510

Pro Gly Thr Asp Thr Phe Asn Thr Met Val Ser Asn Val Ala Phe Ala
        515                 520                 525

Ala Asp Glu Phe Leu Ser Thr Met Glu His Tyr Ala Ala Thr Asn Gly
    530                 535                 540

Ser Met Ser Glu Gln Phe Asn Arg Glu Thr Gly Ser Leu Thr Gly Ala
545                 550                 555                 560

Arg Asp Leu Thr Trp Ser His Ala Ala Phe Ile Thr Ala Gly Lys Ala
                565                 570                 575

Lys Leu Gly Ile Pro Ser Phe
            580
```

<210> SEQ ID NO 73
<211> LENGTH: 585
<212> TYPE: PRT
<213> ORGANISM: Mucor cordense

<400> SEQUENCE: 73

```
Glu Thr Val Pro Thr Thr Ala Asn Val Leu Val Lys Ser Tyr Thr Trp
1               5                   10                  15

Asp Gly Ala Thr Leu Ser Gly Gln Ile Tyr Ile Lys Asn Leu Ala Tyr
            20                  25                  30

Ala Lys Val Val Ser Val Ile Tyr Ser Asp Ala Asn Asp Asn Trp Asn
        35                  40                  45

Asn Asn Gly Asn Lys Val Ala Ala Ser Tyr Ser Ala Gly Ile Asp Gly
    50                  55                  60

Thr Asn Tyr Glu Tyr Trp Thr Phe Ser Gly Ala Val Ser Gly Ile Lys
65                  70                  75                  80

Gln Phe Tyr Val Lys Tyr Asp Val Ser Gly Thr Ser Tyr Tyr Asp Asn
                85                  90                  95

Asn Gly Thr Lys Asn Tyr Gln Val Thr Lys Thr Ser Thr Thr Thr Thr
            100                 105                 110

Ala Ala Thr Thr Thr Thr Thr Ala Thr Thr Thr Thr Gly Gly Thr Gly
        115                 120                 125

Thr Thr Thr Thr Thr Thr Ala Thr Ala Thr Ala Thr Ser Thr Asp Phe
    130                 135                 140

Pro Thr Gly Asn Ser Thr Ile Thr Thr Trp Leu Lys Ser Gln Glu Asp
145                 150                 155                 160

Ile Ser Arg Gly Ala Met Leu Arg Asn Ile Asn Pro Pro Gly Ala Ala
                165                 170                 175

Thr Gly Phe Ile Ala Ala Ser Leu Ser Thr Ser Gly Pro Asp Tyr Tyr
            180                 185                 190

Tyr Ala Trp Thr Arg Asp Ser Ala Leu Thr Ser His Val Ile Ala His
        195                 200                 205

Asp Tyr Asn Thr Thr Leu Ala Gly Asn Thr Thr Ile Leu Asn Ile Leu
    210                 215                 220

Lys Asp Tyr Val Thr Phe Ser Val Lys Ser Gln Ser Val Ser Thr Val
225                 230                 235                 240

Cys Asn Cys Leu Gly Glu Pro Lys Phe Asn Pro Asp Gly Ser Ser Tyr
                245                 250                 255

Thr Gly Ala Trp Gly Arg Pro Gln Asn Asp Gly Pro Ala Glu Arg Ala
            260                 265                 270

Ser Thr Phe Ile Leu Phe Gly Asp Ser Tyr Leu Lys Gln Thr Gly Asp
        275                 280                 285

Ala Thr Tyr Val Thr Gly Thr Leu Ala Pro Ala Ile Tyr Lys Asp Leu
    290                 295                 300

Asp Tyr Val Val Asn Thr Trp Ser Asn Gly Cys Phe Asp Leu Trp Glu
305                 310                 315                 320

Glu Val Asn Gly Val His Phe Tyr Thr Leu Met Ser Met Arg Arg Gly
                325                 330                 335

Leu Leu Asp Gly Ala Asn Phe Ala Lys Arg Asn Gly Asp Thr Thr Arg
            340                 345                 350

Ala Thr Thr Tyr Thr Asn Thr Ala Ala Ser Ile Ala Thr Lys Ile Asp
        355                 360                 365

Thr Phe Trp Val Ser Ser Gly Asn Tyr Val Gln Val Ser Gln Ser Val
    370                 375                 380
```

```
Thr Gly Gly Val Ser Lys Ala Gly Tyr Asp Cys Ala Asn Ile Leu Ala
385                 390                 395                 400

Ala Asn Met Ala Ala Asn His Asp Gly Phe Tyr Thr Pro Gly Ser Ser
                405                 410                 415

Lys Ile Leu Ala Thr Ala Val Ala Ile Glu Ser Lys Phe Ala Ser Leu
            420                 425                 430

Tyr Ser Ile Asn Ser Gly Leu Ala Ser Trp Leu Gly Thr Ala Ile Gly
        435                 440                 445

Arg Tyr Pro Glu Asp Thr Tyr Asn Gly Asn Gly Asn Ser Gln Gly Asn
    450                 455                 460

Pro Trp Phe Ile Cys Thr Asn Ala Phe Ala Glu Leu Tyr Tyr Arg Ala
465                 470                 475                 480

Ile Lys Glu Trp Thr Gln Ala Gly Ser Val Thr Val Asp Ser Thr Ser
                485                 490                 495

Leu Asn Phe Phe Lys Lys Phe Asp Ser Ser Ala Ala Ala Gly Thr Lys
            500                 505                 510

Tyr Thr Val Gly Thr Ser Ala Phe Thr Asn Leu Val Gln Asn Ile Ala
        515                 520                 525

Asn Gly Ala Asp Lys Phe Leu Ser Thr Ser Lys Phe His Ala Ala Thr
    530                 535                 540

Asn Gly Ser Met Ser Glu Gln Tyr Asn Arg Asp Ser Gly Leu Met Thr
545                 550                 555                 560

Gly Ala Arg Asp Leu Thr Trp Ser His Ala Ser Leu Ile Ser Ala Ser
                565                 570                 575

Arg Ala Lys Ala Gly Ser Pro Ser Leu
            580                 585


<210> SEQ ID NO 74
<211> LENGTH: 590
<212> TYPE: PRT
<213> ORGANISM: Phascolomyces articulosus

<400> SEQUENCE: 74

Asp Val Pro Thr Ser Ala Asn Ile Glu Leu Asp Tyr Tyr Thr Tyr Lys
1               5                   10                  15

Asp Lys Val Phe Ser Gly Arg Ile Tyr Val Lys Asn Ile Ala Tyr Glu
            20                  25                  30

Lys Thr Val Ala Val Tyr Trp Ser Asp Ala Ser Gly Asp Trp Asn Asn
        35                  40                  45

Asn Gly Asn Asn Val Ala Ala Ser Tyr Ser Glu Ser Ile Ser Gly Thr
    50                  55                  60

Asp Tyr Glu Tyr Trp Asp Phe Ser Thr Thr Ile Gly Ser Gly Gly Ile
65                  70                  75                  80

Lys Gln Ser Tyr Leu Lys Tyr Thr Val Ser Gly Asn Thr Tyr Tyr Asp
                85                  90                  95

Asn Asn Gly Ser Asn Asn Tyr Asp Ile Thr Glu Thr Thr Ala Thr Thr
            100                 105                 110

Thr Thr Thr Thr Thr Thr Thr Thr Thr Thr Gly Ser Thr Ala Thr Thr
        115                 120                 125

Ser Thr Thr Ser Gly Pro Thr Ser Thr Thr Ser Thr Thr Pro Gly Pro
    130                 135                 140

Thr Pro Thr Asn Val Pro Asp Gly Asn Val Thr Val Thr Glu Trp Val
145                 150                 155                 160

Asn Thr Gln Phe Ala Ile Ser Trp Pro Thr Leu Leu Lys Asn Val Asn
                165                 170                 175
```

```
Pro Ser Gly Thr Val Lys Gly Phe Ile Ala Ala Ser Leu Ser Thr Asn
            180                 185                 190

Asn Pro Asp Tyr Phe Tyr Ser Trp Thr Arg Asp Ser Ala Leu Val Ala
        195                 200                 205

His Thr Met Thr Tyr Leu Tyr Asn Thr Ser Glu Ala Gly Asp Ser Thr
    210                 215                 220

Ile Glu Ser Ala Leu Lys Asp Tyr Val Thr Phe Ser Ile Asn Ala Met
225                 230                 235                 240

Asn Ala Ala Thr Val Cys Asn Cys Leu Gly Glu Pro Lys Phe Asn Thr
                245                 250                 255

Asp Gly Ser Gly Tyr Thr Gly Ala Trp Gly Arg Pro Gln Asn Asp Gly
            260                 265                 270

Pro Ala Ser Arg Ala Thr Thr Met Ile Leu Phe Ala Asp Ser Phe Leu
        275                 280                 285

Ala Gln Gly Gly Asp Val Ser Tyr Val Ile Asn Thr Leu Lys Pro Ala
    290                 295                 300

Ile Tyr Lys Asp Leu Asp Tyr Val Val Ser Thr Trp Ser Asn Thr Cys
305                 310                 315                 320

Tyr Asp Leu Trp Glu Glu Val Asn Gly Val His Ile Tyr Thr Leu Ser
                325                 330                 335

Val Met Arg Arg Ala Leu Ile Asp Gly Ala Asn Phe Ala Gln Arg Asn
            340                 345                 350

Gly Asp Thr Ser Arg Val Ser Gly Tyr Thr Ser Thr Ala Thr Thr Ile
        355                 360                 365

Lys Thr Arg Leu Glu Ser Phe Trp Ser Asp Ser Asn Asn Tyr Ile Thr
    370                 375                 380

Val Thr Gln Ser Tyr Ser Gly Gly Val Gln Lys Ala Gly Leu Asp Val
385                 390                 395                 400

Ser Thr Leu Ile Ala Ala Asn Ile Gly Ser Val Gly Asp Gly Phe Tyr
                405                 410                 415

Thr Pro Gly Ser Asp Lys Val Leu Ala Thr Ala Val Ala Ile Glu Lys
            420                 425                 430

Ser Phe Ala Asn Leu Tyr Thr Ile Asn Gln Asn Lys Pro Ser Trp Leu
        435                 440                 445

Gly Asn Ala Ile Gly Arg Tyr Pro Glu Asp Thr Tyr Asp Gly Tyr Gly
    450                 455                 460

Asn Ser Lys Gly Asn Pro Trp Phe Ile Ala Thr Ala Thr Tyr Ala Glu
465                 470                 475                 480

Leu Tyr Tyr Arg Ala Ile Leu Glu Trp Gln Gln Gln Ala Ser Val Thr
                485                 490                 495

Val Asn Ser Ile Asn Leu Gly Phe Phe Ser Lys Phe Asp Ser Ser Ala
            500                 505                 510

Ser Val Gly Thr Val Tyr Thr Pro Gly Thr Asp Ser Phe Ala Asn Met
        515                 520                 525

Val Ser Asn Val Ala Phe Ala Ala Asp Glu Phe Leu Ser Thr Ile Asp
    530                 535                 540

Tyr His Ala Met Asn Asn Gly Ser Met His Glu Gln Tyr Asn Arg Asp
545                 550                 555                 560

Thr Gly Ile Ser Gln Gly Ala Arg Asp Leu Thr Trp Ser His Ala Ala
                565                 570                 575

Phe Ile Thr Ala Ala Lys Ala Lys Leu Gly Ala Pro Ala Phe
            580                 585                 590
```

<210> SEQ ID NO 75
<211> LENGTH: 578
<212> TYPE: PRT
<213> ORGANISM: Rhizopus microsporus

<400> SEQUENCE: 75

Val Pro Thr Ser Ala Ala Val Gln Val Glu Ser Tyr Lys Tyr Asp Gly
1               5                   10                  15

Thr Thr Phe Ser Gly Arg Ile Phe Val Lys Asn Ile Ala Tyr Ser Lys
            20                  25                  30

Val Val Thr Val Ile Tyr Ser Asp Gly Ser Asp Asn Trp Asn Asn Asn
        35                  40                  45

Asn Asn Lys Ile Ser Ala Ala Tyr Ser Glu Ala Ile Ser Gly Ser Asn
    50                  55                  60

Tyr Glu Tyr Trp Thr Phe Ser Ala Lys Leu Ser Gly Ile Lys Gln Phe
65                  70                  75                  80

Tyr Val Lys Tyr Glu Val Ser Gly Ser Thr Tyr Tyr Asp Asn Asn Gly
                85                  90                  95

Thr Lys Asn Tyr Gln Val Gln Ala Thr Ser Ala Thr Ser Thr Thr Ala
            100                 105                 110

Thr Ala Thr Thr Thr Thr Ser Thr Ser Thr Thr Thr Thr Ser Thr Gly
        115                 120                 125

Pro Thr Ser Thr Ala Ser Val Ser Phe Pro Thr Gly Asn Ser Thr Ile
    130                 135                 140

Ser Ser Trp Ile Lys Asn Gln Glu Glu Ile Ser Arg Phe Ala Met Leu
145                 150                 155                 160

Arg Asn Ile Asn Pro Pro Gly Ser Ala Thr Gly Phe Ile Ala Ala Ser
                165                 170                 175

Leu Ser Thr Ala Gly Pro Asp Tyr Tyr Tyr Ser Trp Thr Arg Asp Ser
            180                 185                 190

Ala Leu Thr Ala Asn Val Ile Ala Tyr Glu Tyr Asn Thr Thr Phe Ala
        195                 200                 205

Gly Asn Thr Thr Leu Leu Lys Tyr Leu Lys Asp Tyr Val Thr Phe Ser
    210                 215                 220

Val Lys Ser Gln Ser Val Ser Thr Val Cys Asn Cys Leu Gly Glu Pro
225                 230                 235                 240

Lys Phe Asn Ala Asp Gly Ser Ser Tyr Thr Gly Pro Trp Gly Arg Pro
                245                 250                 255

Gln Asn Asp Gly Pro Ala Glu Arg Ala Val Thr Phe Met Leu Ile Ala
            260                 265                 270

Asp Ser Tyr Leu Thr Gln Thr Lys Asp Ala Ser Tyr Val Thr Gly Thr
        275                 280                 285

Leu Lys Pro Ala Ile Phe Lys Asp Leu Asp Tyr Val Val Ser Val Trp
    290                 295                 300

Ser Asn Gly Cys Tyr Asp Leu Trp Glu Glu Val Asn Gly Val His Phe
305                 310                 315                 320

Tyr Thr Leu Met Val Met Arg Lys Gly Leu Ile Leu Gly Ala Asp Phe
                325                 330                 335

Ala Ala Arg Asn Gly Asp Ser Ser Arg Ala Ser Thr Tyr Lys Asn Thr
            340                 345                 350

Ala Ser Thr Met Glu Ser Lys Ile Ser Ser Phe Trp Ser Asp Ser Asn
        355                 360                 365

Asn Tyr Val Gln Val Ser Gln Ser Val Thr Ala Gly Val Ser Lys Lys
    370                 375                 380

```
Gly Leu Asp Val Ser Thr Leu Leu Ala Ala Asn Ile Gly Ser Leu Pro
385                 390                 395                 400

Asp Gly Phe Phe Thr Pro Gly Ser Glu Lys Ile Leu Ala Thr Ala Val
                405                 410                 415

Ala Leu Glu Asn Ala Phe Ala Ser Leu Tyr Pro Ile Asn Ser Asn Leu
            420                 425                 430

Pro Ser Tyr Leu Gly Asn Ser Ile Gly Arg Tyr Pro Glu Asp Thr Tyr
        435                 440                 445

Asn Gly Asn Gly Asn Ser Gln Gly Asn Pro Trp Phe Leu Ala Val Asn
    450                 455                 460

Ala Tyr Ala Glu Leu Tyr Tyr Arg Ala Ile Lys Glu Trp Ile Ser Asn
465                 470                 475                 480

Gly Lys Val Thr Val Ser Asn Ile Ser Leu Pro Phe Phe Lys Lys Phe
                485                 490                 495

Asp Ser Ser Ala Thr Ser Gly Lys Thr Tyr Thr Ala Gly Thr Ser Asp
            500                 505                 510

Phe Asn Asn Leu Ala Gln Asn Ile Ala Leu Gly Ala Asp Arg Phe Leu
        515                 520                 525

Ser Thr Val Lys Phe His Ala Tyr Asn Asn Gly Ser Leu Ser Glu Glu
    530                 535                 540

Tyr Asp Arg Ser Thr Gly Met Ser Thr Gly Ala Arg Asp Leu Thr Trp
545                 550                 555                 560

Ser His Ala Ser Leu Ile Thr Ala Ala Tyr Ala Lys Ala Gly Ser Pro
                565                 570                 575

Ala Ala


<210> SEQ ID NO 76
<211> LENGTH: 443
<212> TYPE: PRT
<213> ORGANISM: Spinellus fusiger

<400> SEQUENCE: 76

Val Pro Ser Gly Asn Ser Thr Ile Thr Ala Trp Gly Ser Lys Gln Asp
1               5                   10                  15

Gly Ile Ser Phe Ser Thr Met Leu Gly Asn Ile Asn Pro Pro Gly Ser
            20                  25                  30

Ser Lys Gly Phe Ile Ala Ala Ser Leu Ser Thr Ala Gly Pro Asn Tyr
        35                  40                  45

Tyr Tyr Ser Trp Thr Arg Asp Ser Ala Leu Val Ala Arg Ala Ile Thr
    50                  55                  60

Tyr Lys Tyr Ser Thr Ser Tyr Gln Asn Asp Pro Lys Ile Leu Gly Leu
65                  70                  75                  80

Leu Lys Asp Tyr Val Thr Tyr Gln Val Asn Glu Gln Thr Glu Ser Thr
                85                  90                  95

Val Cys Asn Cys Leu Gly Glu Pro Lys Phe Asn Pro Asp Gly Ser Ser
            100                 105                 110

Phe Ser Gly Pro Trp Gly Arg Pro Gln Asn Asp Gly Pro Ala Glu Arg
        115                 120                 125

Ala Ser Thr Met Ile Leu Phe Ala Lys Ser Tyr Tyr Ala Gln Thr Asn
    130                 135                 140

Asp Val Gly Tyr Val Ser Asn Thr Leu Lys Pro Ala Ile Tyr Lys Asp
145                 150                 155                 160

Leu Asp Tyr Ile Val Asn Val Trp Gly Asn Asn Cys Phe Asp Leu Trp
                165                 170                 175
```

```
Glu Glu Val Asn Gly Val His Phe Tyr Thr Leu Met Met Met Arg His
            180                 185                 190

Gly Leu Val Gln Gly Ser Ile Phe Ala Asn Thr Leu Gly Asp Ser Thr
        195                 200                 205

Arg Ala Asn Thr Tyr Lys Thr Ala Ala Gln Asn Ile Lys Asn Arg Ile
    210                 215                 220

Asp Thr Phe Trp Glu Ser Gly Ser Asn Tyr Ile Val Val Thr Gln Asn
225                 230                 235                 240

Gln Ser Ala Gly Val Asn Lys Pro Ser Gly Leu Asp Val Ala Val Leu
                245                 250                 255

Leu Ala Ala Asn Gln Gly Gly Leu Gly Asp Gly Val Tyr Thr Pro Gly
            260                 265                 270

Ser Asp Lys Val Leu Ala Thr Ala Val Ala Leu Glu Lys Ser Phe Ala
        275                 280                 285

Ser Leu Tyr Pro Ile Asn Lys Asn Leu Pro Ser Tyr Tyr Gly Thr Ala
    290                 295                 300

Ile Gly Arg Tyr Pro Glu Asp Thr Tyr Asn Gly Asn Gly Asn Ser Glu
305                 310                 315                 320

Ala Asn Pro Trp Phe Ile Ala Thr Thr Thr Tyr Ala Glu Leu Tyr Tyr
                325                 330                 335

Arg Ala Ile Ser Glu Trp Thr Asn Gly Ser Gly Val Thr Val Asn Ser
            340                 345                 350

Ile Asn Lys Glu Phe Phe Ser Lys Phe Asp Ala Ser Ala Thr Asn Gly
        355                 360                 365

Lys Val Tyr Thr Pro Gly Ser Asp Ser Phe Asn Ser Leu Val Asn Asn
    370                 375                 380

Val Ala Ile Ala Ala Asp Asn Phe Leu Ser Thr Val Arg Tyr His Gln
385                 390                 395                 400

Thr Ser Asn Gly Ser Leu Ser Glu Gln Phe Asn Arg Tyr Thr Gly Phe
                405                 410                 415

Met Thr Gly Ala Arg Asp Leu Thr Trp Ser His Ala Ala Met Val Thr
            420                 425                 430

Ala Leu Ala Ala Lys Ala Gly Thr Pro Ser Pro
        435                 440


<210> SEQ ID NO 77
<211> LENGTH: 588
<212> TYPE: PRT
<213> ORGANISM: Syncephalastrum racemosum

<400> SEQUENCE: 77

Ala Thr Val Pro Thr Thr Gln Val Gln Leu Asp Tyr Tyr Thr Tyr Ser
1               5                   10                  15

Asn Asn Val Leu Ser Gly Arg Ile Tyr Val Gln Asn Ile Ala Tyr Ser
            20                  25                  30

Lys Val Val Lys Val Ile Tyr Ser Asp Ala Ser Gly Asn Trp Asn Asn
        35                  40                  45

Asn Gly Asn Thr Ile Ser Ala Ser Tyr Val Glu Ser Ile Ser Gly Thr
    50                  55                  60

Asn Tyr Glu Tyr Trp Asp Phe Ser Ala Thr Ile Gly Thr Ala Gly Ile
65                  70                  75                  80

Lys Gln Phe Tyr Leu Arg Tyr Asp Val Ser Gly Ser Thr Tyr Tyr Asp
                85                  90                  95

Asn Asn Gly Gly Asp Asn Asn Asn Tyr Asn Val Val Ala Thr Thr Ser
```

-continued

```
            100                 105                 110

Thr Thr Ser Ser Ser Thr Thr Thr Thr Thr Ala Thr Thr Thr Thr Ala
        115                 120                 125

Thr Lys Thr Thr Ser Thr Thr Ser Ala Thr Ala Thr Pro Thr Ser Ser
    130                 135                 140

Ala Thr Phe Pro Ser Gly Asn Ser Thr Ile Thr Thr Trp Ala Lys Ser
145                 150                 155                 160

Gln Lys Asp Ile Ser Trp Lys Thr Leu Leu Thr Ser Leu Asn Pro Ser
                165                 170                 175

Gly Thr Ala Lys Gly Phe Ile Ala Ala Ser Leu Ser Thr Ser Asn Pro
            180                 185                 190

Asp Tyr Tyr Tyr Ala Trp Thr Arg Asp Ser Ala Leu Val Ala Arg Thr
        195                 200                 205

Met Val Asn Met Tyr Asn Thr Thr Glu Ala Gly Ser Ala Ser Val Leu
    210                 215                 220

Gly Leu Leu Gln Asp Tyr Val Thr Phe Gln Ile Asn Ala Met Ser Thr
225                 230                 235                 240

Ser Thr Val Cys Asn Cys Leu Gly Glu Pro Lys Phe Asn Pro Asp Gly
                245                 250                 255

Ser Ser Tyr Thr Gly Ala Trp Gly Arg Pro Gln Asn Asp Gly Pro Ala
            260                 265                 270

Glu Arg Ala Ser Thr Phe Ile Leu Phe Ala Asp Ser Tyr Ile Ala Gln
        275                 280                 285

Gly Gly Gln Leu Ser Tyr Val Thr Gly Thr Leu Ala Pro Ala Ile Tyr
    290                 295                 300

Lys Asp Leu Asn Tyr Val Val Ser Thr Trp Ser Asn Asn Cys Phe Asp
305                 310                 315                 320

Leu Trp Glu Glu Val Asn Gly Arg His Met Phe Thr Leu Ala Val Met
                325                 330                 335

Arg Arg Ala Leu Leu Asp Gly Val Asn Phe Ala Ser Arg Ile Gly Asp
            340                 345                 350

Thr Thr Tyr Ser Ser Thr Trp Ser Ser Thr Ala Ser Ser Ile Gln Ser
        355                 360                 365

Thr Leu Ser Gly Tyr Tyr Leu Ser Ser Gly Asn Tyr Ile Thr Thr Val
    370                 375                 380

Gln Asn Phe Gln Ser Gly Val Ser Lys Ala Gly Tyr Asp Val Ser Thr
385                 390                 395                 400

Leu Ile Ala Ala Asn Val Ala Gly Met Gly Asp Gly Phe Phe Thr Pro
                405                 410                 415

Gly Ser Asp Glu Val Leu Ala Thr Ala Val Ala Ile Glu Asn Lys Phe
            420                 425                 430

Ser Ser Leu Tyr Gly Val Asn Ala Asn Lys Ala Ser Tyr Leu Gly Thr
        435                 440                 445

Ala Ile Gly Arg Tyr Pro Glu Asp Thr Tyr Asn Gly Tyr Gly Asn Gly
    450                 455                 460

Gln Gly Asn Pro Trp Phe Ile Ala Thr Ala Ala Tyr Ala Glu Leu Tyr
465                 470                 475                 480

Tyr Arg Ala Ile Leu Glu Trp Gln Thr Lys Ser Ser Ile Val Val Asn
                485                 490                 495

Ser Lys Asn Leu Gly Phe Phe Ser Lys Phe Asp Ser Ser Ala Ala Val
            500                 505                 510

Gly Thr Thr Tyr Thr Pro Gly Thr Thr Ala Tyr Ser Asn Met Val Gln
        515                 520                 525
```

```
Asn Val Ala Leu Ala Ala Asp Arg Phe Leu Ser Thr Val Gln Leu His
    530                 535                 540

Ala Ala Thr Asn Gly Ser Met Ser Glu Gln Phe Asn Arg Asp Thr Gly
545                 550                 555                 560

Val Met Gln Gly Ala Arg Asp Leu Thr Trp Ser His Ser Ala Phe Ile
                565                 570                 575

Thr Ala Ala Arg Ala Lys Leu Gly Ser Pro Val Tyr
            580                 585


<210> SEQ ID NO 78
<211> LENGTH: 448
<212> TYPE: PRT
<213> ORGANISM: Syncephalastrum racemosum

<400> SEQUENCE: 78

Ala Asn Ser Thr Val Pro Asp Gly Asn Ser Thr Thr Thr Ala Trp Val
1               5                   10                  15

Lys Lys Gln Glu Ala Ile Ser Trp Thr Asp Leu Lys Thr Asn Val Asn
            20                  25                  30

Pro Glu Gly Ala Ala Lys Gly Phe Ile Ala Ala Ser Leu Ser Thr Ser
        35                  40                  45

Glu Pro Asp Tyr Tyr Tyr Ala Trp Thr Arg Asp Ser Ala Leu Val Ala
    50                  55                  60

Arg Val Met Val Asn Lys Tyr Asn Thr Thr Asp Ala Gly Asp Ala Asn
65                  70                  75                  80

Leu Leu Gly Leu Leu Gln Asp Tyr Val Ser Phe Gln Ile Asn Ala Met
                85                  90                  95

Gly Glu Ser Thr Val Cys Asn Cys Leu Gly Glu Pro Lys Phe Asn Pro
            100                 105                 110

Asp Gly Ser Ser Tyr Thr Gly Ala Trp Gly Arg Pro Gln Asn Asp Gly
        115                 120                 125

Pro Ala Glu Arg Ala Ser Thr Phe Ile Leu Leu Ala Asp Ser Met Ile
    130                 135                 140

Ala Gln Lys Ser Ala Asn Gly Ser Tyr Val Ser Asp Thr Leu Ala Pro
145                 150                 155                 160

Ala Ile Tyr Lys Asp Leu Ala Tyr Val Ala Ser Thr Trp Glu Asn Ala
                165                 170                 175

Cys Tyr Asp Leu Trp Glu Glu Val Asn Gly Lys His Met Tyr Thr Leu
            180                 185                 190

Ser Val Met Arg Arg Ala Leu Leu Asp Gly Ala Asp Phe Ala Ser Arg
        195                 200                 205

Gln Gly Gln Thr Ala Asn Val Thr Ser Trp Lys Ser Thr Ala Asp Lys
    210                 215                 220

Ile Lys Ser Ser Leu Glu Gly Phe Phe Ser Ser Asp Asn Gly Tyr Ile
225                 230                 235                 240

Glu Val Thr Gln Asp Met Gln Gly Gly Val Gln Lys Lys Gly Leu Asp
                245                 250                 255

Val Ser Thr Leu Ile Ala Ala Asn Ile Gly Ser Met Gly Asp Gly Phe
            260                 265                 270

Tyr Thr Pro Gly Ser Asp Glu Val Leu Ala Thr Ala Val Ala Val Glu
        275                 280                 285

Ala Ala Phe Ala Asp Leu Tyr Lys Ile Asn Gln Asn Thr Asn Ser Thr
    290                 295                 300

Gly Leu Gly Thr Ala Ile Gly Arg Tyr Pro Glu Asp Thr Tyr Asn Gly
```

```
305                 310                 315                 320

Val Gly Asn Ser Gln Gly Asn Pro Trp Phe Ile Ala Thr Asn Thr Phe
                325                 330                 335

Ala Glu Leu Tyr Tyr Arg Ala Ile Leu Glu Trp Gln Asn Lys Gly Thr
            340                 345                 350

Ile Thr Val Asn Ser Val Asn Ala Ala Phe Phe Ser Lys Phe Asp Ser
        355                 360                 365

Ser Ala Lys Ala Gly Thr Thr Tyr Lys Ser Gly Ser Thr Glu Phe Asp
    370                 375                 380

Ser Leu Ile Asn Lys Val Ala Leu Ala Ala Asp Ala Phe Leu Asn Thr
385                 390                 395                 400

Val Gln Thr Tyr Ala Ala Ser Asn Gly Ser Met Ser Glu Gln Tyr Asn
                405                 410                 415

Arg Asp Thr Gly Ala Leu Thr Gly Ala Arg Asp Leu Thr Trp Ser His
            420                 425                 430

Ala Ser Leu Ile Thr Ala Ala Asn Ala Lys Leu Gly Thr Pro Tyr Asn
        435                 440                 445


<210> SEQ ID NO 79
<211> LENGTH: 452
<212> TYPE: PRT
<213> ORGANISM: Thermomucor sp.

<400> SEQUENCE: 79

Val Val Thr Ala Ala Ala Ala Ala Ser Val Pro Ser Gly Asn Ala Thr
1               5                   10                  15

Ile Thr Ser Trp Ile Gln Glu Gln Leu Ala Ile Ser Trp Asn Thr Met
            20                  25                  30

Leu Thr Ser Val Asn Pro Val Gly Ala Val Thr Gly Phe Ile Ala Ala
        35                  40                  45

Ser Leu Ser Thr Ala Asn Pro Asp Tyr Tyr Tyr Cys Trp Thr Arg Asp
    50                  55                  60

Ala Ala Leu Val Ala Arg Val Met Thr Phe Met Tyr Asn Thr Thr Gln
65                  70                  75                  80

Ala Gly Asp Ser Gly Leu Leu Gly Ile Leu Gln Asp Tyr Val Ser Phe
                85                  90                  95

Gln Ile His Ala Met Gly Glu Ser Thr Val Cys Asn Cys Leu Gly Glu
            100                 105                 110

Pro Lys Phe Asn Pro Asp Gly Ser Ser Tyr Thr Gly Ala Trp Gly Arg
        115                 120                 125

Pro Gln Asn Asp Gly Pro Ala Glu Arg Ala Ser Thr Phe Ile Lys Ile
    130                 135                 140

Ala Asp Ser Tyr Leu Thr Gln Thr Gly Asp Val Ser Tyr Val Thr Asn
145                 150                 155                 160

Thr Leu Lys Pro Ala Ile Tyr Glu Asp Leu Asp Tyr Ile Val Asn Val
                165                 170                 175

Trp Gln Asn Thr Cys Phe Asp Leu Trp Glu Glu Val Tyr Gly Met His
            180                 185                 190

Met Tyr Thr Leu Ala Val Met Arg Arg Gly Leu Leu Asp Gly Ala Asp
        195                 200                 205

Phe Ala Thr Arg Asn Gly Asp Thr Asp Lys Ala Ser Thr Tyr Thr Ser
    210                 215                 220

Thr Ala Thr Ser Ile Gln Thr Arg Leu Ala Thr Phe Trp Ser Asp Ser
225                 230                 235                 240
```

```
Asn Gly Tyr Ile Thr Val Thr Gln Asp Tyr Gln Ser Gly Val Ser Lys
                245                 250                 255

Ala Gly Leu Asp Val Ser Thr Leu Ile Ala Ala Asn Val Ala Gly Met
            260                 265                 270

Asn Asp Gly Phe Phe Thr Pro Gly Ser Asp Glu Ile Leu Ala Thr Ala
        275                 280                 285

Val Lys Val Glu Ala Ala Phe Ala Asn Leu Tyr Gly Ile Asn Ile Asn
    290                 295                 300

Lys Ala Ser Tyr Leu Gly Asn Ala Ile Gly Arg Tyr Pro Glu Asp Thr
305                 310                 315                 320

Tyr Asn Gly Asn Gly Asn Ser Glu Gly Asn Pro Trp Phe Ile Ala Thr
                325                 330                 335

Ala Ala Phe Ala Glu Leu Tyr Tyr Arg Ala Ile Met Glu Trp Gln Leu
            340                 345                 350

Arg Gly Ser Ser Ile Thr Val Asn Ser Val Asn Gln Gly Phe Phe Thr
        355                 360                 365

Lys Phe Asp Pro Ser Ala Thr Ala Gly Thr Thr Tyr Thr Pro Gly Thr
    370                 375                 380

Asp Ala Phe Asn Ser Leu Ile Asp Asn Val Ala Leu Ala Ala Asp Gln
385                 390                 395                 400

Phe Phe Ser Thr Ile His Leu His Arg Ala Thr Asn Gly Ser Met Ser
                405                 410                 415

Glu Gln Tyr Asn Arg Asp Thr Gly Phe Met Gln Gly Ala Arg Asp Leu
            420                 425                 430

Thr Trp Ser His Ala Ala Phe Ile Thr Ala Ala Lys Ala Lys Gln Gly
        435                 440                 445

Thr Pro Ser Phe
    450


<210> SEQ ID NO 80
<211> LENGTH: 589
<212> TYPE: PRT
<213> ORGANISM: Zychaea mexicana

<400> SEQUENCE: 80

Val Asp Val Pro Ser Val Pro Ile Gln Leu Glu Ser Tyr Thr Tyr Ser
1               5                   10                  15

Glu Asn Val Phe Ala Gly Arg Ile Phe Val Gln Asn Ile Ala Tyr Thr
            20                  25                  30

Lys Glu Val Asn Val Phe Trp Ser Asp Ala Ser Asp Asp Trp Asn Asp
        35                  40                  45

Asn Gly Asn Ser Val Ala Ala Ser Tyr Ser Glu Ser Ile Ala Asp Thr
    50                  55                  60

Asn Tyr Glu Tyr Trp Glu Phe Ser Thr Thr Ile Gly Ser Ala Gly Ile
65                  70                  75                  80

Ser Gln Ser Tyr Leu Arg Tyr Asp Val Ser Gly Ser Ile Tyr Tyr Asp
                85                  90                  95

Asn Asn Asp Ser Gln Asn Tyr Asp Ile Thr Glu Thr Ser Thr Pro Thr
            100                 105                 110

Thr Thr Thr Ala Ala Pro Thr Ser Thr Thr Ser Thr Pro Thr Thr Thr
        115                 120                 125

Thr Asp Gly Gly Ser Thr Thr Thr Thr Thr Ala Thr Ser Val Pro Thr
    130                 135                 140

Ser Thr Gly Val Pro Glu Gly Asn Ala Thr Ile Ser Glu Trp Ala Ser
145                 150                 155                 160
```

-continued

Ala Gln Leu Asp Ile Ser Trp Pro Asn Leu Met Met Asn Val Asn Pro
165 170 175

Ser Gly Ala Val Thr Gly Ser Ile Val Ala Ser Leu Ser Thr Ser Asn
180 185 190

Pro Asp Tyr Phe Tyr Ile Trp Thr Arg Asp Ala Ala Met Val Ala Arg
195 200 205

Val Met Val Tyr Met Tyr Asn Thr Thr Glu Ala Gly Asp Thr Asn Leu
210 215 220

Leu Asn Ala Leu Thr Asp Tyr Val Thr Phe Ser Ile Ser Ser Met Asn
225 230 235 240

Val Asp Thr Val Cys Asp Cys Leu Gly Glu Pro Lys Phe Asn Val Asp
245 250 255

Gly Ser Gly Tyr Thr Gly Ala Trp Gly Arg Pro Gln Asn Asp Gly Pro
260 265 270

Ala Glu Arg Ala Ser Thr Met Ile Leu Ile Ala Asp Ser Tyr Ile Ala
275 280 285

Gln Gly Gly Asp Val Ser Tyr Val Thr Asp Thr Leu Lys Pro Ala Ile
290 295 300

Tyr Thr Asp Leu Asp Tyr Val Val Asp Thr Trp Ser Asn Val Cys Phe
305 310 315 320

Asp Leu Trp Glu Glu Val Asn Gly Ile His Met Tyr Thr Leu Ser Val
325 330 335

Met Arg Lys Ala Leu Leu Asp Gly Ala Asn Phe Ala Thr Arg Asn Gly
340 345 350

Asp Thr Ser Arg Val Ser Gly Tyr Glu Ser Thr Ala Ser Ser Ile Lys
355 360 365

Thr Arg Leu Glu Ser Phe Trp Ser Ser Ser Asn Asn Tyr Ile Thr Val
370 375 380

Thr Gln Ser Phe Ser Gly Gly Val Ser Lys Ala Gly Leu Asp Val Ser
385 390 395 400

Thr Leu Ile Ala Ala Asn Leu Ala Ser Met Asn Asp Gly Phe Tyr Thr
405 410 415

Pro Gly Ser Asp Glu Ile Leu Ala Thr Ala Val Ala Ile Glu Asn Ser
420 425 430

Phe Ile Ser Glu Tyr Thr Leu Asn Gln Asn Arg Pro Ser Trp Leu Ser
435 440 445

Thr Ala Ile Gly Arg Tyr Pro Glu Asp Ser Tyr Asp Gly Tyr Gly Asn
450 455 460

Ser Gln Gly Asn Pro Trp Phe Ile Ala Thr Ala Thr Tyr Ala Glu Leu
465 470 475 480

Tyr Tyr Arg Ala Ile Leu Glu Trp Gln Gln Gln Ala Ser Ile Ser Val
485 490 495

Asn Ser Val Asn Leu Gly Phe Phe Ser Lys Phe Asp Ser Asp Ala Ser
500 505 510

Val Gly Thr Val Tyr Thr Pro Gly Thr Glu Asp Phe Ala Asn Met Val
515 520 525

Ser Asn Val Ala Phe Ala Ala Asp Glu Phe Leu Ala Thr Ile Glu Asn
530 535 540

His Ser Ala Val Asn Gly Ser Leu Ser Glu Gln Tyr Asn Arg Asp Thr
545 550 555 560

Gly Ile Met Gln Gly Ala Arg Asp Leu Thr Trp Ser His Ala Ala Phe
565 570 575

Ile Thr Ala Ala Lys Ala Lys Gln Gly Ala Pro Ile His
580 585

<210> SEQ ID NO 81
<211> LENGTH: 432
<212> TYPE: PRT
<213> ORGANISM: Saksenaea vasiformis

<400> SEQUENCE: 81

Trp Val Ser Lys Gln Glu Asp Ile Ser Phe Ser Glu Met Leu Arg Asn
1 5 10 15

Val Asn Pro Glu Gly Thr Ala Lys Gly Phe Val Ala Ala Ser Leu Ser
20 25 30

Thr Ala Gly Pro Asp Tyr Phe Tyr Thr Trp Thr Arg Asp Ala Ala Leu
35 40 45

Val Ser Arg Val Ile Ala Tyr Lys Tyr Asn Thr Thr Asn Ala Gly Asp
50 55 60

Ser Lys Ile His Gly Val Leu Asp Asp Tyr Val Asn Phe Gln Ile Asn
65 70 75 80

Thr Gln Ser Glu Ser Thr Pro Cys Asn Cys Leu Gly Glu Pro Lys Phe
85 90 95

Asn Pro Asp Gly Ser Ser Phe Thr Gly Pro Trp Gly Arg Pro Gln Asn
100 105 110

Asp Gly Pro Ala Glu Arg Ala Ser Ser Phe Met Leu Ile Ala Asp Ser
115 120 125

Phe Leu Ser Gln Thr Lys Asn Ala Ser Tyr Phe Thr Asn Thr Leu Lys
130 135 140

Pro Ala Ile Tyr Lys Asp Leu Asp Tyr Val Val Asp Thr Trp Ser Asn
145 150 155 160

Pro Cys Phe Asp Leu Trp Glu Glu Val Asn Gly Ile His Phe Tyr Thr
165 170 175

Leu Met Val Met Arg Arg Ser Leu Leu Asp Gly Ala Asn Phe Ala Thr
180 185 190

Arg Asn Gly Asp Asn Ser Lys Ala Ser Thr Tyr Ser Gly Val Ala Ala
195 200 205

Lys Ile Gln Ala Arg Leu Asn Ser Phe Trp Asp Ala Gly Lys Asn Tyr
210 215 220

Ile Thr Val Thr Gln Asp Tyr Lys Asn Gly Val Glu Lys Pro Ser Gly
225 230 235 240

Leu Asp Val Ser Thr Leu Ile Ala Ala Asn Val Ala Gly Met Gly Asp
245 250 255

Gly Phe Tyr Thr Pro Gly Ser Glu Arg Ile Leu Ala Thr Ala Leu Ala
260 265 270

Phe Glu Lys Ser Met Ala Ser Leu Tyr Pro Leu Asn Asn Asn Leu Pro
275 280 285

Ser His Leu Gly Asn Ala Ile Gly Arg Tyr Pro Glu Asp Thr Tyr Asn
290 295 300

Gly Asn Gly Asn Ser Gln Gly Asn Pro Trp Phe Leu Ala Thr Thr Ala
305 310 315 320

Phe Thr Glu Leu Tyr Tyr Arg Ala Ile Leu Glu Trp Lys Asn Thr Gly
325 330 335

Val Thr Val Thr Pro Ile Ser Lys Asp Phe Phe Val Arg Phe Asp Ser
340 345 350

Ser Ala Ala Pro Gly Lys Lys Tyr Asn Pro Gly Ser Gln Glu Phe Ala
355 360 365

```
Thr Leu Thr Gln Ser Ile Ala Ala Ala Ala Asp Arg Phe Met Ser Thr
    370                 375                 380

Val Gln Tyr His Gln Asn Pro Asn Gly Ser Leu Ser Glu Glu Phe Asp
385                 390                 395                 400

Arg Ser Ser Gly Tyr Met Thr Gly Ala Arg Asp Leu Thr Trp Ser His
                405                 410                 415

Ala Ala Phe Ile Thr Ala Ala Gln Ala Arg Ala Gly Ser Pro Ser Phe
            420                 425                 430


<210> SEQ ID NO 82
<211> LENGTH: 432
<212> TYPE: PRT
<213> ORGANISM: Backusella circina

<400> SEQUENCE: 82

Trp Ser Pro Ser Gln His Ser Ile Ser Leu Tyr Ala Met Leu Arg Asn
1               5                   10                  15

Ile Asn Pro Pro Gly Ser Ala Ala Gly Phe Ile Ser Ala Ser Leu Ser
            20                  25                  30

Thr Ser Gly Pro Asp Tyr Tyr Tyr Ser Trp Thr Arg Asp Ser Ala Leu
        35                  40                  45

Val Ala His Val Ile Val Asn Glu Tyr Asn Thr Thr Tyr Gln Gly Asn
    50                  55                  60

Ser Thr Leu Leu Gly Ile Leu Lys Asp Tyr Val Thr Tyr Ser Leu Asn
65                  70                  75                  80

Ala Gln Thr Thr Ser Thr Val Cys Asn Cys Leu Gly Glu Pro Lys Phe
                85                  90                  95

Asn Pro Asp Gly Ser Ser Phe Thr Gly Ala Trp Gly Arg Pro Gln Asn
            100                 105                 110

Asp Gly Pro Ala Glu Arg Ala Val Ser Phe Ile Tyr Phe Ala Asp Ser
        115                 120                 125

Tyr Leu Thr Gln Thr Ser Asp Ser Ser Tyr Val Thr Gly Thr Leu Ala
    130                 135                 140

Pro Ala Ile Tyr Lys Asp Leu Asp Tyr Val Val Ser Val Trp Ser Asn
145                 150                 155                 160

Gly Cys Phe Asp Leu Trp Glu Glu Val Asn Gly Ile His Phe Tyr Thr
                165                 170                 175

Leu Met Phe Met Arg Arg Gly Leu Leu Asp Gly Ala Asn Phe Ala Ser
            180                 185                 190

Arg Asn Gly Asp Ser Thr Arg Ala Ser Thr Tyr Thr Ser Thr Ala Ala
        195                 200                 205

Ser Ile Lys Thr Lys Ile Asp Gly Phe Trp Val Ser Ser Gly Asn Tyr
    210                 215                 220

Val Gln Val Ser Gln Ser Val Thr Ser Gly Val Ser Lys Ala Gly Tyr
225                 230                 235                 240

Asp Ala Ser Thr Leu Ile Ala Ala Asn Gln Ala Ser Arg Gly Asp Gly
                245                 250                 255

Phe Tyr Thr Pro Gly Ser Asp Lys Met Leu Ala Thr Ala Val Ala Ile
            260                 265                 270

Glu Ser Gln Phe Ser Ser Leu Tyr Ser Ile Asn Thr Asn Lys Ala Ser
        275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Phe Leu Cys Thr Asn Ala Phe
```

```
305                 310                 315                 320

Gly Glu Leu Phe Tyr Arg Ala Ile Ser Glu Trp Asn Ala Ala Gly Ser
                325                 330                 335

Val Thr Val Asn Ser Val Asn Leu Ala Phe Phe Lys Lys Tyr Asp Ser
            340                 345                 350

Ser Thr Ser Ser Gly Thr Thr Tyr Thr Val Gly Thr Ser Ala Tyr Asn
        355                 360                 365

Asn Leu Val Gln Asn Val Ala Leu Ala Ala Asp Ala Tyr Phe Ser Thr
    370                 375                 380

Val Lys Tyr His Ala Leu Thr Asn Gly Ser Met Ser Glu Gln Tyr Asp
385                 390                 395                 400

Arg Ser Ser Gly Met Ala Thr Gly Ala Arg Asp Leu Thr Trp Ser His
                405                 410                 415

Ala Ala Met Ile Thr Ala Leu Lys Ala Lys Ser Gly Thr Pro Val Tyr
            420                 425                 430


<210> SEQ ID NO 83
<211> LENGTH: 432
<212> TYPE: PRT
<213> ORGANISM: Backusella circina

<400> SEQUENCE: 83

Trp Ile Lys Gly Gln Glu Asp Thr Ser Arg Ser Val Met Leu Gly Asn
1               5                   10                  15

Ile Asn Pro Pro Gly Ser Ala Thr Gly Phe Ile Ser Ala Ser Leu Ser
            20                  25                  30

Thr Ser Gly Pro Asp Tyr Tyr Tyr His Trp Thr Arg Asp Ala Ala Leu
        35                  40                  45

Val Ala His Val Ile Val Asn Asp Tyr Asn Thr Thr Leu Ser Gly Asp
    50                  55                  60

Ser Ser Thr Leu Gln Val Ile Lys Asp Tyr Val Thr Phe Ser Val Asn
65                  70                  75                  80

Ser Gln Ser Glu Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Thr Thr Phe Ile Phe Phe Ala Asp Thr
        115                 120                 125

Tyr Leu Ala Gln Gly Gly Asp Ser Ser Tyr Val Thr Gly Thr Leu Ala
    130                 135                 140

Pro Ala Ile Tyr Ala Asp Leu Asp Tyr Val Val Asn Asn Trp Ser Thr
145                 150                 155                 160

Gly Cys Tyr Asp Leu Trp Glu Glu Val Asn Gly Ile His Phe Tyr Thr
                165                 170                 175

Leu Met Val Met Arg Arg Gly Leu Ile Asp Gly Ala Ser Phe Ala Ser
            180                 185                 190

Arg Asn Gly Asp Ser Thr Arg Ser Ser Ser Tyr Thr Ser Thr Ala Lys
        195                 200                 205

Ser Ile Ala Thr Lys Ile Asp Ser Phe Trp Ser Ala Ser Asn Asn Tyr
    210                 215                 220

Val Ala Val Ser Gln Ser Val Thr Ser Gly Val Ser Lys Ala Gly Tyr
225                 230                 235                 240

Asp Ala Ser Thr Ile Ile Ala Ala Asn Gln Ala Ser Leu Gly Asp Gly
                245                 250                 255
```

```
Phe Tyr Thr Pro Gly Ser Asp Lys Met Leu Ala Thr Ser Val Ala Val
            260                 265                 270

Glu Asn Ala Phe Ser Ser Leu Tyr Thr Val Asn Thr Gly Lys Ala Ser
        275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Tyr Leu Cys Thr Asn Ala Leu
305                 310                 315                 320

Gly Glu Leu Tyr Tyr Arg Ala Ile Lys Glu Trp Asn Ala Ala Gly Ser
                325                 330                 335

Val Thr Val Asn Ser Val Asn Leu Gly Phe Phe Gln Lys Ile Asp Ser
            340                 345                 350

Ser Ile Ser Ser Gly Thr Thr Phe Thr Leu Gly Thr Ser Asp Tyr Ser
        355                 360                 365

Thr Leu Val Asp Asn Val Ala Leu Ala Ala Asp Lys Phe Phe Ala Val
    370                 375                 380

Val Gln Tyr His Glu Arg Ser Asn Gly Ser Met Pro Glu Gln Phe Gly
385                 390                 395                 400

Arg Glu Asp Gly Leu Pro Thr Gly Ala Arg Asp Leu Thr Trp Ser His
                405                 410                 415

Ala Ala Met Ile Ser Ala Ala Arg Ala Lys Ala Gly Thr Pro Val Tyr
            420                 425                 430


<210> SEQ ID NO 84
<211> LENGTH: 432
<212> TYPE: PRT
<213> ORGANISM: Benjaminiella poitrasii

<400> SEQUENCE: 84

Trp Leu Lys Ser Gln Ile Gly Ile Ser Arg Tyr Ala Met Leu Arg Asn
1               5                   10                  15

Ile Asn Pro Ala Gly Ser Ala Val Gly Phe Ile Ala Ala Ser Leu Ser
            20                  25                  30

Thr Ala Asn Pro Asp Tyr Tyr Tyr Ala Trp Thr Arg Asp Ser Ala Leu
        35                  40                  45

Thr Ser Tyr Val Ile Ala Asn Asp Tyr Asn Ser Thr Leu Ala Gly Asn
    50                  55                  60

Ser Thr Ile Leu Gln Ile Met Lys Asp Tyr Val Thr Phe Ser Val Lys
65                  70                  75                  80

Ser Gln Ser Val Ser Thr Ala Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Thr Thr Phe Ile Leu Phe Ala Asp Ser
        115                 120                 125

Tyr Leu Lys Gln Thr Gly Asp Ala Ser Tyr Val Thr Gly Thr Leu Lys
    130                 135                 140

Pro Ala Ile Phe Lys Asp Leu Asp Tyr Val Val Asn Thr Trp Thr Asn
145                 150                 155                 160

Gly Cys Phe Asp Leu Trp Glu Glu Val Asn Gly Val His Phe Tyr Thr
                165                 170                 175

Leu Met Val Met Arg Lys Gly Leu Ile Arg Gly Ala Asn Phe Ala Thr
            180                 185                 190

Arg Asn Gly Asp Ser Thr Arg Ala Ser Thr Tyr Thr Asn Thr Ala Ala
        195                 200                 205
```

```
Ser Ile Lys Thr Lys Met Asp Ser Phe Trp Ser Ser Gly Asn Asn Tyr
    210                 215                 220

Ile Ala Val Ser Gln Ser Val Thr Gly Gly Val Ser Lys Ala Gly Tyr
225                 230                 235                 240

Asp Val Ala Asn Ile Ile Ala Ala Asn Val Gly Ser Leu Gln Asp Gly
                245                 250                 255

Val Tyr Thr Pro Gly Ser Asp Arg Ile Leu Ala Thr Ala Val Ala Val
            260                 265                 270

Glu Ala Lys Phe Ala Ser Leu Tyr Gly Val Asn Ser Asn Leu Pro Gly
        275                 280                 285

Tyr Leu Gly Asn Ser Ile Gly Arg Tyr Pro Glu Asp Thr Tyr Asn Gly
    290                 295                 300

Asn Gly Asn Ser Gln Gly Asn Pro Trp Phe Leu Ala Thr Asn Ala Tyr
305                 310                 315                 320

Ala Glu Leu Tyr Tyr Arg Ala Ile Arg Glu Trp Tyr Asp Asn Gly Gly
                325                 330                 335

Val Thr Val Asn Ser Val Asn Leu Pro Phe Phe Lys Lys Phe Asp Ser
            340                 345                 350

Ser Ala Ala Ser Gly Thr Thr Tyr Thr Val Gly Thr Thr Ala Phe Asn
        355                 360                 365

Thr Met Val Ser Asn Val Ala Ala Ala Ala Asp Lys Phe Phe Ser Thr
    370                 375                 380

Val Lys Phe His Ala Tyr Thr Asn Gly Ser Met Ser Glu Gln Phe Gly
385                 390                 395                 400

Arg Asn Asp Gly Leu Cys Thr Gly Ala Arg Asp Leu Thr Trp Ser His
                405                 410                 415

Ala Ser Leu Ile Ser Ala Ala Leu Ala Lys Ala Gly Thr Pro Ser Val
            420                 425                 430


<210> SEQ ID NO 85
<211> LENGTH: 432
<212> TYPE: PRT
<213> ORGANISM: Choanephora cucurbitarum

<400> SEQUENCE: 85

Trp Ile Asp Lys Gln Ile Asp Ile Ser Arg Ser Ala Met Leu Lys Asn
1               5                   10                  15

Ile Asn Pro Ala Gly Thr Val Lys Gly Phe Ile Ala Ala Ser Leu Ser
            20                  25                  30

Thr Ser Asn Pro Asp Tyr Phe Tyr Ala Trp Thr Arg Asp Ala Ala Leu
        35                  40                  45

Val Ala His Val Val Ala Asn Asp Tyr Asn Arg Thr Lys Ser Gly Asp
    50                  55                  60

Ala Thr Tyr Leu Gly Leu Leu Lys Asp Tyr Val Thr Phe Ser Ile Asn
65                  70                  75                  80

Ser Gln Asn Thr Pro Thr Ala Cys Asn Cys Leu Gly Glu Pro Lys Phe
                85                  90                  95

Asn Lys Asp Gly Ser Gly Tyr Asn Gly Pro Trp Gly Arg Pro Gln Asn
            100                 105                 110

Asp Gly Pro Ala Glu Arg Ala Asp Thr Phe Val Leu Ile Ala Asp Ser
        115                 120                 125

Ile Leu Thr Gln Thr Lys Asp Val Ser Tyr Val Thr Gly Thr Leu Arg
    130                 135                 140

Pro Ala Ile Tyr Thr Asp Leu Asp Tyr Val Val Arg Thr Trp Ser Asn
```

```
145                 150                 155                 160

Gly Cys Phe Asp Leu Trp Glu Glu Val Asn Gly Val His Phe Tyr Thr
                165                 170                 175

Leu Met Val Met Arg Arg Ala Leu Leu Val Gly Ala Asn Phe Ala Ser
            180                 185                 190

Arg Asn Gly Asp Ser Ala Arg Ala Ser Asn Tyr Asn Asn Ala Ala Asn
        195                 200                 205

Ser Ile Lys Ser Lys Ile Asp Ser Phe Trp Ser Ser Asn Asn Asn Tyr
    210                 215                 220

Val Ala Val Ser Gln Ser Val Thr Gly Gly Val Ser Lys Ala Gly Tyr
225                 230                 235                 240

Asp Val Ser Thr Leu Ile Ala Ala Asn Val Gly Ser Leu Ser Asp Gly
                245                 250                 255

Phe Tyr Thr Pro Gly Ser Glu Arg Met Leu Ala Thr Ala Val Ala Ile
            260                 265                 270

Glu Asp Lys Phe Ala Asn Leu Tyr Gly Ile Asn Arg Asn Leu Asp Ser
        275                 280                 285

Ser Leu Gly Asn Ala Ile Gly Arg Tyr Pro Glu Asp Thr Tyr Asn Gly
    290                 295                 300

Asn Gly Asn Ser Gln Gly Asn Pro Trp Phe Ile Ala Thr Asn Ala Tyr
305                 310                 315                 320

Ala Glu Leu Tyr Tyr Arg Ala Ile Lys Glu Trp Asn Asn Asn Gly Gly
                325                 330                 335

Val Thr Val Thr Asn Val Asn Leu Asn Phe Phe Lys Lys Phe Asp Gly
            340                 345                 350

Ser Ala Ser Val Gly Thr Lys Tyr Thr Ala Gly Ser Ala Ala Tyr Asn
        355                 360                 365

Thr Leu Thr Gln Asn Ile Ala Leu Ala Ala Asp Lys Phe Phe Asn Thr
    370                 375                 380

Val Lys Val His Ala Ala Thr Asn Gly Ser Met Ser Glu Gln Tyr His
385                 390                 395                 400

Arg Asp Thr Gly Ser Met Thr Gly Ala Arg Asp Leu Thr Trp Ser His
                405                 410                 415

Ala Ser Leu Ile Thr Ala Ala Leu Ala Lys Ala Gly Thr Pro Val Ala
            420                 425                 430


<210> SEQ ID NO 86
<211> LENGTH: 432
<212> TYPE: PRT
<213> ORGANISM: Rhizopus stolonifer

<400> SEQUENCE: 86

Trp Ile Lys Arg Gln Glu Lys Ile Ser Arg Phe Ala Met Leu Arg Asn
1               5                   10                  15

Ile Asn Pro Pro Gly Ser Ala Ala Gly Phe Ile Ala Ala Ser Leu Ser
            20                  25                  30

Thr Ser Gly Pro Asp Tyr Tyr Tyr Ser Trp Thr Arg Asp Ser Ala Leu
        35                  40                  45

Thr Ser Asn Leu Ile Ala Tyr Glu Tyr Asn Thr Thr Leu Ser Gly Asn
    50                  55                  60

Thr Thr Ile Leu Asn Ile Leu Lys Asp Tyr Val Lys Phe Ser Ile Ser
65                  70                  75                  80

Ser Gln Thr Thr Ser Thr Val Cys Asn Cys Leu Gly Glu Pro Lys Phe
                85                  90                  95
```

```
Asn His Asp Gly Ser Ser Tyr Thr Gly Ala Trp Gly Arg Pro Gln Asn
            100                 105                 110

Asp Gly Pro Ala Glu Arg Ala Asn Thr Phe Ile Leu Phe Ala Asp Ser
        115                 120                 125

Tyr Leu Asp Gln Thr Lys Asp Ala Ser Tyr Val Thr Gly Thr Leu Lys
    130                 135                 140

Pro Ala Ile Phe Lys Asp Leu Asp Tyr Val Val Asn Val Trp Ser Asn
145                 150                 155                 160

Gly Cys Tyr Asp Leu Trp Glu Glu Val Asn Gly Val His Phe Tyr Thr
                165                 170                 175

Leu Met Val Met Arg Lys Gly Leu Leu Leu Gly Ala Asp Phe Ala Lys
            180                 185                 190

Arg Asn Gly Asp Ser Thr Arg Ala Ser Thr Tyr Thr Asn Thr Ala Ser
        195                 200                 205

Thr Ile Ala Thr Lys Ile Ser Ser Phe Trp Val Ser Ser Ser Asn Trp
    210                 215                 220

Ile Gln Val Ser Gln Ser Val Thr Ala Gly Val Ser Lys Lys Gly Leu
225                 230                 235                 240

Asp Val Ser Thr Leu Leu Ala Ala Asn Leu Gly Ser Val Glu Asp Gly
                245                 250                 255

Phe Phe Thr Pro Gly Ser Glu Lys Ile Leu Ala Thr Ala Val Ala Ile
            260                 265                 270

Glu Asp Ala Phe Ala Ser Leu Tyr Pro Ile Asn Ser Asn Leu Pro Ser
        275                 280                 285

Tyr Leu Gly Asn Ser Ile Gly Arg Tyr Pro Glu Asp Thr Tyr Asn Gly
    290                 295                 300

Asn Gly Asn Ser Gln Gly Asn Pro Trp Phe Leu Ala Val Asn Gly Phe
305                 310                 315                 320

Ala Glu Leu Tyr Tyr Arg Ala Ile Lys Glu Trp Val Asn Asn Gly Ser
                325                 330                 335

Val Thr Val Ser Asn Ile Ser Leu Ser Phe Phe Lys Lys Phe Asp Ser
            340                 345                 350

Ser Ala Thr Ala Gly Lys Thr Tyr Thr Ala Gly Thr Ala Asp Phe Asn
        355                 360                 365

Asn Leu Ala Gln Asn Ile Ala Leu Gly Ala Asp Arg Phe Leu Ser Thr
    370                 375                 380

Val Gln Thr His Ala Phe Asn Asn Gly Ser Leu Ala Glu Glu Tyr Asp
385                 390                 395                 400

Arg Thr Thr Gly Val Ser Thr Gly Ala Arg Asp Leu Thr Trp Ser His
                405                 410                 415

Ala Ser Leu Ile Thr Ala Ala Tyr Ala Lys Ala Gly Ser Pro Ala Ala
            420                 425                 430
```

<210> SEQ ID NO 87
<211> LENGTH: 432
<212> TYPE: PRT
<213> ORGANISM: Mucor circinelloides

<400> SEQUENCE: 87

```
Trp Ile Asp Gly Gln Thr Ser Val Ser Arg Tyr Ala Met Leu Arg Asn
1               5                   10                  15

Ile Asn Pro Ala Gly Ala Val Ser Gly Phe Ile Ala Ala Ser Met Ser
            20                  25                  30

Thr Ser Gly Pro Asp Tyr Phe Tyr Ala Trp Thr Arg Asp Ser Ala Leu
        35                  40                  45
```

```
Thr Ser His Val Val Ala Tyr Asp Tyr Asn Thr Thr Leu Ala Gly Asn
    50                  55                  60

Ser Thr Ile Leu Gly Leu Leu Lys Asn Tyr Val Thr Phe Ser Ile Asn
65                  70                  75                  80

Ser Gln Thr Thr Ser Thr Val Cys Asn Cys Leu Gly Glu Pro Lys Phe
                85                  90                  95

Asn Lys Asp Gly Ser Ser Tyr Thr Gly Ala Trp Gly Arg Pro Gln Asn
            100                 105                 110

Asp Gly Pro Ala Ser Arg Ala Asp Thr Phe Ile Leu Ile Ala Asp Ser
        115                 120                 125

Ile Leu Lys Gln Thr Gly Asp Ala Thr Tyr Val Thr Gly Thr Leu Ala
    130                 135                 140

Pro Ala Ile Tyr Lys Asp Leu Asp Tyr Val Val Ser Thr Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Gly Leu Ile Lys Gly Ala Asn Phe Ala Ser
            180                 185                 190

Arg Asn Gly Asp Asn Thr Arg Ala Asn Thr Tyr Thr Asn Thr Ala Ala
        195                 200                 205

Ser Ile Lys Thr Lys Ile Asp Ser Phe Trp Asn Ser Asn Gly Asn Tyr
    210                 215                 220

Val Thr Val Ser Gln Ser Val Thr Gly Gly Val Ser Lys Ala Gly Tyr
225                 230                 235                 240

Asp Ala Ser Val Leu Ile Ala Ala Asn Leu Gly Ser Val Gln Asp Gly
                245                 250                 255

Phe Tyr Thr Pro Gly Ser Asp Lys Met Leu Ala Thr Ala Val Ala Ile
            260                 265                 270

Glu Ser Lys Phe Ala Ser Leu Tyr Ser Ile Asn Gln Asn Leu Asn Gly
        275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Phe Asn Asn Gly Gly
                325                 330                 335

Val Thr Val Thr Ser Ile Ser Leu Asn Phe Phe Lys Lys Phe Asp Ser
            340                 345                 350

Ser Ala Ala Val Gly Thr Lys Tyr Thr Val Gly Thr Ser Ala Phe Asn
        355                 360                 365

Ser Leu Val Gln Asn Val Ala Val Ala Ala Asp Ala Phe Phe Ser Thr
    370                 375                 380

Val Lys Phe His Ala Ala Thr Asn Gly Ser Met Ser Glu Gln Tyr Gly
385                 390                 395                 400

Arg Ser Asp Gly Leu Met Thr Gly Ala Arg Asp Leu Thr Trp Ser His
                405                 410                 415

Ala Ser Leu Ile Ser Ala Ser Tyr Ala Lys Ala Gly Ser Pro Ala Ala
            420                 425                 430
```

<210> SEQ ID NO 88
<211> LENGTH: 431
<212> TYPE: PRT
<213> ORGANISM: Dichotomocladium elegans

<400> SEQUENCE: 88

```
Trp Ala Asp Ser Gln His Lys Ile Ser Trp Lys Ala Met Leu Ala Asn
1               5                   10                  15

Ile Asn Pro Pro Gly Ser Ala Thr Gly Phe Ile Ala Ala Ser Leu Ser
            20                  25                  30

Thr Ser Gly Pro Asp Tyr Tyr Tyr Ala Trp Thr Arg Asp Ala Ala Met
        35                  40                  45

Val Ala His Val Ile Val Asn Ala Tyr Asn Thr Thr Lys Ala Gly Asp
    50                  55                  60

Ala Thr Thr Leu Gly Val Leu Lys Asp Phe Val Thr Phe Gln Ile Lys
65                  70                  75                  80

Ala Met Ala Thr Ser Thr Val Cys Asn Cys Leu Gly Glu Pro Lys Phe
                85                  90                  95

Asn Pro Asp Gly Ser Ser Tyr Thr Gly Pro Trp Gly Arg Pro Gln Asn
            100                 105                 110

Asp Gly Pro Ala Glu Arg Ala Thr Thr Phe Ile Leu Phe Ala Asp Ser
        115                 120                 125

Tyr Leu Ser Gln Thr Gly Asp Ala Ala Tyr Val Thr Thr Leu Lys Arg
    130                 135                 140

Ala Ile Phe Thr Asp Leu Asp Tyr Val Val Thr Thr Trp Gln Asp Asn
145                 150                 155                 160

Cys Phe Asp Leu Trp Glu Glu Val Asn Gly Leu His Met Tyr Thr Leu
                165                 170                 175

Ala Val Met Arg Arg Ser Leu Val Asp Gly Ala Ser Phe Ala Ala Arg
            180                 185                 190

Asn Gly Asp Asn Thr Arg Ala Ser Thr Tyr Thr Asn Thr Ala Lys Ser
        195                 200                 205

Ile Glu Thr Lys Leu Ala Ser Phe Tyr Asn Ser Ser Ser Asn Tyr Val
    210                 215                 220

Val Val Thr Lys Asn Phe Ala Gly Gly Val Asn Lys Ala Gly Leu Asp
225                 230                 235                 240

Thr Ser Thr Leu Ile Ala Ala Asn Thr Ala Gly Leu Gly Asp Gly Phe
                245                 250                 255

Phe Thr Pro Gly Ser Pro Glu Ile Leu Ala Thr Ala Ala Ala Ile Glu
            260                 265                 270

Lys Ser Phe Ala Asp Leu Tyr Gly Ile Asn Lys Gln Ile Pro Asn Trp
        275                 280                 285

Leu Gly Thr Ala Ile Gly Arg Tyr Pro Glu Asp Thr Tyr Asn Gly Asn
    290                 295                 300

Gly Asn Ser Gln Gly Asn Pro Trp Phe Ile Cys Thr Ala Thr Phe Ala
305                 310                 315                 320

Glu Leu Tyr Tyr Arg Ala Ile Leu Glu Trp Gln His Ala Gly Ser Val
                325                 330                 335

Thr Val Asn Asn Val Asn Leu Pro Phe Phe Lys Lys Phe Asp Ser Ser
            340                 345                 350

Thr Ser Ser Gly Thr Thr Tyr Thr Val Gly Thr Ser Ser Phe Asp Ser
        355                 360                 365

Leu Ile Ser Lys Val Ala Tyr Ala Ala Asp Asn Phe Phe Ser Thr Ile
    370                 375                 380

Lys Tyr His Ala Ala Thr Asn Gly Ser Met Ser Glu Gln Phe Asn Arg
385                 390                 395                 400

Asp Thr Gly Phe Met Thr Gly Ala Arg Asp Leu Thr Trp Ser His Ala
                405                 410                 415
```

```
Ala Phe Ile Thr Ala Ala Lys Ala Lys Ala Gly Thr Pro Val Tyr
            420                 425                 430


<210> SEQ ID NO 89
<211> LENGTH: 432
<212> TYPE: PRT
<213> ORGANISM: Fennellomyces sp.

<400> SEQUENCE: 89

Trp Val Asn Asp Gln Leu Glu Ile Ser Trp Pro Ser Leu Leu Lys Asn
1               5                   10                  15

Val Asn Pro Ser Gly Ala Val Thr Gly Phe Ile Ala Ala Ser Leu Ser
            20                  25                  30

Thr Asn Asp Pro Asp Tyr Phe Tyr Cys Trp Thr Arg Asp Ala Ala Leu
        35                  40                  45

Val Ala Arg Val Met Val Tyr Met Tyr Asn Thr Thr Glu Ala Gly Asp
    50                  55                  60

Thr Ser Leu Arg Ser Lys Leu Gln Asp Tyr Val Thr Phe Gln Ile Asn
65                  70                  75                  80

Ser Met Lys Thr Ala Thr Val Cys Asn Cys Leu Gly Glu Pro Lys Phe
                85                  90                  95

Asn Lys Asp Gly Ser Gly Tyr Ser Gly Ala Trp Gly Arg Pro Gln Asn
            100                 105                 110

Asp Gly Pro Ala Asp Arg Ala Ile Thr Leu Ile Leu Phe Ala Asp Ser
        115                 120                 125

Phe Ile Ala Gln Gly Gly Asp Val Ser Tyr Ile Thr Asn Thr Leu Lys
    130                 135                 140

Pro Ala Ile Tyr Thr Asn Leu Asp Tyr Val Val Asn Thr Trp Ser Asn
145                 150                 155                 160

Val Cys Phe Asp Leu Trp Glu Glu Val Asn Gly Val His Ile Tyr Thr
                165                 170                 175

Leu Ser Val Met Arg Lys Gly Leu Leu Glu Gly Ala Asp Phe Ala Ser
            180                 185                 190

Arg Asn Gly Asp Ser Thr Arg Ala Asn Thr Tyr Arg Ser Thr Ala Ser
        195                 200                 205

Ser Ile Lys Thr Arg Leu Glu Ser Phe Trp Ser Ser Ser Asn Asn Tyr
    210                 215                 220

Ile Thr Val Thr Gln Ser Tyr Ser Gly Gly Val Asn Lys Ala Gly Leu
225                 230                 235                 240

Asp Val Ser Thr Leu Leu Ala Ala Asn Gly Ala Ser Met Asn Asp Gly
                245                 250                 255

Phe Tyr Thr Pro Gly Ser Asp Lys Met Leu Ala Thr Ala Val Ala Ile
            260                 265                 270

Glu Asn Ser Phe Ala Gly Ile Tyr Ala Val Asn Gln Asn Arg Pro Asp
        275                 280                 285

Trp Lys Gly Thr Ala Ile Gly Arg Tyr Pro Glu Asp Thr Tyr Asp Gly
    290                 295                 300

His Gly Asn Ser Gln Gly Asn Pro Trp Phe Ile Ala Thr Ala Ala Tyr
305                 310                 315                 320

Ala Glu Met Tyr Tyr Arg Ala Ile Leu Glu Trp Gln Gln Gln Pro Ser
                325                 330                 335

Ile Thr Val Asn Ser Ile Asn Leu Ser Phe Phe Lys Lys Phe Asp Ser
            340                 345                 350

Ser Ala Ala Val Gly Thr Val Tyr Lys Pro Gly Thr Gln Ala Phe Asn
```

```
        355                 360                 365

Asn Met Val Ser Asn Val Ala Phe Ala Ala Asp Glu Phe Phe Ser Thr
    370                 375                 380

Met Asn Phe His Ser Ala Thr Asn Gly Ser Met Ser Glu Gln Tyr Asn
385                 390                 395                 400

Arg Asn Thr Gly Ile Met Gln Gly Ala Arg Asp Leu Thr Trp Ser His
                405                 410                 415

Ala Ala Phe Ile Thr Ala Ala Lys Ala Lys Leu Gly Thr Pro Val Phe
            420                 425                 430


<210> SEQ ID NO 90
<211> LENGTH: 432
<212> TYPE: PRT
<213> ORGANISM: Gilbertella persicaria

<400> SEQUENCE: 90

Trp Leu Lys Gly Gln Ile Glu Thr Ser Arg Phe Ala Met Leu Arg Asn
1               5                   10                  15

Ile Asn Pro Ala Gly Thr Val Lys Gly Phe Ile Ala Ala Ser Leu Ser
            20                  25                  30

Thr Ala Asn Pro Asp Tyr Phe Tyr Ala Trp Thr Arg Asp Ala Ala Leu
        35                  40                  45

Val Gly His Val Ile Ala Asn Asp Tyr Asn Arg Thr Leu Ala Gly Asn
    50                  55                  60

Ser Thr Tyr Leu Gly Leu Leu Lys Asp Tyr Val Thr Phe Ser Val Asn
65                  70                  75                  80

Ser Gln Ser Thr Ser Thr Ile Cys Asn Cys Leu Gly Glu Pro Lys Phe
                85                  90                  95

Asn Lys Asp Gly Ser Gly Tyr Ser Gly Ala Trp Gly Arg Pro Gln Asn
            100                 105                 110

Asp Gly Pro Ala Glu Arg Ala Asp Thr Phe Ile Leu Ile Ala Asp Ser
        115                 120                 125

Ile Leu Lys Gln Thr Gly Asp Ala Thr Tyr Val Thr Gly Thr Leu Arg
    130                 135                 140

Pro Ala Ile Tyr Lys Asp Leu Asp Tyr Val Val Asn Val Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Ser Leu Ile Leu Gly Ala Asn Phe Ala Ser
            180                 185                 190

Arg Asn Gly Asp Ser Thr Arg Ala Ser Thr Tyr Thr Asn Thr Ala Asn
        195                 200                 205

Ser Ile Lys Thr Lys Ile Asp Thr Phe Trp Ser Ser Ser Asn Asn Tyr
    210                 215                 220

Val Ala Val Ser Gln Ser Val Thr Gly Gly Val Asn Lys Ala Gly Tyr
225                 230                 235                 240

Asp Val Ala Asn Leu Ile Ala Ala Asn Val Gly Ser Leu Asp Asp Gly
                245                 250                 255

Phe Tyr Thr Pro Gly Ser Glu Arg Ile Leu Ala Thr Ala Val Ala Val
            260                 265                 270

Glu Ser Lys Phe Ala Ser Ile Tyr Gly Val Asn Gln Asn Leu Pro Ser
        275                 280                 285

Trp Leu Gly Asn Ser Ile Gly Arg Tyr Pro Glu Asp Thr Tyr Asn Gly
    290                 295                 300
```

```
Asn Gly Asn Ser Gln Gly Asn Pro Trp Phe Ile Ala Thr Asn Thr Tyr
305                 310                 315                 320

Ala Glu Leu Tyr Tyr Arg Ala Ile Lys Glu Trp Thr Asn Asn Gly Gly
                325                 330                 335

Val Thr Val Thr Asn Val Asn Phe Asn Phe Phe Lys Lys Phe Asp Ser
            340                 345                 350

Ser Ala Ser Val Gly Thr Lys Tyr Thr Val Gly Thr Ser Ala Phe Asn
        355                 360                 365

Thr Leu Thr Gln Asn Val Ala Leu Ala Ala Asp Asn Phe Phe Ser Thr
    370                 375                 380

Val Lys Val His Ala Ala Thr Asn Gly Ser Met Ser Glu Gln Phe Gly
385                 390                 395                 400

Arg Asp Ser Gly Val Met Thr Gly Ala Arg Asp Leu Thr Trp Ser His
                405                 410                 415

Ala Ser Leu Ile Thr Ala Ala Leu Ala Lys Thr Gly Ala Pro Val Ala
            420                 425                 430


<210> SEQ ID NO 91
<211> LENGTH: 432
<212> TYPE: PRT
<213> ORGANISM: Mucor circinelloides

<400> SEQUENCE: 91

Trp Ile Asp Gly Gln Thr Ser Val Ser Arg Tyr Ala Met Leu Arg Asn
1               5                   10                  15

Ile Asn Pro Ala Gly Ala Val Thr Gly Phe Ile Ala Ala Ser Met Ser
            20                  25                  30

Thr Ser Gly Pro Asp Tyr Phe Tyr Ala Trp Thr Arg Asp Ser Ala Leu
        35                  40                  45

Thr Ser His Val Val Ala Tyr Asp Tyr Asn Thr Thr Leu Ala Gly Asn
    50                  55                  60

Ser Thr Ile Leu Gly Leu Leu Lys Asn Tyr Val Thr Phe Ser Leu Asn
65                  70                  75                  80

Ser Gln Thr Thr Ser Thr Val Cys Asn Cys Leu Gly Glu Pro Lys Phe
                85                  90                  95

Asn Lys Asp Gly Ser Gly Tyr Ser Gly Ala Trp Gly Arg Pro Gln Asn
            100                 105                 110

Asp Gly Pro Ala Ser Arg Ala Asp Thr Phe Ile Leu Ile Ala Asp Ser
        115                 120                 125

Ile Leu Lys Gln Thr Gly Asp Ala Thr Tyr Val Thr Gly Thr Leu Ala
    130                 135                 140

Pro Ala Ile Tyr Lys Asp Leu Asp Tyr Val Val Ser Thr Trp Ser Asn
145                 150                 155                 160

Gly Cys Phe Asp Leu Trp Glu Glu Val Asn Gly Val His Phe Tyr Thr
                165                 170                 175

Leu Met Val Met Arg Arg Gly Leu Val Lys Gly Ala Asn Phe Ala Ser
            180                 185                 190

Arg Asn Gly Asp Ser Thr Arg Ala Thr Thr Tyr Thr Asn Thr Ala Ala
        195                 200                 205

Ser Ile Lys Thr Lys Ile Asp Ser Phe Trp Asn Ser Asn Gly Gln Tyr
    210                 215                 220

Val Ser Val Ser Gln Ser Val Thr Gly Gly Val Ser Lys Ala Gly Tyr
225                 230                 235                 240

Asp Ala Ser Val Leu Ile Ala Ser Asn Leu Gly Ser Leu Gln Asp Gly
                245                 250                 255
```

```
Phe Tyr Thr Pro Gly Ser Asp Lys Met Leu Ala Thr Ala Val Ala Ile
            260                 265                 270

Glu Ser Lys Phe Ala Ser Leu Tyr Ser Ile Asn Gln Asn Leu Asn Gly
        275                 280                 285

Tyr Leu Gly Asn Ala Ile Gly Arg Tyr Pro Glu Asp Thr Tyr Asn Gly
    290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Phe Asn Asn Gly Gly
                325                 330                 335

Val Thr Val Thr Ser Ile Ser Leu Asn Phe Phe Lys Lys Phe Asp Ser
            340                 345                 350

Ser Ala Ala Val Gly Thr Lys Tyr Thr Val Gly Thr Ser Ser Phe Asn
        355                 360                 365

Ser Leu Val Gln Asn Val Ala Val Ala Ala Asp Ala Phe Phe Ser Thr
    370                 375                 380

Ile Lys Phe His Ala Ala Thr Asn Gly Ser Met Ser Glu Gln Tyr Gly
385                 390                 395                 400

Arg Thr Asp Gly Leu Met Thr Gly Ala Arg Asp Leu Thr Trp Ser His
                405                 410                 415

Ala Ser Leu Ile Ser Ala Ser Tyr Ala Lys Ala Gly Ser Pro Ala Ala
            420                 425                 430


<210> SEQ ID NO 92
<211> LENGTH: 432
<212> TYPE: PRT
<213> ORGANISM: Circinella umbellata

<400> SEQUENCE: 92

Trp Val Asn Lys Gln Leu Lys Ile Ser Trp Ser Asp Leu Leu Gln Asn
1               5                   10                  15

Val Asn Pro Ser Gly Thr Val Thr Gly Phe Ile Ala Ala Ser Leu Ser
            20                  25                  30

Thr Ser Asn Pro Asp Tyr Phe Tyr Cys Trp Thr Arg Asp Ala Ala Met
        35                  40                  45

Val Ala Arg Val Met Thr Tyr Met Tyr Asn Thr Thr Glu Ala Gly Asp
    50                  55                  60

Ser Ser Leu Glu Ser Ala Leu Lys Asp Tyr Ile Thr Phe Gln Ile Asn
65                  70                  75                  80

Ser Met Lys Thr Ala Thr Ala Cys Asn Cys Leu Gly Glu Pro Lys Phe
                85                  90                  95

Asn Thr Asp Gly Ser Gly Tyr Ser Gly Pro Trp Gly Arg Pro Gln Asn
            100                 105                 110

Asp Gly Pro Ala Glu Arg Ala Thr Thr Met Ile Leu Phe Ala Asp Ser
        115                 120                 125

Tyr Leu Ala Gln Gly Gly Asp Thr Ser Tyr Val Thr Asn Thr Leu Lys
    130                 135                 140

Pro Ala Ile Tyr Thr Asn Leu Asp Tyr Val Val Gly Thr Trp Ser Asn
145                 150                 155                 160

Asn Cys Phe Asp Leu Trp Glu Glu Val Asn Gly Val His Ile Phe Thr
                165                 170                 175

Leu Ala Val Met Arg Lys Ser Leu Leu Asp Gly Ala Asp Phe Ala Ala
            180                 185                 190

Arg Asn Gly Asp Thr Ser Arg Val Ser Gly Tyr Gln Ser Thr Ala Ser
```

```
        195                 200                 205

Ser Ile Lys Thr Lys Leu Glu Ser Phe Trp Ser Ser Ser Asn Asn Tyr
    210                 215                 220

Ile Thr Val Thr Gln Ser Tyr Ser Gly Gly Val Gln Lys Ala Gly Leu
225                 230                 235                 240

Asp Val Ser Thr Leu Ile Ala Ala Asn Gln Gly Ser Met Gly Asp Gly
                245                 250                 255

Phe Tyr Thr Pro Gly Ser Asp Lys Met Leu Ala Thr Ala Val Ala Ile
            260                 265                 270

Glu Asn Ser Phe Ala Asn Ile Tyr Thr Ile Asn Lys Asn Lys Pro Ser
        275                 280                 285

Trp Leu Gly Thr Ala Ile Gly Arg Tyr Pro Glu Asp Thr Tyr Asn Gly
    290                 295                 300

Asn Gly Asn Gly Gln Gly Asn Pro Trp Phe Ile Ala Thr Ala Thr Tyr
305                 310                 315                 320

Ala Glu Leu Tyr Tyr Arg Ala Ile Leu Glu Trp Gln Gln Gln Glu Ser
                325                 330                 335

Val Thr Val Asn Ser Val Asn Phe Asp Phe Phe Ser Lys Phe Asp Ser
            340                 345                 350

Ser Ala Lys Val Gly Thr Val Tyr Thr Pro Gly Thr Asp Thr Phe Asn
        355                 360                 365

Thr Met Val Ser Asn Val Ala Phe Ala Ala Asp Glu Phe Leu Ser Thr
    370                 375                 380

Met Glu His Tyr Ala Ala Thr Asn Gly Ser Met Ser Glu Gln Phe Asn
385                 390                 395                 400

Arg Glu Thr Gly Ser Leu Thr Gly Ala Arg Asp Leu Thr Trp Ser His
                405                 410                 415

Ala Ala Phe Ile Thr Ala Gly Lys Ala Lys Leu Gly Ile Pro Ser Phe
            420                 425                 430


<210> SEQ ID NO 93
<211> LENGTH: 432
<212> TYPE: PRT
<213> ORGANISM: Mucor cordense

<400> SEQUENCE: 93

Trp Leu Lys Ser Gln Glu Asp Ile Ser Arg Gly Ala Met Leu Arg Asn
1               5                   10                  15

Ile Asn Pro Pro Gly Ala Ala Thr Gly Phe Ile Ala Ala Ser Leu Ser
            20                  25                  30

Thr Ser Gly Pro Asp Tyr Tyr Tyr Ala Trp Thr Arg Asp Ser Ala Leu
        35                  40                  45

Thr Ser His Val Ile Ala His Asp Tyr Asn Thr Thr Leu Ala Gly Asn
    50                  55                  60

Thr Thr Ile Leu Asn Ile Leu Lys Asp Tyr Val Thr Phe Ser Val Lys
65                  70                  75                  80

Ser Gln Ser Val Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Ser Thr Phe Ile Leu Phe Gly Asp Ser
        115                 120                 125

Tyr Leu Lys Gln Thr Gly Asp Ala Thr Tyr Val Thr Gly Thr Leu Ala
    130                 135                 140
```

```
Pro Ala Ile Tyr Lys Asp Leu Asp Tyr Val Val Asn Thr Trp Ser Asn
145                 150                 155                 160

Gly Cys Phe Asp Leu Trp Glu Glu Val Asn Gly Val His Phe Tyr Thr
                165                 170                 175

Leu Met Ser Met Arg Arg Gly Leu Leu Asp Gly Ala Asn Phe Ala Lys
            180                 185                 190

Arg Asn Gly Asp Thr Thr Arg Ala Thr Thr Tyr Thr Asn Thr Ala Ala
        195                 200                 205

Ser Ile Ala Thr Lys Ile Asp Thr Phe Trp Val Ser Ser Gly Asn Tyr
    210                 215                 220

Val Gln Val Ser Gln Ser Val Thr Gly Gly Val Ser Lys Ala Gly Tyr
225                 230                 235                 240

Asp Cys Ala Asn Ile Leu Ala Ala Asn Met Ala Ala Asn His Asp Gly
                245                 250                 255

Phe Tyr Thr Pro Gly Ser Ser Lys Ile Leu Ala Thr Ala Val Ala Ile
            260                 265                 270

Glu Ser Lys Phe Ala Ser Leu Tyr Ser Ile Asn Ser Gly Leu Ala Ser
        275                 280                 285

Trp Leu Gly Thr Ala Ile Gly Arg Tyr Pro Glu Asp Thr Tyr Asn Gly
    290                 295                 300

Asn Gly Asn Ser Gln Gly Asn Pro Trp Phe Ile Cys Thr Asn Ala Phe
305                 310                 315                 320

Ala Glu Leu Tyr Tyr Arg Ala Ile Lys Glu Trp Thr Gln Ala Gly Ser
                325                 330                 335

Val Thr Val Asp Ser Thr Ser Leu Asn Phe Phe Lys Lys Phe Asp Ser
            340                 345                 350

Ser Ala Ala Ala Gly Thr Lys Tyr Thr Val Gly Thr Ser Ala Phe Thr
        355                 360                 365

Asn Leu Val Gln Asn Ile Ala Asn Gly Ala Asp Lys Phe Leu Ser Thr
    370                 375                 380

Ser Lys Phe His Ala Ala Thr Asn Gly Ser Met Ser Glu Gln Tyr Asn
385                 390                 395                 400

Arg Asp Ser Gly Leu Met Thr Gly Ala Arg Asp Leu Thr Trp Ser His
                405                 410                 415

Ala Ser Leu Ile Ser Ala Ser Arg Ala Lys Ala Gly Ser Pro Ser Leu
            420                 425                 430


<210> SEQ ID NO 94
<211> LENGTH: 432
<212> TYPE: PRT
<213> ORGANISM: Phascolomyces articulosus

<400> SEQUENCE: 94

Trp Val Asn Thr Gln Phe Ala Ile Ser Trp Pro Thr Leu Leu Lys Asn
1               5                   10                  15

Val Asn Pro Ser Gly Thr Val Lys Gly Phe Ile Ala Ala Ser Leu Ser
            20                  25                  30

Thr Asn Asn Pro Asp Tyr Phe Tyr Ser Trp Thr Arg Asp Ser Ala Leu
        35                  40                  45

Val Ala His Thr Met Thr Tyr Leu Tyr Asn Thr Ser Glu Ala Gly Asp
    50                  55                  60

Ser Thr Ile Glu Ser Ala Leu Lys Asp Tyr Val Thr Phe Ser Ile Asn
65                  70                  75                  80

Ala Met Asn Ala Ala Thr Val Cys Asn Cys Leu Gly Glu Pro Lys Phe
                85                  90                  95
```

```
Asn Thr Asp Gly Ser Gly Tyr Thr Gly Ala Trp Gly Arg Pro Gln Asn
            100                 105                 110

Asp Gly Pro Ala Ser Arg Ala Thr Thr Met Ile Leu Phe Ala Asp Ser
        115                 120                 125

Phe Leu Ala Gln Gly Gly Asp Val Ser Tyr Val Ile Asn Thr Leu Lys
    130                 135                 140

Pro Ala Ile Tyr Lys Asp Leu Asp Tyr Val Val Ser Thr Trp Ser Asn
145                 150                 155                 160

Thr Cys Tyr Asp Leu Trp Glu Glu Val Asn Gly Val His Ile Tyr Thr
                165                 170                 175

Leu Ser Val Met Arg Arg Ala Leu Ile Asp Gly Ala Asn Phe Ala Gln
            180                 185                 190

Arg Asn Gly Asp Thr Ser Arg Val Ser Gly Tyr Thr Ser Thr Ala Thr
        195                 200                 205

Thr Ile Lys Thr Arg Leu Glu Ser Phe Trp Ser Asp Ser Asn Asn Tyr
    210                 215                 220

Ile Thr Val Thr Gln Ser Tyr Ser Gly Gly Val Gln Lys Ala Gly Leu
225                 230                 235                 240

Asp Val Ser Thr Leu Ile Ala Ala Asn Ile Gly Ser Val Gly Asp Gly
                245                 250                 255

Phe Tyr Thr Pro Gly Ser Asp Lys Val Leu Ala Thr Ala Val Ala Ile
            260                 265                 270

Glu Lys Ser Phe Ala Asn Leu Tyr Thr Ile Asn Gln Asn Lys Pro Ser
        275                 280                 285

Trp Leu Gly Asn Ala Ile Gly Arg Tyr Pro Glu Asp Thr Tyr Asp Gly
    290                 295                 300

Tyr Gly Asn Ser Lys Gly Asn Pro Trp Phe Ile Ala Thr Ala Thr Tyr
305                 310                 315                 320

Ala Glu Leu Tyr Tyr Arg Ala Ile Leu Glu Trp Gln Gln Gln Ala Ser
                325                 330                 335

Val Thr Val Asn Ser Ile Asn Leu Gly Phe Phe Ser Lys Phe Asp Ser
            340                 345                 350

Ser Ala Ser Val Gly Thr Val Tyr Thr Pro Gly Thr Asp Ser Phe Ala
        355                 360                 365

Asn Met Val Ser Asn Val Ala Phe Ala Ala Asp Glu Phe Leu Ser Thr
    370                 375                 380

Ile Asp Tyr His Ala Met Asn Asn Gly Ser Met His Glu Gln Tyr Asn
385                 390                 395                 400

Arg Asp Thr Gly Ile Ser Gln Gly Ala Arg Asp Leu Thr Trp Ser His
                405                 410                 415

Ala Ala Phe Ile Thr Ala Ala Lys Ala Lys Leu Gly Ala Pro Ala Phe
            420                 425                 430
```

<210> SEQ ID NO 95
<211> LENGTH: 432
<212> TYPE: PRT
<213> ORGANISM: Rhizopus microsporus

<400> SEQUENCE: 95

```
Trp Ile Lys Asn Gln Glu Glu Ile Ser Arg Phe Ala Met Leu Arg Asn
1               5                   10                  15

Ile Asn Pro Pro Gly Ser Ala Thr Gly Phe Ile Ala Ala Ser Leu Ser
            20                  25                  30

Thr Ala Gly Pro Asp Tyr Tyr Tyr Ser Trp Thr Arg Asp Ser Ala Leu
```

```
        35                  40                  45

Thr Ala Asn Val Ile Ala Tyr Glu Tyr Asn Thr Thr Phe Ala Gly Asn
    50                  55                  60

Thr Thr Leu Leu Lys Tyr Leu Lys Asp Tyr Val Thr Phe Ser Val Lys
65                  70                  75                  80

Ser Gln Ser Val Ser Thr Val Cys Asn Cys Leu Gly Glu Pro Lys Phe
                85                  90                  95

Asn Ala Asp Gly Ser Ser Tyr Thr Gly Pro Trp Gly Arg Pro Gln Asn
            100                 105                 110

Asp Gly Pro Ala Glu Arg Ala Val Thr Phe Met Leu Ile Ala Asp Ser
        115                 120                 125

Tyr Leu Thr Gln Thr Lys Asp Ala Ser Tyr Val Thr Gly Thr Leu Lys
    130                 135                 140

Pro Ala Ile Phe Lys Asp Leu Asp Tyr Val Val Ser Val Trp Ser Asn
145                 150                 155                 160

Gly Cys Tyr Asp Leu Trp Glu Glu Val Asn Gly Val His Phe Tyr Thr
                165                 170                 175

Leu Met Val Met Arg Lys Gly Leu Ile Leu Gly Ala Asp Phe Ala Ala
            180                 185                 190

Arg Asn Gly Asp Ser Ser Arg Ala Ser Thr Tyr Lys Asn Thr Ala Ser
        195                 200                 205

Thr Met Glu Ser Lys Ile Ser Ser Phe Trp Ser Asp Ser Asn Asn Tyr
    210                 215                 220

Val Gln Val Ser Gln Ser Val Thr Ala Gly Val Ser Lys Lys Gly Leu
225                 230                 235                 240

Asp Val Ser Thr Leu Leu Ala Ala Asn Ile Gly Ser Leu Pro Asp Gly
                245                 250                 255

Phe Phe Thr Pro Gly Ser Glu Lys Ile Leu Ala Thr Ala Val Ala Leu
            260                 265                 270

Glu Asn Ala Phe Ala Ser Leu Tyr Pro Ile Asn Ser Asn Leu Pro Ser
        275                 280                 285

Tyr Leu Gly Asn Ser Ile Gly Arg Tyr Pro Glu Asp Thr Tyr Asn Gly
    290                 295                 300

Asn Gly Asn Ser Gln Gly Asn Pro Trp Phe Leu Ala Val Asn Ala Tyr
305                 310                 315                 320

Ala Glu Leu Tyr Tyr Arg Ala Ile Lys Glu Trp Ile Ser Asn Gly Lys
                325                 330                 335

Val Thr Val Ser Asn Ile Ser Leu Pro Phe Phe Lys Lys Phe Asp Ser
            340                 345                 350

Ser Ala Thr Ser Gly Lys Thr Tyr Thr Ala Gly Thr Ser Asp Phe Asn
        355                 360                 365

Asn Leu Ala Gln Asn Ile Ala Leu Gly Ala Asp Arg Phe Leu Ser Thr
    370                 375                 380

Val Lys Phe His Ala Tyr Asn Asn Gly Ser Leu Ser Glu Glu Tyr Asp
385                 390                 395                 400

Arg Ser Thr Gly Met Ser Thr Gly Ala Arg Asp Leu Thr Trp Ser His
                405                 410                 415

Ala Ser Leu Ile Thr Ala Ala Tyr Ala Lys Ala Gly Ser Pro Ala Ala
            420                 425                 430
```

<210> SEQ ID NO 96
<211> LENGTH: 433
<212> TYPE: PRT
<213> ORGANISM: Spinellus fusiger

<400> SEQUENCE: 96

Trp Gly Ser Lys Gln Asp Gly Ile Ser Phe Ser Thr Met Leu Gly Asn
1               5                   10                  15

Ile Asn Pro Pro Gly Ser Ser Lys Gly Phe Ile Ala Ala Ser Leu Ser
            20                  25                  30

Thr Ala Gly Pro Asn Tyr Tyr Tyr Ser Trp Thr Arg Asp Ser Ala Leu
        35                  40                  45

Val Ala Arg Ala Ile Thr Tyr Lys Tyr Ser Thr Ser Tyr Gln Asn Asp
    50                  55                  60

Pro Lys Ile Leu Gly Leu Leu Lys Asp Tyr Val Thr Tyr Gln Val Asn
65                  70                  75                  80

Glu Gln Thr Glu Ser Thr Val Cys Asn Cys Leu Gly Glu Pro Lys Phe
                85                  90                  95

Asn Pro Asp Gly Ser Ser Phe Ser Gly Pro Trp Gly Arg Pro Gln Asn
            100                 105                 110

Asp Gly Pro Ala Glu Arg Ala Ser Thr Met Ile Leu Phe Ala Lys Ser
        115                 120                 125

Tyr Tyr Ala Gln Thr Asn Asp Val Gly Tyr Val Ser Asn Thr Leu Lys
    130                 135                 140

Pro Ala Ile Tyr Lys Asp Leu Asp Tyr Ile Val Asn Val Trp Gly Asn
145                 150                 155                 160

Asn Cys Phe Asp Leu Trp Glu Glu Val Asn Gly Val His Phe Tyr Thr
                165                 170                 175

Leu Met Met Met Arg His Gly Leu Val Gln Gly Ser Ile Phe Ala Asn
            180                 185                 190

Thr Leu Gly Asp Ser Thr Arg Ala Asn Thr Tyr Lys Thr Ala Ala Gln
        195                 200                 205

Asn Ile Lys Asn Arg Ile Asp Thr Phe Trp Glu Ser Gly Ser Asn Tyr
    210                 215                 220

Ile Val Val Thr Gln Asn Gln Ser Ala Gly Val Asn Lys Pro Ser Gly
225                 230                 235                 240

Leu Asp Val Ala Val Leu Leu Ala Ala Asn Gln Gly Gly Leu Gly Asp
                245                 250                 255

Gly Val Tyr Thr Pro Gly Ser Asp Lys Val Leu Ala Thr Ala Val Ala
            260                 265                 270

Leu Glu Lys Ser Phe Ala Ser Leu Tyr Pro Ile Asn Lys Asn Leu Pro
        275                 280                 285

Ser Tyr Tyr Gly Thr Ala Ile Gly Arg Tyr Pro Glu Asp Thr Tyr Asn
    290                 295                 300

Gly Asn Gly Asn Ser Glu Ala Asn Pro Trp Phe Ile Ala Thr Thr Thr
305                 310                 315                 320

Tyr Ala Glu Leu Tyr Tyr Arg Ala Ile Ser Glu Trp Thr Asn Gly Ser
                325                 330                 335

Gly Val Thr Val Asn Ser Ile Asn Lys Glu Phe Phe Ser Lys Phe Asp
            340                 345                 350

Ala Ser Ala Thr Asn Gly Lys Val Tyr Thr Pro Gly Ser Asp Ser Phe
        355                 360                 365

Asn Ser Leu Val Asn Asn Val Ala Ile Ala Ala Asp Asn Phe Leu Ser
    370                 375                 380

Thr Val Arg Tyr His Gln Thr Ser Asn Gly Ser Leu Ser Glu Gln Phe
385                 390                 395                 400

Asn Arg Tyr Thr Gly Phe Met Thr Gly Ala Arg Asp Leu Thr Trp Ser

```
                405                 410                 415

His Ala Ala Met Val Thr Ala Leu Ala Ala Lys Ala Gly Thr Pro Ser
            420                 425                 430

Pro


<210> SEQ ID NO 97
<211> LENGTH: 432
<212> TYPE: PRT
<213> ORGANISM: Syncephalastrum racemosum

<400> SEQUENCE: 97

Trp Ala Lys Ser Gln Lys Asp Ile Ser Trp Lys Thr Leu Leu Thr Ser
1               5                   10                  15

Leu Asn Pro Ser Gly Thr Ala Lys Gly Phe Ile Ala Ala Ser Leu Ser
            20                  25                  30

Thr Ser Asn Pro Asp Tyr Tyr Tyr Ala Trp Thr Arg Asp Ser Ala Leu
        35                  40                  45

Val Ala Arg Thr Met Val Asn Met Tyr Asn Thr Thr Glu Ala Gly Ser
    50                  55                  60

Ala Ser Val Leu Gly Leu Leu Gln Asp Tyr Val Thr Phe Gln Ile Asn
65                  70                  75                  80

Ala Met Ser Thr Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Ser Thr Phe Ile Leu Phe Ala Asp Ser
        115                 120                 125

Tyr Ile Ala Gln Gly Gly Gln Leu Ser Tyr Val Thr Gly Thr Leu Ala
    130                 135                 140

Pro Ala Ile Tyr Lys Asp Leu Asn Tyr Val Val Ser Thr Trp Ser Asn
145                 150                 155                 160

Asn Cys Phe Asp Leu Trp Glu Glu Val Asn Gly Arg His Met Phe Thr
                165                 170                 175

Leu Ala Val Met Arg Arg Ala Leu Leu Asp Gly Val Asn Phe Ala Ser
            180                 185                 190

Arg Ile Gly Asp Thr Thr Tyr Ser Ser Thr Trp Ser Ser Thr Ala Ser
        195                 200                 205

Ser Ile Gln Ser Thr Leu Ser Gly Tyr Tyr Leu Ser Ser Gly Asn Tyr
    210                 215                 220

Ile Thr Thr Val Gln Asn Phe Gln Ser Gly Val Ser Lys Ala Gly Tyr
225                 230                 235                 240

Asp Val Ser Thr Leu Ile Ala Ala Asn Val Ala Gly Met Gly Asp Gly
                245                 250                 255

Phe Phe Thr Pro Gly Ser Asp Glu Val Leu Ala Thr Ala Val Ala Ile
            260                 265                 270

Glu Asn Lys Phe Ser Ser Leu Tyr Gly Val Asn Ala Asn Lys Ala Ser
        275                 280                 285

Tyr Leu Gly Thr Ala Ile Gly Arg Tyr Pro Glu Asp Thr Tyr Asn Gly
    290                 295                 300

Tyr Gly Asn Gly Gln Gly Asn Pro Trp Phe Ile Ala Thr Ala Ala Tyr
305                 310                 315                 320

Ala Glu Leu Tyr Tyr Arg Ala Ile Leu Glu Trp Gln Thr Lys Ser Ser
                325                 330                 335

Ile Val Val Asn Ser Lys Asn Leu Gly Phe Phe Ser Lys Phe Asp Ser
```

```
            340                 345                 350

Ser Ala Ala Val Gly Thr Thr Tyr Thr Pro Gly Thr Thr Ala Tyr Ser
        355                 360                 365

Asn Met Val Gln Asn Val Ala Leu Ala Ala Asp Arg Phe Leu Ser Thr
    370                 375                 380

Val Gln Leu His Ala Ala Thr Asn Gly Ser Met Ser Glu Gln Phe Asn
385                 390                 395                 400

Arg Asp Thr Gly Val Met Gln Gly Ala Arg Asp Leu Thr Trp Ser His
                405                 410                 415

Ser Ala Phe Ile Thr Ala Ala Arg Ala Lys Leu Gly Ser Pro Val Tyr
            420                 425                 430


<210> SEQ ID NO 98
<211> LENGTH: 434
<212> TYPE: PRT
<213> ORGANISM: Syncephalastrum racemosum

<400> SEQUENCE: 98

Trp Val Lys Lys Gln Glu Ala Ile Ser Trp Thr Asp Leu Lys Thr Asn
1               5                   10                  15

Val Asn Pro Glu Gly Ala Ala Lys Gly Phe Ile Ala Ala Ser Leu Ser
            20                  25                  30

Thr Ser Glu Pro Asp Tyr Tyr Tyr Ala Trp Thr Arg Asp Ser Ala Leu
        35                  40                  45

Val Ala Arg Val Met Val Asn Lys Tyr Asn Thr Thr Asp Ala Gly Asp
    50                  55                  60

Ala Asn Leu Leu Gly Leu Leu Gln Asp Tyr Val Ser Phe Gln Ile Asn
65                  70                  75                  80

Ala Met Gly Glu Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Ser Thr Phe Ile Leu Leu Ala Asp Ser
        115                 120                 125

Met Ile Ala Gln Lys Ser Ala Asn Gly Ser Tyr Val Ser Asp Thr Leu
    130                 135                 140

Ala Pro Ala Ile Tyr Lys Asp Leu Ala Tyr Val Ala Ser Thr Trp Glu
145                 150                 155                 160

Asn Ala Cys Tyr Asp Leu Trp Glu Glu Val Asn Gly Lys His Met Tyr
                165                 170                 175

Thr Leu Ser Val Met Arg Arg Ala Leu Leu Asp Gly Ala Asp Phe Ala
            180                 185                 190

Ser Arg Gln Gly Gln Thr Ala Asn Val Thr Ser Trp Lys Ser Thr Ala
        195                 200                 205

Asp Lys Ile Lys Ser Ser Leu Glu Gly Phe Phe Ser Ser Asp Asn Gly
    210                 215                 220

Tyr Ile Glu Val Thr Gln Asp Met Gln Gly Gly Val Gln Lys Lys Gly
225                 230                 235                 240

Leu Asp Val Ser Thr Leu Ile Ala Ala Asn Ile Gly Ser Met Gly Asp
                245                 250                 255

Gly Phe Tyr Thr Pro Gly Ser Asp Glu Val Leu Ala Thr Ala Val Ala
            260                 265                 270

Val Glu Ala Ala Phe Ala Asp Leu Tyr Lys Ile Asn Gln Asn Thr Asn
        275                 280                 285
```

```
Ser Thr Gly Leu Gly Thr Ala Ile Gly Arg Tyr Pro Glu Asp Thr Tyr
    290                 295                 300

Asn Gly Val Gly Asn Ser Gln Gly Asn Pro Trp Phe Ile Ala Thr Asn
305                 310                 315                 320

Thr Phe Ala Glu Leu Tyr Tyr Arg Ala Ile Leu Glu Trp Gln Asn Lys
                325                 330                 335

Gly Thr Ile Thr Val Asn Ser Val Asn Ala Ala Phe Phe Ser Lys Phe
            340                 345                 350

Asp Ser Ser Ala Lys Ala Gly Thr Thr Tyr Lys Ser Gly Ser Thr Glu
        355                 360                 365

Phe Asp Ser Leu Ile Asn Lys Val Ala Leu Ala Ala Asp Ala Phe Leu
    370                 375                 380

Asn Thr Val Gln Thr Tyr Ala Ala Ser Asn Gly Ser Met Ser Glu Gln
385                 390                 395                 400

Tyr Asn Arg Asp Thr Gly Ala Leu Thr Gly Ala Arg Asp Leu Thr Trp
                405                 410                 415

Ser His Ala Ser Leu Ile Thr Ala Ala Asn Ala Lys Leu Gly Thr Pro
            420                 425                 430

Tyr Asn


<210> SEQ ID NO 99
<211> LENGTH: 433
<212> TYPE: PRT
<213> ORGANISM: Thermomucor sp.

<400> SEQUENCE: 99

Trp Ile Gln Glu Gln Leu Ala Ile Ser Trp Asn Thr Met Leu Thr Ser
1               5                   10                  15

Val Asn Pro Val Gly Ala Val Thr Gly Phe Ile Ala Ala Ser Leu Ser
            20                  25                  30

Thr Ala Asn Pro Asp Tyr Tyr Tyr Cys Trp Thr Arg Asp Ala Ala Leu
        35                  40                  45

Val Ala Arg Val Met Thr Phe Met Tyr Asn Thr Thr Gln Ala Gly Asp
    50                  55                  60

Ser Gly Leu Leu Gly Ile Leu Gln Asp Tyr Val Ser Phe Gln Ile His
65                  70                  75                  80

Ala Met Gly Glu Ser Thr Val Cys Asn Cys Leu Gly Glu Pro Lys Phe
                85                  90                  95

Asn Pro Asp Gly Ser Ser Tyr Thr Gly Ala Trp Gly Arg Pro Gln Asn
            100                 105                 110

Asp Gly Pro Ala Glu Arg Ala Ser Thr Phe Ile Lys Ile Ala Asp Ser
        115                 120                 125

Tyr Leu Thr Gln Thr Gly Asp Val Ser Tyr Val Thr Asn Thr Leu Lys
    130                 135                 140

Pro Ala Ile Tyr Glu Asp Leu Asp Tyr Ile Val Asn Val Trp Gln Asn
145                 150                 155                 160

Thr Cys Phe Asp Leu Trp Glu Glu Val Tyr Gly Met His Met Tyr Thr
                165                 170                 175

Leu Ala Val Met Arg Arg Gly Leu Leu Asp Gly Ala Asp Phe Ala Thr
            180                 185                 190

Arg Asn Gly Asp Thr Asp Lys Ala Ser Thr Tyr Thr Ser Thr Ala Thr
        195                 200                 205

Ser Ile Gln Thr Arg Leu Ala Thr Phe Trp Ser Asp Ser Asn Gly Tyr
    210                 215                 220
```

```
Ile Thr Val Thr Gln Asp Tyr Gln Ser Gly Val Ser Lys Ala Gly Leu
225                 230                 235                 240

Asp Val Ser Thr Leu Ile Ala Ala Asn Val Ala Gly Met Asn Asp Gly
                245                 250                 255

Phe Phe Thr Pro Gly Ser Asp Glu Ile Leu Ala Thr Ala Val Lys Val
            260                 265                 270

Glu Ala Ala Phe Ala Asn Leu Tyr Gly Ile Asn Ile Asn Lys Ala Ser
        275                 280                 285

Tyr Leu Gly Asn Ala Ile Gly Arg Tyr Pro Glu Asp Thr Tyr Asn Gly
    290                 295                 300

Asn Gly Asn Ser Glu Gly Asn Pro Trp Phe Ile Ala Thr Ala Ala Phe
305                 310                 315                 320

Ala Glu Leu Tyr Tyr Arg Ala Ile Met Glu Trp Gln Leu Arg Gly Ser
                325                 330                 335

Ser Ile Thr Val Asn Ser Val Asn Gln Gly Phe Phe Thr Lys Phe Asp
            340                 345                 350

Pro Ser Ala Thr Ala Gly Thr Thr Tyr Thr Pro Gly Thr Asp Ala Phe
        355                 360                 365

Asn Ser Leu Ile Asp Asn Val Ala Leu Ala Ala Asp Gln Phe Phe Ser
    370                 375                 380

Thr Ile His Leu His Arg Ala Thr Asn Gly Ser Met Ser Glu Gln Tyr
385                 390                 395                 400

Asn Arg Asp Thr Gly Phe Met Gln Gly Ala Arg Asp Leu Thr Trp Ser
                405                 410                 415

His Ala Ala Phe Ile Thr Ala Ala Lys Ala Lys Gln Gly Thr Pro Ser
            420                 425                 430

Phe


<210> SEQ ID NO 100
<211> LENGTH: 432
<212> TYPE: PRT
<213> ORGANISM: Zychaea mexicana

<400> SEQUENCE: 100

Trp Ala Ser Ala Gln Leu Asp Ile Ser Trp Pro Asn Leu Met Met Asn
1               5                   10                  15

Val Asn Pro Ser Gly Ala Val Thr Gly Ser Ile Val Ala Ser Leu Ser
            20                  25                  30

Thr Ser Asn Pro Asp Tyr Phe Tyr Ile Trp Thr Arg Asp Ala Ala Met
        35                  40                  45

Val Ala Arg Val Met Val Tyr Met Tyr Asn Thr Thr Glu Ala Gly Asp
    50                  55                  60

Thr Asn Leu Leu Asn Ala Leu Thr Asp Tyr Val Thr Phe Ser Ile Ser
65                  70                  75                  80

Ser Met Asn Val Asp Thr Val Cys Asp Cys Leu Gly Glu Pro Lys Phe
                85                  90                  95

Asn Val Asp Gly Ser Gly Tyr Thr Gly Ala Trp Gly Arg Pro Gln Asn
            100                 105                 110

Asp Gly Pro Ala Glu Arg Ala Ser Thr Met Ile Leu Ile Ala Asp Ser
        115                 120                 125

Tyr Ile Ala Gln Gly Gly Asp Val Ser Tyr Val Thr Asp Thr Leu Lys
    130                 135                 140

Pro Ala Ile Tyr Thr Asp Leu Asp Tyr Val Val Asp Thr Trp Ser Asn
145                 150                 155                 160
```

```
Val Cys Phe Asp Leu Trp Glu Glu Val Asn Gly Ile His Met Tyr Thr
                165                 170                 175

Leu Ser Val Met Arg Lys Ala Leu Leu Asp Gly Ala Asn Phe Ala Thr
            180                 185                 190

Arg Asn Gly Asp Thr Ser Arg Val Ser Gly Tyr Glu Ser Thr Ala Ser
        195                 200                 205

Ser Ile Lys Thr Arg Leu Glu Ser Phe Trp Ser Ser Ser Asn Asn Tyr
    210                 215                 220

Ile Thr Val Thr Gln Ser Phe Ser Gly Gly Val Ser Lys Ala Gly Leu
225                 230                 235                 240

Asp Val Ser Thr Leu Ile Ala Ala Asn Leu Ala Ser Met Asn Asp Gly
                245                 250                 255

Phe Tyr Thr Pro Gly Ser Asp Glu Ile Leu Ala Thr Ala Val Ala Ile
            260                 265                 270

Glu Asn Ser Phe Ile Ser Glu Tyr Thr Leu Asn Gln Asn Arg Pro Ser
        275                 280                 285

Trp Leu Ser Thr Ala Ile Gly Arg Tyr Pro Glu Asp Ser Tyr Asp Gly
    290                 295                 300

Tyr Gly Asn Ser Gln Gly Asn Pro Trp Phe Ile Ala Thr Ala Thr Tyr
305                 310                 315                 320

Ala Glu Leu Tyr Tyr Arg Ala Ile Leu Glu Trp Gln Gln Gln Ala Ser
                325                 330                 335

Ile Ser Val Asn Ser Val Asn Leu Gly Phe Phe Ser Lys Phe Asp Ser
            340                 345                 350

Asp Ala Ser Val Gly Thr Val Tyr Thr Pro Gly Thr Glu Asp Phe Ala
        355                 360                 365

Asn Met Val Ser Asn Val Ala Phe Ala Ala Asp Glu Phe Leu Ala Thr
    370                 375                 380

Ile Glu Asn His Ser Ala Val Asn Gly Ser Leu Ser Glu Gln Tyr Asn
385                 390                 395                 400

Arg Asp Thr Gly Ile Met Gln Gly Ala Arg Asp Leu Thr Trp Ser His
                405                 410                 415

Ala Ala Phe Ile Thr Ala Ala Lys Ala Lys Gln Gly Ala Pro Ile His
            420                 425                 430


<210> SEQ ID NO 101
<211> LENGTH: 609
<212> TYPE: PRT
<213> ORGANISM: Mucor ambiguus

<400> SEQUENCE: 101

Met Lys Phe Ser Ser Leu Leu Lys Lys Pro Leu Leu Leu Ile Ala Gly
1               5                   10                  15

Ile Leu Ala Ala Thr Val Val Ala Glu Thr Val Pro Thr Thr Ala Glu
            20                  25                  30

Val Lys Val Lys Ser Phe Thr Tyr Asp Gly Ser Thr Phe Ala Gly Gln
        35                  40                  45

Ile Tyr Ile Lys Asn Ile Ala Tyr Thr Lys Thr Val Thr Val Ile Tyr
    50                  55                  60

Ser Asp Gly Ser Asn Asn Trp Asn Asn Asn Gly Asn Thr Ile Ala Ala
65                  70                  75                  80

Ser Tyr Ser Ala Ala Ile Ser Gly Ser Asn Tyr Glu Tyr Trp Thr Phe
                85                  90                  95

Ser Ala Pro Val Ser Ser Ile Lys Gln Phe Tyr Val Lys Tyr Val Val
            100                 105                 110
```

```
Ser Gly Thr Thr Tyr Tyr Asp Asn Asn Ser Ser Gly Asn Tyr Gln Val
        115                 120                 125

Ser Thr Thr Thr Thr Thr Thr Thr Ala Pro Thr Thr Thr Thr Ser Gly
    130                 135                 140

Gly Ser Ser Thr Thr Thr Gly Gly Ser Thr Thr Thr Ala Thr Ser Val
145                 150                 155                 160

Pro Thr Ala Val Pro Ser Gly Phe Pro Thr Gly Asn Ser Thr Ile Ser
                165                 170                 175

Ser Trp Ile Asp Gly Gln Thr Ser Val Ser Arg Tyr Ala Met Leu Arg
            180                 185                 190

Asn Ile Asn Pro Ala Gly Thr Val Thr Gly Phe Ile Ala Ala Ser Met
        195                 200                 205

Ser Thr Ser Gly Pro Asp Tyr Phe Tyr Ala Trp Thr Arg Asp Ser Ala
    210                 215                 220

Leu Thr Ser His Val Val Ala Tyr Asp Tyr Asn Thr Thr Leu Ala Gly
225                 230                 235                 240

Asn Ser Thr Ile Leu Gly Leu Leu Lys Asn Tyr Val Thr Phe Ser Leu
                245                 250                 255

Asn Ser Gln Thr Thr Ser Thr Val Cys Asn Cys Leu Gly Glu Pro Lys
            260                 265                 270

Phe Asn Lys Asp Gly Ser Ser Tyr Thr Gly Ala Trp Gly Arg Pro Gln
        275                 280                 285

Asn Asp Gly Pro Ala Ser Arg Ala Asp Thr Phe Ile Leu Ile Ala Asp
    290                 295                 300

Ser Ile Leu Lys Gln Thr Gly Asp Ala Thr Tyr Val Thr Gly Thr Leu
305                 310                 315                 320

Ala Pro Ala Ile Tyr Lys Asp Leu Asp Tyr Val Val Ser Thr Trp Ser
                325                 330                 335

Asn Gly Cys Phe Asp Leu Trp Glu Glu Val Asn Gly Val His Phe Tyr
            340                 345                 350

Thr Leu Met Val Met Arg Arg Gly Leu Val Lys Gly Ala Ser Phe Ala
        355                 360                 365

Ser Arg Asn Gly Asp Ser Thr Arg Ala Asn Thr Tyr Thr Asn Thr Ala
    370                 375                 380

Ala Ser Ile Lys Thr Lys Ile Asp Ser Phe Trp Asn Ser Asn Gly Gln
385                 390                 395                 400

Tyr Val Ser Val Ser Gln Ser Val Thr Gly Gly Val Ser Lys Ala Gly
                405                 410                 415

Tyr Asp Ala Ser Val Leu Ile Ala Ser Asn Leu Gly Ser Leu Gln Asp
            420                 425                 430

Gly Phe Tyr Thr Pro Gly Ser Asp Lys Met Leu Ala Thr Ala Val Ala
        435                 440                 445

Ile Glu Ser Lys Phe Ala Ser Leu Tyr Ser Ile Asn Gln Asn Leu Asn
    450                 455                 460

Gly Tyr Leu Gly Asn Ala Ile Gly Arg Tyr Pro Glu Asp Thr Tyr Asn
465                 470                 475                 480

Gly Asn Gly Asn Ser Gln Gly Asn Pro Trp Phe Ile Cys Thr Asn Ala
                485                 490                 495

Phe Ala Glu Leu Tyr Tyr Arg Ala Ile Lys Glu Trp Phe Asn Asn Gly
            500                 505                 510

Gly Val Thr Val Thr Ser Ile Ser Leu Asn Phe Phe Lys Lys Phe Asp
        515                 520                 525
```

```
Ser Ser Ala Ala Val Gly Thr Lys Tyr Thr Val Gly Thr Ser Ala Phe
    530                 535                 540

Asn Ser Leu Val Gln Asn Val Ala Val Ala Ala Asp Ala Phe Phe Ser
545                 550                 555                 560

Thr Ile Lys Phe His Ala Ala Thr Asn Gly Ser Met Ser Glu Gln Tyr
                565                 570                 575

Gly Arg Thr Asp Gly Leu Met Thr Gly Ala Arg Asp Leu Thr Trp Ser
            580                 585                 590

His Ala Ser Leu Ile Ser Ala Ser Tyr Ala Lys Ala Gly Ser Pro Ala
        595                 600                 605

Ala


<210> SEQ ID NO 102
<211> LENGTH: 605
<212> TYPE: PRT
<213> ORGANISM: Rhizopus microsporus

<400> SEQUENCE: 102

Met Lys Leu Met Asn Pro Ser Ile Lys Ala Cys Val Phe Phe Ile Leu
1               5                   10                  15

Ser Tyr Leu Ser Leu Leu Val Ser Ser Ala Ala Val Pro Thr Ser Ala
            20                  25                  30

Ala Val Gln Val Glu Ser Tyr Lys Tyr Asp Gly Thr Thr Phe Ser Gly
        35                  40                  45

Arg Ile Phe Val Lys Asn Ile Ala Tyr Ser Lys Val Val Thr Val Ile
    50                  55                  60

Tyr Ser Asp Gly Ser Asp Asn Trp Asn Asn Asn Asn Asn Lys Ile Ser
65                  70                  75                  80

Ala Ala Tyr Ser Glu Ala Ile Ser Gly Ser Asn Tyr Glu Tyr Trp Thr
                85                  90                  95

Phe Ser Ala Lys Val Ser Gly Ile Lys Gln Phe Tyr Val Lys Tyr Glu
            100                 105                 110

Val Ser Gly Ser Thr Tyr Tyr Asp Asn Asn Gly Thr Lys Asn Tyr Gln
        115                 120                 125

Val Gln Ala Thr Ser Ala Thr Ser Thr Thr Ala Thr Ala Thr Thr Thr
    130                 135                 140

Thr Thr Thr Ser Thr Pro Ala Thr Ser Thr Gly Pro Ala Asn Asn Ala
145                 150                 155                 160

Pro Val Ser Phe Pro Thr Gly Asn Ser Thr Ile Ser Ser Trp Ile Lys
                165                 170                 175

Lys Gln Glu Glu Ile Ser Arg Phe Ala Met Leu Arg Asn Ile Asn Pro
            180                 185                 190

Pro Gly Ser Ala Thr Gly Phe Ile Ala Ala Ser Leu Ser Thr Ala Gly
        195                 200                 205

Pro Asp Tyr Tyr Tyr Ser Trp Thr Arg Asp Ser Ala Leu Thr Ala Asn
    210                 215                 220

Val Ile Ala Tyr Glu Tyr Asn Thr Thr Phe Thr Gly Asn Thr Thr Leu
225                 230                 235                 240

Leu Lys Tyr Leu Lys Asp Tyr Val Thr Phe Ser Val Lys Ser Gln Ser
                245                 250                 255

Val Ser Thr Val Cys Asn Cys Leu Gly Glu Pro Lys Phe Asn Ala Asp
            260                 265                 270

Gly Ser Ser Tyr Thr Gly Pro Trp Gly Arg Pro Gln Asn Asp Gly Pro
        275                 280                 285
```

Ala Glu Arg Ala Val Thr Phe Met Leu Ile Ala Asp Ser Tyr Leu Thr
290 295 300

Gln Thr Lys Asp Ala Ser Tyr Val Thr Gly Thr Leu Lys Pro Ala Ile
305 310 315 320

Phe Lys Asp Leu Asp Tyr Val Val Ser Val Trp Ser Asn Gly Cys Tyr
325 330 335

Asp Leu Trp Glu Glu Val Asn Gly Val His Phe Tyr Thr Leu Met Val
340 345 350

Met Arg Lys Gly Leu Ile Leu Gly Ala Asp Phe Ala Ala Arg Asn Gly
355 360 365

Asp Ser Ser Arg Ala Ser Thr Tyr Lys Lys Thr Ala Ser Thr Met Glu
370 375 380

Ser Lys Ile Ser Ser Phe Trp Ser Asp Ser Asn Asn Tyr Ile Gln Val
385 390 395 400

Ser Gln Ser Val Thr Ala Gly Val Ser Lys Lys Gly Leu Asp Val Ser
405 410 415

Thr Leu Leu Ala Ala Asn Ile Gly Ser Leu Pro Asp Gly Phe Phe Thr
420 425 430

Pro Gly Ser Glu Lys Ile Leu Ala Thr Ala Val Ala Leu Glu Asn Ala
435 440 445

Phe Ala Ser Leu Tyr Pro Ile Asn Ser Asn Leu Pro Ser Tyr Leu Gly
450 455 460

Asn Ser Ile Gly Arg Tyr Pro Glu Asp Thr Tyr Asn Gly Asn Gly Asn
465 470 475 480

Ser Gln Gly Asn Pro Trp Phe Leu Ala Val Asn Ala Tyr Ala Glu Leu
485 490 495

Tyr Tyr Arg Ala Ile Ser Glu Trp Ile Ser Asn Gly Lys Val Thr Val
500 505 510

Ser Asn Ile Ser Leu Pro Phe Phe Lys Lys Phe Asp Pro Ser Ala Thr
515 520 525

Ser Gly Lys Thr Tyr Thr Ala Gly Thr Ser Asp Phe Asp Asn Leu Ala
530 535 540

Gln Asn Ile Ala Leu Gly Ala Asp Arg Phe Leu Ser Thr Val Lys Phe
545 550 555 560

His Ala Tyr Thr Asn Gly Ser Leu Ser Glu Glu Tyr Asp Arg Ser Thr
565 570 575

Gly Met Ser Thr Gly Ala Arg Asp Leu Thr Trp Ser His Ala Ser Leu
580 585 590

Ile Thr Ala Ala Tyr Ala Lys Ala Gly Ser Pro Ala Ala
595 600 605

<210> SEQ ID NO 103
<211> LENGTH: 605
<212> TYPE: PRT
<213> ORGANISM: Rhizopus azygosporus

<400> SEQUENCE: 103

Met Lys Leu Met Asn Pro Ser Met Lys Ala Cys Val Phe Phe Ile Leu
1 5 10 15

Ser Tyr Phe Ser Leu Leu Val Ser Ser Ala Ala Val Pro Thr Ser Ala
20 25 30

Ala Val Gln Val Glu Ser Tyr Asn Tyr Asp Gly Thr Thr Phe Ser Gly
35 40 45

Arg Ile Phe Val Lys Asn Ile Ala Tyr Ser Lys Val Val Thr Val Ile
50 55 60

```
His Ser Asp Gly Ser Asp Asn Trp Asn Asn Asn Asn Asn Lys Val Ser
65                  70                  75                  80

Ala Ala Tyr Ser Glu Ala Ile Ser Gly Ser Asn Tyr Glu Tyr Trp Thr
                85                  90                  95

Phe Ser Ala Lys Leu Ser Gly Ile Lys Gln Phe Tyr Val Lys Tyr Glu
            100                 105                 110

Val Ser Gly Ser Thr Tyr Tyr Asp Asn Asn Gly Thr Lys Asn Tyr Gln
        115                 120                 125

Val Gln Ala Thr Ser Ala Thr Ser Thr Thr Ala Thr Ala Thr Thr Thr
    130                 135                 140

Thr Ala Thr Gly Thr Thr Thr Thr Ser Thr Gly Pro Thr Ser Thr Ala
145                 150                 155                 160

Ser Val Ser Phe Pro Thr Gly Asn Ser Thr Ile Ser Ser Trp Ile Lys
                165                 170                 175

Asn Gln Glu Glu Ile Ser Arg Phe Ala Met Leu Arg Asn Ile Asn Pro
            180                 185                 190

Pro Gly Ser Ala Thr Gly Phe Ile Ala Ala Ser Leu Ser Thr Ala Gly
        195                 200                 205

Pro Asp Tyr Tyr Tyr Ser Trp Thr Arg Asp Ser Ala Leu Thr Ala Asn
    210                 215                 220

Val Ile Ala Tyr Glu Tyr Asn Thr Thr Phe Thr Gly Asn Thr Thr Leu
225                 230                 235                 240

Leu Lys Tyr Leu Lys Asp Tyr Val Thr Phe Ser Val Lys Ser Gln Ser
                245                 250                 255

Val Ser Thr Val Cys Asn Cys Leu Gly Glu Pro Lys Phe Asn Ala Asp
            260                 265                 270

Gly Ser Ser Phe Thr Gly Pro Trp Gly Arg Pro Gln Asn Asp Gly Pro
        275                 280                 285

Ala Glu Arg Ala Val Thr Phe Met Leu Ile Ala Asp Ser Tyr Leu Thr
    290                 295                 300

Gln Thr Lys Asp Ala Ser Tyr Val Thr Gly Thr Leu Lys Pro Ala Ile
305                 310                 315                 320

Phe Lys Asp Leu Asp Tyr Val Val Ser Val Trp Ser Asn Gly Cys Tyr
                325                 330                 335

Asp Leu Trp Glu Glu Val Asn Gly Val His Phe Tyr Thr Leu Met Val
            340                 345                 350

Met Arg Lys Gly Leu Ile Leu Gly Ala Asp Phe Ala Ala Arg Asn Gly
        355                 360                 365

Asp Ser Ser Arg Ala Ser Thr Tyr Lys Lys Thr Ala Ser Thr Met Glu
    370                 375                 380

Ser Lys Ile Ser Ser Phe Trp Ser Asp Ser Asn Asn Tyr Ile Gln Val
385                 390                 395                 400

Ser Gln Ser Val Thr Ala Gly Val Ser Lys Lys Gly Leu Asp Val Ser
                405                 410                 415

Thr Leu Leu Ala Ala Asn Ile Gly Ser Leu Pro Asp Gly Phe Phe Thr
            420                 425                 430

Pro Gly Ser Glu Lys Ile Leu Ala Thr Ala Val Ala Leu Glu Asn Ala
        435                 440                 445

Phe Ala Ser Leu Tyr Pro Ile Asn Ser Asn Leu Pro Ser Tyr Leu Gly
    450                 455                 460

Asn Ser Ile Gly Arg Tyr Pro Glu Asp Thr Tyr Asn Gly Asn Gly Asn
465                 470                 475                 480
```

```
Ser Gln Gly Asn Pro Trp Phe Leu Ala Val Asn Ala Tyr Ala Glu Leu
                485                 490                 495

Tyr Tyr Arg Ala Ile Lys Glu Trp Ile Ser Asn Gly Lys Val Thr Val
            500                 505                 510

Ser Asn Ile Ser Leu Pro Phe Phe Lys Lys Phe Asp Ser Ser Ala Thr
        515                 520                 525

Ser Gly Lys Thr Tyr Thr Ala Gly Thr Ser Asp Phe Asn Asn Leu Ala
    530                 535                 540

Gln Asn Ile Ala Leu Gly Ala Asp Arg Phe Leu Ser Thr Val Lys Phe
545                 550                 555                 560

His Ala Tyr Thr Asn Gly Ser Leu Ser Glu Glu Tyr Asp Arg Ser Thr
                565                 570                 575

Gly Met Ser Thr Gly Ala Arg Asp Leu Thr Trp Ser His Ala Ser Leu
            580                 585                 590

Ile Thr Ala Ala Tyr Ala Lys Ala Gly Ser Pro Ala Ala
        595                 600                 605


<210> SEQ ID NO 104
<211> LENGTH: 468
<212> TYPE: PRT
<213> ORGANISM: Saksenaea vasiformis

<400> SEQUENCE: 104

Met Pro Ser Trp Lys Thr Leu Phe Leu Leu Leu Gly Pro Ile Ala Thr
1               5                   10                  15

Ala Ala Ala Ala Pro Val Asp Lys Gln Ser Leu Pro Thr Gly Asn Ser
            20                  25                  30

Thr Ile Ser Ser Trp Val Ser Lys Gln Glu Asp Ile Ser Phe Ser Glu
        35                  40                  45

Met Leu Arg Asn Val Asn Pro Glu Gly Thr Ala Lys Gly Phe Val Ala
    50                  55                  60

Ala Ser Leu Ser Thr Ala Gly Pro Asp Tyr Phe Tyr Thr Trp Thr Arg
65                  70                  75                  80

Asp Ala Ala Leu Val Ser Arg Val Ile Ala Tyr Lys Tyr Asn Thr Thr
                85                  90                  95

Asn Ala Gly Asp Ser Lys Ile His Gly Val Leu Asp Asp Tyr Val Asn
            100                 105                 110

Phe Gln Ile Asn Thr Gln Ser Glu Pro Thr Pro Cys Asn Cys Leu Gly
        115                 120                 125

Glu Pro Lys Phe Asn Pro Asp Gly Ser Ser Phe Thr Gly Pro Trp Gly
    130                 135                 140

Arg Pro Gln Asn Asp Gly Pro Ala Glu Arg Ala Ser Ser Phe Met Leu
145                 150                 155                 160

Ile Ala Asp Ser Phe Leu Ser Gln Thr Lys Asn Ala Ser Tyr Phe Thr
                165                 170                 175

Asn Thr Leu Lys Pro Ala Ile Tyr Lys Asp Leu Asp Tyr Val Val Asp
            180                 185                 190

Thr Trp Ser Asn Pro Cys Phe Asp Leu Trp Glu Glu Val Asn Gly Ile
        195                 200                 205

His Phe Tyr Thr Leu Met Val Met Arg Arg Ser Leu Leu Asp Gly Ala
    210                 215                 220

Asn Phe Ala Thr Arg Asn Gly Asp Asn Ser Lys Ala Ser Thr Tyr Ser
225                 230                 235                 240

Gly Val Ala Ala Lys Ile Gln Ala Arg Leu Asn Ser Phe Trp Asp Ala
                245                 250                 255
```

```
Gly Lys Asn Tyr Ile Thr Val Thr Gln Asp Tyr Lys Asn Gly Val Glu
            260                 265                 270

Lys Pro Ser Gly Leu Asp Val Ser Thr Leu Ile Ala Ala Asn Val Ala
        275                 280                 285

Gly Met Gly Asp Gly Phe Tyr Thr Pro Gly Ser Glu Arg Ile Leu Ala
    290                 295                 300

Thr Ala Leu Ala Phe Glu Lys Ser Met Ala Ser Leu Tyr Pro Leu Asn
305                 310                 315                 320

Asn Asn Leu Pro Ser His Leu Gly Asn Ala Ile Gly Arg Tyr Pro Glu
                325                 330                 335

Asp Thr Tyr Asn Gly Asn Gly Asn Ser Gln Gly Asn Pro Trp Phe Leu
            340                 345                 350

Ala Thr Thr Ala Phe Thr Glu Leu Tyr Tyr Arg Ala Ile Leu Glu Trp
        355                 360                 365

Lys Asn Thr Gly Val Thr Val Thr Pro Ile Ser Lys Asp Phe Phe Val
    370                 375                 380

Arg Phe Asp Ser Ser Ala Ala Pro Gly Lys Lys Tyr Asn Pro Gly Ser
385                 390                 395                 400

Gln Glu Phe Ala Thr Leu Thr Gln Ser Ile Ala Ala Ala Ala Asp Arg
                405                 410                 415

Phe Met Ser Thr Val Gln Tyr His Gln Asn Pro Asn Gly Ser Leu Ser
            420                 425                 430

Glu Glu Phe Asp Arg Ser Ser Gly Tyr Met Thr Gly Ala Arg Asp Leu
        435                 440                 445

Thr Trp Ser His Ala Ala Phe Ile Thr Ala Ala Gln Ala Arg Ala Gly
    450                 455                 460

Ser Pro Ser Phe
465
```

<210> SEQ ID NO 105
<211> LENGTH: 640
<212> TYPE: PRT
<213> ORGANISM: Aspergillus niger

<400> SEQUENCE: 105

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
```

```
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575
```

```
Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640


<210> SEQ ID NO 106
<211> LENGTH: 631
<212> TYPE: PRT
<213> ORGANISM: Aspergillus fumigatus

<400> SEQUENCE: 106

Met Pro Arg Leu Ser Tyr Ala Leu Cys Ala Leu Ser Leu Gly His Ala
1               5                   10                  15

Ala Ile Ala Ala Pro Gln Leu Ser Ala Arg Ala Thr Gly Ser Leu Asp
            20                  25                  30

Ser Trp Leu Gly Thr Glu Thr Thr Val Ala Leu Asn Gly Ile Leu Ala
        35                  40                  45

Asn Ile Gly Ala Asp Gly Ala Tyr Ala Lys Ser Ala Lys Pro Gly Ile
    50                  55                  60

Ile Ile Ala Ser Pro Ser Thr Ser Glu Pro Asp Tyr Tyr Tyr Thr Trp
65                  70                  75                  80

Thr Arg Asp Ala Ala Leu Val Thr Lys Val Leu Val Asp Leu Phe Arg
                85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Asn Pro Ser Gly Gly Leu Ala Ser
        115                 120                 125

Gly Gly Leu Ala Glu Pro Lys Tyr Asn Val Asp Met Thr Ala Phe Thr
    130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
        195                 200                 205

Asn Ser Met Ser Phe Phe Thr Val Ala Val Gln His Arg Ala Leu Val
    210                 215                 220

Glu Gly Ser Thr Phe Ala Lys Arg Val Gly Ala Ser Cys Ser Trp Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ala Asn Thr Val Leu Ala Ser Ile His Thr Phe Asp Pro Glu Ala Gly
        275                 280                 285

Cys Asp Asp Thr Thr Phe Gln Pro Cys Ser Pro Arg Ala Leu Ala Asn
    290                 295                 300

His Lys Val Tyr Thr Asp Ser Phe Arg Ser Val Tyr Ala Ile Asn Ser
```

305 310 315 320

Gly Ile Pro Gln Gly Ala Ala Val Ser Ala Gly Arg Tyr Pro Glu Asp
325 330 335

Val Tyr Tyr Asn Gly Asn Pro Trp Phe Leu Thr Thr Leu Ala Ala Ala
340 345 350

Glu Gln Leu Tyr Asp Ala Ile Tyr Gln Trp Lys Lys Ile Gly Ser Ile
355 360 365

Ser Ile Thr Ser Thr Ser Leu Ala Phe Phe Lys Asp Ile Tyr Ser Ser
370 375 380

Ala Ala Val Gly Thr Tyr Ala Ser Ser Thr Ser Thr Phe Thr Asp Ile
385 390 395 400

Ile Asn Ala Val Lys Thr Tyr Ala Asp Gly Tyr Val Ser Ile Val Gln
405 410 415

Ala His Ala Met Asn Asn Gly Ser Leu Ser Glu Gln Phe Asp Lys Ser
420 425 430

Ser Gly Leu Ser Leu Ser Ala Arg Asp Leu Thr Trp Ser Tyr Ala Ala
435 440 445

Phe Leu Thr Ala Asn Met Arg Arg Asn Gly Val Val Pro Ala Pro Trp
450 455 460

Gly Ala Ala Ser Ala Asn Ser Val Pro Ser Ser Cys Ser Met Gly Ser
465 470 475 480

Ala Thr Gly Thr Tyr Ser Thr Ala Thr Ala Thr Ser Trp Pro Ser Thr
485 490 495

Leu Thr Ser Gly Ser Pro Gly Ser Thr Thr Thr Val Gly Thr Thr Thr
500 505 510

Ser Thr Thr Ser Gly Thr Ala Ala Glu Thr Ala Cys Ala Thr Pro Thr
515 520 525

Ala Val Ala Val Thr Phe Asn Glu Ile Ala Thr Thr Thr Tyr Gly Glu
530 535 540

Asn Val Tyr Ile Val Gly Ser Ile Ser Glu Leu Gly Asn Trp Asp Thr
545 550 555 560

Ser Lys Ala Val Ala Leu Ser Ala Ser Lys Tyr Thr Ser Ser Asn Asn
565 570 575

Leu Trp Tyr Val Ser Val Thr Leu Pro Ala Gly Thr Thr Phe Glu Tyr
580 585 590

Lys Tyr Ile Arg Lys Glu Ser Asp Gly Ser Ile Val Trp Glu Ser Asp
595 600 605

Pro Asn Arg Ser Tyr Thr Val Pro Ala Ala Cys Gly Val Ser Thr Ala
610 615 620

Thr Glu Asn Asp Thr Trp Gln
625 630

<210> SEQ ID NO 107
<211> LENGTH: 567
<212> TYPE: PRT
<213> ORGANISM: Fibroporia radiculosa

<400> SEQUENCE: 107

Met Leu Phe Leu Leu Ala Ala Leu Gly Leu Ala Cys Ser Ala Ala Ala
1 5 10 15

Gln Ser Thr Ser Val Ser Ala Tyr Ile Ala Ser Glu Ser Pro Val Ala
20 25 30

Lys Ala Gly Val Leu Ala Asn Ile Gly Thr Glu Gly Ser Leu Ser Ser
35 40 45

```
Gly Ala Tyr Ser Gly Val Val Ile Ala Ser Pro Ser Thr Val Asn Pro
    50                  55                  60

Asp Tyr Leu Tyr Thr Trp Val Arg Asp Ser Ser Leu Thr Phe Gln Ala
65                  70                  75                  80

Leu Ile Asp Gln Tyr Val Tyr Gly Glu Asp Pro Thr Leu Arg Ser Leu
                85                  90                  95

Ile Asp Glu Phe Ile Thr Ala Glu Ser Ile Leu Gln Gln Thr Thr Asn
            100                 105                 110

Pro Ser Gly Thr Val Ser Thr Gly Gly Leu Gly Glu Pro Lys Phe Asn
        115                 120                 125

Ile Asn Glu Thr Ala Phe Thr Gly Pro Trp Gly Arg Pro Gln Arg Asp
    130                 135                 140

Gly Pro Ala Leu Arg Ser Thr Ala Ile Ile Thr Tyr Ala Thr Tyr Leu
145                 150                 155                 160

Trp Asn Ser Gly Asn Thr Ser Tyr Val Ser Asp Ser Leu Trp Pro Ile
                165                 170                 175

Ile Glu Leu Asp Leu Asn Tyr Ile Ala Thr Tyr Trp Asn Phe Ser Thr
            180                 185                 190

Phe Asp Leu Trp Glu Glu Ile Asp Ser Ser Ser Phe Trp Thr Thr Ala
        195                 200                 205

Val Gln His Arg Ala Leu Arg Gln Gly Ile Thr Phe Ala Asn Leu Ile
    210                 215                 220

Gly Gln Thr Ser Pro Val Ser Asn Tyr Glu Thr Gln Ala Gly Asp Ile
225                 230                 235                 240

Leu Cys Phe Leu Gln Thr Tyr Trp Asn Pro Thr Gly Asn Tyr Met Thr
                245                 250                 255

Ala Asn Thr Gly Gly Gly Arg Ser Gly Lys Asp Ser Asn Thr Val Leu
            260                 265                 270

Ala Ser Val His Thr Phe Asp Pro Asp Ala Gly Cys Asp Ser Thr Thr
        275                 280                 285

Phe Gln Pro Cys Ser Asp Lys Ala Leu Ser Asn Leu Lys Val Tyr Val
    290                 295                 300

Asp Ser Phe Arg Ser Leu Tyr Ala Ile Asn Asp Gly Ile Ala Ser Asp
305                 310                 315                 320

Ala Ala Val Ala Thr Gly Arg Tyr Pro Glu Asp Val Tyr Tyr Gly Gly
                325                 330                 335

Asn Pro Trp Tyr Leu Cys Thr Phe Ala Val Ala Glu Gln Leu Tyr Asp
            340                 345                 350

Ala Leu Ile Val Trp Ser Ser Gln Gly Tyr Leu Glu Ile Thr Asp Leu
        355                 360                 365

Ser Leu Ala Phe Phe Gln Gln Phe Asp Ser Asp Val Gly Thr Gly Thr
    370                 375                 380

Tyr Asp Ser Gly Ser Ser Thr Tyr Ser Thr Leu Thr Ser Ala Ile Arg
385                 390                 395                 400

Thr Phe Ala Asp Gly Phe Val Leu Thr Asn Ala Lys Tyr Thr Pro Thr
                405                 410                 415

Asn Gly Ser Leu Ser Glu Glu Tyr Thr Ser Ala Asp Gly Thr Pro Ile
            420                 425                 430

Ser Ala Tyr Asp Leu Thr Trp Ser Tyr Ala Ser Ala Leu Thr Val Phe
        435                 440                 445

Ala Ala Glu Ala Gly Thr Thr Tyr Gly Ser Trp Gly Ala Ala Gly Leu
    450                 455                 460

Thr Val Pro Ser Thr Cys Thr Ser Gly Val Ala Val Thr Phe Glu Val
```

465 470 475 480

Asp Tyr Asp Thr Glu Tyr Gly Glu Asn Val Tyr Ile Thr Gly Ser Val
485 490 495

Asn Ala Leu Glu Asn Trp Ser Ala Thr Asn Ala Leu Ile Met Ser Ala
500 505 510

Ala Asp Tyr Pro Thr Trp Ser Ile Thr Val Tyr Leu Pro Pro Ser Thr
515 520 525

Thr Ile Gln Tyr Lys Tyr Leu Thr Gln Tyr Asn Gly Glu Val Thr Trp
530 535 540

Glu Asp Asp Pro Asn Asn Glu Ile Thr Thr Pro Ala Ser Gly Ser Met
545 550 555 560

Thr Gln Val Asp Ser Trp His
565

<210> SEQ ID NO 108
<211> LENGTH: 582
<212> TYPE: PRT
<213> ORGANISM: Fusarium verticillioides

<400> SEQUENCE: 108

Met Phe Thr Gln Ile Leu Tyr Gly Leu Thr Ala Leu Ser Ala Leu Gln
1 5 10 15

Gly Gln Val Thr Ala Ser Pro Gly Gly Ser Ser Leu Asp Arg Phe Ile
20 25 30

Ser Lys Glu Ala Asp Ile Ser Ile Lys Gly Val Leu Ala Asn Ile Gly
35 40 45

Ala Asp Gly Lys Arg Ala Gln Gly Ala Ala Pro Gly Ala Val Val Ala
50 55 60

Ser Pro Ser Arg Thr Asp Pro Asp Tyr Trp Tyr Thr Trp Thr Arg Asp
65 70 75 80

Ser Ala Leu Thr Tyr Lys Val Leu Val Glu Arg Phe Ile His Gly Asp
85 90 95

Lys Ser Leu Gln Arg Lys Ile Asp Glu Tyr Val Ser Ala Gln Ala Lys
100 105 110

Leu Gln Gly Val Thr Asn Pro Ser Gly Gly Pro Glu Ser Gly Gly Leu
115 120 125

Gly Glu Pro Lys Phe His Val Asn Leu Thr Ala Phe Thr Gly Ser Trp
130 135 140

Gly Arg Pro Gln Arg Asp Gly Pro Pro Leu Arg Ala Thr Ala Leu Thr
145 150 155 160

Leu Tyr Ala Asn Trp Leu Val Ser His Gly Asp Arg Ser Lys Ala Val
165 170 175

Asn Lys Val Trp Pro Val Ile Glu Lys Asp Leu Ala Tyr Thr Val Lys
180 185 190

Phe Trp Asn Arg Thr Gly Tyr Asp Leu Trp Glu Glu Val Asn Gly Ser
195 200 205

Ser Phe Phe Thr Leu Ser Ala Ser His Arg Ala Leu Val Glu Gly Ala
210 215 220

Ala Leu Ala Lys Lys Leu Gly Lys Ser Cys Ser Asp Cys Ala Thr Asn
225 230 235 240

Ala Pro Arg Val Leu Cys Phe Met Gln Ser Phe Trp Thr Gly Ser Tyr
245 250 255

Ile Asp Ser Asn Ile Asn Val Asn Asp Gly Arg Lys Gly Leu Asp Ala
260 265 270

```
Asn Ser Ile Leu Ser Ser Ile His Thr Phe Asp Pro Ser Ser Lys Cys
        275                 280                 285

Thr Asp Ser Thr Phe Gln Pro Cys Ser Ser Arg Ala Leu Ala Asn His
    290                 295                 300

Lys Glu Val Val Asp Ser Phe Arg Ser Ile Tyr Gly Val Asn Lys Asn
305                 310                 315                 320

Arg Gly Lys Gly Lys Ala Ala Ala Val Gly Arg Tyr Ser Glu Asp Val
                325                 330                 335

Tyr Tyr Asp Gly Asn Pro Trp Tyr Leu Ala Thr Leu Ala Ala Ala Glu
            340                 345                 350

Gln Leu Tyr Ala Ala Val Tyr Gln Trp Asn Lys Ile Gly Ser Ile Thr
        355                 360                 365

Val Asp Ser Val Ser Leu Pro Phe Phe Ser Asp Leu Val Pro Lys Val
    370                 375                 380

Ser Lys Gly Thr Tyr Arg Lys Asn Ser Lys Thr Tyr Lys Ala Ile Ile
385                 390                 395                 400

Lys Ala Val Thr Ser Tyr Ala Asp Gly Phe Val Ala Val Val Gln Thr
                405                 410                 415

Tyr Thr Pro Lys Asp Gly Ser Leu Ala Glu Gln Phe Asp Lys Ser Thr
            420                 425                 430

Gly Thr Pro Lys Ser Ala Val His Leu Thr Trp Ser Tyr Ala Ser Phe
        435                 440                 445

Val Gly Ala Ala Glu Arg Arg Thr Gly Val Val Pro Pro Ala Trp Gly
    450                 455                 460

Glu Ser Asn Ala Asn Lys Val Pro Ala Val Cys Glu Ala Ala Pro Ala
465                 470                 475                 480

Cys Asp Thr Thr Ile Thr Phe Asn Val Lys Asn Val Asp Val Thr Ser
                485                 490                 495

Asp Gln Lys Val Tyr Ile Val Gly Gly Ile Thr Gln Leu Ser Asn Trp
            500                 505                 510

Ala Pro Ala Asp Gly Ile Ala Leu Glu Glu Ser Thr Ser Thr Lys Gly
        515                 520                 525

Leu Trp Thr Val Lys Val Lys Ile Pro Ser Asp Thr Ser Phe Glu Tyr
    530                 535                 540

Lys Tyr Ile Lys Lys Thr Ser Asp Gly Thr Val Thr Trp Glu Ser Asp
545                 550                 555                 560

Pro Asn Asn Ser Ala Ala Thr Gly Ser Lys Cys Gly Ser Ser Ser Thr
                565                 570                 575

Ile Asn Asp Glu Trp Arg
            580
```

<210> SEQ ID NO 109
<211> LENGTH: 576
<212> TYPE: PRT
<213> ORGANISM: Gloeophyllum trabeum

<400> SEQUENCE: 109

```
Met Tyr Arg Phe Leu Val Cys Ala Leu Gly Leu Leu Gly Thr Val Leu
1               5                   10                  15

Ala Gln Ser Val Asp Ser Tyr Val Gly Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ala Ala Gly Val Val Val Ala Ser Pro Ser Lys Ser Asp Pro Asp
    50                  55                  60
```

```
Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Ser
                85                  90                  95

Leu Ile Asp Ser Phe Val Ile Ala Glu Ala Asn Ile Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ala Thr Ala Leu Ile Thr Tyr Gly Asn Trp
145                 150                 155                 160

Leu Leu Ser Asn Gly Asn Thr Thr Trp Val Thr Ser Thr Leu Trp Pro
                165                 170                 175

Ile Ile Gln Asn Asp Leu Asn Tyr Val Val Gln Tyr Trp Asn Gln Thr
            180                 185                 190

Thr Phe Asp Leu Trp Glu Glu Val Asn Ser Ser Ser Phe Phe Thr Thr
        195                 200                 205

Ala Val Gln His Arg Ala Leu Arg Glu Gly Ala Ala Phe Ala Thr Lys
    210                 215                 220

Ile Gly Gln Thr Ser Ser Val Ser Ser Tyr Thr Thr Gln Ala Ala Asn
225                 230                 235                 240

Leu Leu Cys Phe Leu Gln Ser Tyr Trp Asn Pro Thr Ser Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Thr
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Ile Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Ala Ala Gln Gly Ser Leu Asn Val Thr Ser
        355                 360                 365

Ile Ser Leu Pro Phe Phe Gln Gln Phe Ser Ser Ser Val Thr Ala Gly
    370                 375                 380

Thr Tyr Ala Ser Ser Ser Thr Thr Tyr Thr Thr Leu Thr Ser Ala Ile
385                 390                 395                 400

Lys Ser Phe Ala Asp Gly Phe Val Ala Ile Asn Ala Gln Tyr Thr Pro
                405                 410                 415

Ser Asn Gly Gly Leu Ala Glu Gln Phe Ser Arg Ser Asn Gly Ala Pro
            420                 425                 430

Val Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Val Gly
    450                 455                 460

Leu Thr Val Pro Thr Ser Cys Ser Ser Asn Ser Gly Gly Gly Gly Gly
465                 470                 475                 480
```

```
Ser Thr Val Ala Val Thr Phe Asn Val Asn Ala Gln Thr Val Trp Gly
                485                 490                 495

Glu Asn Ile Tyr Ile Thr Gly Ser Val Asp Ala Leu Ser Asn Trp Ser
            500                 505                 510

Pro Asp Asn Ala Leu Leu Leu Ser Ser Ala Asn Tyr Pro Thr Trp Ser
        515                 520                 525

Ile Thr Val Asn Leu Pro Ala Ser Thr Ala Ile Gln Tyr Lys Tyr Ile
    530                 535                 540

Arg Lys Asn Asn Gly Ala Val Thr Trp Glu Ser Asp Pro Asn Asn Ser
545                 550                 555                 560

Ile Thr Thr Pro Ala Ser Gly Ser Val Thr Glu Asn Asp Thr Trp Arg
                565                 570                 575


<210> SEQ ID NO 110
<211> LENGTH: 616
<212> TYPE: PRT
<213> ORGANISM: Penicillium oxalicum

<400> SEQUENCE: 110

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
        275                 280                 285
```

Ile His Thr Phe Asp Pro Glu Ala Ala Cys Asp Asp Ala Thr Phe Gln
    290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
        515                 520                 525

Asn Val Phe Met Ser Gly Asn Ile Thr Ala Leu Gly Asn Trp Asp Ala
    530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
    610                 615

<210> SEQ ID NO 111
<211> LENGTH: 632
<212> TYPE: PRT
<213> ORGANISM: Trichoderma reesei

<400> SEQUENCE: 111

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn

```
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
        435                 440                 445

Ala Leu His Leu Thr Trp Ser Tyr Ala Ser Phe Leu Thr Ala Thr Ala
    450                 455                 460
```

Arg Arg Ala Gly Ile Val Pro Pro Ser Trp Ala Asn Ser Ser Ala Ser
465 470 475 480

Thr Ile Pro Ser Thr Cys Ser Gly Ala Ser Val Val Gly Ser Tyr Ser
485 490 495

Arg Pro Thr Ala Thr Ser Phe Pro Pro Ser Gln Thr Pro Lys Pro Gly
500 505 510

Val Pro Ser Gly Thr Pro Tyr Thr Pro Leu Pro Cys Ala Thr Pro Thr
515 520 525

Ser Val Ala Val Thr Phe His Glu Leu Val Ser Thr Gln Phe Gly Gln
530 535 540

Thr Val Lys Val Ala Gly Asn Ala Ala Ala Leu Gly Asn Trp Ser Thr
545 550 555 560

Ser Ala Ala Val Ala Leu Asp Ala Val Asn Tyr Ala Asp Asn His Pro
565 570 575

Leu Trp Ile Gly Thr Val Asn Leu Glu Ala Gly Asp Val Val Glu Tyr
580 585 590

Lys Tyr Ile Asn Val Gly Gln Asp Gly Ser Val Thr Trp Glu Ser Asp
595 600 605

Pro Asn His Thr Tyr Thr Val Pro Ala Val Ala Cys Val Thr Gln Val
610 615 620

Val Lys Glu Asp Thr Trp Gln Ser
625 630

<210> SEQ ID NO 112
<211> LENGTH: 569
<212> TYPE: PRT
<213> ORGANISM: Wolfiporia cocos

<400> SEQUENCE: 112

Met Arg Leu Ser Leu Ala Ser Val Phe Ala Leu Ala Gly Gly Ala Leu
1 5 10 15

Ala Gln Thr Thr Ser Val Thr Ser Tyr Ile Ala Ser Glu Ser Pro Ile
20 25 30

Ala Lys Ala Gly Val Leu Ala Asn Ile Gly Ala Asp Gly Ser Leu Ser
35 40 45

Ser Gly Ala Tyr Ser Gly Ile Val Ile Ala Ser Pro Ser Thr Val Asn
50 55 60

Pro Asn Tyr Leu Tyr Thr Trp Thr Arg Asp Ser Ser Leu Thr Phe Met
65 70 75 80

Glu Leu Ile Asn Gln Tyr Ile Tyr Gly Glu Asp Asp Thr Leu Arg Thr
85 90 95

Leu Ile Asp Glu Phe Val Ser Ala Glu Ala Thr Leu Gln Gln Val Thr
100 105 110

Asn Pro Ser Gly Thr Val Ser Thr Gly Gly Leu Gly Glu Pro Lys Phe
115 120 125

Asn Ile Asn Glu Thr Ala Phe Thr Gly Pro Trp Gly Arg Pro Gln Arg
130 135 140

Asp Gly Pro Ala Leu Arg Ala Thr Ala Ile Met Ala Tyr Ala Thr Tyr
145 150 155 160

Leu Tyr Glu Asn Gly Asn Thr Ser Tyr Val Thr Asp Thr Leu Trp Pro
165 170 175

Ile Ile Glu Leu Asp Leu Gly Tyr Val Ala Glu Tyr Trp Asn Glu Ser
180 185 190

Thr Phe Asp Leu Trp Glu Glu Ile Asp Ser Ser Ser Phe Phe Thr Thr

```
        195                 200                 205

Ala Val Gln His Arg Ala Leu Arg Ala Gly Val Thr Phe Ala Asn Leu
    210                 215                 220

Ile Gly Glu Thr Ser Asp Val Ser Asn Tyr Gln Glu Asn Ala Asp Asp
225                 230                 235                 240

Leu Leu Cys Phe Leu Gln Ser Tyr Trp Asn Pro Thr Gly Ser Tyr Val
                245                 250                 255

Thr Ala Asn Thr Gly Gly Gly Arg Ser Gly Lys Asp Ala Asn Thr Leu
            260                 265                 270

Leu Ala Ser Ile His Thr Phe Asp Pro Asp Ala Gly Cys Asn Ala Thr
        275                 280                 285

Thr Phe Gln Pro Cys Ser Asp Lys Ala Leu Ser Asn His Lys Val Tyr
    290                 295                 300

Val Asp Ser Phe Arg Ser Leu Tyr Ala Ile Asn Asp Asp Ile Ser Ser
305                 310                 315                 320

Asp Ala Ala Val Ala Thr Gly Arg Tyr Pro Glu Asp Val Tyr Tyr Asn
                325                 330                 335

Gly Asn Pro Trp Tyr Leu Cys Thr Leu Ala Ala Ala Glu Gln Leu Tyr
            340                 345                 350

Asp Ser Leu Ile Val Trp Lys Ala Gln Gly Tyr Ile Glu Val Thr Ser
        355                 360                 365

Leu Ser Leu Ala Phe Phe Gln Gln Phe Asp Ala Ser Val Ser Ala Gly
    370                 375                 380

Thr Tyr Asp Ser Ser Ser Asp Thr Tyr Thr Thr Leu Leu Asp Ala Val
385                 390                 395                 400

Gln Thr Tyr Ala Asp Gly Phe Val Leu Met Val Ala Gln Tyr Thr Pro
                405                 410                 415

Ala Asn Gly Ser Leu Ser Glu Gln Tyr Ala Lys Ala Asp Gly Ser Pro
            420                 425                 430

Thr Ser Ala Tyr Asp Leu Thr Trp Ser Phe Ala Ala Ala Leu Thr Ala
        435                 440                 445

Phe Ala Ala Arg Asp Gly Lys Thr Tyr Gly Ser Trp Gly Ala Ala Asp
    450                 455                 460

Leu Ser Ser Thr Cys Ser Gly Ser Thr Asp Thr Val Ala Val Thr Phe
465                 470                 475                 480

Glu Val Gln Tyr Asp Thr Gln Tyr Gly Glu Asn Leu Tyr Ile Thr Gly
                485                 490                 495

Ser Val Ser Gln Leu Glu Asp Trp Ser Ala Asp Asp Ala Leu Ile Met
            500                 505                 510

Ser Ser Ala Asp Tyr Pro Thr Trp Ser Ile Thr Val Asp Leu Pro Pro
        515                 520                 525

Ser Thr Leu Ile Gln Tyr Lys Tyr Leu Thr Lys Tyr Asn Gly Asp Val
    530                 535                 540

Thr Trp Glu Asp Asp Pro Asn Asn Glu Ile Thr Thr Pro Ala Ser Gly
545                 550                 555                 560

Ser Tyr Thr Gln Val Asp Ser Trp His
                565


<210> SEQ ID NO 113
<211> LENGTH: 8
<212> TYPE: PRT
<213> ORGANISM: Mucorales
<220> FEATURE:
<221> NAME/KEY: MISC_FEATURE
<222> LOCATION: (2)..(2)
```

<223> OTHER INFORMATION: N or S
<220> FEATURE:
<221> NAME/KEY: MISC_FEATURE
<222> LOCATION: (3)..(3)
<223> OTHER INFORMATION: T, S, or R
<220> FEATURE:
<221> NAME/KEY: MISC_FEATURE
<222> LOCATION: (5)..(6)
<223> OTHER INFORMATION: Any amino acid
<220> FEATURE:
<221> NAME/KEY: MISC_FEATURE
<222> LOCATION: (7)..(7)
<223> OTHER INFORMATION: G or N
<220> FEATURE:
<221> NAME/KEY: MISC_FEATURE
<222> LOCATION: (8)..(8)
<223> OTHER INFORMATION: D, N, or S

<400> SEQUENCE: 113

Tyr Xaa Xaa Thr Xaa Xaa Xaa Xaa
1               5

<210> SEQ ID NO 114
<211> LENGTH: 8
<212> TYPE: PRT
<213> ORGANISM: Mucorales
<220> FEATURE:
<221> NAME/KEY: MISC_FEATURE
<222> LOCATION: (5)..(5)
<223> OTHER INFORMATION: Any amino acid

<400> SEQUENCE: 114

Tyr Asn Thr Thr Xaa Ala Gly Asp
1               5

<210> SEQ ID NO 115
<211> LENGTH: 9
<212> TYPE: PRT
<213> ORGANISM: Mucorales
<220> FEATURE:
<221> NAME/KEY: MISC_FEATURE
<222> LOCATION: (1)..(1)
<223> OTHER INFORMATION: S or A
<220> FEATURE:
<221> NAME/KEY: MISC_FEATURE
<222> LOCATION: (2)..(2)
<223> OTHER INFORMATION: T, N, or V
<220> FEATURE:
<221> NAME/KEY: MISC_FEATURE
<222> LOCATION: (3)..(4)
<223> OTHER INFORMATION: L or I
<220> FEATURE:
<221> NAME/KEY: MISC_FEATURE
<222> LOCATION: (8)..(8)
<223> OTHER INFORMATION: Any amino acid
<220> FEATURE:
<221> NAME/KEY: MISC_FEATURE
<222> LOCATION: (9)..(9)
<223> OTHER INFORMATION: A or G

<400> SEQUENCE: 115

Xaa Xaa Xaa Xaa Ala Ala Asn Xaa Xaa
1               5

<210> SEQ ID NO 116
<211> LENGTH: 9
<212> TYPE: PRT
<213> ORGANISM: Mucorales
<220> FEATURE:
<221> NAME/KEY: MISC_FEATURE
<222> LOCATION: (8)..(8)
<223> OTHER INFORMATION: Any amino acid

<400> SEQUENCE: 116

Ser Thr Leu Ile Ala Ala Asn Xaa Ala
1               5

<210> SEQ ID NO 117
<211> LENGTH: 7
<212> TYPE: PRT
<213> ORGANISM: Mucorales
<220> FEATURE:
<221> NAME/KEY: MISC_FEATURE
<222> LOCATION: (1)..(1)
<223> OTHER INFORMATION: N or D
<220> FEATURE:
<221> NAME/KEY: MISC_FEATURE
<222> LOCATION: (3)..(3)
<223> OTHER INFORMATION: Any amino acid
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
<223> OTHER INFORMATION: Q, K, or E

<400> SEQUENCE: 117

Xaa Gly Xaa Gly Asn Xaa Xaa
1               5

<210> SEQ ID NO 118
<211> LENGTH: 7
<212> TYPE: PRT
<213> ORGANISM: Mucorales

<400> SEQUENCE: 118

Asn Gly Asn Gly Asn Ser Gln
1               5

<210> SEQ ID NO 119
<211> LENGTH: 468
<212> TYPE: PRT
<213> ORGANISM: Saksenaea oblongispora

<400> SEQUENCE: 119

Met Pro Ser Trp Lys Thr Leu Ile Phe Leu Leu Gly Pro Ile Thr Ala
1               5                   10                  15

Ala Leu Ala Ala Pro Val Asn Lys Gln Ser Phe Pro Thr Gly Asn Pro
            20                  25                  30

Asp Ile Ser Ser Trp Val Ser Lys Gln Glu Gly Ile Ser Phe Ser Glu
        35                  40                  45

Met Leu Arg Asn Val Asn Pro Pro Gly Thr Ala Lys Gly Phe Val Ala
    50                  55                  60

Ala Ser Leu Ser Thr Ala Gly Pro Asp Tyr Phe Tyr Thr Trp Thr Arg
65                  70                  75                  80

Asp Ala Ala Leu Val Ser Arg Val Ile Ala Tyr Lys Tyr Asn Thr Thr
                85                  90                  95

Asn Ala Gly Asp Asn Asn Ile His Gly Ala Leu Gln Asp Tyr Val Thr
            100                 105                 110

Phe Gln Ile Asn Thr Gln Thr Glu Ser Thr Pro Cys Asn Cys Leu Gly
        115                 120                 125

Glu Pro Lys Phe Asn Pro Asp Gly Ser Ser Phe Thr Gly Pro Trp Gly
    130                 135                 140

Arg Pro Gln Asn Asp Gly Pro Ala Glu Arg Ala Ser Ser Met Ile Leu

```
145                 150                 155                 160

Ile Ala Asp Ser Phe Leu Ala Gln Thr Lys Asp Thr Ala Tyr Val Thr
                165                 170                 175

Asn Thr Leu Lys Pro Ala Ile Tyr Lys Asp Leu Asp Tyr Val Val Asn
            180                 185                 190

Thr Trp Ser Asn Pro Cys Phe Asp Leu Trp Glu Glu Val Asn Gly Val
        195                 200                 205

His Phe Tyr Thr Leu Met Val Met Arg Arg Gly Leu Leu Asp Gly Ala
    210                 215                 220

Asp Phe Ala Thr Arg Asn Gly Asp Ala Ser Lys Ala Ser Ser Tyr Ser
225                 230                 235                 240

Asp Ala Ala Ser Lys Ile Lys Thr Arg Leu Asp Ser Phe Trp Val Ser
                245                 250                 255

Asp Lys Asn Tyr Ile Thr Val Thr Gln Asp Tyr Lys Glu Gly Val Lys
            260                 265                 270

Lys Asp Thr Gly Leu Asp Val Ser Thr Leu Ile Ala Ala Asn Val Ala
        275                 280                 285

Gly Lys Asp Asp Gly Phe Tyr Thr Pro Gly Ser Asp Lys Ile Leu Ala
    290                 295                 300

Thr Ala Val Ala Phe Glu Asn Ala Met Ala Lys Leu Tyr Pro Leu Asn
305                 310                 315                 320

Gln Asn Leu Asp Ser His Leu Gly Asn Ser Ile Gly Arg Tyr Pro Glu
                325                 330                 335

Asp Thr Tyr Asn Gly Asn Gly Asn Ser Gln Gly Asn Pro Trp Phe Leu
            340                 345                 350

Ala Thr Thr Ala Phe Thr Glu Leu Tyr Tyr Arg Ala Ile Leu Glu Trp
        355                 360                 365

Lys Asp Ser Gly Val Thr Val Thr Pro Val Ser Lys Asp Phe Phe Ala
    370                 375                 380

Lys Phe Asp Ser Asn Ala Val Ala Gly Lys Lys Tyr Ser Pro Asn Ser
385                 390                 395                 400

Glu Glu Phe Ala Thr Leu Thr Ala Asn Ile Ala Ala Ala Ala Asp Arg
                405                 410                 415

Phe Met Ser Thr Val Lys Tyr His Gln Asn Pro Asn Gly Ser Leu Ser
            420                 425                 430

Glu Gln Phe Asp Arg His Ser Gly Tyr Met Thr Gly Ala Arg Asp Leu
        435                 440                 445

Thr Trp Ser His Ala Ala Phe Ile Thr Ala Ala Gln Ala Arg Ala Gly
    450                 455                 460

Thr Pro Ser Phe
465


<210> SEQ ID NO 120
<211> LENGTH: 463
<212> TYPE: PRT
<213> ORGANISM: Apophysomyces ossiformis

<400> SEQUENCE: 120

Met Met Met Ser Trp Lys Ser Leu Leu Leu Leu Leu Gly Pro Ile Ala
1               5                   10                  15

Ala Ala Thr Ala Ala Ile Pro Thr Gly Asn Ser Ser Leu Asn Ala Trp
            20                  25                  30

Val Ser Ser Gln Glu Asp Ile Ser Phe Ser Val Met Leu Gly Asn Ile
        35                  40                  45
```

```
Asn Pro Pro Gly Thr Val Lys Gly Phe Val Ala Ala Ser Leu Ser Thr
    50                  55                  60

Ala Gly Pro Asp Tyr Phe Tyr Ser Trp Val Arg Asp Ser Ala Leu Val
65                  70                  75                  80

Ser Arg Val Val Thr His Lys Tyr Asn Thr Thr Glu Thr Gly Asn Ser
                85                  90                  95

Thr Val Ala Gly Phe Leu Glu Asp Tyr Val His Phe Gln Ile Asn Thr
            100                 105                 110

Gln Thr Glu Ser Thr Val Cys Asn Cys Leu Gly Glu Pro Lys Phe Asn
        115                 120                 125

Pro Asp Gly Ser Ser Tyr Thr Gly Pro Trp Gly Arg Pro Gln Asn Asp
    130                 135                 140

Gly Pro Ala Glu Arg Ala Ser Thr Met Ile Leu Ile Ala Asp Ser Phe
145                 150                 155                 160

Leu Thr Gln Thr Lys Asn Thr Ser Tyr Val Asp Asn Thr Leu Lys Pro
                165                 170                 175

Ala Ile Tyr Lys Asp Leu Asp Tyr Val Val Asn Thr Trp Ser Asn Pro
            180                 185                 190

Cys Phe Asp Leu Trp Glu Glu Val Asn Gly Ile His Phe Tyr Thr Leu
        195                 200                 205

Met Val Met Arg Arg Gly Leu Leu Asp Gly Ala Asn Phe Ala Thr Arg
    210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Asn Lys Asn Tyr Ile
                245                 250                 255

Ile Val Thr Gln Asp Tyr Gln Asn Gly Val Gln Lys Pro Ser Gly Leu
            260                 265                 270

Asp Ile Ser Thr Leu Ile Ala Ala Asn Val Ala Gly Met Asn Asp Gly
        275                 280                 285

Phe Tyr Thr Pro Gly Ser Asp Lys Met Leu Ala Thr Ala Val Ala Ile
    290                 295                 300

Glu Asn Ala Met Ala Asn Leu Tyr Pro Leu Asn Lys Asn Leu Pro Ser
305                 310                 315                 320

Tyr Leu Gly Asn Ala Ile Gly Arg Tyr Pro Glu Asp Thr Tyr Asn Gly
                325                 330                 335

Asp Gly Asn Ser Gln Gly Asn Pro Trp Phe Leu Ala Thr Thr Ala Phe
            340                 345                 350

Ser Glu Leu Tyr Tyr Arg Ala Leu Leu Glu Trp Gln Glu Thr Gly Val
        355                 360                 365

Thr Val Thr Ser Ile Ser Lys Asp Phe Phe Ser Lys Phe Asp Pro Asn
    370                 375                 380

Ala Ser Ala Gly Lys Lys Tyr Ser Pro Gly Ser Asn Glu Phe Ala Ser
385                 390                 395                 400

Leu Ala Gln Asn Ile Ala Ser Ala Ala Asp Arg Phe Leu Ser Thr Val
                405                 410                 415

Asn Tyr His Arg Asn Ser Asn Gly Ser Leu Ser Glu Glu Phe Asp Arg
            420                 425                 430

Asn Thr Gly Tyr Met Thr Gly Ala Arg Asp Leu Thr Trp Ser His Ala
        435                 440                 445

Ala Phe Ile Thr Ala Gly Leu Ala Arg Ala Gly Thr Pro Ser Phe
    450                 455                 460
```

<210> SEQ ID NO 121
<211> LENGTH: 462
<212> TYPE: PRT
<213> ORGANISM: Apophysomyces elegans

<400> SEQUENCE: 121

```
Met Met Met Ser Trp Lys Ser Leu Leu Leu Leu Leu Gly Pro Ile Ala
1               5                   10                  15

Ala Ala Thr Ala Ala Ile Pro Thr Gly Asn Ser Ser Leu Asn Ala Trp
            20                  25                  30

Val Ser Ser Gln Glu Asp Ile Ser Phe Ser Val Met Leu Gly Asn Ile
        35                  40                  45

Asn Pro Pro Gly Thr Val Lys Gly Phe Val Ala Ala Ser Leu Ser Thr
    50                  55                  60

Ala Gly Pro Asp Tyr Phe Tyr Ser Trp Val Arg Asp Ser Ala Leu Val
65                  70                  75                  80

Ser Arg Val Val Thr His Lys Tyr Asn Thr Thr Glu Thr Gly Asn Ser
                85                  90                  95

Thr Val Ala Gly Phe Leu Gln Asp Tyr Val His Phe Gln Ile Asn Thr
            100                 105                 110

Gln Thr Glu Ser Thr Val Cys Asn Cys Leu Gly Glu Pro Lys Phe Asn
        115                 120                 125

Pro Asp Gly Ser Ser Tyr Thr Gly Pro Trp Gly Arg Pro Gln Asn Asp
    130                 135                 140

Gly Pro Ala Glu Arg Ala Ser Thr Met Ile Leu Ile Ala Asp Ser Phe
145                 150                 155                 160

Leu Thr Gln Thr Lys Asn Thr Ser Tyr Val Asp Asn Thr Leu Lys Pro
                165                 170                 175

Ala Ile Tyr Lys Asp Leu Asp Tyr Val Val Asn Thr Trp Ser Asn Pro
            180                 185                 190

Cys Phe Asp Leu Trp Glu Glu Val Asn Gly Ile His Phe Tyr Thr Leu
        195                 200                 205

Met Val Met Arg Arg Gly Leu Leu Asp Gly Ala Asn Phe Ala Thr Arg
    210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Ser Lys Asn Tyr Ile
                245                 250                 255

Met Val Thr Gln Asp Tyr Gln Asn Gly Ile Gln Lys Pro Ser Gly Leu
            260                 265                 270

Asp Ile Ser Thr Leu Ile Ala Ala Asn Val Ala Gly Met Asn Asp Gly
        275                 280                 285

Phe Tyr Thr Pro Gly Ser Asp Lys Met Leu Ala Thr Ala Val Ala Ile
    290                 295                 300

Glu Asn Ala Met Ala Asn Leu Tyr Pro Leu Asn Lys Asn Leu Pro Ser
305                 310                 315                 320

Tyr Leu Gly Asn Ala Ile Gly Arg Tyr Pro Glu Asp Thr Tyr Asn Gly
                325                 330                 335

Asp Gly Asn Ser Gln Gly Asn Pro Trp Phe Leu Ala Thr Thr Ala Phe
            340                 345                 350

Ser Glu Leu Tyr Tyr Arg Ala Leu Leu Glu Trp Gln Glu Thr Gly Val
        355                 360                 365

Thr Val Thr Ser Ile Ser Lys Asp Phe Phe Ser Lys Phe Asp Pro Asn
    370                 375                 380
```

```
Ala Ser Ala Gly Lys Lys Tyr Ser Pro Gly Ser Asp Glu Phe Asn Ser
385                 390                 395                 400

Leu Ala Gln Asn Ile Ala Ser Ala Ala Asp Arg Phe Leu Ser Thr Val
                405                 410                 415

Asn Tyr His Arg Asn Ser Asn Gly Ser Leu Ser Glu Glu Tyr Asp Arg
            420                 425                 430

Asn Ser Gly Tyr Met Thr Gly Ala Arg Asp Leu Thr Trp Ser His Ala
        435                 440                 445

Ala Phe Ile Thr Ala Gly Leu Ala Arg Ala Gly Thr Pro Ser
    450                 455                 460


<210> SEQ ID NO 122
<211> LENGTH: 463
<212> TYPE: PRT
<213> ORGANISM: Apophysomyces variabilis

<400> SEQUENCE: 122

Met Met Met Ser Trp Lys Ser Leu Leu Leu Leu Leu Gly Pro Ile Ala
1               5                   10                  15

Ala Ala Thr Ala Ala Ile Pro Thr Gly Asn Ser Ser Leu Asn Ala Trp
            20                  25                  30

Val Ser Ser Gln Glu Asp Ile Ser Phe Ser Val Met Leu Gly Asn Ile
        35                  40                  45

Asn Pro Pro Gly Thr Val Lys Gly Phe Val Ala Ala Ser Leu Ser Thr
    50                  55                  60

Ala Gly Pro Asp Tyr Phe Tyr Ser Trp Val Arg Asp Ser Ala Leu Val
65                  70                  75                  80

Ser Arg Val Val Thr His Lys Tyr Asn Thr Thr Glu Thr Gly Asn Ser
                85                  90                  95

Thr Val Ala Gly Phe Leu Gln Asp Tyr Val His Phe Gln Ile Asn Thr
            100                 105                 110

Gln Thr Glu Ser Thr Val Cys Asn Cys Leu Gly Glu Pro Lys Phe Asn
        115                 120                 125

Pro Asp Gly Ser Ser Tyr Thr Gly Pro Trp Gly Arg Pro Gln Asn Asp
    130                 135                 140

Gly Pro Ala Glu Arg Ala Ser Thr Met Ile Leu Ile Ala Asp Ser Phe
145                 150                 155                 160

Leu Ala Gln Thr Lys Asn Thr Ser Tyr Val Asp Asn Thr Leu Lys Pro
                165                 170                 175

Ala Ile Tyr Lys Asp Leu Asp Tyr Val Val Asn Thr Trp Ser Asn Pro
            180                 185                 190

Cys Phe Asp Leu Trp Glu Glu Val Asn Gly Ile His Phe Tyr Thr Leu
        195                 200                 205

Met Val Met Arg Arg Gly Leu Leu Asp Gly Ala Asn Phe Ala Thr Arg
    210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Ser Lys Asn Tyr Ile
                245                 250                 255

Met Val Thr Gln Asp Tyr Gln Asn Gly Val Gln Lys Pro Ser Gly Leu
            260                 265                 270

Asp Ile Ser Thr Leu Ile Ala Ala Asn Val Ala Gly Met Asn Asp Gly
        275                 280                 285

Phe Tyr Thr Pro Gly Ser Asp Lys Met Leu Ala Thr Ala Val Ala Ile
    290                 295                 300
```

Glu Asn Ala Met Ala Asn Leu Tyr Pro Leu Asn Lys Asn Leu Pro Ser
305 310 315 320

Tyr Leu Gly Asn Ala Ile Gly Arg Tyr Pro Glu Asp Thr Tyr Asn Gly
325 330 335

Asp Gly Asn Ser Gln Gly Asn Pro Trp Phe Leu Ala Thr Thr Ala Phe
340 345 350

Ser Glu Leu Tyr Tyr Arg Ala Leu Leu Glu Trp Gln Glu Thr Gly Val
355 360 365

Thr Val Thr Ser Ile Ser Lys Asp Phe Phe Ser Lys Phe Asp Pro Asn
370 375 380

Ala Ser Ala Gly Lys Lys Tyr Ser Pro Gly Ser Asp Glu Phe Asn Ser
385 390 395 400

Leu Ala Gln Asn Ile Ala Ser Ala Ala Asp Arg Phe Leu Ser Thr Val
405 410 415

Asn Tyr His Arg Asn Ser Asn Gly Ser Leu Ser Glu Glu Tyr Asp Arg
420 425 430

Asn Ser Gly Tyr Met Thr Gly Ala Arg Asp Leu Thr Trp Ser His Ala
435 440 445

Ala Phe Ile Thr Ala Gly Leu Ala Arg Ala Gly Thr Pro Ser Phe
450 455 460

<210> SEQ ID NO 123
<211> LENGTH: 463
<212> TYPE: PRT
<213> ORGANISM: Apophysomyces trapeziformis

<400> SEQUENCE: 123

Met Met Met Ser Trp Lys Ser Leu Leu Leu Leu Leu Gly Pro Ile Ala
1 5 10 15

Ala Ala Thr Ala Ala Ile Pro Thr Gly Asn Ser Ser Leu Asn Ala Trp
20 25 30

Val Ser Ser Gln Glu Asp Ile Ser Phe Ser Val Met Leu Gly Asn Ile
35 40 45

Asn Pro Pro Gly Thr Val Lys Gly Phe Val Ala Ala Ser Leu Ser Thr
50 55 60

Ala Gly Pro Asp Tyr Phe Tyr Ser Trp Val Arg Asp Ser Ala Leu Val
65 70 75 80

Ser Arg Val Val Thr His Lys Tyr Asn Thr Thr Glu Thr Gly Asn Ser
85 90 95

Thr Val Ala Gly Phe Leu Gln Asp Tyr Val His Phe Gln Ile Asn Thr
100 105 110

Gln Thr Glu Ser Thr Val Cys Asn Cys Leu Gly Glu Pro Lys Phe Asn
115 120 125

Pro Asp Gly Ser Ser Tyr Thr Gly Pro Trp Gly Arg Pro Gln Asn Asp
130 135 140

Gly Pro Ala Glu Arg Ala Ser Thr Met Ile Leu Ile Ala Asp Ser Phe
145 150 155 160

Leu Thr Gln Thr Lys Asn Thr Ser Tyr Val Asp Asn Thr Leu Lys Pro
165 170 175

Ala Ile Tyr Lys Asp Leu Asp Tyr Val Val Asn Thr Trp Ser Asn Pro
180 185 190

Cys Phe Asp Leu Trp Glu Glu Val Asn Gly Ile His Phe Tyr Thr Leu
195 200 205

Met Val Met Arg Arg Gly Leu Leu Asp Gly Ala Asn Phe Ala Thr Arg

```
    210                 215                 220

Asn Gly Asp Thr Ser Lys Ala Ser Ser Tyr Ser Ser Thr Ala Ser Gln
225                 230                 235                 240

Ile Gln Asn Lys Ile Asp Ser Phe Trp Ser Ser Ser Lys Asn Tyr Ile
                245                 250                 255

Ile Val Thr Gln Asp Tyr Gln Asn Gly Val Gln Lys Pro Ser Gly Leu
            260                 265                 270

Asp Val Ser Thr Leu Ile Ala Ala Asn Val Ala Gly Met Asn Asp Gly
        275                 280                 285

Phe Tyr Thr Pro Gly Ser Asp Lys Met Leu Ala Thr Ala Val Ala Ile
    290                 295                 300

Glu Asn Ala Met Ala Asn Leu Tyr Pro Leu Asn Lys Asn Leu Pro Ser
305                 310                 315                 320

Tyr Leu Gly Asn Ala Ile Gly Arg Tyr Pro Glu Asp Thr Tyr Asn Gly
                325                 330                 335

Asp Gly Asn Ser Gln Gly Asn Pro Trp Phe Leu Ala Thr Thr Ala Phe
            340                 345                 350

Ser Glu Leu Tyr Tyr Arg Ala Leu Leu Glu Trp Gln Glu Thr Gly Val
        355                 360                 365

Thr Val Thr Ser Ile Ser Lys Asp Phe Phe Ser Lys Phe Asp Pro Asn
    370                 375                 380

Ala Ser Ala Gly Lys Lys Tyr Ser Pro Gly Ser Asn Glu Tyr Ala Ser
385                 390                 395                 400

Leu Ala Gln Asn Ile Ala Ser Ala Ala Asp Arg Phe Leu Ser Thr Val
                405                 410                 415

Asn Tyr His Arg Asn Pro Asn Gly Ser Leu Ser Glu Glu Tyr Asp Arg
            420                 425                 430

Asn Thr Gly Tyr Met Thr Gly Ala Arg Asp Leu Thr Trp Ser His Ala
        435                 440                 445

Ala Phe Ile Thr Ala Gly Leu Ala Arg Ala Gly Thr Pro Ser Phe
    450                 455                 460
```

<210> SEQ ID NO 124
<211> LENGTH: 1404
<212> TYPE: DNA
<213> ORGANISM: Artificial Sequence
<220> FEATURE:
<223> OTHER INFORMATION: codon modified

<400> SEQUENCE: 124

```
atgccttctt ggaagaccct gattttcctc ctgggcccta ttaccgccgc tctggctgct     60

cctgttaaca agcagtcttt ccctaccggc aaccccgaca tcagctcttg ggtttctaag    120

caggagggca ttagcttcag cgagatgctc cgaaacgtca accctcccgg caccgctaag    180

ggcttcgttg ctgctagcct cagcaccgcc ggccccgact acttctacac ctggacccga    240

gacgccgctc tcgtctcccg cgtcatcgct tacaagtaca acaccaccaa cgctggcgac    300

aacaacattc acggcgctct gcaggactac gtcaccttcc agattaacac ccagaccgag    360

tccacccctt gcaactgcct gggcgagcct aagttcaacc ccgacggcag ctctttcacc    420

ggcccttggg gccgacctca gaacgacggc cctgctgagc gcgctagcag catgattctc    480

attgctgaca gcttcctcgc ccagaccaag gacaccgctt acgttaccaa caccctgaag    540

cctgccattt acaaggacct ggactacgtt gttaacacct ggtctaaccc ttgcttcgac    600

ctgtgggagg aggttaacgg cgtccacttc tacaccctca tggttatgcg acgaggcctc    660
```

```
ctcgacggcg ctgacttcgc tacccgaaac ggcgacgcct ctaaggctag ctcttactct    720

gacgctgcta gcaagatcaa gacccgactg gactctttct gggtcagcga caagaactac    780

attaccgtta cccaggacta caaggagggc gtcaagaagg acaccggcct cgacgttagc    840

accctcattg ctgccaacgt tgccggcaag gacgacggct tctacacccc cggcagcgac    900

aagattctgg ctaccgctgt tgccttcgag aacgccatgg ctaagctgta ccctctgaac    960

cagaacctcg acagccacct gggcaactct attggccgat accctgagga cacctacaac   1020

ggcaacggca actcccaggg caacccttgg ttcctcgcca ccaccgcttt caccgagctg   1080

tactaccgag ccatcttgga atggaaggac agcggcgtta ccgtcacccc cgtttccaag   1140

gacttcttcg ccaagttcga ctccaacgcc gttgccggca agaagtactc tcctaactct   1200

gaggagttcg ccaccctgac cgctaacatc gctgctgccg ctgaccgatt catgtctacc   1260

gttaagtacc accagaaccc taacggctct ctgtccgagc agttcgaccg ccacagcggc   1320

tacatgaccg gcgcccgaga cctgacctgg tctcacgctg ctttcattac cgccgcccag   1380

gctcgcgctg gcacccctag cttc                                          1404
```

```
<210> SEQ ID NO 125
<211> LENGTH: 19
<212> TYPE: PRT
<213> ORGANISM: Artificial Sequence
<220> FEATURE:
<223> OTHER INFORMATION: signal peptide

<400> SEQUENCE: 125

Met Pro Ser Trp Lys Thr Leu Ile Phe Leu Leu Gly Pro Ile Thr Ala
1               5                   10                  15

Ala Leu Ala


<210> SEQ ID NO 126
<211> LENGTH: 449
<212> TYPE: PRT
<213> ORGANISM: Saksenaea oblongispora

<400> SEQUENCE: 126

Ala Pro Val Asn Lys Gln Ser Phe Pro Thr Gly Asn Pro Asp Ile Ser
1               5                   10                  15

Ser Trp Val Ser Lys Gln Glu Gly Ile Ser Phe Ser Glu Met Leu Arg
            20                  25                  30

Asn Val Asn Pro Pro Gly Thr Ala Lys Gly Phe Val Ala Ala Ser Leu
        35                  40                  45

Ser Thr Ala Gly Pro Asp Tyr Phe Tyr Thr Trp Thr Arg Asp Ala Ala
    50                  55                  60

Leu Val Ser Arg Val Ile Ala Tyr Lys Tyr Asn Thr Thr Asn Ala Gly
65                  70                  75                  80

Asp Asn Asn Ile His Gly Ala Leu Gln Asp Tyr Val Thr Phe Gln Ile
                85                  90                  95

Asn Thr Gln Thr Glu Ser Thr Pro Cys Asn Cys Leu Gly Glu Pro Lys
            100                 105                 110

Phe Asn Pro Asp Gly Ser Ser Phe Thr Gly Pro Trp Gly Arg Pro Gln
        115                 120                 125

Asn Asp Gly Pro Ala Glu Arg Ala Ser Ser Met Ile Leu Ile Ala Asp
    130                 135                 140

Ser Phe Leu Ala Gln Thr Lys Asp Thr Ala Tyr Val Thr Asn Thr Leu
145                 150                 155                 160
```

```
Lys Pro Ala Ile Tyr Lys Asp Leu Asp Tyr Val Val Asn Thr Trp Ser
                165                 170                 175

Asn Pro Cys Phe Asp Leu Trp Glu Glu Val Asn Gly Val His Phe Tyr
            180                 185                 190

Thr Leu Met Val Met Arg Arg Gly Leu Leu Asp Gly Ala Asp Phe Ala
        195                 200                 205

Thr Arg Asn Gly Asp Ala Ser Lys Ala Ser Ser Tyr Ser Asp Ala Ala
    210                 215                 220

Ser Lys Ile Lys Thr Arg Leu Asp Ser Phe Trp Val Ser Asp Lys Asn
225                 230                 235                 240

Tyr Ile Thr Val Thr Gln Asp Tyr Lys Glu Gly Val Lys Lys Asp Thr
                245                 250                 255

Gly Leu Asp Val Ser Thr Leu Ile Ala Ala Asn Val Ala Gly Lys Asp
            260                 265                 270

Asp Gly Phe Tyr Thr Pro Gly Ser Asp Lys Ile Leu Ala Thr Ala Val
        275                 280                 285

Ala Phe Glu Asn Ala Met Ala Lys Leu Tyr Pro Leu Asn Gln Asn Leu
    290                 295                 300

Asp Ser His Leu Gly Asn Ser Ile Gly Arg Tyr Pro Glu Asp Thr Tyr
305                 310                 315                 320

Asn Gly Asn Gly Asn Ser Gln Gly Asn Pro Trp Phe Leu Ala Thr Thr
                325                 330                 335

Ala Phe Thr Glu Leu Tyr Tyr Arg Ala Ile Leu Glu Trp Lys Asp Ser
            340                 345                 350

Gly Val Thr Val Thr Pro Val Ser Lys Asp Phe Phe Ala Lys Phe Asp
        355                 360                 365

Ser Asn Ala Val Ala Gly Lys Lys Tyr Ser Pro Asn Ser Glu Glu Phe
    370                 375                 380

Ala Thr Leu Thr Ala Asn Ile Ala Ala Ala Ala Asp Arg Phe Met Ser
385                 390                 395                 400

Thr Val Lys Tyr His Gln Asn Pro Asn Gly Ser Leu Ser Glu Gln Phe
                405                 410                 415

Asp Arg His Ser Gly Tyr Met Thr Gly Ala Arg Asp Leu Thr Trp Ser
            420                 425                 430

His Ala Ala Phe Ile Thr Ala Ala Gln Ala Arg Ala Gly Thr Pro Ser
        435                 440                 445

Phe
```

<210> SEQ ID NO 127
<211> LENGTH: 1389
<212> TYPE: DNA
<213> ORGANISM: Artificial Sequence
<220> FEATURE:
<223> OTHER INFORMATION: codon modified

<400> SEQUENCE: 127

```
atgatgatgt cttggaagtc tctgctcctc ctgctgggcc ctatcgccgc tgctaccgct     60

gccatcccta ccggcaacag cagcctgaac gcttgggtta gctcccagga ggacatctct    120

ttctccgtca tgctgggcaa cattaaccct cccggcaccg tcaagggctt cgttgccgct    180

agcctgtcca ccgctggccc cgactacttc tactcttggg tccgagacag cgccctcgtt    240

tcccgcgtcg tcacccacaa gtacaacacc accgagaccg gcaactctac cgttgccggc    300

ttcttggagg actacgttca cttccagatt aacacccaga ccgagtctac cgtttgcaac    360

tgcctgggcg agcctaagtt caaccccgac ggcagctctt acaccggccc ttggggccgc    420
```

```
cctcagaacg acggccccgc tgagcgagct agcaccatga ttctgattgc cgactctttc    480

ctgacccaga ccaagaacac ctcttacgtt gacaacaccc tgaagcccgc catttacaag    540

gacctggact acgttgttaa cacctggtct aacccttgct tcgacctgtg ggaggaggtt    600

aacggcattc acttctacac cctcatggtt atgcgacgag gcctcctcga cggcgccaac    660

ttcgccaccc gaaacggcga cacctctaag gctagctctt acagcagcac cgctagccag    720

attcagaaca agattgactc cttctggagc tccaacaaga actacattat tgttacccag    780

gactaccaga acggcgtcca gaagcctagc ggcctcgaca tcagcaccct cattgctgcc    840

aacgtcgctg gcatgaacga cggcttctac accccggct ctgacaagat gctcgccacc    900

gccgttgcta ttgagaacgc catggctaac ctgtaccccc tcaacaagaa cctgccttct    960

tacctgggca acgctattgg ccgataccct gaggacacct acaacggcga cggcaactcc   1020

cagggcaacc cttggttcct cgccaccacc gctttcagcg agctgtacta ccgagctctg   1080

ctggagtggc aggagaccgg cgttaccgtt accagcattt ctaaggactt cttcagcaag   1140

ttcgacccta acgctagcgc tggcaagaag tactctcccg gctctaacga gttcgcttct   1200

ctggctcaga acattgctag cgctgctgac cgattcctgt ccaccgtcaa ctaccaccga   1260

aactccaacg gcagcctgtc tgaggagttc gaccgaaaca ccggctacat gaccggcgcc   1320

cgagacctga cctggtctca cgccgctttc attaccgctg gcctcgctcg cgctggcacc   1380

cctagcttc                                                            1389
```

<210> SEQ ID NO 128
<211> LENGTH: 20
<212> TYPE: PRT
<213> ORGANISM: Artificial Sequence
<220> FEATURE:
<223> OTHER INFORMATION: signal peptide

<400> SEQUENCE: 128

```
Met Met Met Ser Trp Lys Ser Leu Leu Leu Leu Leu Gly Pro Ile Ala
1               5                   10                  15

Ala Ala Thr Ala
            20
```

<210> SEQ ID NO 129
<211> LENGTH: 443
<212> TYPE: PRT
<213> ORGANISM: Apophysomyces ossiformis

<400> SEQUENCE: 129

```
Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Glu Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110
```

```
Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Thr Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
    210                 215                 220

Ile Asp Ser Phe Trp Ser Ser Asn Lys Asn Tyr Ile Ile Val Thr Gln
225                 230                 235                 240

Asp Tyr Gln Asn Gly Val Gln Lys Pro Ser Gly Leu Asp Ile Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
        355                 360                 365

Lys Lys Tyr Ser Pro Gly Ser Asn Glu Phe Ala Ser Leu Ala Gln Asn
    370                 375                 380

Ile Ala Ser Ala Ala Asp Arg Phe Leu Ser Thr Val Asn Tyr His Arg
385                 390                 395                 400

Asn Ser Asn Gly Ser Leu Ser Glu Glu Phe Asp Arg Asn Thr Gly Tyr
                405                 410                 415

Met Thr Gly Ala Arg Asp Leu Thr Trp Ser His Ala Ala Phe Ile Thr
            420                 425                 430

Ala Gly Leu Ala Arg Ala Gly Thr Pro Ser Phe
        435                 440
```

<210> SEQ ID NO 130
<211> LENGTH: 1386
<212> TYPE: DNA
<213> ORGANISM: Artificial Sequence
<220> FEATURE:
<223> OTHER INFORMATION: codon optimized

<400> SEQUENCE: 130

```
atgatgatgt cttggaagtc tctgctcctg ctcctgggcc ctattgctgc cgccaccgct      60

gccatcccta ccggcaactc tagcctcaac gcttgggtta gcagccagga ggacatttct     120

ttcagcgtca tgctgggcaa cattaaccct cccggcaccg tcaagggctt cgttgctgct     180
```

```
agcctgtcca ccgctggccc cgactacttc tactcttggg ttcgagacag cgctctcgtt    240

tctcgcgtcg ttacccacaa gtacaacacc accgagaccg gcaacagcac cgttgctggc    300

ttcctgcagg actacgttca cttccagatt aacacccaga ccgagtccac cgtttgcaac    360

tgcctgggcg agcctaagtt caaccccgac ggcagctctt acaccggccc ttggggccgc    420

cctcagaacg acggccccgc tgagcgagct agcaccatga ttctgattgc tgactccttc    480

ctgacccaga ccaagaacac ctcttacgtt gacaacaccc tgaagcccgc tatttacaag    540

gacctggact acgtcgtcaa cacctggtct aacccttgct tcgacctgtg ggaggaggtt    600

aacggcattc acttctacac cctcatggtt atgcgacgag gcctcctgga cggcgccaac    660

ttcgccaccc gaaacggcga caccagcaag gctagctctt acagcagcac cgcttctcag    720

atccagaaca agattgactc tttctggtct agctctaaga actacatcat ggttacccag    780

gactaccaga acggcattca gaagcctagc ggcctcgaca ttagcaccct catcgccgct    840

aacgtcgctg gcatgaacga cggcttctac accccccggct ccgacaagat gctcgctacc    900

gccgttgcta ttgagaacgc catggctaac ctgtaccctc tgaacaagaa cctgccttct    960

tacctgggca acgccattgg ccgatacccc gaggacacct acaacggcga cggcaactct   1020

cagggcaacc cttggttcct cgccaccacc gctttcagcg agctgtacta ccgcgctctc   1080

ctggagtggc aggagaccgg cgttaccgtc accagcattt ccaaggactt cttctctaag   1140

ttcgacccta acgctagcgc tggcaagaag tactcccccg gctctgacga gttcaactcc   1200

ctcgcccaga acattgccag cgctgccgac cgattcctgt ctaccgttaa ctaccaccga   1260

aactccaacg gctctctgtc tgaggagtac gaccgaaaca gcggctacat gaccggcgcc   1320

cgagacctga cctggtccca cgccgctttc attaccgccg gcctcgcgag agctggcacc   1380

cctagc                                                                1386
```

<210> SEQ ID NO 131
<211> LENGTH: 20
<212> TYPE: PRT
<213> ORGANISM: Artificial Sequence
<220> FEATURE:
<223> OTHER INFORMATION: signal peptide

<400> SEQUENCE: 131

```
Met Met Met Ser Trp Lys Ser Leu Leu Leu Leu Leu Gly Pro Ile Ala
1               5                   10                  15

Ala Ala Thr Ala
            20
```

<210> SEQ ID NO 132
<211> LENGTH: 442
<212> TYPE: PRT
<213> ORGANISM: Apophysomyces elegans

<400> SEQUENCE: 132

```
Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60
```

```
Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Thr Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
    210                 215                 220

Ile Asp Ser Phe Trp Ser Ser Ser Lys Asn Tyr Ile Met Val Thr Gln
225                 230                 235                 240

Asp Tyr Gln Asn Gly Ile Gln Lys Pro Ser Gly Leu Asp Ile Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
        355                 360                 365

Lys Lys Tyr Ser Pro Gly Ser Asp Glu Phe Asn Ser Leu Ala Gln Asn
    370                 375                 380

Ile Ala Ser Ala Ala Asp Arg Phe Leu Ser Thr Val Asn Tyr His Arg
385                 390                 395                 400

Asn Ser Asn Gly Ser Leu Ser Glu Glu Tyr Asp Arg Asn Ser Gly Tyr
                405                 410                 415

Met Thr Gly Ala Arg Asp Leu Thr Trp Ser His Ala Ala Phe Ile Thr
            420                 425                 430

Ala Gly Leu Ala Arg Ala Gly Thr Pro Ser
        435                 440
```

<210> SEQ ID NO 133
<211> LENGTH: 1389
<212> TYPE: DNA
<213> ORGANISM: Artificial Sequence
<220> FEATURE:
<223> OTHER INFORMATION: codon modified

<400> SEQUENCE: 133

```
atgatgatgt cttggaagtc tctgctcctc ctgctgggcc ctattgccgc tgccaccgct     60
gccattccta ccggcaacag cagcctcaac gcttgggtta gctcccagga ggacatttct    120
ttcagcgtca tgctgggcaa cattaaccct cccggcaccg ttaagggctt cgttgccgct    180
agcctgtcta ccgccggccc cgactacttc tactcttggg tccgagacag cgccctcgtt    240
tcccgcgtcg tcacccacaa gtacaacacc accgagaccg gcaacagcac cgttgctggc    300
ttcctgcagg actacgtcca cttccagatt aacacccaga ccgagtccac cgtttgcaac    360
tgcctgggcg agcctaagtt caaccccgac ggcagctctt acaccggccc ttggggccga    420
cctcagaacg acggccccgc tgagcgcgct agcaccatga ttctgattgc tgactccttc    480
ctcgctcaga ccaagaacac ctcttacgtt gacaacaccc tgaagcctgc catttacaag    540
gacctggact acgtcgttaa cacctggtct aacccttgct tcgacctgtg ggaggaggtt    600
aacggcattc acttctacac cctcatggtt atgcgacgag gcctcctgga cggcgccaac    660
ttcgccaccc gaaacggcga cacctccaag gctagctctt acagcagcac cgctagccag    720
atccagaaca agattgactc tttctggtct agctccaaga actacatcat ggttacccag    780
gactaccaga acggcgttca gaagcctagc ggcctcgaca ttagcaccct catcgccgct    840
aacgttgctg gcatgaacga cggcttctac acccctggct ctgacaagat gctcgccacc    900
gccgttgcta ttgagaacgc tatggctaac ctgtaccctc tgaacaagaa cctgccttct    960
tacctgggca acgccattgg ccgatacccc gaggacacct acaacggcga cggcaactcc   1020
cagggcaacc cttggttcct cgctaccacc gctttcagcg agctgtacta ccgagctctg   1080
ttagagtggc aggagaccgg cgtcaccgtt accagcatct ctaaggactt cttctccaag   1140
ttcgacccta acgctagcgc cggcaagaag tactcccccg gcagcgacga gttcaactct   1200
ctcgcccaga acatcgccag cgccgctgac cgattcctgt ctaccgtcaa ctaccaccga   1260
aactctaacg gctctctgtc tgaggagtac gaccgaaact ccggctacat gaccggcgcg   1320
agagacctga cctggtctca cgctgctttc attaccgctg gcctcgcccg agctggcacc   1380
ccttctttc                                                           1389
```

<210> SEQ ID NO 134
<211> LENGTH: 20
<212> TYPE: PRT
<213> ORGANISM: Artificial Sequence
<220> FEATURE:
<223> OTHER INFORMATION: signal peptide

<400> SEQUENCE: 134

```
Met Met Met Ser Trp Lys Ser Leu Leu Leu Leu Leu Gly Pro Ile Ala
1               5                   10                  15

Ala Ala Thr Ala
            20
```

<210> SEQ ID NO 135
<211> LENGTH: 443
<212> TYPE: PRT
<213> ORGANISM: Apophysomyces variabilis

<400> SEQUENCE: 135

```
Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
```

```
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Ala Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
    210                 215                 220

Ile Asp Ser Phe Trp Ser Ser Ser Lys Asn Tyr Ile Met Val Thr Gln
225                 230                 235                 240

Asp Tyr Gln Asn Gly Val Gln Lys Pro Ser Gly Leu Asp Ile Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
        355                 360                 365

Lys Lys Tyr Ser Pro Gly Ser Asp Glu Phe Asn Ser Leu Ala Gln Asn
    370                 375                 380

Ile Ala Ser Ala Ala Asp Arg Phe Leu Ser Thr Val Asn Tyr His Arg
385                 390                 395                 400

Asn Ser Asn Gly Ser Leu Ser Glu Glu Tyr Asp Arg Asn Ser Gly Tyr
                405                 410                 415

Met Thr Gly Ala Arg Asp Leu Thr Trp Ser His Ala Ala Phe Ile Thr
            420                 425                 430

Ala Gly Leu Ala Arg Ala Gly Thr Pro Ser Phe
        435                 440
```

<210> SEQ ID NO 136
<211> LENGTH: 1389
<212> TYPE: DNA
<213> ORGANISM: Artificial Sequence
<220> FEATURE:
<223> OTHER INFORMATION: codon modified

<400> SEQUENCE: 136

```
atgatgatgt cttggaagtc tctgctcctc ctgctgggcc ctatcgccgc tgccaccgct     60

gccatcccta ccggcaacag cagcctcaac gcttgggtta gctctcagga ggacatctct    120

ttcagcgtca tgctgggcaa catcaaccct cccggcaccg tcaagggctt cgttgccgct    180

agcctgtcta ccgctggccc cgactacttc tactcttggg tccgagacag cgctctcgtt    240

tctcgcgttg ttacccacaa gtacaacacc accgagaccg gcaacagcac cgttgctggc    300

ttcctgcagg actacgttca cttccagatt aacacccaga ccgagtccac cgtttgcaac    360

tgcctgggcg agcctaagtt caaccccgac ggcagctctt acaccggccc ttggggccgc    420

cctcagaacg acggccccgc tgagcgcgct agcaccatga ttctgatcgc tgactccttc    480

ctgacccaga ccaagaacac ctcttacgtt gacaacaccc tgaagcccgc tatttacaag    540

gacctcgact acgtcgttaa cacctggtct aacccttgct tcgacctgtg ggaggaggtt    600

aacggcattc acttctacac cctcatggtt atgcgacgag gcctcctgga cggcgccaac    660

ttcgccaccc gaaacggcga caccagcaag gctagctctt actccagcac cgcttcccag    720

attcagaaca agattgactc tttctggagc agctccaaga actacattat tgttacccag    780

gactaccaga acggcgtcca gaagcctagc ggcctcgacg tcagcaccct cattgctgcc    840

aacgtcgctg gcatgaacga cggcttctac acccccggca gcgacaagat gctcgccacc    900

gccgttgcca ttgagaacgc catggctaac ctgtaccctc tgaacaagaa cctgccttct    960

tacctgggca acgctattgg ccgatacccc gaggacacct acaacggcga cggcaactcc   1020

cagggcaacc cttggttcct cgccaccacc gctttcagcg agctgtacta ccgagctctg   1080

cttgaatggc aggagaccgg cgtcaccgtt accagcattt ctaaggactt cttctctaag   1140

ttcgacccta acgctagcgc cggcaagaag tactcccccg gctccaacga gtacgctagc   1200

ctcgcccaga acattgctag cgccgctgac cgattcctgt ctaccgttaa ctaccaccga   1260

aaccctaacg gctctctgtc tgaggagtac gaccgaaaca ccggctacat gaccggcgcc   1320

cgagacctga cctggtctca cgctgctttc attaccgccg gcctggccag ggctggcacc   1380

ccttctttc                                                           1389
```

<210> SEQ ID NO 137
<211> LENGTH: 20
<212> TYPE: PRT
<213> ORGANISM: Artificial Sequence
<220> FEATURE:
<223> OTHER INFORMATION: signal peptide

<400> SEQUENCE: 137

```
Met Met Met Ser Trp Lys Ser Leu Leu Leu Leu Leu Gly Pro Ile Ala
1               5                   10                  15

Ala Ala Thr Ala
            20
```

<210> SEQ ID NO 138
<211> LENGTH: 443
<212> TYPE: PRT

<213> ORGANISM: Apophysomyces trapeziformis

<400> SEQUENCE: 138

```
Ala Ile Pro Thr Gly Asn Ser Ser Leu Asn Ala Trp Val Ser Ser Gln
1               5                   10                  15

Glu Asp Ile Ser Phe Ser Val Met Leu Gly Asn Ile Asn Pro Pro Gly
            20                  25                  30

Thr Val Lys Gly Phe Val Ala Ala Ser Leu Ser Thr Ala Gly Pro Asp
        35                  40                  45

Tyr Phe Tyr Ser Trp Val Arg Asp Ser Ala Leu Val Ser Arg Val Val
    50                  55                  60

Thr His Lys Tyr Asn Thr Thr Glu Thr Gly Asn Ser Thr Val Ala Gly
65                  70                  75                  80

Phe Leu Gln Asp Tyr Val His Phe Gln Ile Asn Thr Gln Thr Glu Ser
                85                  90                  95

Thr Val Cys Asn Cys Leu Gly Glu Pro Lys Phe Asn Pro Asp Gly Ser
            100                 105                 110

Ser Tyr Thr Gly Pro Trp Gly Arg Pro Gln Asn Asp Gly Pro Ala Glu
        115                 120                 125

Arg Ala Ser Thr Met Ile Leu Ile Ala Asp Ser Phe Leu Thr Gln Thr
    130                 135                 140

Lys Asn Thr Ser Tyr Val Asp Asn Thr Leu Lys Pro Ala Ile Tyr Lys
145                 150                 155                 160

Asp Leu Asp Tyr Val Val Asn Thr Trp Ser Asn Pro Cys Phe Asp Leu
                165                 170                 175

Trp Glu Glu Val Asn Gly Ile His Phe Tyr Thr Leu Met Val Met Arg
            180                 185                 190

Arg Gly Leu Leu Asp Gly Ala Asn Phe Ala Thr Arg Asn Gly Asp Thr
        195                 200                 205

Ser Lys Ala Ser Ser Tyr Ser Ser Thr Ala Ser Gln Ile Gln Asn Lys
    210                 215                 220

Ile Asp Ser Phe Trp Ser Ser Ser Lys Asn Tyr Ile Ile Val Thr Gln
225                 230                 235                 240

Asp Tyr Gln Asn Gly Val Gln Lys Pro Ser Gly Leu Asp Val Ser Thr
                245                 250                 255

Leu Ile Ala Ala Asn Val Ala Gly Met Asn Asp Gly Phe Tyr Thr Pro
            260                 265                 270

Gly Ser Asp Lys Met Leu Ala Thr Ala Val Ala Ile Glu Asn Ala Met
        275                 280                 285

Ala Asn Leu Tyr Pro Leu Asn Lys Asn Leu Pro Ser Tyr Leu Gly Asn
    290                 295                 300

Ala Ile Gly Arg Tyr Pro Glu Asp Thr Tyr Asn Gly Asp Gly Asn Ser
305                 310                 315                 320

Gln Gly Asn Pro Trp Phe Leu Ala Thr Thr Ala Phe Ser Glu Leu Tyr
                325                 330                 335

Tyr Arg Ala Leu Leu Glu Trp Gln Glu Thr Gly Val Thr Val Thr Ser
            340                 345                 350

Ile Ser Lys Asp Phe Phe Ser Lys Phe Asp Pro Asn Ala Ser Ala Gly
        355                 360                 365

Lys Lys Tyr Ser Pro Gly Ser Asn Glu Tyr Ala Ser Leu Ala Gln Asn
    370                 375                 380

Ile Ala Ser Ala Ala Asp Arg Phe Leu Ser Thr Val Asn Tyr His Arg
385                 390                 395                 400
```

```
Asn Pro Asn Gly Ser Leu Ser Glu Glu Tyr Asp Arg Asn Thr Gly Tyr
                405                 410                 415

Met Thr Gly Ala Arg Asp Leu Thr Trp Ser His Ala Ala Phe Ile Thr
            420                 425                 430

Ala Gly Leu Ala Arg Ala Gly Thr Pro Ser Phe
        435                 440
```

```
<210> SEQ ID NO 139
<211> LENGTH: 1404
<212> TYPE: DNA
<213> ORGANISM: Artificial Sequence
<220> FEATURE:
<223> OTHER INFORMATION: Sequence is synthesized

<400> SEQUENCE: 139

atgccttctt ggaaaaccct gttcctcctc ctgggcccta tcgccaccgc tgccgctgct     60

cccgttgaca agcagtctct gcctaccggc aacagcacca ttagctcttg ggtcagcaag    120

caggaggaca tcagcttcag cgagatgctc cgaaacgtca accctgaggg caccgccaag    180

ggcttcgttg ccgcgtcgct cagcaccgct ggccccgact acttctacac ctggacccga    240

gacgccgctc tcgcctcccg agttattgct tacaagtaca acaccaccaa cgctggcgac    300

tctaagatcc acggcgttct ggacgactac gttaacttcc agattaacac ccagtctgag    360

cccacccctt gcaactgcct gggcgagcct aagttcaacc ctgacggcag ctctttcacc    420

ggcccttggg gccgcccccca gaacgacggc cccgctgagc gagcctccag tttcatgctg    480

attgccgact ctttcctcag ccagaccaag aacgcctctt acttcaccaa caccctcaag    540

cctgccattt acaaggacct cgactacgtc gttgacacct ggtctaaccc ttgcttcgac    600

ctgtgggagg aggttaacgg catccacttc tacaccctca tggttatgcg acgatctctc    660

ctcgacggcg ctaacttcgc cacccgaaac ggcgacaact ccaaggcctc aacctactcc    720

ggcgtcgccg ccaagattca ggctcgactg aactctttct gggacgccgg caagaactac    780

attaccgtta cccaggacta caagaacggc gttgagaagc ctagcggcct cgacgttagc    840

accctcattg ctgctaacgt cgctggcatg ggcgacggct tctacacccc cggcagcgag    900

cgcatcctcg ctaccgctct ggctttcgag aagagcatgg caagtctgta ccctctgaac    960

aacaacctgc ctagccacct gggcaacgcc attggccgat accccgagga cacctacaac   1020

ggcaacggca actcccaggg caacccttgg ttcctcgcta ccaccgcttt caccgagctg   1080

tactaccgcg ccattctgga gtggaagaac accggcgtta ccgtcacccc tatttctaag   1140

gacttcttcg tccgattcga cagcagcgct gctcctggca agaagtacaa ccccggctcc   1200

caggagttcg ctaccctgac ccagtctatt gctgccgccg ctgaccgatt catgtccacc   1260

gtccagtacc accagaaccc taacggctct ctgtctgagg agttcgaccg atctagcggc   1320

tacatgaccg gcgcccgaga cctgacctgg agtcacgctg ctttcattac cgctgctcag   1380

gcccgagctg gctctccttc tttc                                          1404
```

```
<210> SEQ ID NO 140
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 140

Ala Pro Val Asp Lys Gln Ser Leu Pro Thr Gly Asn Ser Thr Ile Ser
1               5                   10                  15
```

-continued

```
Ser Trp Val Ser Lys Gln Glu Asp Ile Ser Phe Ser Glu Met Leu Arg
            20                  25                  30

Asn Val Asn Pro Glu Gly Thr Ala Lys Gly Phe Val Ala Ala Ser Leu
        35                  40                  45

Ser Thr Ala Gly Pro Asp Tyr Phe Tyr Thr Trp Thr Arg Asp Ala Ala
    50                  55                  60

Leu Ala Ser Arg Val Ile Ala Tyr Lys Tyr Asn Thr Thr Asn Ala Gly
65                  70                  75                  80

Asp Ser Lys Ile His Gly Val Leu Asp Asp Tyr Val Asn Phe Gln Ile
                85                  90                  95

Asn Thr Gln Ser Glu Pro Thr Pro Cys Asn Cys Leu Gly Glu Pro Lys
            100                 105                 110

Phe Asn Pro Asp Gly Ser Ser Phe Thr Gly Pro Trp Gly Arg Pro Gln
        115                 120                 125

Asn Asp Gly Pro Ala Glu Arg Ala Ser Ser Phe Met Leu Ile Ala Asp
    130                 135                 140

Ser Phe Leu Ser Gln Thr Lys Asn Ala Ser Tyr Phe Thr Asn Thr Leu
145                 150                 155                 160

Lys Pro Ala Ile Tyr Lys Asp Leu Asp Tyr Val Val Asp Thr Trp Ser
                165                 170                 175

Asn Pro Cys Phe Asp Leu Trp Glu Glu Val Asn Gly Ile His Phe Tyr
            180                 185                 190

Thr Leu Met Val Met Arg Arg Ser Leu Leu Asp Gly Ala Asn Phe Ala
        195                 200                 205

Thr Arg Asn Gly Asp Asn Ser Lys Ala Ser Thr Tyr Ser Gly Val Ala
    210                 215                 220

Ala Lys Ile Gln Ala Arg Leu Asn Ser Phe Trp Asp Ala Gly Lys Asn
225                 230                 235                 240

Tyr Ile Thr Val Thr Gln Asp Tyr Lys Asn Gly Val Glu Lys Pro Ser
                245                 250                 255

Gly Leu Asp Val Ser Thr Leu Ile Ala Ala Asn Val Ala Gly Met Gly
            260                 265                 270

Asp Gly Phe Tyr Thr Pro Gly Ser Glu Arg Ile Leu Ala Thr Ala Leu
        275                 280                 285

Ala Phe Glu Lys Ser Met Ala Ser Leu Tyr Pro Leu Asn Asn Asn Leu
    290                 295                 300

Pro Ser His Leu Gly Asn Ala Ile Gly Arg Tyr Pro Glu Asp Thr Tyr
305                 310                 315                 320

Asn Gly Asn Gly Asn Ser Gln Gly Asn Pro Trp Phe Leu Ala Thr Thr
                325                 330                 335

Ala Phe Thr Glu Leu Tyr Tyr Arg Ala Ile Leu Glu Trp Lys Asn Thr
            340                 345                 350

Gly Val Thr Val Thr Pro Ile Ser Lys Asp Phe Phe Val Arg Phe Asp
        355                 360                 365

Ser Ser Ala Ala Pro Gly Lys Lys Tyr Asn Pro Gly Ser Gln Glu Phe
    370                 375                 380

Ala Thr Leu Thr Gln Ser Ile Ala Ala Ala Ala Asp Arg Phe Met Ser
385                 390                 395                 400

Thr Val Gln Tyr His Gln Asn Pro Asn Gly Ser Leu Ser Glu Glu Phe
                405                 410                 415

Asp Arg Ser Ser Gly Tyr Met Thr Gly Ala Arg Asp Leu Thr Trp Ser
            420                 425                 430
```

His Ala Ala Phe Ile Thr Ala Ala Gln Ala Arg Ala Gly Ser Pro Ser
435 440 445

Phe

<210> SEQ ID NO 141
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 141

Ala Pro Val Asp Lys Gln Ser Leu Pro Thr Gly Asn Ser Thr Ile Ser
1 5 10 15

Ser Trp Val Ser Lys Gln Glu Asp Ile Ser Phe Ser Glu Met Leu Arg
20 25 30

Asn Val Asn Pro Glu Gly Thr Ala Lys Gly Phe Val Ala Ala Ser Leu
35 40 45

Ser Thr Ala Gly Pro Asp Tyr Phe Tyr Thr Trp Thr Arg Asp Ala Ala
50 55 60

Leu Val Ser Arg Val Ile Ala Tyr Lys Tyr Asn Thr Thr Asn Ala Gly
65 70 75 80

Asp Ser Lys Ile His Gly Val Leu Asp Asp Tyr Val Asn Phe Gln Ile
85 90 95

Asn Thr Gln Ser Glu Pro Thr Pro Cys Asn Cys Leu Gly Glu Pro Lys
100 105 110

Phe Asn Pro Asp Gly Ser Ser Phe Thr Gly Pro Trp Gly Arg Pro Gln
115 120 125

Asn Asp Gly Pro Ala Glu Arg Ala Ser Ser Phe Met Leu Ile Ala Asp
130 135 140

Ser Phe Leu Ser Gln Thr Lys Asn Ala Ser Tyr Phe Thr Asn Thr Leu
145 150 155 160

Lys Pro Ala Ile Tyr Lys Asp Leu Asp Tyr Val Val Asp Thr Trp Ser
165 170 175

Asn Pro Cys Phe Asp Leu Trp Glu Glu Val Asn Gly Ile His Phe Tyr
180 185 190

Thr Leu Met Val Met Arg Arg Ser Leu Leu Asp Gly Ala Asn Phe Ala
195 200 205

Thr Arg Asn Gly Asp Asn Ser Lys Ala Ser Thr Tyr Ser Gly Val Ala
210 215 220

Ala Lys Ile Gln Ala Arg Leu Asn Ser Phe Trp Asp Ala Gly Lys Asn
225 230 235 240

Tyr Ile Thr Val Thr Gln Asp Tyr Lys Asn Gly Val Glu Lys Pro Ser
245 250 255

Gly Leu Asp Val Ser Thr Leu Ile Ala Ala Asn Val Ala Gly Met Gly
260 265 270

Asp Gly Phe Tyr Thr Pro Gly Ser Glu Arg Ile Leu Ala Thr Ala Leu
275 280 285

Ala Phe Glu Lys Ser Met Ala Ser Leu Tyr Pro Leu Asn Asn Asn Leu
290 295 300

Pro Ser His Leu Gly Asn Ala Ile Gly Arg Tyr Pro Glu Asp Thr Tyr
305 310 315 320

Asn Gly Asn Gly Asn Ser Gln Gly Asn Pro Trp Phe Leu Ala Thr Thr
325 330 335

Ala Phe Thr Glu Leu Tyr Tyr Arg Ala Ile Leu Glu Trp Lys Asn Thr

```
            340                 345                 350

Gly Val Thr Val Thr Pro Ile Ser Lys Asp Phe Phe Val Arg Phe Asp
        355                 360                 365

Ser Ser Ala Ala Pro Gly Lys Lys Tyr Asn Pro Gly Ser Gln Glu Phe
    370                 375                 380

Ala Thr Leu Thr Gln Ser Ile Ala Ala Ala Ala Asp Arg Phe Met Ser
385                 390                 395                 400

Thr Val Gln Tyr His Gln Asn Pro Asn Gly Ser Leu Ser Glu Glu Phe
                405                 410                 415

Asp Arg Ser Ser Gly Tyr Met Thr Gly Ala Arg Asp Leu Thr Trp Ser
            420                 425                 430

His Ala Ala Phe Ile Thr Ala Ala Gln Ala Arg Ala Gly Ser Pro Ser
        435                 440                 445

Phe


<210> SEQ ID NO 142
<211> LENGTH: 468
<212> TYPE: PRT
<213> ORGANISM: Saksenaea vasiformis

<400> SEQUENCE: 142

Met Pro Ser Trp Lys Thr Leu Phe Leu Leu Leu Gly Pro Ile Ala Thr
1               5                   10                  15

Ala Ala Ala Ala Pro Val Asp Lys Gln Ser Leu Pro Thr Gly Asn Ser
            20                  25                  30

Thr Ile Ser Ser Trp Val Ser Lys Gln Glu Asp Ile Ser Phe Ser Glu
        35                  40                  45

Met Leu Arg Asn Val Asn Pro Glu Gly Thr Ala Lys Gly Phe Val Ala
    50                  55                  60

Ala Ser Leu Ser Thr Ala Gly Pro Asp Tyr Phe Tyr Thr Trp Thr Arg
65                  70                  75                  80

Asp Ala Ala Leu Val Ser Arg Val Ile Ala Tyr Lys Tyr Asn Thr Thr
                85                  90                  95

Asn Ala Gly Asp Ser Lys Ile His Gly Val Leu Asp Asp Tyr Val Asn
            100                 105                 110

Phe Gln Ile Asn Thr Gln Ser Glu Ser Thr Pro Cys Asn Cys Leu Gly
        115                 120                 125

Glu Pro Lys Phe Asn Pro Asp Gly Ser Ser Phe Thr Gly Pro Trp Gly
    130                 135                 140

Arg Pro Gln Asn Asp Gly Pro Ala Glu Arg Ala Ser Ser Phe Met Leu
145                 150                 155                 160

Ile Ala Asp Ser Phe Leu Ser Gln Thr Lys Asn Ala Ser Tyr Phe Thr
                165                 170                 175

Asn Thr Leu Lys Pro Ala Ile Tyr Lys Asp Leu Asp Tyr Val Val Asp
            180                 185                 190

Thr Trp Ser Asn Pro Cys Phe Asp Leu Trp Glu Glu Val Asn Gly Ile
        195                 200                 205

His Phe Tyr Thr Leu Met Val Met Arg Arg Ser Leu Leu Asp Gly Ala
    210                 215                 220

Asn Phe Ala Thr Arg Asn Gly Asp Asn Ser Lys Ala Ser Thr Tyr Ser
225                 230                 235                 240

Gly Val Ala Ala Lys Ile Gln Ala Arg Leu Asn Ser Phe Trp Asp Ala
                245                 250                 255

Gly Lys Asn Tyr Ile Thr Val Thr Gln Asp Tyr Lys Asn Gly Val Glu
```

```
            260                 265                 270

Lys Pro Ser Gly Leu Asp Val Ser Thr Leu Ile Ala Ala Asn Val Ala
        275                 280                 285

Gly Met Gly Asp Gly Phe Tyr Thr Pro Gly Ser Glu Arg Ile Leu Ala
    290                 295                 300

Thr Ala Leu Ala Phe Glu Lys Ser Met Ala Ser Leu Tyr Pro Leu Asn
305                 310                 315                 320

Asn Asn Leu Pro Ser His Leu Gly Asn Ala Ile Gly Arg Tyr Pro Glu
                325                 330                 335

Asp Thr Tyr Asn Gly Asn Gly Asn Ser Gln Gly Asn Pro Trp Phe Leu
            340                 345                 350

Ala Thr Thr Ala Phe Thr Glu Leu Tyr Tyr Arg Ala Ile Leu Glu Trp
        355                 360                 365

Lys Asn Thr Gly Val Thr Val Thr Pro Ile Ser Lys Asp Phe Phe Val
    370                 375                 380

Arg Phe Asp Ser Ser Ala Ala Pro Gly Lys Lys Tyr Asn Pro Gly Ser
385                 390                 395                 400

Gln Glu Phe Ala Thr Leu Thr Gln Ser Ile Ala Ala Ala Ala Asp Arg
                405                 410                 415

Phe Met Ser Thr Val Gln Tyr His Gln Asn Pro Asn Gly Ser Leu Ser
            420                 425                 430

Glu Glu Phe Asp Arg Ser Ser Gly Tyr Met Thr Gly Ala Arg Asp Leu
        435                 440                 445

Thr Trp Ser His Ala Ala Phe Ile Thr Ala Ala Gln Ala Arg Ala Gly
    450                 455                 460

Ser Pro Ser Phe
465


<210> SEQ ID NO 143
<211> LENGTH: 444
<212> TYPE: PRT
<213> ORGANISM: Saksenaea vasiformis

<400> SEQUENCE: 143

Gln Ser Leu Pro Thr Gly Asn Ser Thr Ile Ser Ser Trp Val Ser Lys
1               5                   10                  15

Gln Glu Asp Ile Ser Phe Ser Glu Met Leu Arg Asn Val Asn Pro Glu
            20                  25                  30

Gly Thr Ala Lys Gly Phe Val Ala Ala Ser Leu Ser Thr Ala Gly Pro
        35                  40                  45

Asp Tyr Phe Tyr Thr Trp Thr Arg Asp Ala Ala Leu Val Ser Arg Val
    50                  55                  60

Ile Ala Tyr Lys Tyr Asn Thr Thr Asn Ala Gly Asp Ser Lys Ile His
65                  70                  75                  80

Gly Val Leu Asp Asp Tyr Val Asn Phe Gln Ile Asn Thr Gln Ser Glu
                85                  90                  95

Ser Thr Pro Cys Asn Cys Leu Gly Glu Pro Lys Phe Asn Pro Asp Gly
            100                 105                 110

Ser Ser Phe Thr Gly Pro Trp Gly Arg Pro Gln Asn Asp Gly Pro Ala
        115                 120                 125

Glu Arg Ala Ser Ser Phe Met Leu Ile Ala Asp Ser Phe Leu Ser Gln
    130                 135                 140

Thr Lys Asn Ala Ser Tyr Phe Thr Asn Thr Leu Lys Pro Ala Ile Tyr
145                 150                 155                 160
```

-continued

```
Lys Asp Leu Asp Tyr Val Val Asp Thr Trp Ser Asn Pro Cys Phe Asp
                165                 170                 175

Leu Trp Glu Glu Val Asn Gly Ile His Phe Tyr Thr Leu Met Val Met
            180                 185                 190

Arg Arg Ser Leu Leu Asp Gly Ala Asn Phe Ala Thr Arg Asn Gly Asp
        195                 200                 205

Asn Ser Lys Ala Ser Thr Tyr Ser Gly Val Ala Ala Lys Ile Gln Ala
    210                 215                 220

Arg Leu Asn Ser Phe Trp Asp Ala Gly Lys Asn Tyr Ile Thr Val Thr
225                 230                 235                 240

Gln Asp Tyr Lys Asn Gly Val Glu Lys Pro Ser Gly Leu Asp Val Ser
                245                 250                 255

Thr Leu Ile Ala Ala Asn Val Ala Gly Met Gly Asp Gly Phe Tyr Thr
            260                 265                 270

Pro Gly Ser Glu Arg Ile Leu Ala Thr Ala Leu Ala Phe Glu Lys Ser
        275                 280                 285

Met Ala Ser Leu Tyr Pro Leu Asn Asn Asn Leu Pro Ser His Leu Gly
    290                 295                 300

Asn Ala Ile Gly Arg Tyr Pro Glu Asp Thr Tyr Asn Gly Asn Gly Asn
305                 310                 315                 320

Ser Gln Gly Asn Pro Trp Phe Leu Ala Thr Thr Ala Phe Thr Glu Leu
                325                 330                 335

Tyr Tyr Arg Ala Ile Leu Glu Trp Lys Asn Thr Gly Val Thr Val Thr
            340                 345                 350

Pro Ile Ser Lys Asp Phe Phe Val Arg Phe Asp Ser Ser Ala Ala Pro
        355                 360                 365

Gly Lys Lys Tyr Asn Pro Gly Ser Gln Glu Phe Ala Thr Leu Thr Gln
    370                 375                 380

Ser Ile Ala Ala Ala Ala Asp Arg Phe Met Ser Thr Val Gln Tyr His
385                 390                 395                 400

Gln Asn Pro Asn Gly Ser Leu Ser Glu Glu Phe Asp Arg Ser Ser Gly
                405                 410                 415

Tyr Met Thr Gly Ala Arg Asp Leu Thr Trp Ser His Ala Ala Phe Ile
            420                 425                 430

Thr Ala Ala Gln Ala Arg Ala Gly Ser Pro Ser Phe
        435                 440
```